(12) United States Patent
Kanai et al.

(10) Patent No.: US 8,140,191 B2
(45) Date of Patent: Mar. 20, 2012

(54) ENVIRONMENT CONTROL DEVICE, ENVIRONMENT CONTROL METHOD, ENVIRONMENT CONTROL PROGRAM, AND COMPUTER-READABLE RECORDING MEDIUM CONTAINING THE ENVIRONMENT CONTROL PROGRAM

(75) Inventors: Etsuko Kanai, Kyoto (JP); Masami Funakura, Osaka (JP); Yasutaka Maeda, Osaka (JP)

(73) Assignee: Panasonic Corporation, Osaka (JP)

( * ) Notice: Subject to any disclaimer, the term of this patent is extended or adjusted under 35 U.S.C. 154(b) by 787 days.

(21) Appl. No.: 11/995,287

(22) PCT Filed: Jul. 6, 2006

(86) PCT No.: PCT/JP2006/313477
§ 371 (c)(1),
(2), (4) Date: Sep. 29, 2008

(87) PCT Pub. No.: WO2007/007632
PCT Pub. Date: Jan. 18, 2007

(65) Prior Publication Data
US 2009/0276062 A1    Nov. 5, 2009

(30) Foreign Application Priority Data

Jul. 11, 2005  (JP) ................ 2005-202129
Jul. 12, 2005  (JP) ................ 2005-203194
Dec. 5, 2005   (JP) ................ 2005-351343
Dec. 5, 2005   (JP) ................ 2005-351344

(51) Int. Cl.
*G06G 7/70* (2006.01)
*G06F 19/00* (2006.01)
*G06F 15/18* (2006.01)
*A61B 5/02* (2006.01)
*A61B 5/04* (2006.01)
*G05B 13/02* (2006.01)
*G05B 13/00* (2006.01)
*G01N 1/22* (2006.01)
*B60T 7/12* (2006.01)

(52) U.S. Cl. .......... 700/276; 700/274; 700/275; 700/47; 700/49; 600/500; 600/483; 600/546; 706/12; 706/13; 706/14; 706/45; 701/96; 701/111; 436/181

(58) Field of Classification Search .................... None
See application file for complete search history.

(56) References Cited

U.S. PATENT DOCUMENTS
6,216,118 B1 * 4/2001 Iokibe et al. ............... 706/12
(Continued)

FOREIGN PATENT DOCUMENTS
JP        2833082        6/1991
(Continued)

OTHER PUBLICATIONS
Daniel Kaplan, Chaotic Statistics of Biomedical Time Series, 1991, IEEE, CH2997-5/91/0000-0033501.00.*
(Continued)

*Primary Examiner* — Albert Decady
*Assistant Examiner* — Sunray Chang
(74) *Attorney, Agent, or Firm* — Wenderoth, Lind & Ponack, L.L.P.

(57) ABSTRACT

An environment control device, an environment control method, an environment control program, and a computer-readable recording medium containing the environment control program for enabling the user to actually have a comfortable feeling in a reliable manner and further to maintain such a comfortable state, are provided. A biological information measuring portion acquires time-series data of the biological information of the user. A chaos analysis portion calculates a parameter about the biological information through chaos analysis of the time-series data acquired by the biological information measuring portion. A state inferring portion infers a comfortable feeling of the user on the basis of the parameter calculated by the chaos analysis portion. A device control portion controls generation of a stimulus to be given to the user on the basis of the result of inference made by the state inferring portion.

9 Claims, 61 Drawing Sheets

U.S. PATENT DOCUMENTS

| | | | |
|---|---|---|---|
| 2002/0103512 A1* | 8/2002 | Echauz et al. | 607/9 |
| 2002/0156392 A1* | 10/2002 | Arai et al. | 600/546 |
| 2002/0196141 A1* | 12/2002 | Boone et al. | 340/540 |
| 2004/0137639 A1* | 7/2004 | Miyazaki et al. | 436/181 |
| 2005/0121530 A1* | 6/2005 | Song | 236/44 C |
| 2005/0215844 A1* | 9/2005 | Ten Eyck et al. | 600/22 |
| 2006/0247542 A1* | 11/2006 | Watanabe et al. | 600/500 |
| 2007/0213786 A1* | 9/2007 | Sackellares et al. | 607/45 |

FOREIGN PATENT DOCUMENTS

| | | |
|---|---|---|
| JP | 2816799 | 3/1995 |
| JP | 7-299040 | 11/1995 |
| JP | 2000-354683 | 12/2000 |
| JP | 2001-141306 | 5/2001 |
| JP | 2002-17687 A * | 1/2002 |
| JP | 2003-42509 | 2/2003 |
| JP | 2003-227654 | 8/2003 |
| JP | 2004-73520 | 3/2004 |
| JP | 2004-73520 A * | 3/2004 |
| JP | 2004-351184 | 12/2004 |

OTHER PUBLICATIONS

JP 2002017687 translation.*
Masaya Koyama et al., Quantitative Symptom Discrimination by Chaotic, Feb. 2000, IEICE Trans. Funamentals, vol. E83-A, No. 2, 6 pages.*
Mitsuyuki Amada et al., A pattern assessment of attractors structured by acceleration plethysmogram time series data, Sep. 2004.*
JP 2004073520 translation.*
International Search Report issued Oct. 3, 2006 in the International (PCT) Application No. PCT/JP2006/313477.

* cited by examiner

FIG.6A
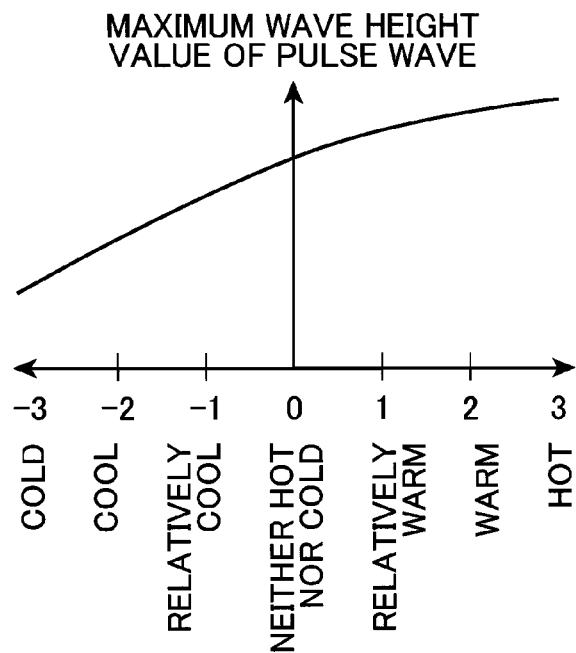
FIG.6B
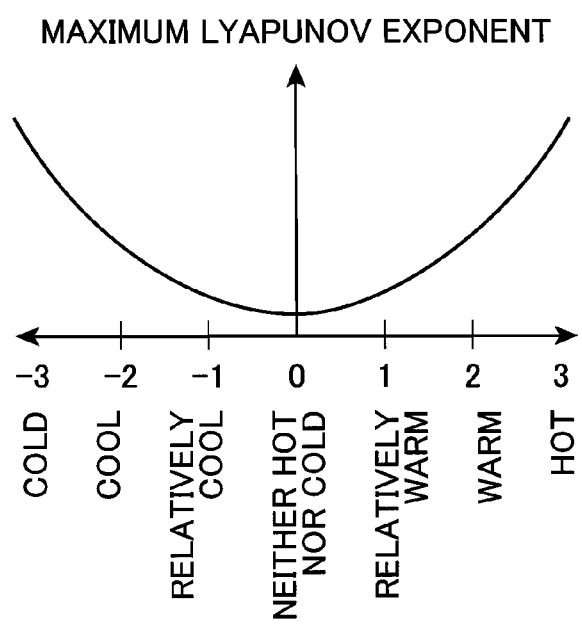
FIG.6C
|  |  | MAXIMUM WAVE HEIGHT VALUE OF PULSE WAVE | |
|---|---|---|---|
|  |  | INCREASE | DECREASE |
| MAXIMUM LYAPUNOV EXPONENT | INCREASE | 0→HOT | 0→COLD |
|  | DECREASE | COLD→0 | HOT→0 |

FIG.8

| INFERENCE DATA | CONTROL DATA |
|---|---|
| COLD→0<br>HOT→0 | NO DATA |
| 0→COLD | WARM CONTROL |
| 0→HOT | COOL CONTROL |

FIG.11

|  |  | ROOM TEMPERATURE ||
|  |  | RISE | DROP |
| --- | --- | --- | --- |
| MAXIMUM LYAPUNOV EXPONENT | INCREASE | 0→HOT | 0→COLD |
|  | DECREASE | COLD→0 | HOT→0 |

FIG.14A

|  |  | COOLING PERFORMANCE | |
|---|---|---|---|
|  |  | INCREASE | DECREASE |
| MAXIMUM LYAPUNOV EXPONENT | INCREASE | 0→COLD | 0→HOT |
|  | DECREASE | HOT→0 | COLD→0 |

FIG.14B

|  |  | HEATING PERFORMANCE | |
|---|---|---|---|
|  |  | INCREASE | DECREASE |
| MAXIMUM LYAPUNOV EXPONENT | INCREASE | 0→HOT | 0→COLD |
|  | DECREASE | COLD→0 | HOT→0 |

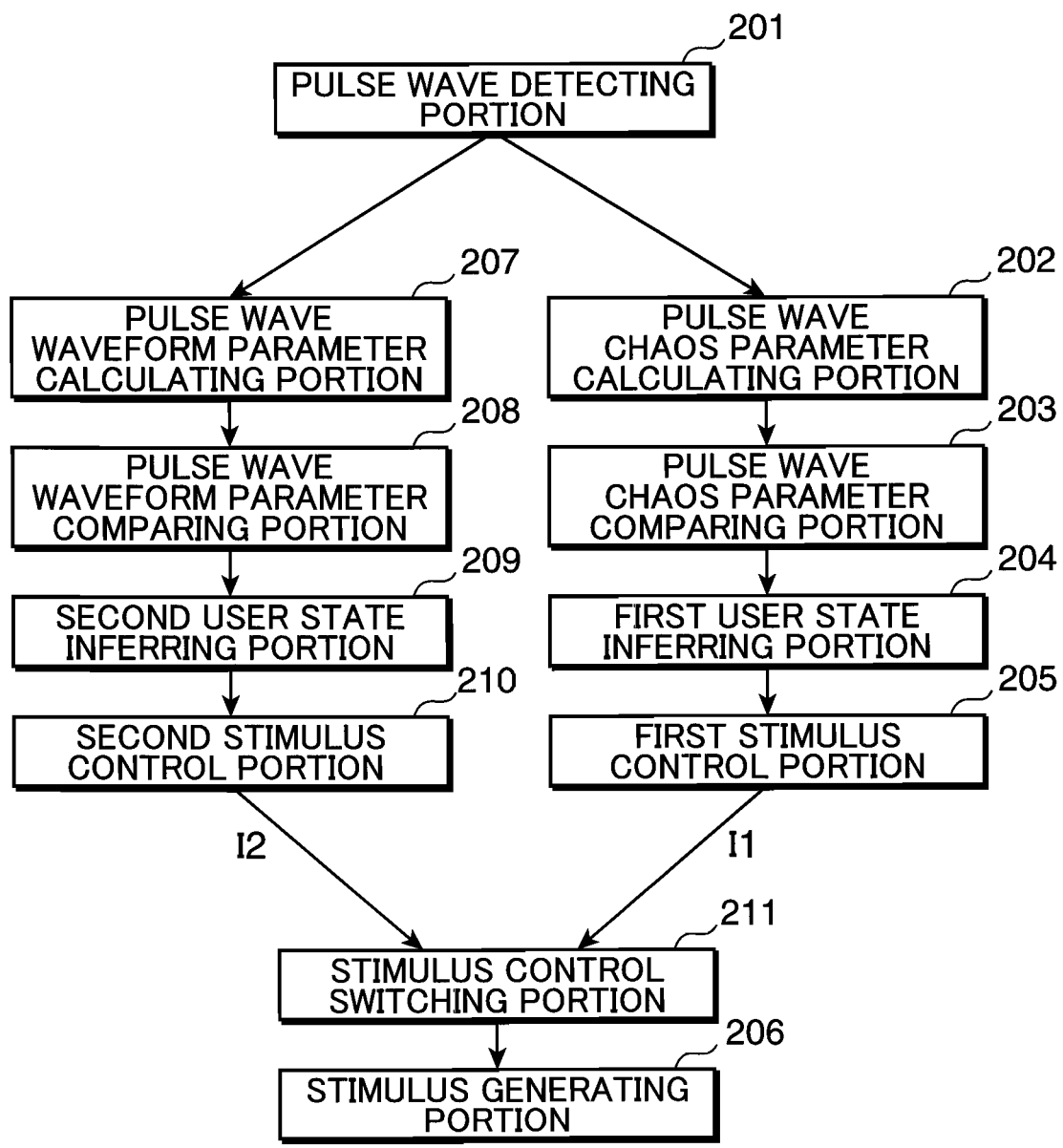

FIG.55

| FIRST THERMAL SENSATION CHANGE INFERRING PORTION | SECOND THERMAL SENSATION CHANGE INFERRING PORTION | THERMAL SENSATION CHANGE DETERMINING PORTION |
|---|---|---|
| THERMAL SENSATION HAS INCREASED | THERMAL SENSATION HAS INCREASED | THERMAL SENSATION HAS INCREASED k=1 |
| THERMAL SENSATION HAS INCREASED | NO CHANGE | THERMAL SENSATION HAS INCREASED k=0.5 |
| THERMAL SENSATION HAS INCREASED | THERMAL SENSATION HAS DECREASED | NO CHANGE k=0 |
| NO CHANGE | THERMAL SENSATION HAS INCREASED | THERMAL SENSATION HAS INCREASED k=0.5 |
| NO CHANGE | NO CHANGE | NO CHANGE k=0 |
| NO CHANGE | THERMAL SENSATION HAS DECREASED | THERMAL SENSATION HAS DECREASED k=0.5 |
| THERMAL SENSATION HAS DECREASED | THERMAL SENSATION HAS INCREASED | NO CHANGE k=0 |
| THERMAL SENSATION HAS DECREASED | NO CHANGE | THERMAL SENSATION HAS DECREASED k=0.5 |
| THERMAL SENSATION HAS DECREASED | THERMAL SENSATION HAS DECREASED | THERMAL SENSATION HAS DECREASED k=1 |

FIG.58

| FIRST THERMAL SENSATION CHANGE INFERRING PORTION (BASED ON b/a) | SECOND THERMAL SENSATION CHANGE INFERRING PORTION (BASED ON OTHER THAN b/a) | THERMAL SENSATION CHANGE DETERMINING PORTION |
|---|---|---|
| THERMAL SENSATION HAS INCREASED | THERMAL SENSATION HAS INCREASED | THERMAL SENSATION HAS INCREASED k=1 |
| | NO CHANGE | THERMAL SENSATION HAS INCREASED k=0.5 |
| | THERMAL SENSATION HAS DECREASED | NO CHANGE k=0 |
| NO CHANGE | THERMAL SENSATION HAS INCREASED | THERMAL SENSATION HAS INCREASED TO SPECIFIC VALUE OR ABOVE k=1 |
| | NO CHANGE | NO CHANGE k=0 |
| | THERMAL SENSATION HAS DECREASED | THERMAL SENSATION HAS DECREASED k=0.5 |
| THERMAL SENSATION HAS DECREASED | THERMAL SENSATION HAS INCREASED | NO CHANGE k=0 |
| | NO CHANGE | THERMAL SENSATION HAS DECREASED k=0.5 |
| | THERMAL SENSATION HAS DECREASED | THERMAL SENSATION HAS DECREASED k=1 |

ENVIRONMENT CONTROL DEVICE, ENVIRONMENT CONTROL METHOD, ENVIRONMENT CONTROL PROGRAM, AND COMPUTER-READABLE RECORDING MEDIUM CONTAINING THE ENVIRONMENT CONTROL PROGRAM

TECHNICAL FIELD

The present invention relates to an environment control device, an environment control method, an environment control program, and a computer-readable recording medium containing the environment control program for controlling the residential environment by inferring a state of the user on the basis of biological information of the user.

BACKGROUND ART

Regarding the functions of a system, technical developments have been shifting from unidirectional to bidirectional in recent years. Such shifting indicates that achievement of functions that take differences among individuals into account will become the key technology in the future, and various research communities propose systems in which the psychological state of an individual is inferred by any available method and devices are controlled thereafter using the result of inference. As means for inferring the psychological state of an individual, making inference on the basis of biological information of an individual is deemed as the most reliable means, and studies in this field has been actively conducted in recent years.

Generally, a technique of inferring a comfortable feeling of the user by analyzing the brain wave is known extensively. This technique can be said as useful means in a case where evaluation tests or the like are the purpose. However, because this technique requires large-scale equipment and has a requisite to limit movements of an individual, developing this technique actually at home has been thought as infeasible. It can be said also from the foregoing that a point that has to be considered always when acquiring biological information is how easily biological information is acquired without making the user feel uncomfortable to the extent possible.

When considerations are given to this point, in comparison with the collection of the bran wave for which efforts are currently being undertaken, collecting the pulse wave that is said to have the least possibility of making an individual feel uncomfortable is thought as the most effective means. Regarding the pulse wave, there has been revealed a phenomenon in the first place that a blood flow discharged from the heart and delivered to peripheral fingertips comes under a significant influence of physiological conditions, such as a change in property of a heart rate, hemodynamics, and an arteriolovenular system, and such a change is reflected on the waveform of the pulse wave. Accordingly, in the field of health analysis, a currently proposed technique is to collect the pulse wave of the peripheral blood vessel in the fingertips and infer the health condition from the accelerated pulse wave (for example, see Patent Document 1).

FIG. 60 is a view showing the waveform of the accelerated pulse wave described in Patent Document 1. As is shown in FIG. 60, the accelerated pulse wave is made up of five elementary waves denoted as E1, E2, E3, E4, and E5. Because the peak A of the elementary wave E1 coincides with the start of the diastolic wave in the fingertip plethysmogram, a required time from the peak A to the peak E coincides with the systolic time axial length. The elementary wave E1 is a positive wave that is convex upward with respect to the base line, the elementary wave E2 is a negative wave that is convex downward with respect to the base line, and the following elementary waves E3, E4, and E5 are changeable elementary waves that become either a positive wave or a negative wave depending on the physiological conditions, all of which have a strong correlation with the age of the user.

When the pulse wave of the user is measured, the heart rate increases when the user is in a state of tension and the fingertip blood flow tends to decrease. This gives rise to an influence that a distance b to the peak B from the base line decreases whereas a distance d to the peak D from the base line increases. Hence, in the waveform analysis of the accelerated pulse wave, the health condition is determined by a rate of change in the ratio of the distance b to the distance a (b/a) or in the ratio of the distance d to the distance a (d/a).

Also, with the purpose of enabling the user to maintain satisfactory psychological state and feeling, Patent Document 2 proposes a warm air heating device configured in such a manner that an amount of heat generation by heating means or an amount of air flow by air blowing means becomes irregular with time to enable the user to maintain a warm feeling by maintaining an influence on the automatic nerve for a state of relaxation to be enhanced.

FIG. 61 is a block diagram showing the configuration of the warm air heating device described in Patent Document 2. An air blowing portion 1001 shown in FIG. 61 is formed of a fan motor and a heating portion 1002 is formed of a heat source, such as heating oil or a heater. A temperature sensor 1003 to detect the temperature is provided in the vicinity of the heating portion 1002, and detected temperature information is transmitted to a control portion 1004. The control portion 1004 controls an amount of air blow by the air blowing portion 1001 and an amount of heat generation by the heating portion 1002 by outputting an irregular signal generated by an irregular signal generating portion 1005 to the air blowing portion 1001 and the heating portion 1002 at appropriate timing determined according to a timer signal from a timer 1006 and a detected temperature signal from the temperature sensor 1003.

Also, in order to control the residential environment of the user, an environmental control device has been controlled by detecting environment physical quantities, such as a residential environment temperature (hereinafter, referred to as room temperature), a residential environment humidity (hereinafter, referred to as humidity), a residential environment outside air temperature (hereinafter, referred to as outside air temperature), and an amount of solar radiation. Besides the control based on the environment physical quantities as described above, there has been proposed a technique for inferring a state of the user, such as a state of tension, a state of relaxation, and a state of excitation through chaos analysis of biological information of the user to control the environment control device on the basis of the result of inference.

For example, Patent Document 3 proposes a multimedia equipment control device configured to control multimedia equipment by inferring a feeling of tension, a feeling of relaxation, and a feeling of excitement of the user from evaluation made by detecting the skin temperature of fingertips or the like of the user (subject) and evaluating the detected skin temperature through chaos analysis or the like.

Also, Patent Document 4 proposes an environment control device configured to control environment conditions by inferring a psychological state or a physiological state of the user through chaos analysis of time-series data of motions of the user (individual).

Also, Patent Document 5 proposes an electronic device that changes a response from a game machine, such as a pinball game machine, by inferring a state of being bored, a state of excitement, and a state of concentration or distraction of the user with respect to the game machine using the Lyapunov exponent obtained through chaos analysis of the pulse wave, a heart rate, or the like collected from the user (player) of the game machine.

Also, Patent Document 6 proposes a bath device provided with a pulse wave detector on the surface of the bathroom remote controller to detect pulse wave data when the user (an individual taking a bath) puts his fingertip on the detector, so that when pulse wave data different from the normal data is detected, the bath device alerts the user to take a rest, informs the family members of such a detection or performs the control to lower the hot water temperature.

Also, Patent Document 7 proposes a technique for enhancing efficiency of job or study of an individual by performing air-conditioning in response to a change of a physiological amount of the sympathetic nerve system by utilizing a phenomenon that when an individual doing a job or studying in a room is getting irritated because of low efficiency, his automatic nerve, in particular, his sympathetic nerve, increases its activity, which causes the skin temperature to drop as the blood flows to the head by an increase of an amount of sweat or the number of pulses, which are the physiological amount of the sympathetic nerve system.

Also, Patent Document 8 proposes a technique of inferring a psychological state of an individual, chiefly a warm feeling, from the amplitude of the pulse wave of an individual, which is determined as having the least possibility of making an individual feel uncomfortable, because a point that has to be considered always when acquiring biological information is how simply the technique is implemented as a system and how least the user is made feel uncomfortable when biological information is acquired.

With the configuration described in Patent Document 1, the health analysis of the user is made with the use of the pulse wave. However, because a comfortable feeling of the user is not inferred, there is a problem that it is impossible to control a stimulus outputted to the user for the user to maintain a comfortable feeling.

Also, with the configuration described in Patent Document 2, the user is enabled to maintain a satisfactory feeling by providing irregularities to the control on the device side. However, because a comfortable feeling of the user is not inferred, this configuration is susceptible to further improvement for enabling the user to maintain a comfortable feeling in a more reliable manner.

Further, although a state of the user is inferred through chaos analysis in Patent Documents 3 through 5, time-series data of biological information over a sufficiently long period, for example, from a few minutes to about 15 minutes, is necessary to infer a state of the user through chaos analysis. This raises a problem that a state of the user cannot be inferred precisely until the sufficiently long period has passed since the acquisition of biological information was started, which makes it impossible to give a suitable stimulus to the user during such a period. In particular, in a case where chaos analysis is adopted to control a device forming the residential environment of the user, for example, an air conditioning device, a lighting device, a video device, or an audio device, it is anticipated that there is a case where time-series data over a sufficiently long period cannot be acquired. Hence, there is a problem that how accurately a state of the user can be inferred during such a period.

Also, there have been proposed various methods and devices for inferring a state of the user through chaos analysis of biological information of the user as in Patent Documents 3 through 6. However, which state of the user can be inferred through chaos analysis of which biological information is still under study and development. In addition, Patent Document 3 describes that a state of tension, a state of relaxation, and a state of excitement of the user can be inferred through chaos analysis of the skin temperature of the user. However, it fails to disclose a correlation between chaos analysis and a comfortable feeling or a thermal sensation in response to a warm or cool thermal stimulus.

In addition, Patent Document 4 describes that it is possible to control an air conditioner or the like by finding a comfortable feeling in response warm or cool thermal through chaos analysis of motions of the user. However, it fails to disclose a correlation between chaos analysis of biological information other than motions of the user and a degree of comfort in response to warm or cool thermal.

Also, Patent Document 5 describes that a state of being bored, a state of excitement, and a state of concentration or distraction of the user can be inferred through chaos analysis of the pulse wave, a heart rate, and the like of the user. However, it fails to disclose a concrete correlation between the Lyapunov exponent obtained through chaos analysis and a state of the user. It also describes that a response to air conditioning can be changed, too. However, it also fails to disclose a correlation between chaos analysis and a comfortable feeling or a thermal sensation in response to a warm or cool thermal stimulus.

Also, Patent Document 6 describes that the device performs the control to lower the hot water temperature upon detection of pulse wave data different from normal data. However, this is to control the hot water temperature by inferring an abnormality of the user from the pulse wave, and not to control the hot water temperature by inferring a comfortable feeling or a thermal sensation of the user in response to a warm or cool thermal stimulus.

Also, in Patent Document 7, plural physiological amounts of the automatic nerve system are collected as biological information used to infer a psychological state of the user. In this case, however, because plural physiological amounts are measured at one time, plural sensors have to be incorporated into the system, which makes it difficult to put this configuration into practical use. In addition, it describes that a psychological state of an individual is inferred by comprehensively determining the measurement results of these plural physiological amounts of the automatic nerve system. However, it fails to disclose clearly a concrete method for making a comprehensive determination.

Also, Patent Document 8 proposes to use the amplitude characteristic of the pulse wave in response to a warm feeling of an individual for the technique of inferring a warm feeling of an individual using the pulse wave, which is one kind of biological information. However, by taking into account that the absolute value of the amplitude completely varies from individual to individual, it is impossible to avoid an influence of differences among individuals, which deteriorates accuracy of inference.

Patent Document 1: JP-A-2004-351184 (page 7 and FIG. 2)
Patent Document 2: JP-A-2001-141306 (page 10 and FIG. 1)
Patent Document 3: JP-A-7-299040
Patent Document 4: Japanese Patent No. 2816799
Patent Document 5: JP-A-2000-354683
Patent Document 6: JP-A-2003-227654
Patent Document 7: JP-A-2003-42509
Patent Document 8: Japanese Patent No. 2833082

SUMMARY OF THE INVENTION

The invention was devised to solve the problems discussed above, and therefore has an object to provide an environment control device, an environment control method, an environment control program, and a computer-readable recording medium containing the environment control program for enabling the user to actually have a comfortable feeling in a reliable manner and further to maintain such a comfortable state.

An environment control device according to an aspect of the invention includes: a biological information acquiring portion for acquiring time-series data of biological information of a user; a parameter calculating portion for calculating a parameter about the biological information through chaos analysis of the time-series data acquired by the biological information acquiring portion; an inferring portion for inferring a comfortable feeling of the user on the basis of the parameter calculated by the parameter calculating portion; and a stimulus control portion for controlling generation of a stimulus to be given to the user on the basis of a result of inference made by the inferring portion.

An environment control method according to another aspect of the invention includes: a biological information acquiring step of acquiring time-series data of biological information of a user; a parameter calculating step of calculating a parameter about the biological information through chaos analysis of the time-series data acquired in the biological information acquiring step; an inferring step of inferring a comfortable feeling of the user on the basis of the parameter calculated in the parameter calculating step; and a stimulus controlling step of controlling generation of a stimulus to be given to the user on the basis of a result of inference made in the inferring step.

An environment control program according to still another aspect of the invention causes a computer to function as: a biological information acquiring portion for acquiring time-series data of biological information of a user; a parameter calculating portion for calculating a parameter about the biological information through chaos analysis of the time-series data acquired by the biological information acquiring portion; an inferring portion for inferring a comfortable feeling of the user on the basis of the parameter calculated by the parameter calculating portion; and a stimulus control portion for controlling generation of a stimulus to be given to the user on the basis of a result of inference made by the inferring portion.

A computer-readable recording medium containing an environment control program according to still another aspect of the invention has recorded therein an environment control program that causes a computer to function as: a biological information acquiring portion for acquiring time-series data of biological information of a user; a parameter calculating portion for calculating a parameter about the biological information through chaos analysis of the time-series data acquired by the biological information acquiring portion; an inferring portion for inferring a comfortable feeling of the user on the basis of the parameter calculated by the parameter calculating portion; and a stimulus control portion for controlling generation of a stimulus to be given to the user on the basis of a result of inference made by the inferring portion.

According to these configurations, the parameter about the biological information is calculated through chaos analysis of the time-series data of the biological information of the user. A comfortable feeling of the user in response to a stimulus is inferred on the basis of the parameter thus calculated, and the generation of a stimulus to be given to the user is controlled on the basis of the result of inference. In other words, in a case where the result of inference obtained indicates a deterioration of a comfortable feeling of the user, a stimulus such that enhances a comfortable feeling is given to the user.

Hence, because a comfortable feeling is inferred on the basis of the parameter calculated through chaos analysis of the time-series data of the biological information of the user and the generation of a stimulus to be given to the user is controlled on the basis of the result of inference, it is possible to enable the user to actually have a comfortable feeling in a reliable manner and further to maintain such a comfortable state.

An environment control device according to still another aspect of the invention includes: a biological information acquiring portion for acquiring time-series data of biological information of a user; a parameter calculating portion for calculating a parameter about the biological information on the basis of a change of the time-series data acquired by the biological information acquiring portion; an inferring portion for inferring a comfortable feeling of the user on the basis of the parameter calculated by the parameter calculating portion; and a stimulus control portion for controlling generation of a stimulus to be given to the user on the basis of a result of inference made by the inferring means.

An environment control method according to still another aspect of the invention includes: a biological information acquiring step of acquiring time-series data of biological information of a user; a parameter calculating step of calculating a parameter about the biological information on the basis of a change of the time-series data acquired in the biological information acquiring step; an inferring step of inferring a comfortable feeling of the user on the basis of the parameter calculated in the parameter calculating step; and a stimulus controlling step of controlling generation of a stimulus to be given to the user on the basis of a result of inference made in the inferring step.

An environment control program according to still another aspect of the invention causes a computer to function as: a biological information acquiring portion for acquiring time-series data of biological information of a user; a parameter calculating portion for calculating a parameter about the biological information on the basis of a change of the time-series data acquired by the biological information acquiring portion; an inferring portion for inferring a comfortable feeling of the user on the basis of the parameter calculated by the parameter calculating portion; and a stimulus control portion for controlling generation of a stimulus to be given to the user on the basis of a result of inference made by the inferring portion.

A computer-readable recording medium containing an environment control program according to still another aspect of the invention has recorded therein an environment control program that causes a computer to function as: a biological information acquiring portion for acquiring time-series data of biological information of a user; a parameter calculating portion for calculating a parameter about the biological information on the basis of a change of the time-series data acquired by the biological information acquiring portion; an inferring portion for inferring a comfortable feeling of the user on the basis of the parameter calculated by the parameter calculating portion; and a stimulus control portion for controlling generation of a stimulus to be given to the user on the basis of a result of inference made by the inferring portion.

According to these configurations, the parameter about the biological information is calculated on the basis of a change of the time-series data of the biological information of the user. A comfortable feeling of the user in response to a stimulus is inferred on the basis of the parameter thus calculated, and the generation of a stimulus to be given to the user is controlled on the basis of the result of inference. In other words, in a case where the result of inference obtained indicates a deterioration of a comfortable feeling of the user, a stimulus such that enhances a comfortable feeling is given to the user.

Hence, because a comfortable feeling is inferred on the basis of the parameter calculated on the basis of a change of the time-series data of the biological information of the user and the generation of a stimulus to be given to the user is controlled on the basis of the result of inference, it is possible to enable the user to actually have a comfortable feeling in a reliable manner and further to maintain such a comfortable state.

The above and other objects, features, and advantages of the invention will become more apparent from the following detailed description with reference to the accompanying drawings.

BRIEF DESCRIPTION OF THE DRAWINGS

FIG. 6A is a graph indicating a correlation between the maximum wave height value of the pulse wave and a thermal sensation of the user discovered by the inventors from the test conducted on subjects, FIG. 6B is a graph indicating a correlation between the maximum Lyapunov exponent and a thermal sensation of the user, and FIG. 6C is a table in which relations of the maximum wave height value of the pulse wave and the maximum Lyapunov exponent with respect to a thermal sensation shown in FIGS. 6A and 6B are tabulated in a matrix fashion.

FIG. 8 is a view showing a table in which inference data and control data are correlated with each other.

FIG. 11 a view showing a table in which a thermal sensation in response to the maximum Lyapunov exponent and room temperature found in the same manner as in the second embodiment is tabulated in a matrix fashion.

FIG. 14A is a view showing a table in which relations of the maximum Lyapunov exponent and the cooling performance with respect to a thermal sensation are tabulated in a matrix fashion, and FIG. 14B is a view showing a table in which relations of the maximum Lyapunov exponent and the heating performance with respect to a thermal sensation are tabulated in a matrix fashion.

FIG. 15 is a block diagram schematically showing the configuration of an environment control device according to a fifth embodiment of the invention.

FIG. 55 is a view showing an example of a table in which the results of inference made by a first thermal sensation change inferring portion and a second thermal sensation change inferring portion are correlated with a change of a thermal sensation and a coefficient k determined by a thermal sensation change determining portion of the fifteenth embodiment.

FIG. 58 is a view showing an example of a table in which the results of inference made by a first thermal sensation change inferring portion and a second thermal sensation change inferring portion are correlated with a change of a thermal sensation and a coefficient k determined by a thermal sensation change determining portion of a seventeenth embodiment.

DETAILED DESCRIPTION OF THE INVENTION

Hereinafter, embodiments of the invention will be described with reference to the drawings.

First Embodiment

An environment control device according to a first embodiment of the invention will be described. Regarding a warm or cool thermal stimulus (a change in the warm or cool thermal environment), the inventors discovered the presence of a high correlation between a variance of the maximum Lyapunov exponent, which is a degree of fluctuation of the pulse wave of the user converted to an exponent, and a variance of a thermal sensation. The environment control device of the first embodiment therefore infers a thermalسensation of the user using this correlation.

Figure 1:
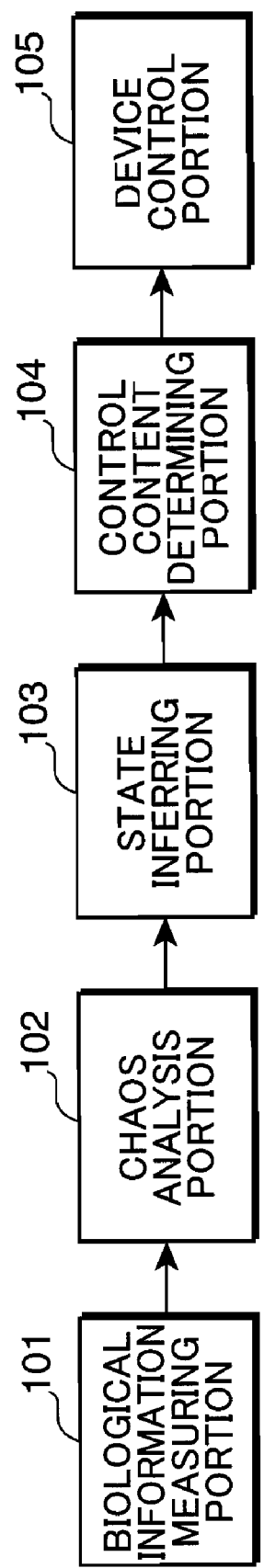
FIG. 1 is a block diagram showing the configuration of an environment control device according to a first embodiment of the invention.

FIG. 1 is a block diagram showing the configuration of the environment control device according to the first embodiment of the invention. The environment control device shown in FIG. 1 is formed of, for example, a known computer, and includes a biological information measuring portion (biological information acquiring portion) 101, a chaos analysis portion (parameter calculating portion) 102, a state inferring portion (inferring portion) 103, a control content determining portion (stimulus control portion) 104, and a device control portion 105. The biological information measuring portion 101 through the device control portion 105 are achieved by running an environment control program of the invention pre-installed in the computer on the CPU.

The biological information measuring portion 101 acquires pulse wave data in time series by sampling the fingertip pulse wave of the user detected by a known transducer or the like at a specific sampling cycle. The chaos analysis portion 102 calculates, as a parameter to evaluate the pulse wave, the maximum Lyapunov exponent, which is a value obtained by converting a degree of fluctuation of the pulse wave to an exponent, through chaos analysis of the pulse wave data over a specific time, and finds an average (so-called a moving average) of a specific number of maximum Lyapunov exponents calculated by successively shifting the specific time for the pulse wave data of interest, so that it accumulates the average as the maximum Lyapunov exponent over a predetermined length of time at a current point in time.

The state inferring portion 103 calculates a variance of the maximum Lyapunov exponent extracted by the chaos analysis portion 102 to infer a thermal sensation of the user from the result of calculation, and outputs inference data, which is the result of inference, to the control content determining portion 104. In this embodiment, the state inferring portion 103 calculates a derivative value of the maximum Lyapunov exponent by dividing a difference between the current value and an intermediately preceding value, which is the value immediately preceding the current value, of the maximum Lyapunov exponent calculated successively in time series since the device control portion 105 started a control operation by a time difference (sampling cycle), and infers a thermal sensation of the user by determining to which of pre-set plural behavioral examples described below this derivative value fits.

The control content determining portion 104 generates control data of the device on the basis of the inference data indicating a thermal sensation of the user at a point in time when the inference data is outputted from the state inferring portion 103, and outputs the control data to the device control portion 105. The device control portion 105 controls the device according to the control data outputted from the control content determining portion 104.

Figure 2:
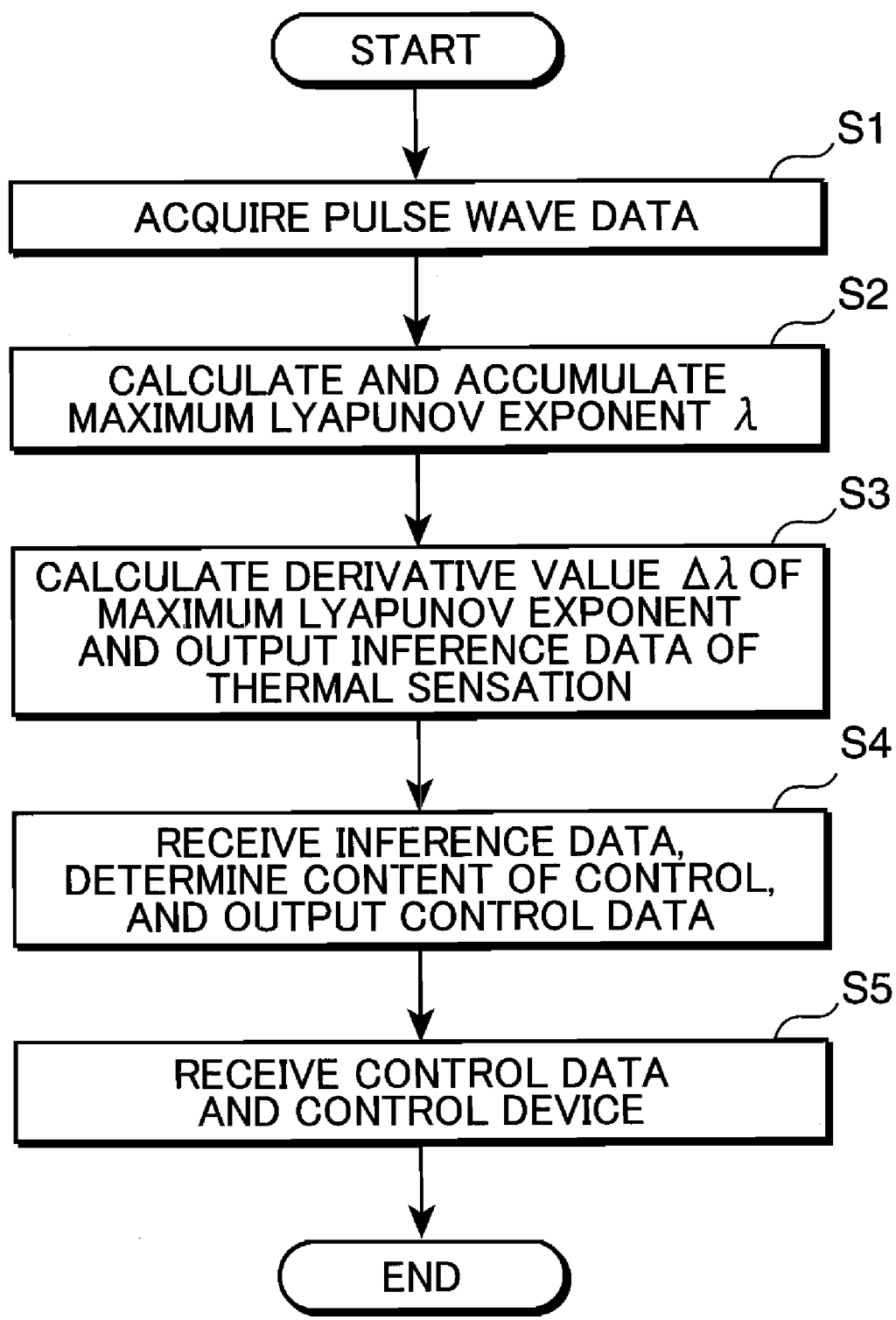
FIG. 2 is a flowchart detailing the flow of the processing by the environment control device according to the first embodiment of the invention.

FIG. 2 is a flowchart detailing the flow of the processing by the environment control device according to the first embodiment of the invention. Initially, the biological information measuring portion 101 acquires time-series data of the pulse wave by measuring the pulse wave of the user (Step S1). Subsequently, the chaos analysis portion 102 calculates the maximum Lyapunov exponent $\lambda$ at regular time intervals on the basis of the time-series data of the pulse wave measured by the biological information measuring portion 101 and accumulates it therein (Step S2). Subsequently, the state inferring portion 103 calculates a derivative value $\Delta\lambda$ of the maximum Lyapunov exponent $\lambda$ by dividing a difference between the current value and an immediately preceding value, which is the value immediately preceding the current value, of the maximum Lyapunov exponent $\lambda$ extracted by the chaos analysis portion 102 by a time difference (sampling cycle). The state inferring portion 103 then infers a thermal sensation of the user on the basis of the derivative value $\Delta\lambda$ of the maximum Lyapunov exponent it has calculated, and outputs the inference data, which is the result of inference, to the control content determining portion 104 (Step S3).

Subsequently, the control content determining portion 104 receives the inference data outputted from the state inferring portion 103. The control content determining portion 104 then determines the content of control of the device on the basis of the inference data outputted from the state inferring portion 103, and outputs the control data, which is the content of control, to the device control portion 105 (Step S4). Subsequently, the device control portion 105 receives the control data outputted from the control content determining portion 104. The device control portion 105 controls the device according to the control data outputted from the control content determining portion 104 (Step S5).

The processing to infer a thermal sensation of the user by the state inferring portion 103 of this embodiment will now be described.

Figure 3:
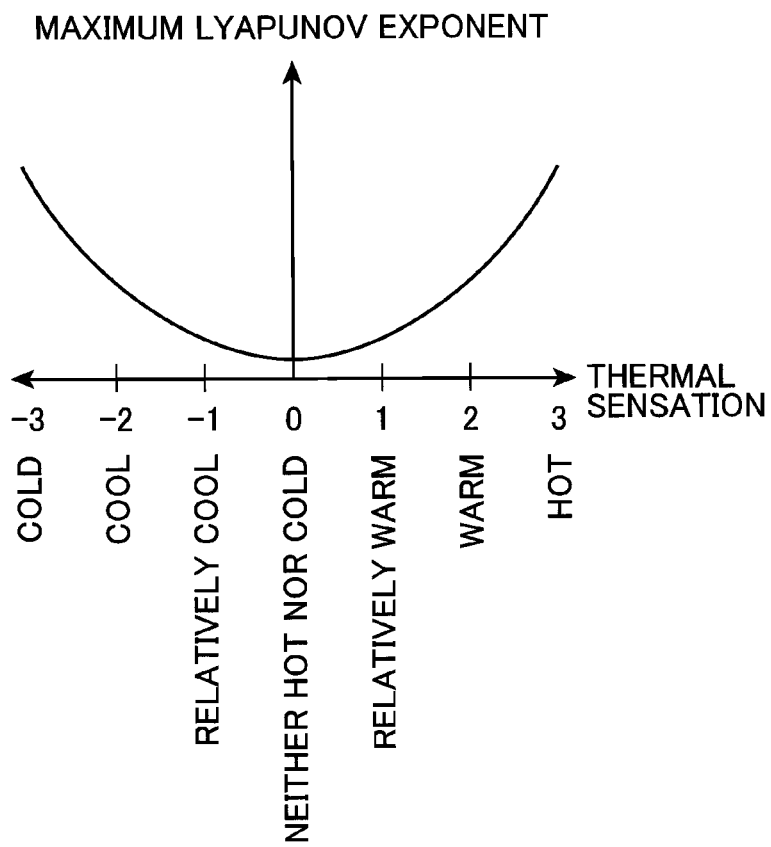
FIG. 3A is a graph indicating a correlation between the maximum Lyapunov exponent and a thermal sensation of the user discovered by the inventors from a test conducted on subjects.
FIG. 3B is a table in which a relation between a variance of the maximum Lyapunov exponent and a variance of a thermal sensation discovered from FIG. 3A is tabulated.

The inventors discovered the presence of a high correlation between a variance of the maximum Lyapunov exponent and a variance of a thermal sensation of the user. FIG. 3A is a graph indicating a correlation between the maximum Lyapunov exponent and a thermal sensation of the user discovered by the inventors from a test conducted on subjects. As is shown in FIG. 3A, it is understood that the maximum Lyapunov exponent and a thermal sensation have a correlation indicated by a downward convex graph such that the maximum Lyapunov exponent takes the external value in the vicinity of a point at which a thermal sensation indicates 0 (a neutral state where it is neither hot nor cold).

FIG. 3B is a table in which the relation between a variance of the maximum Lyapunov exponent and a variance of a thermal sensation discovered from FIG. 3A is tabulated. The state inferring portion 103 holds therein this table in advance. "Increase" shown in this table indicates that the maximum Lyapunov exponent has increased in the graph shown in FIG. 3A. "Thermal sensation improved (cold→0 or hot→0)" indicates that a thermal sensation has changed from a hot state or a cold state to the neutral state where it is neither hot nor cold in the graph shown in FIG. 3A. "Decrease" indicates that the maximum Lyapunov exponent has decreased in the graph shown in FIG. 3A. "Thermal sensation deteriorated (0→cold or 0→hot)" indicates that a thermal sensation has changed from the neutral state where it is neither hot nor cold to a cold state or a hot state in the graph shown in FIG. 3A.

More specifically, in a case where the derivative value $\Delta\lambda$ of the maximum Lyapunov exponent $\lambda$ is equal to 0 or greater after the control by the device forming the warm or cool thermal environment is executed, the state inferring portion 103 determines that the maximum Lyapunov exponent has increased, and infers that a thermal sensation of the user has changed in a direction from the neutral state (0 side) where it is neither hot nor cold to a cold state or in a direction from the neutral state (0 side) where it is neither hot nor cold to a hot state, that is, a thermal sensation has deteriorated. Meanwhile, in a case where the derivative value $\Delta\lambda$ of the maximum Lyapunov exponent $\lambda$ is smaller than 0, the state inferring portion 103 determines that the maximum Lyapunov exponent has decreased, and infers that a thermal sensation of the user has changed in a direction (0 direction) from a cold state to the neutral state where it is neither hot nor cold or in a direction (0 direction) from a hot state to the neutral state where it is neither hot nor cold, that is, a thermal sensation has improved.

In a case where the state inferring portion 103 infers that a thermal sensation of the user has improved, it outputs the inference data exhibiting "thermal sensation improved", and in a case where it infers that a thermal sensation of the user has deteriorated, it outputs the inference data exhibiting "thermal sensation deteriorated".

Upon input of the inference data from the state inferring portion 103, the control content determining portion 104 converts the inference data to the control data of the device. For example, in a case where the inference data inputted therein exhibits "thermal sensation deteriorated", the control data is determined to have the content to improve a thermal sensation. Meanwhile, in a case where the inference data inputted therein exhibits "thermal sensation improved", the control data is determined to have the content indicating "no data" and no control data is outputted.

Regarding the inference of a thermal sensation of the user by the state inferring portion 103, the phrase, "a thermal sensation changes in a direction (0 direction) from a cold state to the neutral state where it is neither hot nor cold", means that a thermal sensation moves in the 0 direction from a given point positioned within a range from −3 to 0 on the abscissa in FIG. 3A. The phrase, "a thermal sensation changes in the direction (0 direction) from a hot state to the neutral state where it is neither hot nor cold", means that a thermal sensation moves in the 0 direction from a given point positioned within a range from +3 to 0 on the abscissa in FIG. 3A. The phase, "a thermal sensation changes in a direction from the neutral state (0 side) where it is neither hot nor cold to a cold state", means that a thermal sensation moves in a −3 direction from a given point positioned within a range from 0 to −3 on the abscissa in FIG. 3A. The phrase, "a thermal sensation changes in a direction from the neutral state (0 side) where it is neither hot nor cold to a hot state", means that a thermal sensation moves in a +3 direction from a given point positioned within a range from 0 to +3 on the abscissa in FIG. 3A.

For the degree of control by the control data outputted from the control content determining portion 104, a pre-determined value may be used, for example, to change the temperature set as room temperature by 2 degrees, or the degree of a change in control may be determined by the state inferring portion 103 on the basis of the magnitude of the derivative value Δλ.

As has been described, according to the environment control device of the first embodiment, a thermal sensation of the user is inferred on the basis of the maximum Lyapunov exponent obtained through chaos analysis of the time-series data of the pulse wave used as the biological information of the user, and the device (in particular, an air conditioning device) forming the residential environment of the user is controlled according to the result of inference. It is thus possible to give the user a warm or cool thermal stimulus such that leads a thermal sensation of the user to a moderate state where it is neither hot nor cold.

Second Embodiment

An environment control device according to a second embodiment of the invention will now be described. It has been known that the absolute value of the amplitude of the pulse wave and a thermal sensation of the user have a high correlation. However, because the absolute value of the amplitude of the pulse wave varies completely from individual to individual, using the absolute value of the amplitude of the pulse wave to infer a thermal sensation of the user is significantly susceptible to differences among individuals, which raises a problem that accuracy of inference is deteriorated.

Under these circumstances, the inventors discovered the presence of a high correlation between a variance of the maximum value of the wave height of the pulse wave (maximum wave height value of the pulse wave), which corresponds to a variance of the amplitude of the pulse wave, and a variance of a thermal sensation of the user. The inventors also discovered the presence of a high correlation between a variance of the maximum Lyapunov exponent, which is a degree of fluctuation of the pulse wave of the user converted an exponent, and a variance of a thermal sensation of the user. The inventors thus discovered that it is possible to achieve the inference of a thermal sensation of the user at a higher degree of accuracy without an influence of differences among individuals by inferring a thermal sensation of the user on the basis of a variance of the maximum wave height value of the pulse wave and a variance of the maximum Lyapunov exponent with respect to a warm or cool thermal stimulus (a change in the warm or cool thermal environment).

The maximum wave height value of the pulse wave referred to herein means the peak value of the waveform of the pulse wave for several pulse beats obtained within a specific time in the pulse wave data. Alternatively, it may be the peak value of the waveform for each pulse beat, the average value of the peak values of the respective waveforms of the pulse wave for several pulse beats, or the amplitude of the pulse wave in the pulse wave data.

Figure 4:
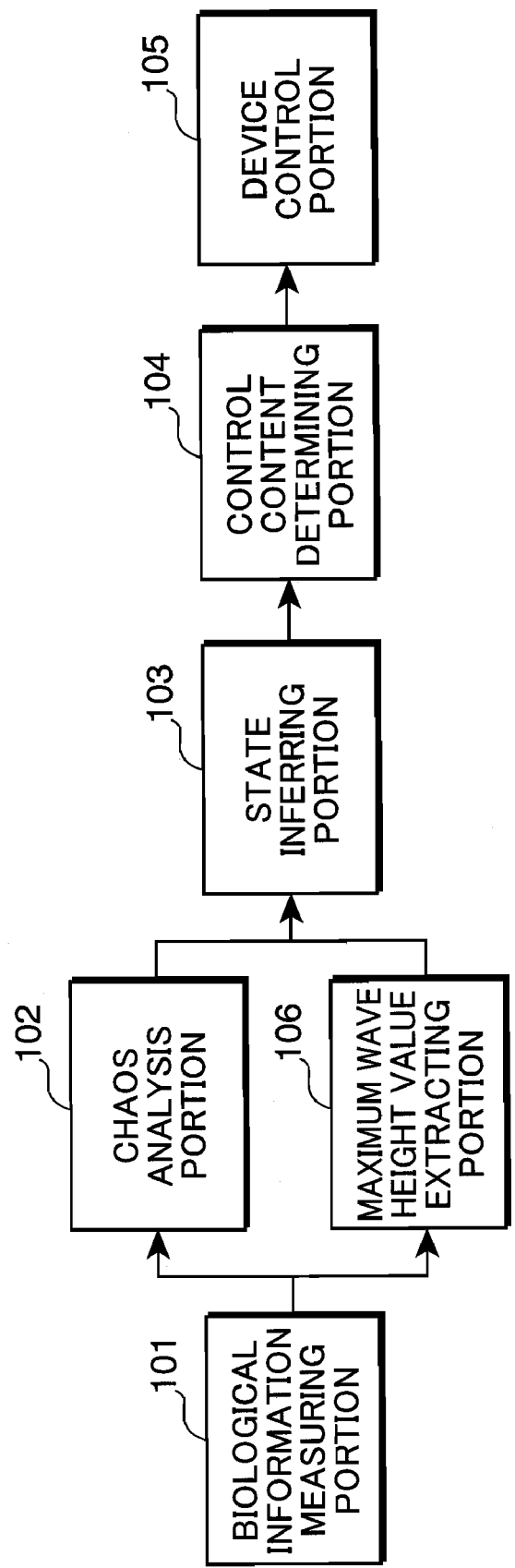
FIG. 4 is a block diagram showing the configuration of an environment control device according to a second embodiment of the invention.

FIG. 4 is a block diagram showing the configuration of the environment control device according to the second embodiment of the invention. Descriptions of components same as those in the first embodiment are omitted and only different components will be described in this embodiment.

The environment control device shown in FIG. 4 includes a maximum wave height value extracting portion 106 in addition to the configuration of the first embodiment, and it is different from the counterpart of the first embedment in that the state inferring portion 103 infers a thermal sensation of the user using the maximum wave height value extracted by the maximum wave height value extracting portion 106 and the maximum Lyapunov exponent analyzed by the chaos analysis portion 102.

The maximum wave height value extracting portion 106 extracts, as a parameter to evaluate the pulse wave, a maximum wave height value of the pulse wave, which is the peak value of the waveforms of the pulse wave for several pulse beats obtained within a specific time in the pulse wave data and accumulates it in an unillustrated memory.

The state inferring portion 103 calculates a variance of the maximum wave height value of the pulse wave extracted by the maximum wave height value extracting portion 106 and a variance of the maximum Lyapunov exponent calculated by the chaos analysis portion 102 to infer a thermal sensation of the user from the result of calculation, and outputs the inference data, which is the result of inference, to the control content determining portion 104 in the same manner as in the first embodiment.

In this embodiment, too, the state inferring portion 103 calculates a derivative value of the maximum wave height value of the pulse wave and a derivative value of the maximum Lyapunov exponent by dividing differences between the current values and immediately preceding values, which are the values immediately preceding the current values, of the maximum wave height value of the pulse wave and the maximum Lyapunov exponent extracted successively in time series since the device control portion 105 started a control operation by a time difference (sampling cycle). The state inferring portion 103 infers a thermal sensation of the user by determining to which of pre-set plural behavioral examples described below these derivative values fit.

Figure 5:
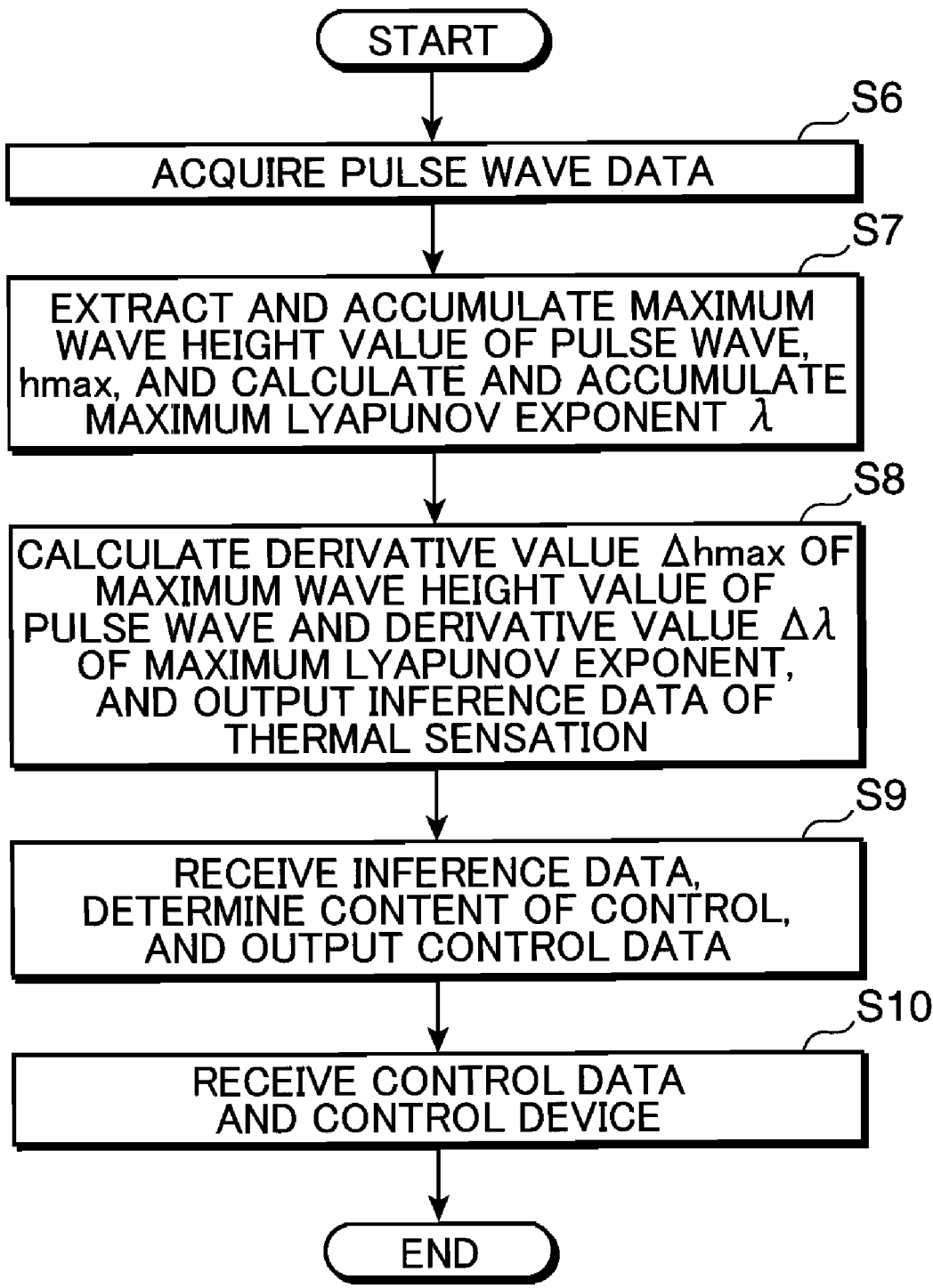
FIG. 5 is a flowchart detailing the flow of the processing by the environment control device according to the second embodiment of the invention.

FIG. 5 is a flowchart detailing the flow of the processing by the environment control device according to the second embodiment of the invention. Initially, the biological information measuring portion 101 acquires time-series data of the pulse wave in the same manner as in the first embodiment (Step S6). Subsequently, the maximum wave height value extracting portion 106 extracts the maximum height wave value of the pulse wave, hmax, at regular time intervals from the time-series data of the pulse wave measured by the biological information measuring portion 101 and accumulates it therein (Step S7).

In parallel with the operation above, the chaos analysis portion 102 calculates the maximum Lyapunov exponent B at regular time intervals from the time-series data of the pulse wave measured by the biological information measuring portion 101 and accumulates it therein (Step S7). Subsequently, the state inferring portion 103 calculates a derivative value $\Delta hmax$ of the maximum wave height value of the pulse wave, hmax, by dividing a difference between the current value and an immediately preceding value, which is the value immediately preceding the current value, of the maximum wave height value of the pulse wave, hmax, extracted by the maximum wave height value extracting portion 106 by a time difference (sampling cycle), and also calculates a derivative value $\Delta\lambda$ of the maximum Lyapunov exponent $\lambda$ by dividing a difference between the current value and an immediately preceding value, which is the value immediately preceding the current value, of the maximum Lyapunov exponent $\lambda$ calculated by the chaos analysis portion 102 by a time difference (sampling cycle) (Step S8).

The state inferring portion 103 then infers a thermal sensation of the user on the basis of the derivative value $\Delta hmax$ of the maximum wave height value of the pulse wave and the derivative value $\Delta\lambda$ of the maximum Lyapunov exponent it has calculated, and outputs the inference data, which is the result of inference, to the control content determining portion 104 (Step S8).

Thereafter, in the same manner as in the first embodiment, the control content determining portion 104 receives the inference data outputted from the state inferring portion 103. The control content determining portion 104 determines the content of control of the device on the basis of the inference data inputted therein from the state inferring portion 103 and outputs the control data indicating the content of control to the device control portion 105 (Step S9). Subsequently, the device control portion 105 receives the control data outputted from the control content determining portion 104. The device control portion 105 thus controls the device according to the control data outputted from the control content determining portion 104 (Step S10).

The processing to infer a thermal sensation of the user by the state inferring portion 103 of this embodiment will now be described. The inventors discovered the presence of a high correlation between a variance of the maximum wave height value of the pulse wave and a variance of a thermal sensation of the user and between a variance of the maximum Lyapunov exponent and a variance of a thermal sensation of the user.

FIG. 6A shows a graph indicating a correlation between the maximum wave height value of the pulse wave and a thermal sensation of the user and FIG. 6B is a graph indicating a correlation between the maximum Lyapunov exponent and a thermal sensation of the user, both of which are discovered by the inventors from the test conducted on subjects. As is shown in FIG. 6B, the maximum Lyapunov exponent and a thermal sensation have a correlation indicated by a downward convex graph such that the maximum Lyapunov exponent takes the external value in the vicinity of a point at which a thermal sensation becomes 0 (a neutral state where it is neither hot nor cold). As is shown in FIG. 6A, the maximum wave height value of the pulse wave and a thermal sensation have a correlation that the maximum wave height value of the pulse wave increases monotonously with a variance of a thermal sensation from a cold (−3) side to a hot (+3) side.

Also, FIG. 6C is a table in which the relations of a thermal sensation with respect to the maximum wave height value of the pulse wave and the maximum Lyapunov exponent shown in FIG. 6A and FIG. 6B, respectively, are tabulated in a matrix fashion. This table is held in the state inferring portion 103 in advance.

More specifically, in a case where the maximum wave height value of the pulse wave has increased and the maximum Lyapunov exponent has increased after the control by the device forming the warm or cool thermal environment is executed, the state inferring portion 103 infers that a thermal sensation of the user has changed in a direction from the neutral state (0 side) where it is neither hot nor cold to a hot state with the use of the table shown in FIG. 6C.

In a case where the maximum wave height value of the pulse wave has increased and the maximum Lyapunov exponent has decreased, the state inferring portion 103 infers that a thermal sensation of the user has changed in a direction (0 direction) from a cold state to the neutral state where it is neither hot nor cold. In a case where the maximum wave height value of the pulse wave has decreased and the maximum Lyapunov exponent has increased, the state inferring portion 103 infers that a thermal sensation of the user has changed in a direction from the neutral state (0 side) where it is neither hot nor cold to a cold state. In a case where the maximum wave height value of the pulse wave has decreased and the maximum Lyapunov exponent has decreased, the state inferring state 103 infers that a thermal sensation of the user has changed in a direction (0 direction) from a hot state to the neutral state where it is neither hot nor cold.

Figure 7:
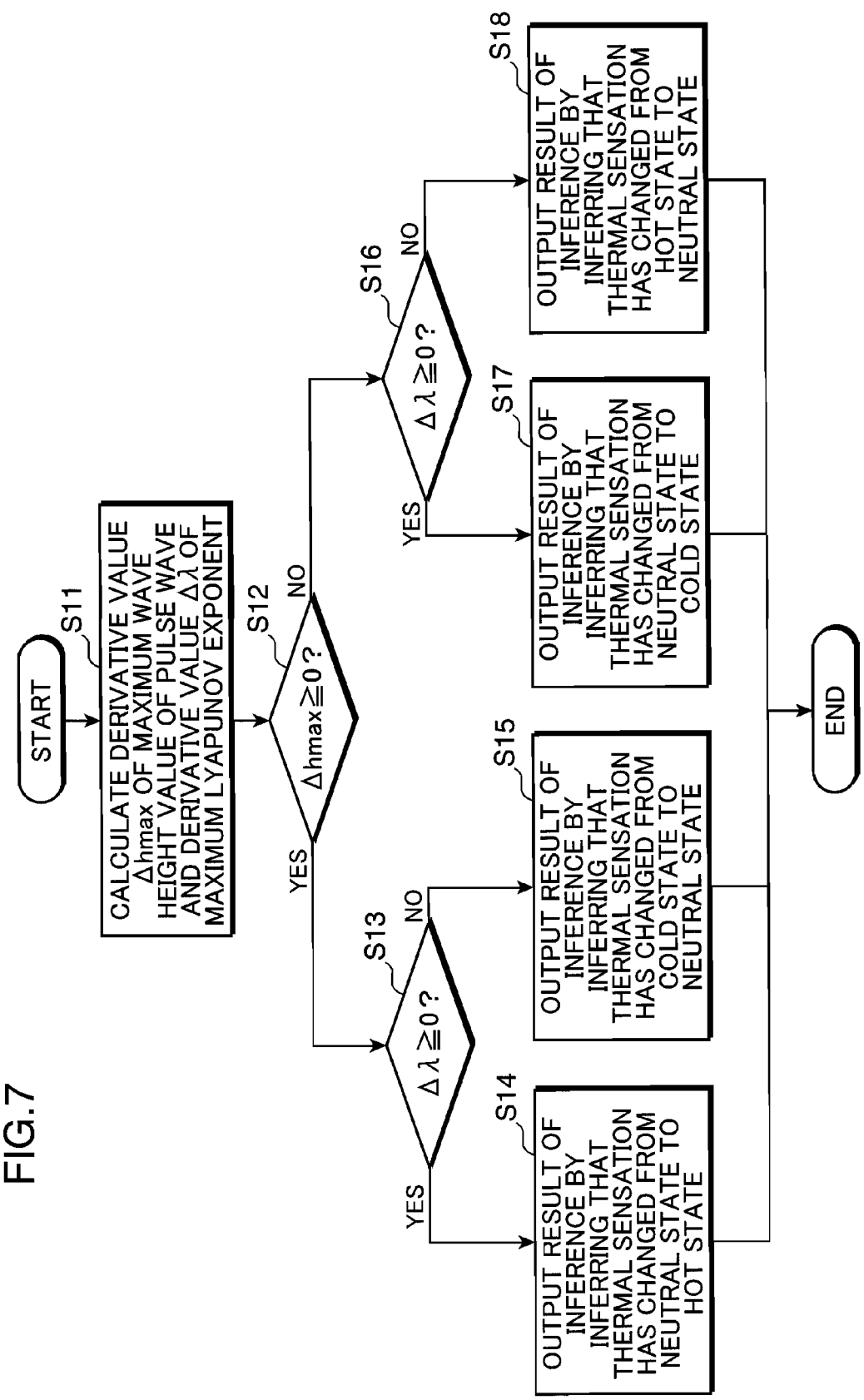
FIG. 7 is a flowchart detailing the flow of the processing by a state inferring portion according to the second embodiment of the invention.

FIG. 7 is a flowchart detailing the flow of processing by the state inferring portion 103 according to the second embodiment of the invention. Initially, the state inferring portion 103 calculates a derivative value $\Delta hmax$ of the maximum wave height value of the pulse wave, hmax, by dividing a difference between the current value and an immediately preceding value, which is the value immediately preceding the current value, of the maximum wave height value of the pulse wave, hmax, extracted by the maximum wave height value extracting portion 106 by a time difference (sampling cycle) (Step S11).

In parallel with the operation above, the state inferring state 103 calculates a derivative value $\Delta\lambda$ of the maximum Lyapunov exponent $\lambda$ by dividing a difference between the current value and an immediately preceding value, which is the value immediately preceding the current value, of the maximum Lyapunov exponent $\lambda$ extracted by the chaos analysis portion 102 by a time difference (sampling cycle) (Step S11).

Subsequently, in Step S12, the state inferring portion 103 makes a determination first for the derivative value $\Delta hmax$ of the maximum wave height value of the pulse wave. To be more concrete, the state inferring portion 103 determines whether the derivative value $\Delta hmax$ of the maximum wave height value of the pulse wave is equal to 0 or greater. In a case where the derivative value $\Delta hmax$ of the maximum wave height value of the pulse wave is equal to 0 or greater (YES in Step S12), the state inferring portion 103 determines that the maximum wave height value of the pulse wave has increased and proceeds to the processing in Step S13.

In Step S13, the state inferring portion 103 determines whether the derivative value $\Delta\lambda$ of the maximum Lyapunov exponent is equal to 0 or greater. In a case where the derivative value $\Delta\lambda$ of the maximum Lyapunov exponent is equal to 0 or greater (YES in Step S13), the state inferring portion 103 determines that the maximum Lyapunov exponent has increased. In this case, the state inferring portion 103 refers to the table of FIG. 6C held therein in advance and infers that a thermal sensation has changed in a direction from the neutral state (0 side) where it is neither hot nor cold to a hot state. It thus outputs the inference data exhibiting the result of inference, "0→hot", to the control content determination portion 104 (Step S14).

Meanwhile, in a case where the derivative value Δλ of the maximum Lyapunov exponent is smaller than 0 (NO in Step S13), the state inferring portion 103 determines that the maximum Lyapunov exponent has decreased. In this case, the state inferring portion 103 refers to the table of FIG. 6C, and infers that a thermal sensation has changed in a direction (0 direction) from a cold state to the neutral state where it is neither hot nor cold. It thus outputs the inference data exhibiting the result of inference, "cold→0", to the control content determining portion 104 (Step S15).

In a case where the derivative value Δhmax of the maximum wave height value of the pulse wave is smaller than 0 (NO in Step S12), the state inferring portion 103 determines that the maximum wave height value of the pulse wave has decreased and proceeds to the processing in Step S16.

In Step S16, the state inferring portion 103 determines whether the derivative value Δλ of the maximum Lyapunov exponent is equal to 0 or greater. In a case where the derivative value Δλ of the maximum Lyapunov exponent is equal to 0 or greater (YES in Step S16), the state inferring portion 103 determines that the maximum Lyapunov exponent has increased. In this case, the state inferring portion 103 refers to the table shown in FIG. 6B and infers that a thermal sensation has changed in a direction from the neural state (0 side) where it is neither hot nor cold to a cold state. It thus outputs the inference data exhibiting the result of inference, "0→cold", to the control content determining portion 104 (Step S17).

Meanwhile, in a case where the derivative value Δλ of the maximum Lyapunov exponent is smaller than 0 (NO in Step S16), the state inferring portion 103 determines that the maximum Lyapunov exponent has decreased. In this case, the state inferring portion 103 infers that a thermal sensation has changed in a direction (0 direction) from a hot state to the neutral state where it is neither hot nor cold. It thus outputs the inference data exhibiting the result of inference, "hot→0", to the control content determining portion 104 (Step S18).

Upon input of the inference data from the sate inferring portion 103, the control content determining portion 104 refers to a table held therein in advance and indicating a relation between the inference data and the control data, and converts the inference data to the control data of the device. FIG. 8 is a view showing the table in which the inference data and the control data are correlated with each other.

The control content determining portion 104 converts the content of the inference data to the control data on the basis of the table shown in FIG. 8. For example, in a case where the inference data exhibits "0→cold", the control content determining portion 104 determines the control data to have the content, "warm control". In a case where the inference data exhibits, "0→hot", the control content determining portion 104 determines the control data to have the content, "cool control". Further, in a case where the inference data exhibits "cold→0" or "hot→0", the control content determining portion 104 determines the control data to have the content, "no data". In this case, the control content determining portion 104 outputs no control data or it outputs the control data for the device to maintain the current state.

"Warm control" referred to herein means the control to raise the temperature set as room temperature with the air conditioning device, the control to increase the heating performance during a heating operation, the control to decrease the cooling performance during a cooling operation, and so forth. "Cool control" referred to herein means the control to lower the temperature set as room temperature with the air conditioning device, the control to decrease the heating performance during a heating operation, the control to increase the cooling performance during a cooling operation, and so forth.

Regarding the inference of a thermal sensation of the user by the state inferring portion 103, the phrase, "a thermal sensation changes in a direction (0 direction) from a cold state to the neutral state where it is neither hot nor cold", means that a thermal sensation moves in the 0 direction from a given point positioned within a range from −3 to 0 on the abscissa in FIG. 6A and FIG. 6B. The phrase, "a thermal sensation changes in a 0 direction (0 direction) from a hot state to the neutral state where it is neither hot nor cold", means that a thermal sensation moves in the 0 direction from a given point positioned within a range from +3 to 0 on the abscissa in FIG. 6A and FIG. 6B. The phrase, "a thermal sensation changes in a direction from the neutral condition (0 side) where it is neither hot nor cold to a cold state", means that a thermal sensation moves in a −3 direction from a given point positioned within a range from 0 to −3 on the abscissa in FIG. 6A and FIG. 6B. The phrase, "a thermal sensation changes in a direction from the neutral state (0 side) where it is neither hot nor cold to a hot state", means that a thermal sensation moves in a +3 direction from a given point positioned within a range from 0 to +3 on the abscissa in FIG. 6A and FIG. 6B.

For the degree of control by the control data outputted from the control content determining portion 104, a pre-determined value may be used, for example, to change the temperature set as room temperature by 2 degrees, or the degree of a change in control may be determined by the state inferring state 103 on the basis of the magnitude of the derivative value Δhmax of the maximum wave height value of the pulse wave and the derivative value Δλ of the maximum Lyapunov exponent it has calculated.

As has been described, according to the environment control device of the second embodiment, a thermal sensation of the user in response to a warm or cool thermal stimulus is inferred, by using the pulse wave alone as the biological information of the user, on the basis of the maximum Lyapunov exponent obtained through chaos analysis of the time-series data of the pulse wave and the maximum wave height value of the pulse wave, which is the peak value of the waveform of the pulse wave for one pulse beat in the pulse wave data, and the device generating a warm or cool thermal stimulus is controlled on the basis of the result of inference. It is thus possible to infer a thermal sensation of the user at a higher degree of accuracy by eliminating an influence of differences of the biological information among individuals. Consequently, a thermal sensation of the user can be brought into a moderate state where it is neither hot nor cold. In this embodiment, the amplitude of the pulse wave may be used instead of the maximum wave height value of the pulse wave.

Third Embodiment

Figure 9:
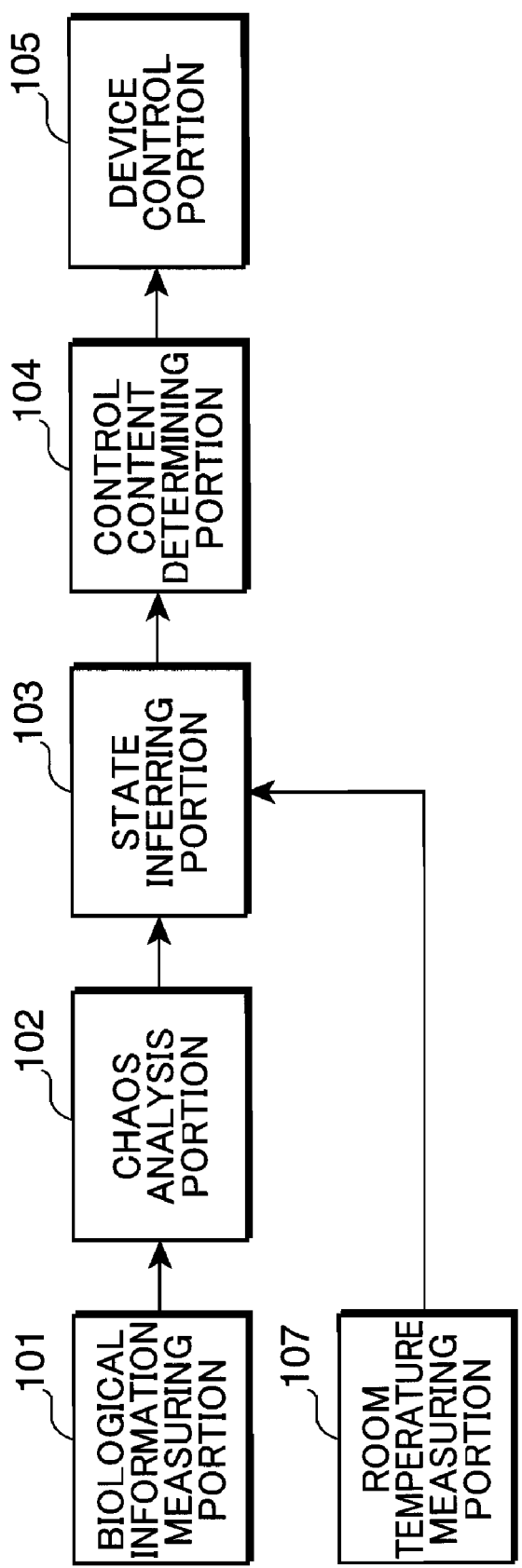
FIG. 9 is a block diagram showing the configuration of an environment control device according to a third embodiment of the invention.

An environment control device according to a third embodiment of the invention will now be described. FIG. 9 is a block diagram showing the configuration of the environment control device according to the third embodiment of the invention. Descriptions of components same as those in the second embodiment are omitted and only different components will be described in this embodiment.

The environment control device shown in FIG. 9 includes a room temperature measuring portion 107 instead of the maximum wave height value extracting portion 106 of the second embodiment, and is different from the counterpart of the second embodiment in that the state inferring portion 103 uses room temperature data measured by the room temperature measuring portion 107 instead of the maximum wave height value of the pulse wave and infers a thermal sensation of the user using the room temperature data and the maximum Lyapunov exponent.

The room temperature measuring portion 107 is formed of a temperature sensor or the like. It measures the temperature inside the room at regular time intervals and accumulates it therein. The state inferring portion 103 calculates a variance of the room temperature data measured by the room temperature measuring portion 107 and a variance of the maximum Lyapunov exponent calculated by the chaos analysis portion 102. It then infers a thermal sensation of the user from the result of calculation and outputs the inference data, which is the result of inference, to the control content determining portion 104 in the same manner as in the second embodiment.

In this embodiment, too, the state inferring portion 103 calculates a derivative value of the room temperature data and a derivative value of the maximum Lyapunov exponent by dividing respective differences of the room temperature data and the maximum Lyapunov exponents extracted successively in time series since the device control portion 105 started a control operation by a time difference (sampling cycle). The state inferring portion 103 infers a thermal sensation of the user by determining to which of pre-set plural behavioral examples described below these derivative values fit.

Figure 10:
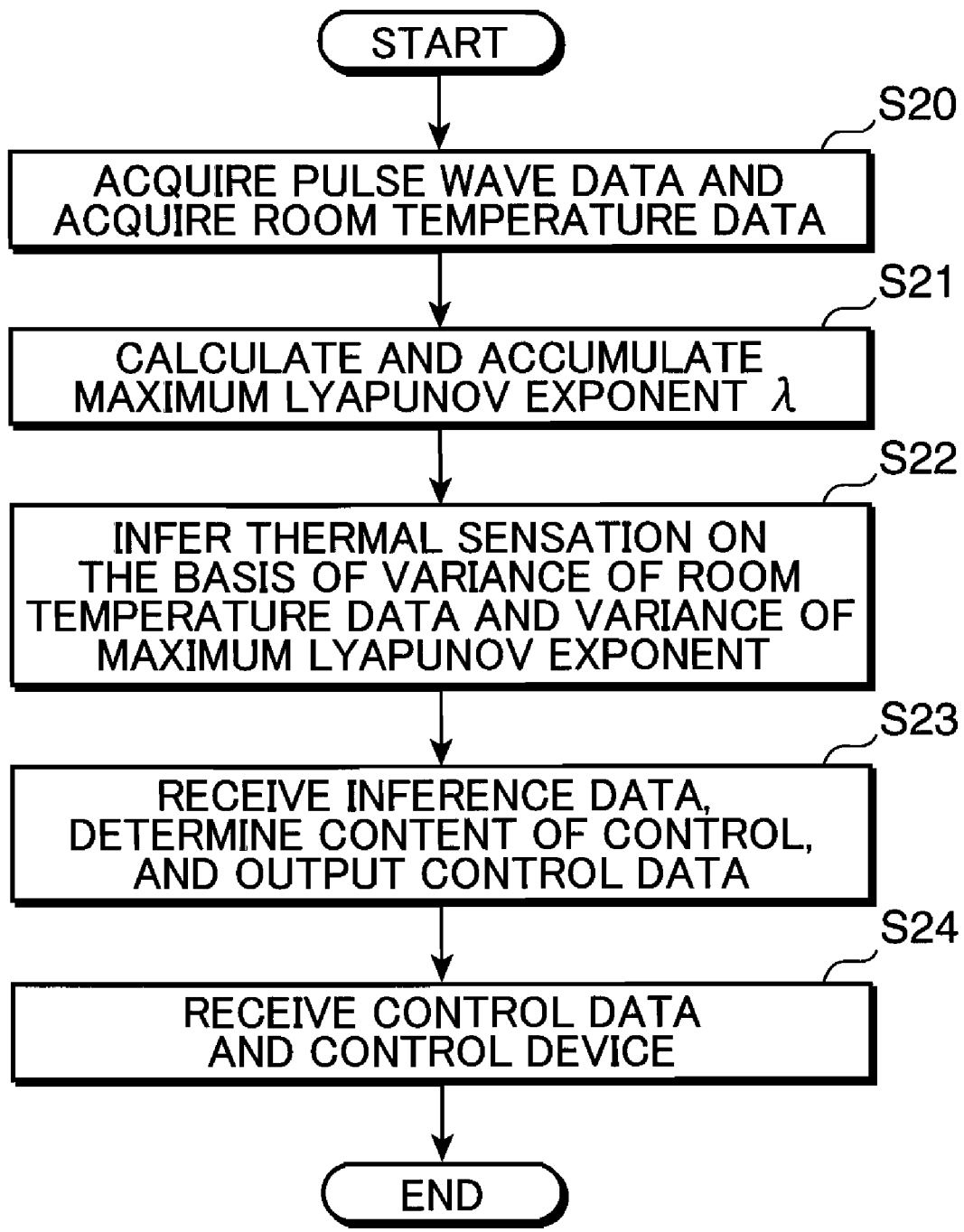
FIG. 10 is a flowchart detailing the flow of the processing by the environment control device according to the third embodiment of the invention.

An operation of the environment control device of this embodiment will now be described using a flowchart of FIG. 10. FIG. 10 is a flowchart detailing the flow of the processing by the environment control device according to the third embodiment of the invention. Initially, the biological information measuring portion 101 acquires time-series data of the pulse wave by measuring the pulse wave in the same manner as in the second embodiment. The room temperature measuring portion 107 acquires the room temperature data by measuring the temperature of the room where the user is in (Step S20).

Subsequently, the chaos analysis portion 102 calculates the maximum Lyapunov exponent at regular time intervals from the time-series data of the pulse wave measured by the biological information measuring portion 101 and accumulates it therein (Step S21).

Subsequently, the state inferring portion 103 infers a thermal sensation of the user on the basis of a variance of the room temperature data and a variance of the maximum Lyapunov exponent, and outputs the inference data to the control content determining portion 104 (Step S22). To be more concrete, the state inferring portion 103 calculates a derivative value $\Delta t$ of the room temperature data by dividing a difference between the current value and an immediately preceding value, which is the value immediately preceding the current value, of the room temperature data acquired by the room temperature measuring portion 107 by a time difference (sampling cycle). In a case where the derivative value $\Delta t$ is positive, the state inferring portion 103 determines that the room temperature has risen, and in a case where the derivative value $\Delta t$ is negative, it determines that the room temperature has dropped.

Also, the state inferring portion 103 calculates a derivative value $\Delta\lambda$ of the maximum Lyapunov exponent $\lambda$ by dividing a difference between the current value and an immediately preceding value, which is the value immediately preceding the current value, of the maximum Lyapunov exponent $\lambda$ calculated by the chaos analysis portion 102 by a time difference (sampling cycle). In a case where the derivative value $\Delta\lambda$ is positive, the state inferring portion 103 determines that the maximum Lyapunov exponent has increased, and in a case where the derivative value $\Delta\lambda$ is a negative value, it determines that the maximum Lyapunov exponent has decreased.

The state inferring portion 103 then refers to a table shown in FIG. 11 to infer a thermal sensation of the user. FIG. 11 is a view showing a table in which a thermal sensation in response to the maximum Lyapunov exponent and the room temperature found in the same manner as in the second embodiment is tabulated in a matrix fashion. This table is held in advance in the state inferring portion 103.

More specifically, after the control by the device forming the warm or cool thermal environment is executed, the state inferring portion 103 refers to the table shown in FIG. 11. In a case where the room temperature has risen and the maximum Lyapunov exponent has increased, it infers that a thermal sensation of the user has changed in a direction from the neutral state (0 side) where it is neither hot nor cold to a hot state, and outputs the inference data exhibiting "0→hot". In a case where the temperature data indicates a rise and the maximum Lyapunov exponent has decreased, the state inferring portion 103 infers that a thermal sensation of the user has changed in a direction (0 direction) from a cold state to the neutral state where it is neither hot nor cold, and outputs the inference data exhibiting "cold→0".

In a case where the room temperature data indicates a drop and the maximum Lyapunov exponent has increased, the state inferring portion 103 infers that a thermal sensation of the user has changed in a direction from the neutral state (0 side) where it is neither hot nor cold to a cold state, and outputs the inference data exhibiting "0→cold". In a case where the room temperature data indicates a drop and the maximum Lyapunov exponent has decreased, the state inferring portion 103 infers that a thermal sensation of the user has changed in a direction (0 direction) from a hot state to the neutral state where it is neither hot nor cold, and outputs the inference data exhibiting "hot→0". The inference data in each case is then outputted to the control content determining portion 104.

Subsequently, upon input of the inference data from the state inferring portion 103, the control content determining portion 104 converts the inference data to the control data of the device by referring to the table shown in FIG. 8 in the same manner as in the second embodiment (Step S23). Subsequently, the device control portion 105 receives the control data outputted from the control content determining portion 104. The device control portion 105 controls the device according to the control data outputted from the control content determining portion 104 (Step S24).

As has been described, according to the environment control device of the third embodiment, because a thermal sensation of the user is inferred on the basis of the maximum Lyapunov exponent and the room temperature, which it is normally measured by the air conditioning device, at a current point in time, it is possible to infer a thermal sensation of the user at a higher degree of accuracy by eliminating an influence of differences of the biological information among individuals. It is thus possible to lead a thermal sensation of the user to a moderate state where it is neither hot nor cold in a reliable manner.

Fourth Embodiment

Figure 12:
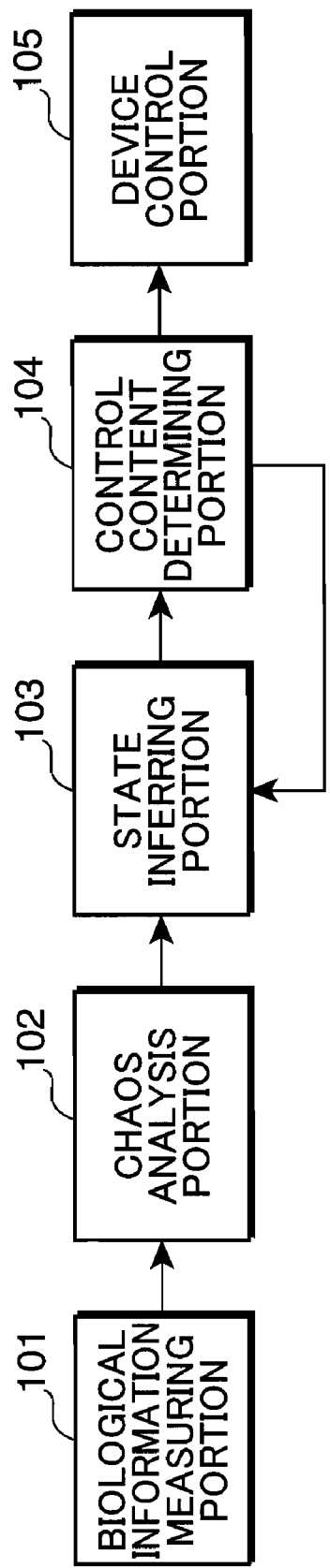
FIG. 12 is a block diagram showing the configuration of an environment control device according to a fourth embodiment of the invention.

An environment control device according to a fourth embodiment of the invention will now be described. FIG. 12 is a block diagram showing the configuration of the environment control device according to the fourth embodiment of the invention. Descriptions of components same as those in the first embodiment are omitted and only different components will be described herein. The environment control device shown in FIG. 12 is of the configuration almost the same as the configuration of the first embodiment, and a difference from the counterpart in the first embodiment is that the control content determining portion 104 determines the control data and outputs the determined control data also to the state inference portion 103, so that the state inferring portion 103 infers a thermal sensation of the user using the control data outputted from the control content determining portion 104 and the maximum Lyapunov exponent.

The state inferring portion 103 calculates a variance of the maximum Lyapunov exponent calculated by the chaos analysis portion 102. It then infers a thermal sensation of the user on the basis of the result of calculation and the control data outputted from the control content determining portion 104, and outputs the inference data, which is the result of inference, to the control content determining portion 104 in the same manner as in the first embodiment. In a case where the device subjected to control is run for cooling, the control data contains data exhibiting "cooling" and data specifying the output strength of the cooling. In a case where the device subjected to control is run for heating, the control data contains data exhibiting "heating" and data specifying the output strength of the heating.

In this embodiment, too, the state inferring portion 103 calculates a derivative value $\Delta\lambda$ of the maximum Lyapunov exponent by dividing a difference of the maximum Lyapunov exponents extracted successively in time series since the device control portion 105 started a control operation by a time difference (sampling cycle). The state inferring portion 103 infers a thermal sensation of the user by determining to which of pre-set plural examples described below a behavior of this derivative value and the content of the control data outputted from the control content determining portion 104 fit.

Figure 13:
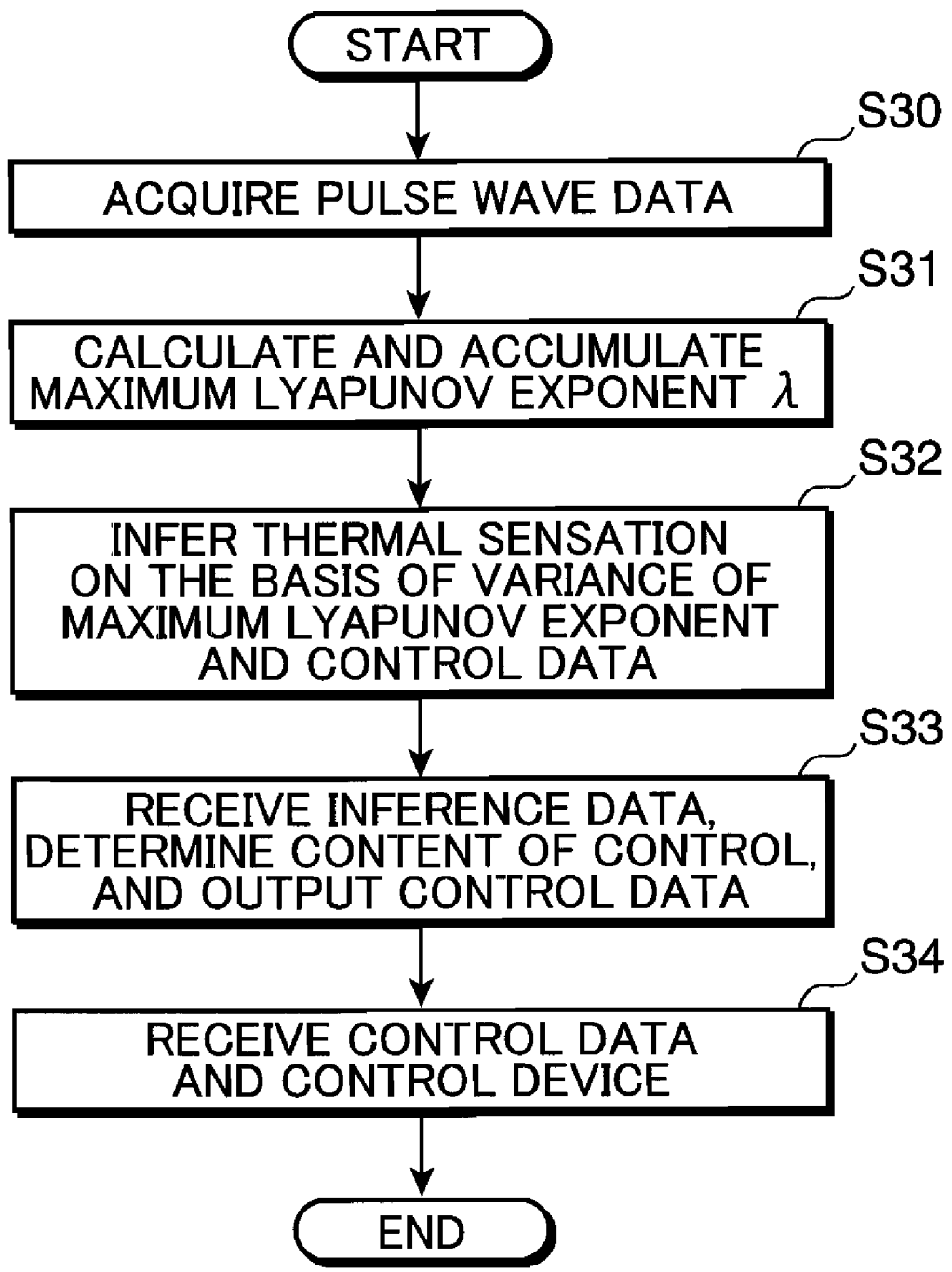
FIG. 13 is a flowchart detailing the flow of the processing by the environment control device according to the fourth embodiment of the invention.

An operation of the environment control device of this embodiment will now be described using a flowchart of FIG. 13. FIG. 13 is a flowchart detailing the flow of the processing by the environment control device according to the fourth embodiment of the invention. Initially, the biological information measuring portion 101 acquires time-series data of the pulse wave by measuring the pulse wave in the same manner as in the first embodiment (Step S30). Subsequently, the chaos analysis portion 102 calculates the maximum Lyapunov exponent $\lambda$ at regular time intervals from the time-series data of the pulse wave measured by the biological information measuring portion 101 and accumulates it therein (Step S31).

Subsequently, the state inferring portion 103 infers a thermal sensation of the user on the basis of a variance of the maximum Lyapunov exponent and the control data outputted from the control content determining portion 104, and outputs the inference data to the control content determining portion 104 (Step S32).

To be more concrete, the state inferring portion 103 calculates a derivative value $\Delta\lambda$ of the maximum Lyapunov exponent $\lambda$ by dividing a difference between the current value and an immediately preceding value, which is the value immediately preceding the current value, of the maximum Lyapunov exponent $\lambda$ calculated by the chaos analysis portion 102 by a time difference (sampling cycle). In a case where the derivative value. A is positive, the state inferring portion 103 determines that the maximum Lyapunov exponent has increased, and in a case where the derivative value $\Delta\lambda$ is negative, it determines that the maximum Lyapunov exponent has decreased.

The state inferring portion 103 determines whether the cooling performance or the heating performance, which indicates the output strength of the device running for cooling or heating, has increased or decreased from the current value and an immediately preceding value, which is the value immediately preceding the current value, of the output strength contained in the control data outputted from the control content determining portion 104.

The state inferring portion 103 then infers a thermal sensation of the user by referring to tables shown in FIG. 14A and FIG. 14B. FIG. 14 is a view showing tables in which a relation between the maximum Lyapunov exponent and a thermal sensation found in the same manner as in the first embodiment and a relation between the control data and a thermal sensation are tabulated in a matrix fashion. FIG. 14A is a view showing a table in which relations of the maximum Lyapunov exponent and the cooling performance with respect to a thermal sensation are tabulated in a matrix fashion. FIG. 14B is a view showing a table in which relations of the maximum Lyapunov exponent and the heating performance with respect to a thermal sensation are tabulated in a matrix fashion. The state inferring portion 103 holds therein these tables in advance.

More specifically, in a case where the control data it received specifies the cooling while the cooling performance has been increased and the maximum Lyapunov exponent has increased, the state inferring portion 103 infers that a thermal sensation of the user has changed in a direction from the neutral state (0 side) where it is neither hot nor cold to a cold state by referring to the table shown in FIG. 14A, and outputs the inference data exhibiting "0→cold".

In a case where the control data it received specifies the cooling while the cooling performance has been decreased and the Lyapunov exponent has increased, the state inferring portion 103 infers that a thermal sensation of the user has changed in a direction from the neutral state (0 side) where it is neither hot nor cold to a hot state by referring to the table shown in FIG. 14A, and outputs the inference data exhibiting "0→hot".

In a case where the control data it received specifies the cooling while the cooling performance has been increased and the maximum Lyapunov exponent has decreased, the state inferring portion 103 infers that a thermal sensation of the user has changed in a direction (0 direction) from a hot state to the neutral state where it is neither hot nor cold by referring to the table shown in FIG. 14A, and outputs the inference data exhibiting "hot→0".

In a case where the control data it received specifies the cooling while the cooling performance has been decreased and the maximum Lyapunov exponent has decreased, the state inferring portion 103 infers that a thermal sensation of the user has changed in a direction (0 direction) from a cold state to the neutral state where it is neither hot nor cold by referring to the table shown in FIG. 14A, and output the inference data exhibiting "cold→0".

Meanwhile, in a case where the control data it received specifies the heating while the heating performance has been increased and the maximum Lyapunov exponent has increased, the state inferring portion 103 infers that a thermal sensation of the user has changed in a direction from the neutral state (0 side) where it is neither hot nor cold to a hot state by referring to the table shown in FIG. 14B, and outputs the inference data exhibiting "0→hot".

In a case where the control data it received specifies the heating while the heating performance has been decreased and the maximum Lyapunov exponent has increased, the state inferring portion 103 infers that a thermal sensation of the user has changed in a direction from the neutral state (0 side) where it is neither hot nor cold to a cold state by referring to the table shown in FIG. 14B, and outputs the inference data exhibiting "0→cold".

In a case where the control data it received specifies the heating while the heating performance has been increased and the maximum Lyapunov exponent has decreased, the state inferring portion 103 infers that a thermal sensation of the user has changed in a direction (0 direction) from a cold state to the neutral state where it is neither hot nor cold by referring to the table shown in FIG. 14B, and outputs the inference data exhibiting "cold→0".

In a case where the control data it received specifies the heating while the heating performance has been decreased and the maximum Lyapunov exponent has decreased, the state inferring portion 103 infers that a thermal sensation of the user has changed in a direction (0 direction) from a hot state to the neutral state where it is neither hot nor cold by referring to the table shown in FIG. 14B, and output the inference data exhibiting "hot→0".

Referring to FIG. 13 again, upon input of the inference data from the state inferring portion 103, the control content determining portion 104 converts the inference data to the control data of the device by referring to the table shown in FIG. 8 in the same manner as in the second embodiment (Step S33). Subsequently, the device control portion 105 receives the control data outputted from the control content determining portion 104. The device control portion 105 controls the device according to the control data outputted from the control content determining portion 104 (Step S34).

"Warm control" during the execution of the control for cooling by the device forming the warm or cool thermal environment means the control to decrease the cooling performance. "Cool control" means the control to increase the cooling performance. Likewise, "warm control" during the execution of the control for heating means the control to increase the heating performance. "Cool control" means the control to decrease the heating performance.

As has been described, according to the environment control device of the fourth embodiment, because a thermal sensation of the user is inferred on the basis of the maximum Lyapunov exponent and the control content corresponding to a warm or cool thermal stimulus at a current point in time, it is possible to infer a thermal sensation of the user in response to a warm or cool thermal stimulus at a higher degree of accuracy by eliminating an influence of differences of the biological information among individuals. It is thus possible to lead a thermal sensation of the user to a moderate state where it is neither hot nor cold in a reliable manner.

Fifth Embodiment

FIG. 15 is a view schematically showing the configuration of an environment control device according to a fifth embodiment of the invention. The environment control device is formed of a known computer, and includes a pulse wave detecting portion (biological information acquiring portion) 201, a pulse wave chaos parameter calculating portion (first parameter calculating portion) 202, a pulse wave chaos parameter comparing portion (first inferring portion) 203, a first user state inferring portion (first inferring portion) 204, a first stimulus control portion (first stimulus control portion) 205, a stimulus generating portion 206, a pulse wave waveform parameter calculating portion (second parameter calculating portion) 207, a pulse wave waveform parameter comparing portion (second inferring portion) 208, a second user state inferring portion (second inferring portion) 209, a second stimulus control portion (second stimulus control portion) 210, and a stimulus control switching portion (stimulus control switching portion) 211.

The pulse wave detecting portion 201 through the stimulus control switching portion 211 are achieved by running an environment control program of the invention pre-installed in the computer on the CPU.

The pulse wave detecting portion 201 acquires pulse wave data (an example of biological information) in time series by sampling the fingertip pulse wave of the user detected by a known transducer or the like at a specific sampling cycle. The pulse wave chaos parameter calculating portion 202 calculates the maximum Lyapunov exponent of the time-series data of the pulse wave detected by and accumulated in the pulse wave detecting portion 201 as a pulse wave chaos parameter. The pulse wave chaos parameter comparing portion 203 compares the value of the pulse wave chaos parameter thus calculated with a reference value K1.

The first user state inferring portion 204 performs a computation to subtract the reference value K1 from the current value N1 of the pulse wave chaos parameter calculated by the pulse wave chaos parameter calculating portion 202 or a computation to subtract the current value N1 from the reference value K1 on the basis of the result of comparison made by the pulse wave chaos parameter comparing portion 203, and infers a state of the user, for example, a relaxed feeling, a comfortable feeling, or a thermal sensation, by comparing the result of computation with a preset threshold value (third specified value) A1.

Adopted as the reference value K1 herein is the value of the pulse wave chaos parameter calculated by the pulse wave chaos parameter calculating portion 202 before the stimulus generating portion 206 gives a stimulus to the user or before it changes the strength or kinds of stimulus. Alternatively, a value (for example, an average value) learned from a change of the value of the pulse wave chaos parameter calculated by the pulse wave chaos parameter calculating portion 202 before the strength or kinds of stimulus are changed during a specific period before the stimulus generating portion 206 gives a stimulus to the user may be adopted.

The first stimulus control portion 205 calculates a stimulus value (first stimulus value) I1 that enables the stimulus generating portion 206 to generate a stimulus at strength sufficient for the user to have a relaxed feeling, a comfortable feeling, a thermal sensation, or the like on the basis of the result of inference made by the first user state inferring portion 204, and outputs the stimulus value I1 it has calculated to the stimulus control switching portion 211.

The pulse wave waveform parameter calculating portion 207 calculates a pulse wave waveform parameter to evaluate the accelerated waveform of the pulse wave, which is a second-order derivative of the pulse wave, on the basis of the pulse wave time-series data. This pulse wave waveform parameter is one example of a change of the time-series data.

Figure 60:
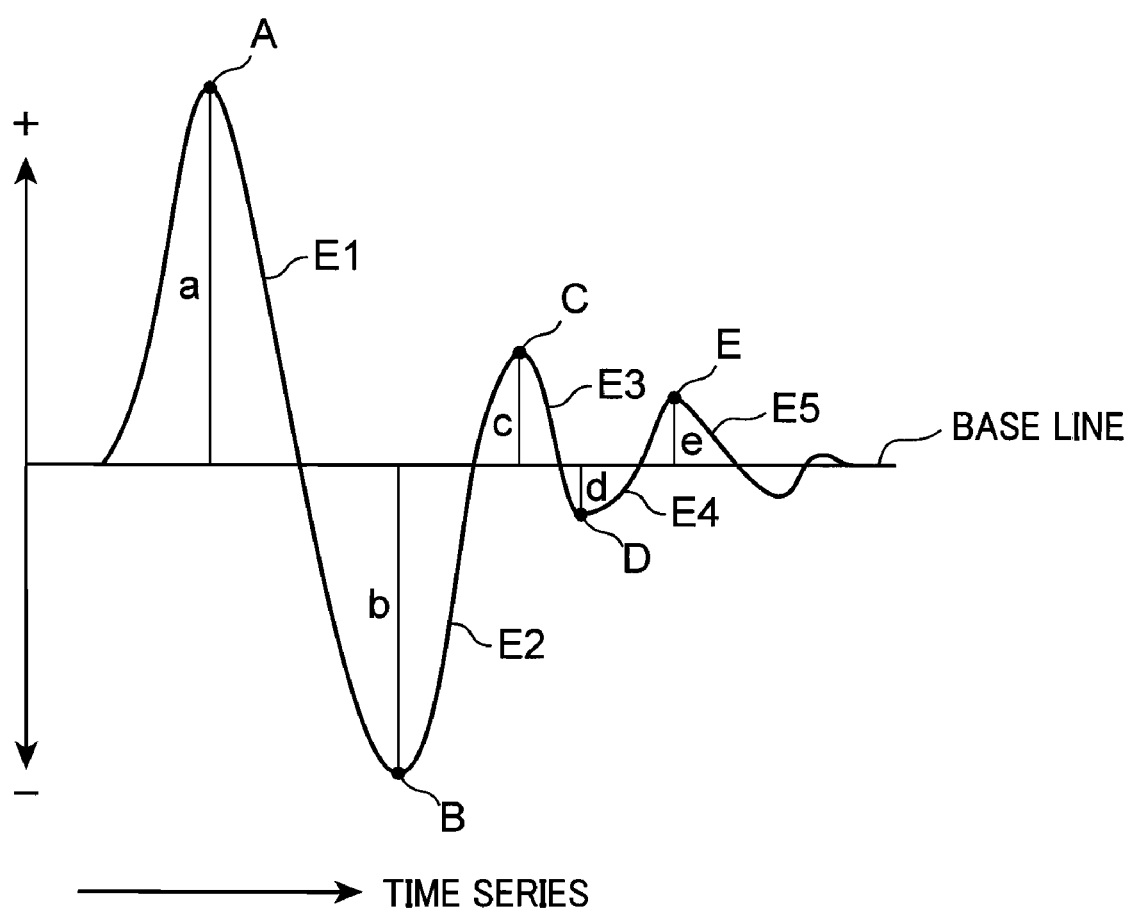
FIG. 60 is a view showing the waveform of the accelerated pulse wave described in Patent Document 1.
Figure 61:
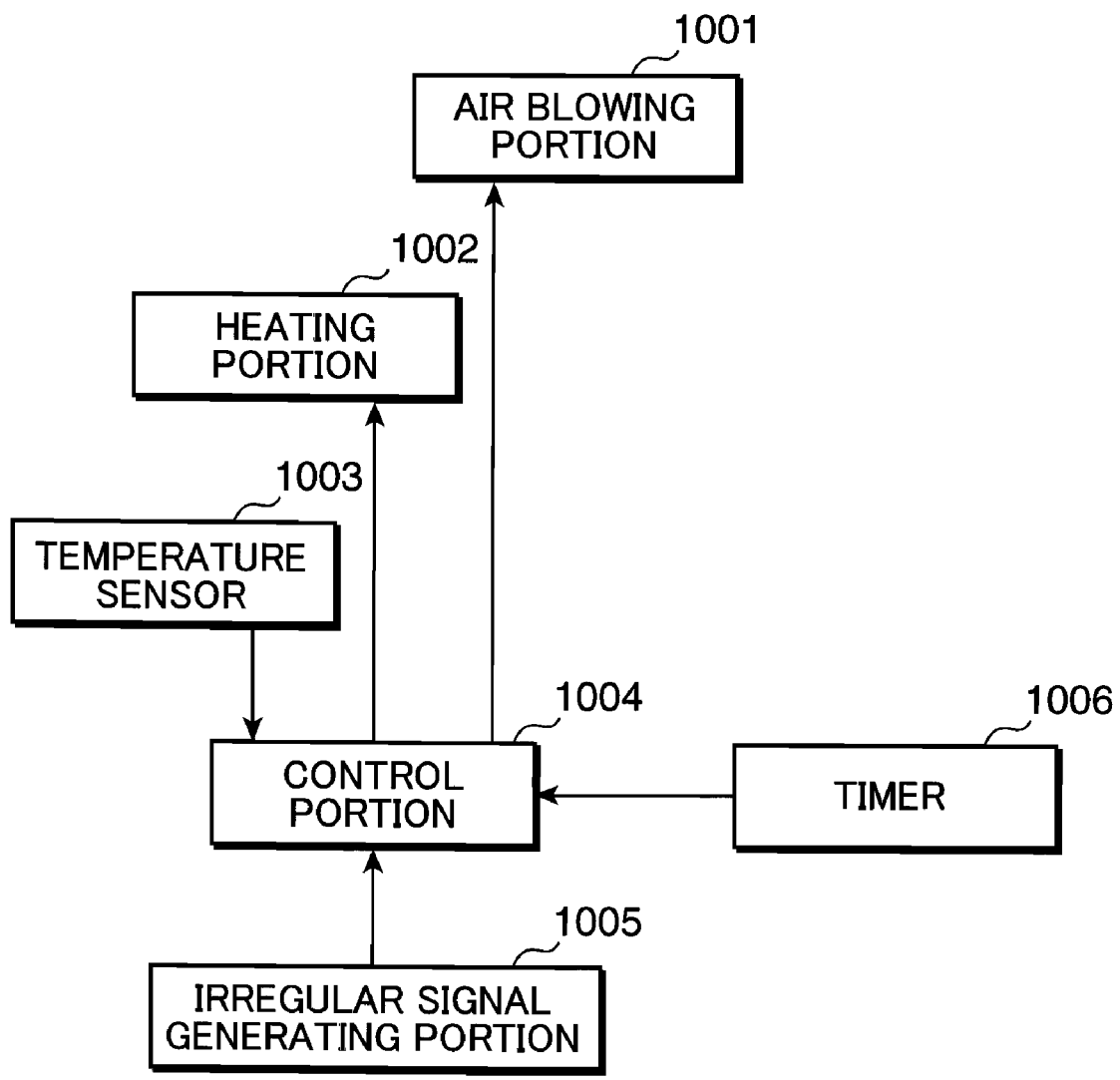
FIG. 61 is a block diagram showing the configuration of a warm fan heating device described in Patent Document 2.

As is shown in FIG. 60, the pulse wave acceleration is made up of five elementary waves denoted as E1, E2, E3, E4, and E5. Because the peak A of the elementary wave E1 coincides with the start of the diastolic wave in the fingertip plethysmogram, a required time from the peak A to the peak E coincides with the systolic time axial length. The elementary wave E1 is a positive wave that is convex upward with respect to the base line, the elementary wave E2 is a negative wave that is convex downward with respect to the base line, and the following elementary waves E3, E4, and E5 are changeable elementary waves that become either a positive wave or a negative wave depending on the physiological conditions, all of which have a strong correlation with the age of the user.

In this embodiment, the pulse wave waveform parameter calculating portion 207 adopts c/a, where the amplitude a is given as the denominator and the amplitude c is given as the numerator, as the pulse wave waveform parameter. It should be noted, however, that b/a or d/a may be adopted as the pulse wave waveform parameter instead of c/a.

The pulse wave waveform parameter comparing portion 208 compares the value of the pulse wave waveform parameter thus calculated with a reference value K2. The second user state inferring portion 209 performs a computation to subtract the specific reference value K2 from the current value N2 of the pulse wave waveform parameter calculated by the pulse wave waveform parameter calculating portion 207 or a computation to subtract the current value N2 from the reference value K2 on the basis of the result of comparison made by the pulse wave waveform parameter comparing portion 208. It then compares the result of computation with a specific threshold value B1 and infers a state of perception of the user in response to a stimulus given to the user by the stimulus generating portion 206 on the basis of the result of comparison. In short, the second user state inferring portion 209 infers whether the user feels the stimulus given to the user by the stimulus generating portion 206 is too strong, moderate, or too weak.

Adopted as the reference value K2 herein is the value of the pulse wave waveform parameter calculated by the pulse wave waveform parameter calculating portion 207 before the stimulus generating portion 206 gives a stimulus to the user or before it changes the strength or kinds of stimulus. Alternatively, a value (for example, an average value) learned from a change of the value of the pulse wave waveform parameter before the strength or kinds of stimulus are changed during a specific period before the stimulus generating portion 206 gives a stimulus to the user may be adopted.

The second stimulus control portion 210 calculates a stimulus value (second stimulus value) I2 that enables the stimulus generating portion 206 to generate a stimulus at strength sufficient for the user to feel that the stimulus is moderate on the basis of the result of inference made by the second user state inferring portion 209, and outputs it to the stimulus control switching portion 211.

The stimulus control switching portion 211 calculates a stimulus output value O1 to specify the strength of a stimulus to be outputted actually on the basis of the stimulus value I1 outputted from the first stimulus control portion 205 and the stimulus value I2 outputted from the second stimulus control portion 210, and outputs it to the stimulus generating portion 206.

Figure 16:
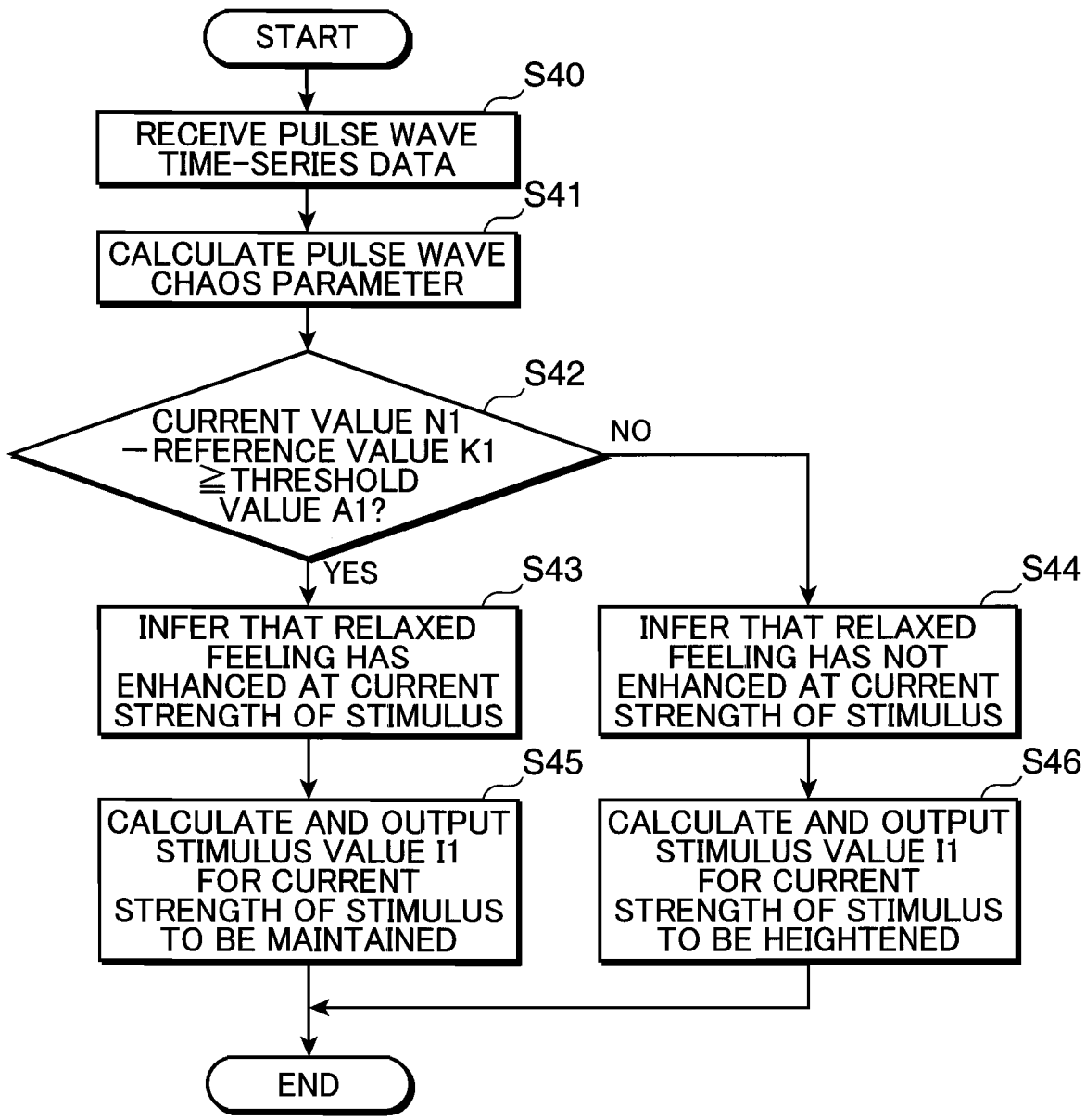
FIG. 16 is a flowchart detailing operations of a pulse wave chaos parameter calculating portion, a pulse wave chaos parameter comparing portion, a first user state inferring portion, and a first stimulus control portion of the embodiment.

FIG. 16 is a flowchart detailing operations of the pulse wave chaos parameter calculating portion 202, the pulse wave chaos parameter comparing portion 203, the first user state inferring portion 204, and the first stimulus control portion 205 of this embodiment.

Initially, the pulse wave chaos parameter calculating portion 202 receives the pulse wave time-series data detected by and accumulated in the pulse wave detecting portion 201 (Step S40). Subsequently, the pulse wave chaos parameter calculating portion 202 calculates the maximum Lyapunov exponent (Ly) on the basis of the pulse wave time-series data it received, and uses the maximum Lyapunov exponent it has calculated as the current value N1 of the pulse wave chaos parameter (Step S41).

Subsequently, the pulse wave chaos parameter comparing portion 203 compares a difference between the reference value K1 and the current value N1 of the pulse wave chaos parameter with the threshold value A1 (Step S42). To be more concrete, the pulse wave chaos parameter comparing portion 203 calculates a difference between the current value N1 and the reference value K1 of the pulse wave chaos parameter, and determines wither the difference it has calculated is equal to the threshold value A1 or greater. In a case where the calculated difference is equal to the threshold value A1 or greater (YES in Step S42), the first user state inferring portion 204 infers that a relaxed feeling, a comfortable feeling, a thermal sensation, or the like has enhanced (Step S43).

Meanwhile, in a case where the difference between the current value N1 and the reference value K1 of the pulse wave chaos parameter is smaller than the specific threshold value A1 (NO in Step S42), the first user state inferring portion 204 infers that a relaxed feeling, a comfortable feeling, a thermal sensation, or the like has not enhanced (Step S44).

In Step S45, the first stimulus control portion 205 calculates the stimulus value I1 for the current strength of stimulus to be maintained, and outputs it to the stimulus control switching portion 211. In Step S46, the first stimulus control portion 205 outputs the stimulus value I1 for the strength to be heightened from the current strength of stimulus to the stimulus control switching portion 211.

Figure 17:
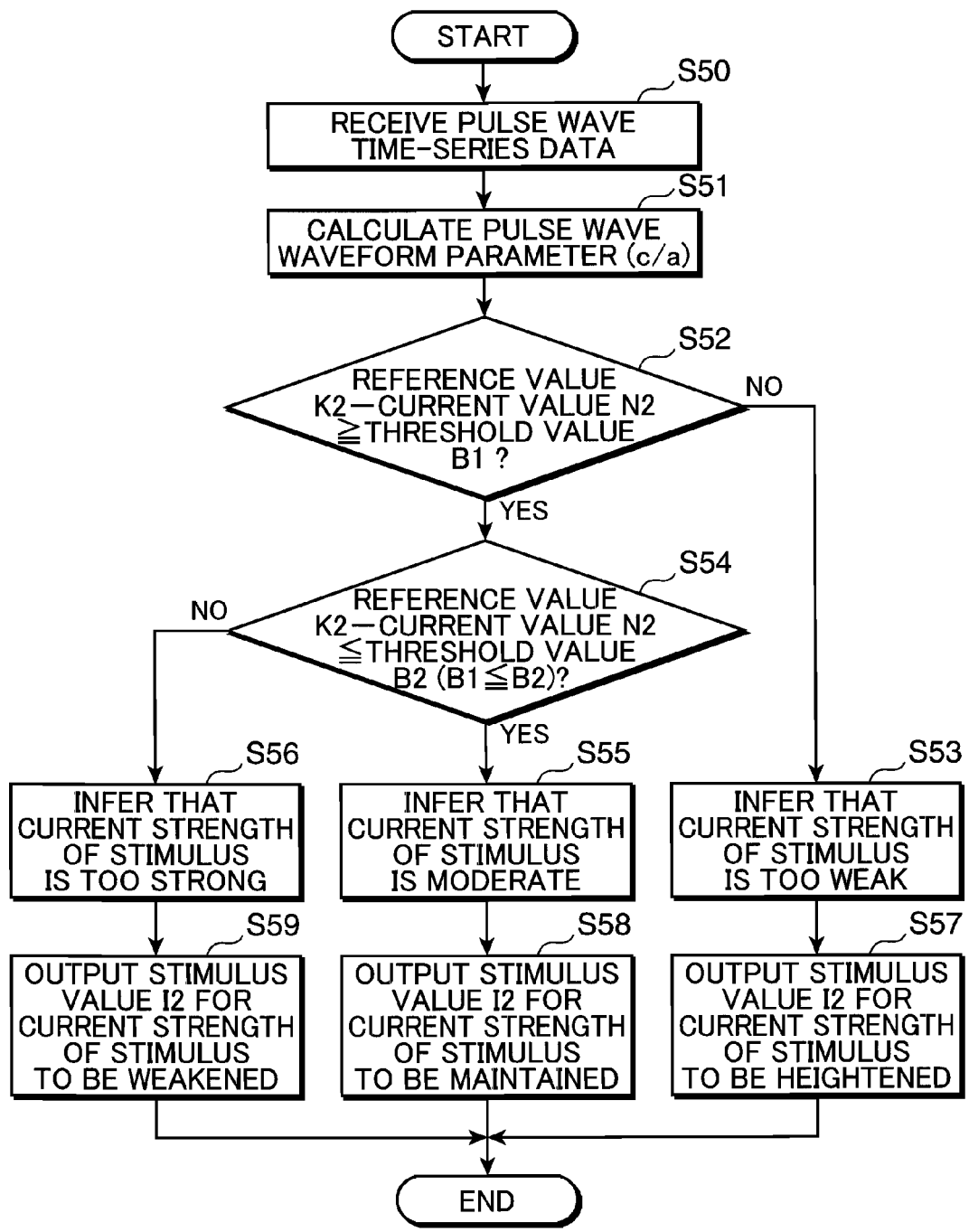
FIG. 17 is a flowchart detailing operations of a pulse wave waveform parameter calculating portion, a pulse wave waveform parameter comparing portion, a second user state inferring portion, and a second stimulus control portion of the embodiment.

FIG. 17 is a flowchart detailing operations of the pulse wave waveform parameter calculating portion 207, the pulse wave waveform parameter comparing portion 208, the second user state inferring portion 209, and the second stimulus control portion 210 of this embodiment.

Initially, the pulse wave waveform parameter calculating portion 207 receives the pulse wave time-series data detected by and accumulated in the pulse wave detecting portion 201 (Step S50). Subsequently, the pulse wave waveform parameter calculates portion 207 calculates a ratio of waveform components of the accelerated pulse wave, c/a, which is the second-order derivative value of the pulse wave, and uses the ratio of pulse wave components, c/a, it has calculated as the current value N2 of the pulse wave waveform parameter (Step S51).

Subsequently, the pulse wave waveform parameter comparing portion 208 compares a difference between the reference value K2 and the current value N2 of the pulse wave waveform parameter c/a with the threshold value B1 (Step S52). To be more concrete, the pulse wave waveform parameter comparing portion 208 calculates a difference between the reference value K2 and the current value N2 of the pulse wave waveform parameter c/a, and determines whether the difference it has calculated is equal to the threshold value B1 or greater. In a case where the calculated difference is smaller than the specific threshold value B1 (NO in Step S52), the second user state inferring portion 209 infers that perception by the user is so low at the current strength of stimulus that the strength stimulus is too weak (Step S53).

Meanwhile, in a case where the difference between the reference value K2 and the current value N2 of the pulse wave waveform parameter c/a is equal to the specific threshold value B1 or greater (YES in Step S52), the pulse wave waveform parameter comparing portion 208 further compares the difference between the reference value K2 and the current value N2 of the pulse wave waveform parameter c/a with a threshold value B2 (Step S54). To be more concrete, the pulse wave waveform parameter comparing portion 208 determines whether the difference between the reference value K2 and the current value N2 of the pulse wave waveform parameter c/a is equal to the threshold value B2 or greater. It should be noted that the threshold value B2 is equal to or greater than the threshold value B1. In a case where the difference is equal to the threshold value B2 or smaller (YES in Step S54), the second user state inferring portion 209 infers that the perception by the user is moderate at the current strength of stimulus, that is, the stimulus is in a suitable range (Step S55).

Meanwhile, in a case where the difference between the reference value K2 and the current value N2 of the pulse wave waveform parameter c/a is greater than the threshold value B2 (NO in Step S54), the second user state inferring portion 209 infers that the perception by the user is so high at the current strength of stimulus that the user feels a pain or is adversely affected (Step S56).

In Step S57, the second stimulus control portion 210 calculates the stimulus value I2 for the current strength of stimulus to be heightened, and outputs it to the stimulus control switching portion 211. In Step S58, the second stimulus control portion 210 calculates the stimulus value I2 for the current strength of stimulus to be maintained, and outputs it to the stimulus control switching portion 211. In Step S59, the second stimulus control portion 210 calculates the stimulus value I2 for the current strength of stimulus to be weakened, and outputs it to the stimulus control switching portion 211. Because the pulse wave waveform parameter can be calculated within several seconds (for example, about five seconds to about ten seconds) from the pulse wave waveform, it can be calculated swiftly for the pulse wave chaos parameter.

Whether the difference between the reference value and the current value of the pulse wave waveform parameter is found by subtracting the current value from the reference value, for example, as with the pulse wave waveform parameter c/a described above, or by subtracting the reference value from the current value, for example, as with the number of pulses, can be selected properly depending on the pulse wave waveform parameter to be calculated. In addition, the specific threshold values (B1 and B2, where $B1 \leq B2$) can be set appropriately.

Figure 18:
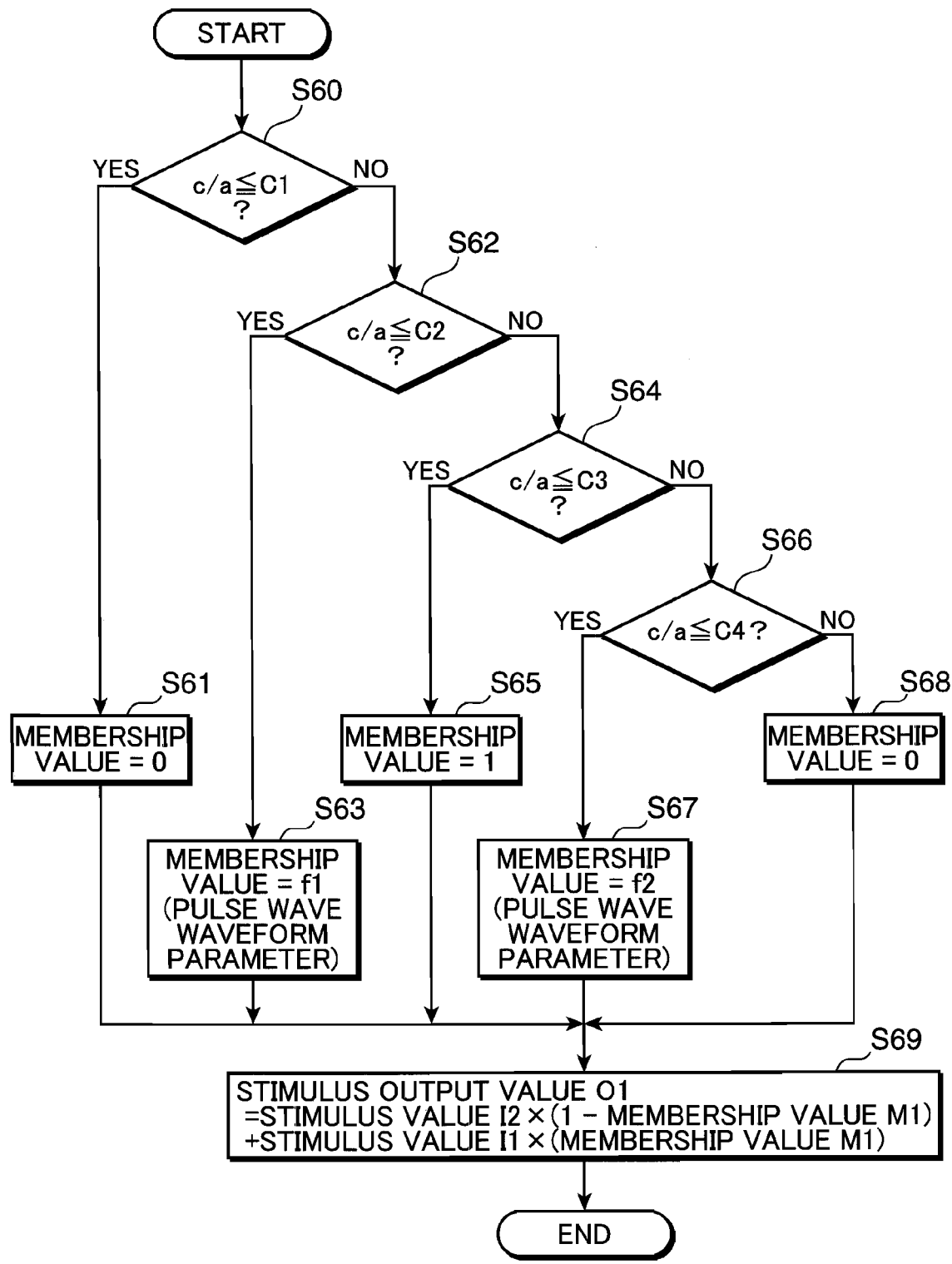
FIG. 18 is a flowchart detailing an operation of a stimulus control switching portion of the embodiment.

FIG. 18 is a flowchart detailing an operation of the stimulus control switching portion 211 of this embodiment. Initially, the stimulus control switching portion 211 compares the pulse wave waveform parameter c/a calculated by the pulse wave waveform parameter calculating portion 207 with a specific first threshold value (the lower limit specified value) C1 (Step S60). In short, the stimulus control switching portion 211 determines whether the pulse wave waveform parameter c/a is equal to the specific first threshold value C1 or smaller. In a case where the pulse wave waveform parameter c/a is equal to the first threshold value C1 or smaller (YES in Step S60), the stimulus control switching portion 211 sets a membership value M1 to 0 (Step S61). The membership value M1 referred to herein means a weighting factor determined according to the pulse wave waveform parameter. The membership value M1 is calculated using a specific membership function f1 that monotonously increases in a range from 0 to 1 with the pulse wave waveform parameter given as an input and the membership M1 as an output.

Meanwhile, in a case where the pulse wave waveform parameter c/a is greater than the first threshold value C1 (NO in Step S60), the stimulus control switching portion 211 compares a specific second threshold value (first specified value) C2 greater than the first threshold value C1 with the pulse wave waveform parameter c/a (Step S62). In short, the stimulus control switching portion 211 determines whether the pulse wave waveform parameter c/a is equal to the specific second threshold value C2 or smaller. In a case where the pulse wave waveform parameter c/a is equal to the second threshold value C2 or smaller (YES in Step S62), the stimulus control switching portion 211 calculates the membership value M1 corresponding to the pulse wave waveform parameter c/a using the membership function f1 (Step S63).

In a case where the pulse wave waveform parameter c/a is greater than the second threshold value C2 (NO in Step S62), the stimulus control switching portion 211 compares a specific third threshold value (second specified value) C3 greater than the second threshold value C2 with the pulse wave waveform parameter c/a (Step S64). In short, the pulse control switching portion 211 determines whether the pulse wave waveform parameter c/a is equal to the specific third threshold value C3 or smaller. In a case where the pulse wave waveform parameter c/a is equal to the third threshold value C3 or smaller (YES in Step S64), the stimulus control switching portion 211 sets the membership value M1 to 1 (Step S65).

Meanwhile, in a case where the pulse wave waveform parameter c/a is greater than the third threshold value C3 (NO in Step S64), the stimulus control switching portion 211 compares a specific fourth threshold value (upper limit specified value) C4 greater than the third threshold value C3 with the pulse wave waveform parameter c/a (Step S66). In short, the stimulus control switching portion 211 determines whether the pulse wave waveform parameter c/a is equal to the specific fourth threshold value C4 or smaller. In a case where the pulse wave waveform parameter c/a is equal to the fourth threshold value C4 or smaller (YES in Step S66), the stimulus control switching portion 211 calculates the membership value M1 corresponding to the pulse wave waveform parameter c/a using a membership function f2 (Step S67).

The membership function f2 is a function that monotonously decreases in a range from 0 to 1 and used to calculate the membership value M1 corresponding to the value of the pulse wave waveform parameter c/a.

Meanwhile, in a case where the pulse wave waveform parameter c/a is greater than the fourth threshold value C4 (NO in Step S66), the stimulus control switching portion 211 sets the membership value M1 to 0 (Step S68).

Figure 19:
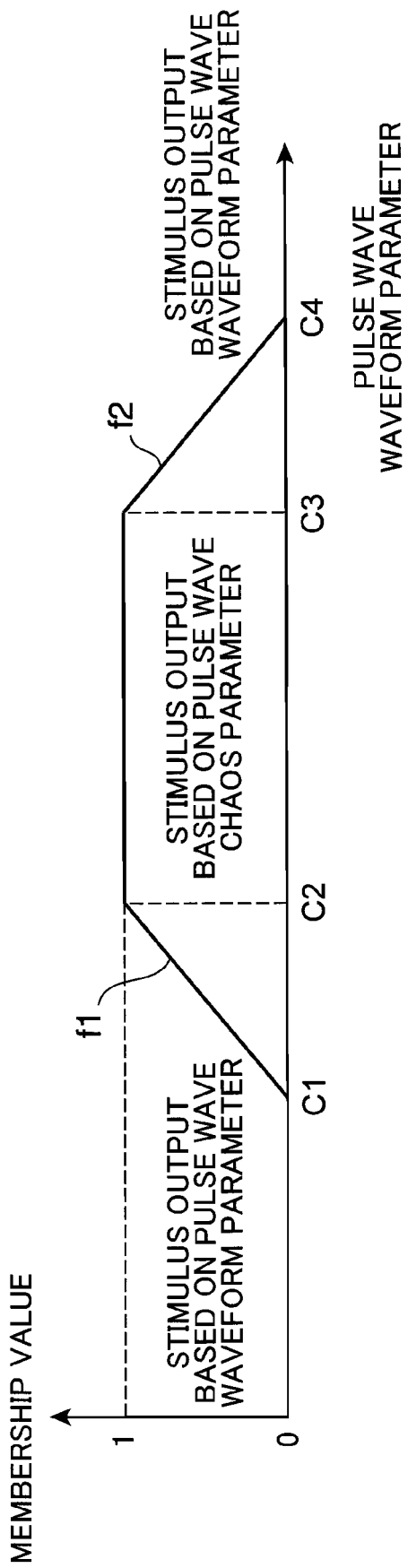
FIG. 19 is a graph indicating a relation between a pulse wave waveform parameter and a membership value.

FIG. 19 is a graph indicting the relation between the pulse wave waveform parameter and the membership value M1. In FIG. 19, the ordinate is used for the membership value M1 and the abscissa is used for the pulse wave waveform parameter. As is shown in FIG. 19, in a case where the pulse wave waveform parameter is equal to the first threshold value C1 or smaller, we obtain, the membership value M1=0. In a case where the pulse wave waveform parameter is greater than the first threshold value C1 and equal to the second threshold hold value C2 or smaller, the membership value M1 monotonously increases in accordance with the membership function f1. In a case where the pulse wave parameter is greater than the second threshold value C2 and equal to the third threshold value C3 or smaller, we obtain, the membership value M1=1. In a case where the pulse wave waveform parameter is greater than the third threshold value C3 and equal to the fourth threshold value C4 or smaller, the membership value M1 monotonously decreases in accordance with the membership function f2. In a case where the pulse wave waveform parameter is greater than the fourth threshold value C4, we obtain, the membership value M1=0.

Referring to FIG. 18 again, in Step S69, the stimulus control switching portion 211 performs a computation in accordance with Equation (1) below using the stimulus values I1 and I2 and the membership value M1 to calculate the stimulus output value O1, and outputs it to the stimulus generating portion 206.

$$\text{stimulus output value } O1 = \text{stimulus value } I2 \times (1 - \text{membership value } M1) + \text{stimulus value } I1 \times (\text{membership value } M1) \qquad (1)$$

Upon receipt of the stimulus output value O1, the stimulus generating portion 206 generates a stimulus at the strength specified by the stimulus output value O1 and gives the stimulus to the user.

As is shown in FIG. 19, in a case where the pulse wave waveform parameter c/a calculated by the pulse wave waveform parameter calculating portion 207 is determined as being equal to the first threshold value C1 or smaller by the stimulus control switching portion 211, it is determined that the strength of stimulus is so weak that it is difficult to enhance a state of the user (for example, a relaxed feeling, a comfortable feeling, or a thermal sensation) by continuing the generation of a stimulus at the same strength of stimulus. The membership value M1 is thus set to 0. Consequently, the weight of the stimulus value I1, which is dominant in enhancing a relaxed feeling, a comfortable feeling, a thermal sensation, or the like takes 0. The stimulus output value O1 is therefore calculated with the use of the stimulus value I2 alone.

Hence, because the stimulus output value O1 is calculated without using the pulse wave chaos parameter which takes a time to calculate, the stimulus output value O1 can be calculated swiftly, which makes it possible to adjust the strength of stimulus to be given to the user swiftly to the moderate strength.

In a case where the pulse wave waveform parameter c/a calculated by the pulse wave waveform parameter calculating portion 207 is determined as being greater than the fourth threshold value C4 by the stimulus control switching portion 211, it is determined that the strength of stimulus is so strong that there is a possibility that the user feels a pain or is adversely affected. The membership value M1 is thus set to 0 as with the description above. Consequently, the stimulus output value O1 is calculated with the use of the stimulus value I2 alone.

Hence, because the stimulus output value O1 is calculated without using the pulse wave chaos parameter that takes a time to calculate, the strength of stimulus to be given to the user is weakened swiftly, which makes it possible to adjust the strength of stimulus swiftly to the moderate strength.

Further, in a case where the pulse wave waveform parameter c/a calculated by the pulse wave waveform calculating portion 207 is determined as being greater than the second threshold value C2 and equal to the third threshold value C3 or smaller by the stimulus control switching portion 211, it is determined that the pulse wave waveform parameter c/a falls within a suitable range and the current strength of stimulus is moderate, so that the user is not adversely affected, such as he feels a pain, by continuously giving the user a stimulus at this strength.

The membership value M1 is then set to 1 by the stimulus control switching portion 211. The weighting factor of the stimulus value I2 thus takes 0, and the stimulus output value O1 is calculated with the use of the stimulus value I1 alone. In this instance, in a case where a difference between the current value N1 and the reference value K1 of the pulse wave chaos parameter is equal to the specific threshold value A1 or greater, the current strength of stimulus is maintained. Meanwhile, in a case where the difference between the current value N1 and the reference value K1 of the pulse wave chaos parameter is smaller than the specific threshold value A1, the current strength of stimulus is heightened.

It is thus possible to enhance a relaxed feeling, a comfortable feeling, a thermal sensation, or the like of the user after it is ensured that the user will not feel a pain or be adversely affected.

Further, in a case where the pulse wave waveform parameter c/a calculated by the pulse wave waveform parameter calculating portion 207 is determined as being greater than the first threshold value C1 and equal to the second threshold value C2 or smaller by the stimulus control switching portion 211, it is determined that because the strength of stimulus is rather weak, although not as weak as the case where it is equal to the first threshold value C1 or smaller, it is rather difficult to enhance a state of the user (for example, a relaxed feeling, a comfortable feeling, or a thermal sensation) by continuing the generation of a stimulus at the same strength of stimulus. In this case, the stimulus output value O1 is calculated by mixing the stimulus value I1 and the stimulus value I2.

It is thus possible to give the user a stimulus at moderate strength that is not too weak, which makes it possible to enhance a relaxed feeling, a feeling of relaxation, a thermal sensation, or the like of the user in a more reliable manner.

Further, in a case where the pulse wave waveform parameter c/a calculated by the pulse wave waveform parameter calculating portion 207 is determined as being greater than the third threshold value C3 and equal to the fourth threshold value C4 or smaller by the stimulus control switching portion 211, it is determined that because the strength of stimulus is rather strong, although not as strong as the case where it is equal to the fourth threshold value C4 or greater, there is a possibility that the user feels a pain or is adversely affected by continuing the generation of a stimulus at the same strength of stimulus. In this case, the stimulus output value O1 is calculated by mixing the stimulus value I1 and the stimulus value I2.

It is thus possible to give the user a stimulus at moderate strength that is not too strong, which makes it possible to enhance a relaxed feeling, a feeling of relaxation, a thermal sensation, or the like of the user in a more reliable manner.

As has been described, according to this environment control device, it is possible to enhance a relaxed feeling, a feeling of relaxation, a thermal sensation, or the like of the user by avoiding an event that the user feels a pain or is adversely affected.

In this embodiment, a stimulus given to the user includes a warm or cool thermal stimulus, such as cooling and heating, an air-flow stimulus, such as cool air and warm air, a physical stimulus, such as massage, a material stimulus, such as oxygen and minus ions, an audio stimulus, such as a pulse tone, music, and ultrasonic waves, a visual stimulus, such as light, illumination, and a video, and so forth.

In the description with reference to FIG. 18 and FIG. 19, the stimulus control switching portion 211 compares the pulse wave waveform parameter with the threshold values (C1, C2, C3, and C4). However, it may be configured in such a manner that a difference between the reference value (K2) and the current value (N2) of the pulse wave waveform parameter is compared with an adequately set threshold value.

The embodiment described above adopts the configuration including the first user state inferring portion 204 that infers a state of the user on the basis of the pulse wave chaos parameter and the second user state inferring portion 209 that infers a state of the user on the basis of the pulse wave waveform parameter. The invention, however, is not limited to this configuration, and the stimulus generating portion 206 may be controlled on the basis of the pulse wave chaos parameter alone. In this case, the pulse wave waveform parameter calculating portion 207 through the stimulus control switching portion 211 can be omitted, and the first stimulus control portion 205 directly controls the stimulus generating portion 206 using the stimulus value I1 it has calculated. According to this configuration, a comfortable feeling or a thermal sensation of the user is inferred using the pulse wave chaos parameter and a stimulus such that enhances a comfortable feeling or a thermal sensation can be given to the user on the basis of the result of inference. It is therefore possible to provide an environment control device sufficiently adaptable to control the device forming the residential environment of the user (in particular, a device that gives the user a warm or cool thermal stimulus, for example, an air conditioning device, a bathroom environment device, such as a water heating device) while making the configuration simpler.

The principle of inference of a comfortable feeling or a thermal sensation of the user in response to a warm or cool thermal stimulus through chaos analysis of the pulse wave employed in the invention will now be described.

In order to achieve the invention, the inventors conducted assiduous studies about inference of a comfortable feeling of an individual in response to a warm or cool thermal stimulus from the biological information, and conducted a warm or cool thermal stimulus test on adolescent female subjects in winter. The test conditions were that after the subjects were rested while they were seated on chairs in a relatively cool environment, they took a foot bath by bathing their feet in hot water as an example of a warm thermal stimulus under the same environment. The subjects were then rested with their feet out of hot water. The pulse waves of the subjects were detected and accumulated in the form of time-series data during the test. Also, the subjects were requested to objectively report changes of a comfortable feeling and a thermal sensation.

Figure 20:
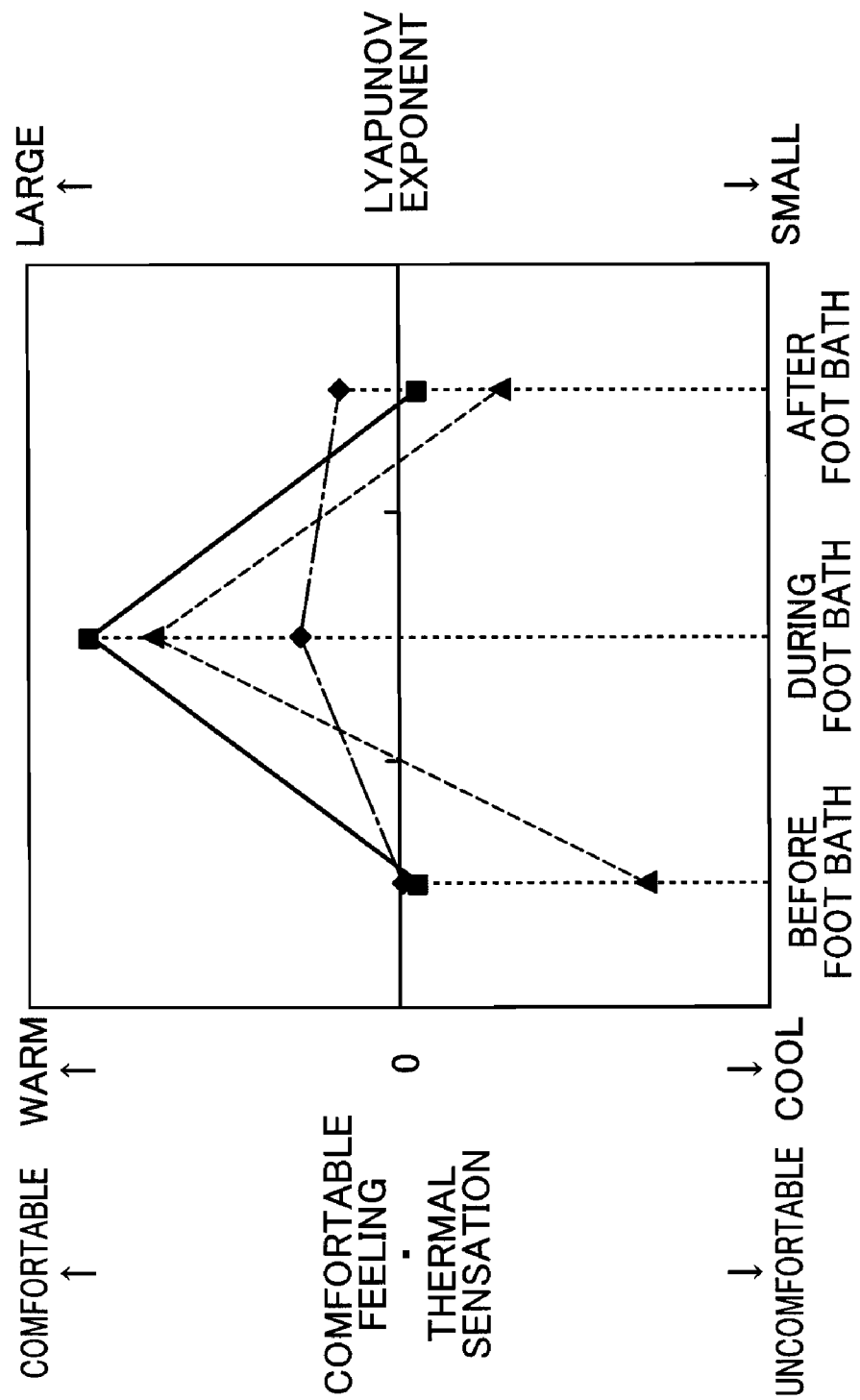
FIG. 20 is a view showing an example of a change of the Lyapunov exponent obtained through chaos analysis of the pulse wave and objectively reported changes of a comfortable feeling and a thermal sensation before, during, and after a foot bath.

FIG. 20 is a view showing an example of a change of the Lyapunov exponent obtained through chaos analysis of the pulse wave, and objectively reported changes of a comfortable feeling and a thermal sensation before, during, and after the foot bath. In FIG. 20, rectangular marks indicate an objectively reported comfortable feeling before, during, and after the foot bath, and triangular marks indicate an objectively reported thermal sensation before, during, and after the foot bath. Rhombic marks indicate the Lyapunov exponents before, during, and after the foot bath.

After the test ended, the inventors made various analyses about the correlation between the pulse wave time-series data of the subjects and objectively reported comfortable feeling and thermal sensation. Consequently, the inventors completed the invention when they discovered the presence of a high correlation between a change of the Lyapunov exponent obtained through chaos analysis of the pulse wave before, during, and after the foot bath and the objectively reported comfortable feeling and thermal sensation as is shown in FIG. 20. More specifically, because the subjects were in a relatively cool environment before they took a foot bath, a comfortable feeling was reported to be almost at the neutral point or on the slightly uncomfortable side, and a thermal sensation was reported to be on the cool side. On the contrary, during the foot bath, both a comfortable feeling and a thermal sensation were reported to be at far ends on the comfortable side and the warm side, respectively. In addition, because the subjects were left in a relatively cool environment after they took the foot bath, a comfortable feeling was reported again to be at almost the neutral point or slightly on the uncomfortable side and a thermal sensation was reported to be on the cool side.

Meanwhile, the Lyapunov exponent, which is the result of chaos analysis of the pulse wave, shows the tendency that it increases markedly from before the foot bath to during the foot bath and decreases again from during the foot bath to after the foot bath. Hence, a high correlation was discovered between the Lyapunov exponent and objectively reported changes of a comfortable feeling and a thermal sensation as described above. By configuring the first user state inferring portion 204 described above by using the correlation between changes of a comfortable feeling and a thermal sensation in response to a warm or cool thermal stimulus and the result of chaos analysis of the pulse wave, it is possible to control the stimulus generating portion 206 that generates a warm or cool thermal stimulus on the basis of the result of inference of a comfortable feeling or a thermal sensation of the user in response to a warm or cool thermal stimulus, which is obtained through chaos analysis of the time-series data of the pulse wave used as the biological information of the user. It is thus possible to give the user a stimulus such that enhances a comfortable feeling or a thermal sensation in response to a warm or cool thermal stimulus. It is therefore possible to provide an environment control device sufficiently adaptable to control the device forming the residential environment of the user (in particular, a device that gives the user a warm or cool thermal stimulus, for example, an air conditioning device, a bathroom environment device, such as a water heating device).

Sixth Embodiment

An environment control device according to a sixth embodiment of the invention will now be described. Firstly, the inference principle of a comfortable feeling of the user using a parameter to evaluate the pulse wave employed in the invention, and the inference principle of a thermal sensation of the user using a parameter to evaluate the pulse wave employed in the invention will be described.

The inventors conducted assiduous studies to understand a comfortable feeling quantitatively from biological information, and discovered the presence of a high correlation between a change of a ratio of waveform components of the accelerated pulse wave and objectively reported enhancement of a comfortable feeling before and after a stimulus such that fosters a comfortable feeling is given to the user.

Also, the inventors conducted assiduous studies to understand better a thermal sensation from the biological information, and discovered the presence of a high correlation between changes of a ratio of waveform components of the accelerated pulse wave and the maximum value of the wave height of the accelerated pulse wave (maximum wave height value of the accelerated pulse wave) or the maximum value of the wave height of the pulse wave (maximum wave height value of the pulse wave) and an objectively reported change of a thermal sensation.

Herein, the largest peak value among plural peak values or an average value of the plural peak values of the accelerated pulse wave waveform for several pulse beats obtained within a specific time and the peak value of the accelerated pulse wave waveform for one pulse beat included in the accelerated pulse wave waveform for several pulse beats obtained within a specific time can be adopted as the maximum wave height value of the accelerated pulse wave.

Also, the largest peak value among plural peak values or an average value of the plural peak values of the pulse wave waveform for several pulse beats obtained within a specific time and the peak value of the pulse wave waveform for one pulse beat included in the pulse wave waveform for several pulse beats obtained within a specific time can be adopted as the maximum wave height value of the pulse wave. Hereinafter, the sixth embodiment of the invention will be described with reference to the drawings.

Figure 21:
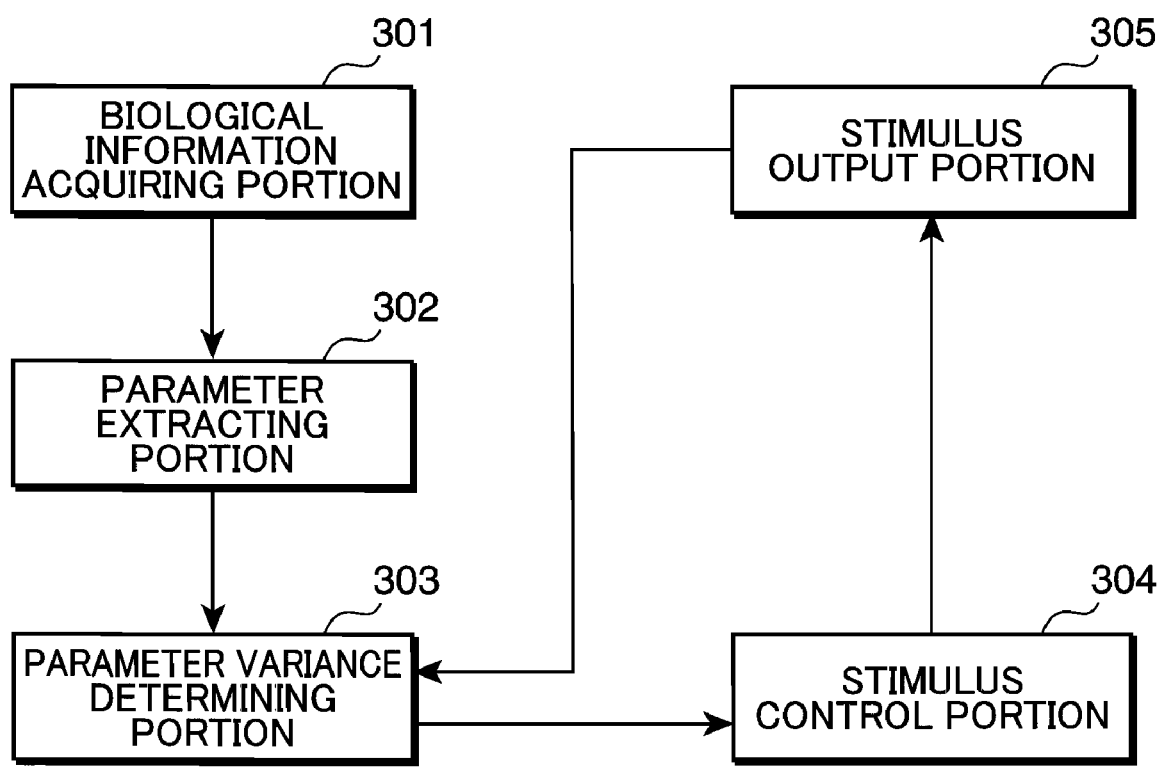
FIG. 21 is a block diagram showing the configuration of an environment control system according to a sixth embodiment of the invention.

FIG. 21 is a block diagram showing the configuration of an environment control system according to the sixth embodiment of the invention. The environment control system shown in FIG. 21 is formed of, for example, a known computer, and includes a biological information acquiring portion (biological information acquiring portion) 301, a parameter extracting portion (parameter calculating portion) 302, a parameter variance determining portion (inferring portion) 303, a stimulus control portion (stimulus control portion) 304, and a stimulus output portion 305. The biological information acquiring portion 301 through the stimulus output portion 305 are achieved by running an environment control program of the invention pre-installed in the computer on the CPU.

The biological information acquiring portion 301 acquires pulse wave data in time series by sampling the fingertip pulse wave of the user detected by a known transducer or the like at a specific sampling cycle. The parameter extracting portion 302 extracts, as a parameter to evaluate the pulse wave, a ratio of waveform components of the accelerated pulse wave obtained by second-order differentiation of the pulse wave waveform obtained from the pulse wave data and accumulates it therein. Herein, the accelerated pulse wave waveform shapes the waveform as shown in FIG. 60. In this embodiment, given the distance a from the base line to the peak A of the accelerated pulse wave waveform as the denominator and the distance c from the base line to the peak C as the numerator, c/a is extracted as the ratio of waveform components. Herein, b/a, d/a, or e/a may be used as the ratio of waveform components instead of c/a; however, c/a has a particularly high correlation with a comfortable feeling.

The parameter variance determining portion 303 calculates a variance of the ratio of waveform components extracted by the parameter extracting portion 302 to infer a comfortable feeling of the user from the result of calculation, and determines the content of stimulus from the result of inference. The parameter variance determining portion 303 then outputs a stimulus output instruction to the stimulus control portion 304 so that a stimulus corresponding to the determined content of stimulus is outputted from the stimulus output portion 305. In this embodiment, the parameter variance determining portion 303 calculates a derivative value of the ratio of waveform components by dividing a difference between the ratio of waveform components extracted immediately after the reception of a stimulus output signal that the stimulus output portion 305 outputs when it outputs a stimulus and the ratio of waveform components extracted immediately before the reception of the stimulus output signal by the sampling cycle. It infers a comfortable feeling of the user by determining within which of pre-set particular ranges 1 through 3 (described below) this derivative value falls.

The stimulus control portion 304 controls the stimulus output portion 305 by outputting a stimulus output instruction to the stimulus output portion 305. The stimulus output portion 305 outputs a stimulus to the user, and at the same time, it outputs a stimulus output signal indicating that it has outputted a stimulus to the parameter variance determining portion 303.

Figure 22:
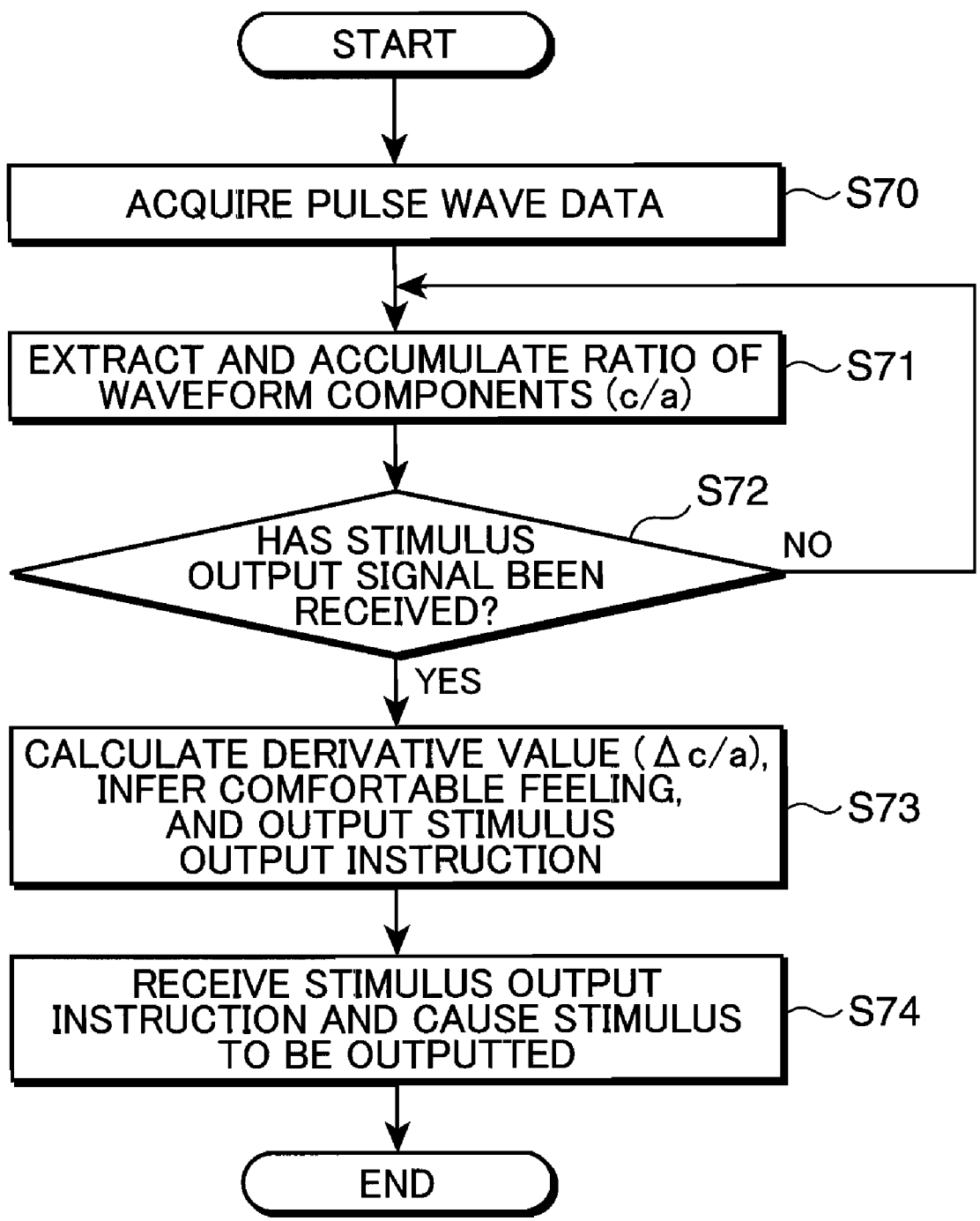
FIG. 22 is a flowchart detailing the processing by the environment control system according to the sixth embodiment of the invention.

FIG. 22 is a flowchart detailing the processing by the environment control system according to the sixth embodiment of the invention. Initially, the biological information acquiring portion 301 acquires time-series data of the pulse wave and accumulates it therein (Step S70).

Subsequently, the parameter extracting portion 302 extracts the ratio of waveform components, c/a, at regular time intervals from the time-series data of the pulse wave acquired by the biological information acquiring portion 301 and accumulates it therein (Step S71). Subsequently, the parameter variance determining portion 303 determines whether it has received a stimulus output signal from the stimulus output portion 305 (Step S72). In a case where it has not received the stimulus output signal from the stimulus output portion 305 (NO in Step S72), it returns to the processing in Step S71, and processing in Step S71 and Step S72 is performed repetitively until the stimulus output signal is received.

Meanwhile, upon receipt of the stimulus output signal from the stimulus output portion 305 (YES in Step S72), the parameter variance determining portion 303 finds a derivative value $\Delta c/a$ of the ratio of waveform components from the ratio of waveform components, c/a, extracted by the parameter extracting portion 302 immediately after the reception of the stimulus output signal and the ratio of waveform components, c/a, extracted by the parameter extracting portion 302 immediately before the reception of the stimulus output signal. It then infers a comfortable feeling of the user on the basis of the derivative value $\Delta c/a$ to determine the content of stimulus from the result of inference, and outputs a stimulus output instruction to the stimulus control portion 304 so that a stimulus according to the determined content of stimulus is outputted from the stimulus output portion 305 (Step S73). Subsequently, the stimulus control portion 304 controls the stimulus output portion 305 to output a stimulus according to the stimulus output instruction outputted from the parameter variance determining portion 303 (Step S74).

Figure 23:
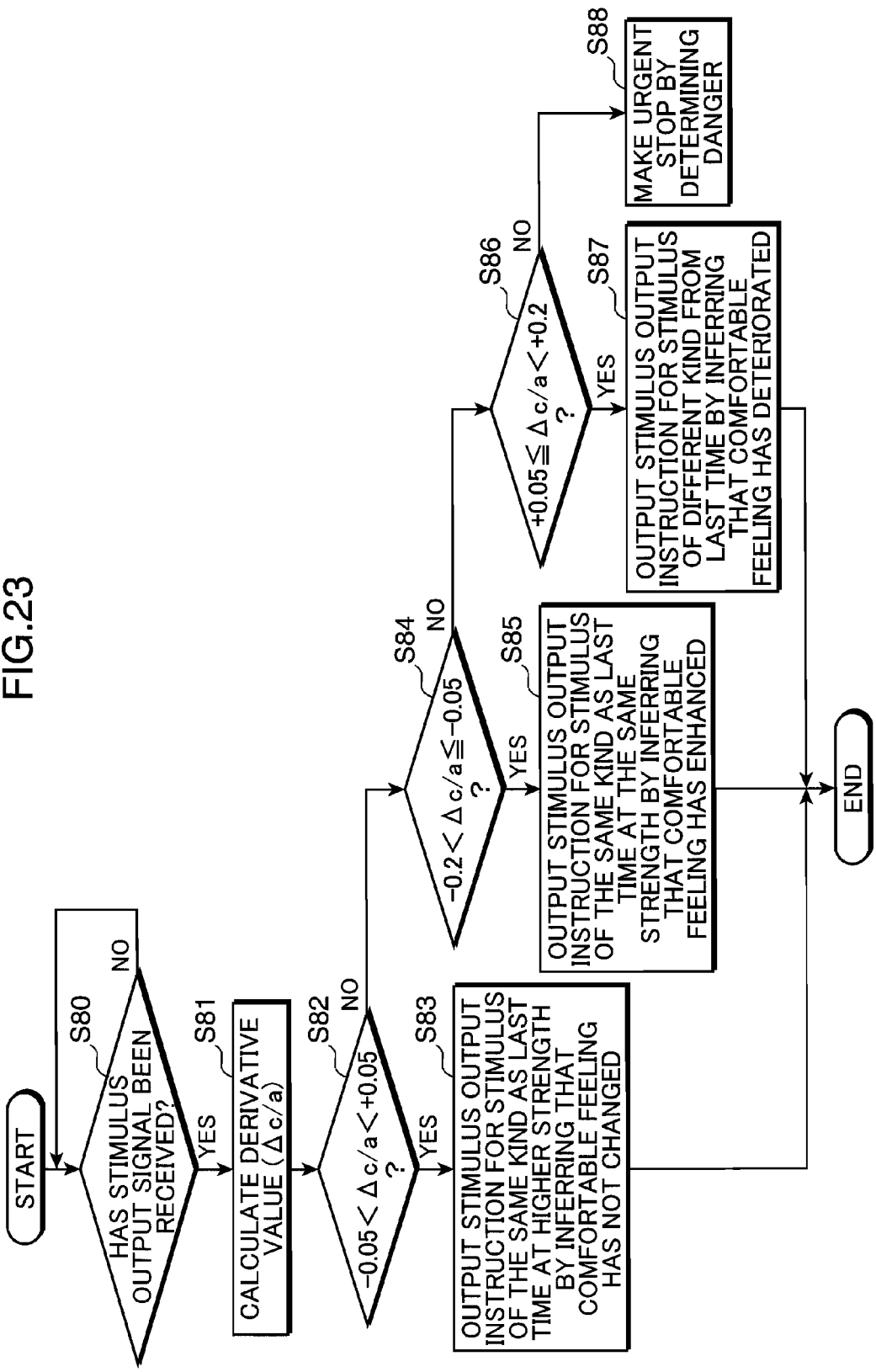
FIG. 23 is a flowchart detailing the processing by a parameter variance determining portion according to the sixth embodiment of the invention.

The processing to infer a comfortable feeling of the user and the processing to determine the content of stimulus by the parameter variance determining portion 303 will now be described. FIG. 23 is a flowchart detailing the processing by the parameter variance determining portion 303 according to the sixth embodiment of the invention.

Initially, the parameter variance determining portion 303 determines whether it has received a stimulus output signal from the stimulus output portion 305 (Step S80). In a case where it has not received the stimulus output signal from the stimulus output portion 305 (NO in Step S80), the processing in Step S80 is performed repetitively at specific timing until the stimulus output signal is received. Upon receipt of the stimulus output signal from the stimulus output portion 305 (YES in Step S80), the parameter variance determining portion 303 calculates a derivative value $\Delta c/a$ on the basis of the ratio of waveform components, c/a, immediately before the reception of the stimulus output signal and the ratio of waveform components, c/a, immediately after the reception among the ratios of waveform components, c/a, extracted by the parameter extracting portion 302 (Step S81).

The inventors discovered the presence of a high correlation between a phenomenon that the ratio of waveform components varies and a phenomenon that a comfortable feeling of the user enhances. This environment control system therefore infers a comfortable feeling of the user on the basis of a variance of the ratio of waveform components.

Subsequently, the parameter variance determining portion 303 determines whether the derivative value $\Delta c/a$ falls within a particular range 1 indicating that the ratio of waveform components, c/a, has hardly varied (Step S82). The particular range 1 is expressed, for example, as, $-0.05 < \Delta c/a < +0.05$. In a case where the derivative value $\Delta c/a$ falls within the particular range 1 (YES in Step S82), the parameter variance determining portion 303 infers that a comfortable feeling of the user has not changed and determines that a stimulus such that enhances a comfortable feeling is necessary. Hence, it outputs a stimulus output instruction to heighten the strength of stimulus for a stimulus of the same kind as the stimulus given last time or to extend a stimulus giving time to the stimulus control portion 304 (Step S83). The user is thus able to have a comfortable feeling.

Meanwhile, in a case where the derivative value $\Delta c/a$ does not fall within the particular range 1 (NO in Step S82), the parameter variance determining portion 303 determines whether the derivative value $\Delta c/a$ of the ratio of waveform components, c/a, falls within a particular range 2 different from the particular range 1 (Step S84). The particular range 2 is expressed, for example, as, $-0.2 < \Delta c/a \leq -0.05$.

In a case where the derivative value $\Delta c/a$ falls within the particular range 2 (YES in Step S84), the parameter variance determining portion 303 infers that a comfortable feeling of the user has enhanced and a stimulus such that maintains or enhances a comfortable feeling is necessary. Hence, it outputs a stimulus output instruction for a stimulus of the same kind and at the same strength as the stimulus given last time to the stimulus control portion 304 (Step S85). This allows the stimulus output portion 305 to continue to output a stimulus such that enables the user to have a comfortable feeling to the user. The user is thus able to maintain a comfortable feeling.

In a case where the derivative value $\Delta c/a$ does not fall within the particular range 2 (NO in Step S84), the parameter variance determining portion 303 determines whether the variance of the ratio of waveform components falls within a particular range 3 different from the particular range 2 (Step S86). The particular range 3 is expressed, for example, as, $+0.05 \leq \Delta c/a < +0.2$. In a case where the derivative value $\Delta c/a$ falls within the particular range 3 (YES in Step S86), the parameter variance determining portion 303 infers that a comfortable feeling of the user has deteriorated and determines that a stimulus such that enhances a comfortable feeling is necessary. Hence, it outputs a stimulus output instruction for a stimulus of a different kind from the stimulus given last time (Step S87). Meanwhile, in a case where the derivative value $\Delta c/a$ does not fall within the particular range 3 (NO in Step S86), the parameter variance determining portion 303 determines that the user is in a state of unexpected danger and stops the system urgently (Step S88).

As has been described, according to the environment control system of the sixth embodiment, because a comfortable feeling of the user is inferred from the pulse wave of the user, it is possible to infer a comfortable feeling of the user without making the user feel uncomfortable. In addition, because a comfortable feeling is inferred from the pulse wave, expensive equipment can be omitted in comparison with a case where a comfortable feeling is inferred from the brain wave. It is thus possible to create the environment to let the user actually have a comfortable feeling readily within the house of the user.

Further, because a comfortable feeling of the user is inferred from a variance of the ratio of waveform components, c/a, before and after the output of a stimulus to the user, it is possible to understand a response of the user to the stimulus in a reliable manner. In addition, because a comfortable feeling is inferred on the basis of the response of the user to the stimulus and the content of stimulus is determined on the basis of the result of inference, it is possible to address differences among individual users when a comfortable feeling is obtained, which enables the user to actually have a comfortable feeling in a reliable manner. Further, by repeating a series of these processing steps, it is possible to enable the user to maintain a comfortable feeling in a reliable manner.

Further, of many pulse wave parameters, the ratio of waveform components of the accelerated pulse wave, c/a, is adopted as the pulse wave parameter. This eliminates the need for complicated processing, which in turn makes it possible to achieve the system with a simpler configuration. It is therefore possible to infer a comfortable feeling at a further higher degree of accuracy using the pulse wave that has not been achieved before.

Further, because the derivative value $\Delta c/a$ of the ratio of waveform components, c/a, is calculated as a variance of the parameter before and after the output of a stimulus and a comfortable feeling is inferred using this derivative value $\Delta c/a$, a response of the user to the stimulus can be extracted in a more reliable manner. Further, because a comfortable feeling is inferred by determining within which of the particular ranges 1 through 3 the derivative value $\Delta c/a$ falls, it is possible to understand a response of the user in detail, which can in turn further enhance the accuracy of the inference of a comfortable feeling of the user.

Further, in a case where the derivative value found on the basis of the ratios before and after the output of a stimulus does not fall within the particular range 3, the system is stopped because a danger is predicted. It is therefore possible to achieve a system that is safer for the user.

In this embodiment, the content of stimulus determined by the parameter variance determining portion 303 includes kinds of stimulus, the strength of stimulus, a stimulus giving time, and so forth. The kinds of stimulus include a warm or cool thermal stimulus, such as cooling and heating, an airflow stimulus, such as cool air and warm air, a physical stimulus, such as massage, a material stimulus, such as oxygen and minus ions, and so forth.

In this embodiment, the parameter variance determining portion 303 may determine whether a variance of the ratio of waveform components falls within a range set by combining the particular range 1 and the particular range 3. In a case where the variance of the ratio of waveform components falls within this range, the parameter variance determining portion 303 infers that a comfortable feeling of the user has not enhanced and determines that a stimulus such that enhances a comfortable feeling is necessary. Hence, it outputs a stimulus output instruction for a stimulus, for example, of a different kind from the stimulus given last time. Meanwhile, in a case where the variance of the ratio of waveform components does not fall within the range set by combining the particular range 1 and the particular range 3, the parameter variance determining portion 303 further determines whether the variance of the ratio of waveform components falls within the particular range 2. In a case where the variance of the ratio of waveform components falls within the particular range 2, the parameter variance determining portion 303 infers that a comfortable feeling of the user has enhanced and determines that a stimulus such that maintains or enhances a comfortable feeling is necessary. Hence, it outputs a stimulus output instruction for a stimulus, for example, of the same kind and at the same strength as the stimulus given last time. In a case where the variance of the ratio of waveform components does not fall within the particular range 2, either, the parameter variance determining portion 303 determines that the user is in a state of unexpected danger and stops the system urgently.

In this embodiment, the parameter variance determining portion 303 calculates a derivative value $\Delta c/a$ on the basis of the ratio of waveform components, c/a, immediately after the output of a stimulus from the stimulus output portion 305 and the ratio of waveform components, c/a, immediately before the output, and infers a comfortable feeling of the user using this derivative value $\Delta c/a$. The invention, however, is not limited to this configuration, and a difference between the ratio of waveform components, c/a, immediately before the output and the ratio of waveform components, c/a, immediately after the output may be calculated, so that a comfortable feeling of the user is inferred on the basis of the difference. In this case, too, as with the case of the derivative value $\Delta c/a$, the parameter variance determining portion 303 infers a comfortable feeling of the user by merely determining to which one of the pre-set three ranges the difference belongs.

Also, in this embodiment, the parameter variance determining portion 303 calculates a derivative value $\Delta c/a$ of the ratio of waveform components on the basis of the ratio of waveform components, c/a, immediately before the reception of the stimulus output signal outputted from the stimulus output portion 305 and the ratio of waveform components, c/a, immediately after the reception. However, an average value of plural ratios of waveform components, c/a, extracted within a specific period in the past since the reception of the stimulus output signal, an average value or a derivative value of respective differences may be calculated, so that a derivative value Δc/a or a difference of the ratios of waveform components is calculated on the basis of the calculated value and the ratio of waveform components, c/a, immediately after the reception of the stimulus output signal to infer a comfortable feeling of the user on the basis of the result of calculation.

Also, in this embodiment, the parameter variance determining portion 303 infers a comfortable feeling of the user and determines the content of stimulus on the basis of the inference. However, the result of inference of a comfortable feeling of the user may be presented to the user by displaying the result on a display portion, such as a monitor.

In this embodiment, the stimulus output portion 305 outputs the stimulus output signal indicating that it has outputted a stimulus to the parameter variance determining portion 303, and the parameter variance determining portion 303 calculates the derivative value from the ratios of waveform components immediately before and after the reception of the stimulus output signal. However, it may be configured in such a manner that the stimulus output portion 305 does not output the stimulus output signal, and instead, the parameter variance determining portion 303 is provided with a timer portion that measures a time, so that it calculates the derivative value from the ratios of waveform components immediately before and after the elapse of a specific time or immediately before and after the elapse of a stimulus giving time included in the content of stimulus.

Alternatively, a rate of change of the ratio of waveform components over a specific time may be used as the derivative value. Further, the timer portion that measures a time may be separated from the parameter variance determining portion 303 as an independent component and the timer portion is connected to the parameter variance determining portion 303 to enable mutual communications, so that the timer portion transmits the start of time measurement and an elapse of time to the parameter variance determining portion 303.

Seventh Embodiment

Regarding a warm thermal stimulus, the inventors also discovered the presence of a high correlation between a phenomenon that the pulse rate PR of the pulse wave increases and a phenomenon that an objectively reported comfortable feeling enhances before and after a stimulus such that fosters a comfortable feeling of the user. The pulse rate PR is so-called the number of pulses and is generally said to decrease in a state of relaxation or in a state of good shape where unpleasant things are removed (passive comfortable space).

However, the fact that a correlation is present between an increase of the pulse rate PR and enhancement of a comfortable feeling reveals that a biophenomenon completely different from the one in the passive comfortable space described above takes place in a place (active comfortable space) where a warm thermal stimulus such that enhances a comfortable feeling transiently is given.

Hence, in this embodiment, a comfortable feeling of the user, which was inferred from a variance of the ratio of waveform components of the accelerated pulse wave, c/a, in the sixth embodiment, is inferred from a variance of the pulse rate PR of the pulse wave. Hereinafter, an environment control system of a seventh embodiment will be described.

Because the environment control device of this embodiment is of the same configuration as the counterpart of the sixth embodiment, the configuration thereof will be described using the same block diagram as the block diagram shown in FIG. 21. Also, descriptions of components same as those in the sixth embodiment are omitted and only different components will be described.

The parameter extracting portion 302 extracts the pulse rate PR of the pulse wave as a parameter. It then extracts the value of the pulse rate PR at regular time intervals, for example, for every sampling cycle, from the pulse wave data acquired by the biological information acquiring portion 301 and accumulates it therein. The parameter variance determining portion 303 infers a comfortable feeling of the user on the basis of a variance between the pulse rates PR immediately before and after the reception of a stimulus output signal from the stimulus output portion 305, and determines the content of stimulus to be outputted from the result of inference.

The processing to infer a comfortable feeling of the user and the processing to determine the content of stimulus to be outputted by the parameter variance determining portion 303 of this embodiment will now be described.

Figure 24:
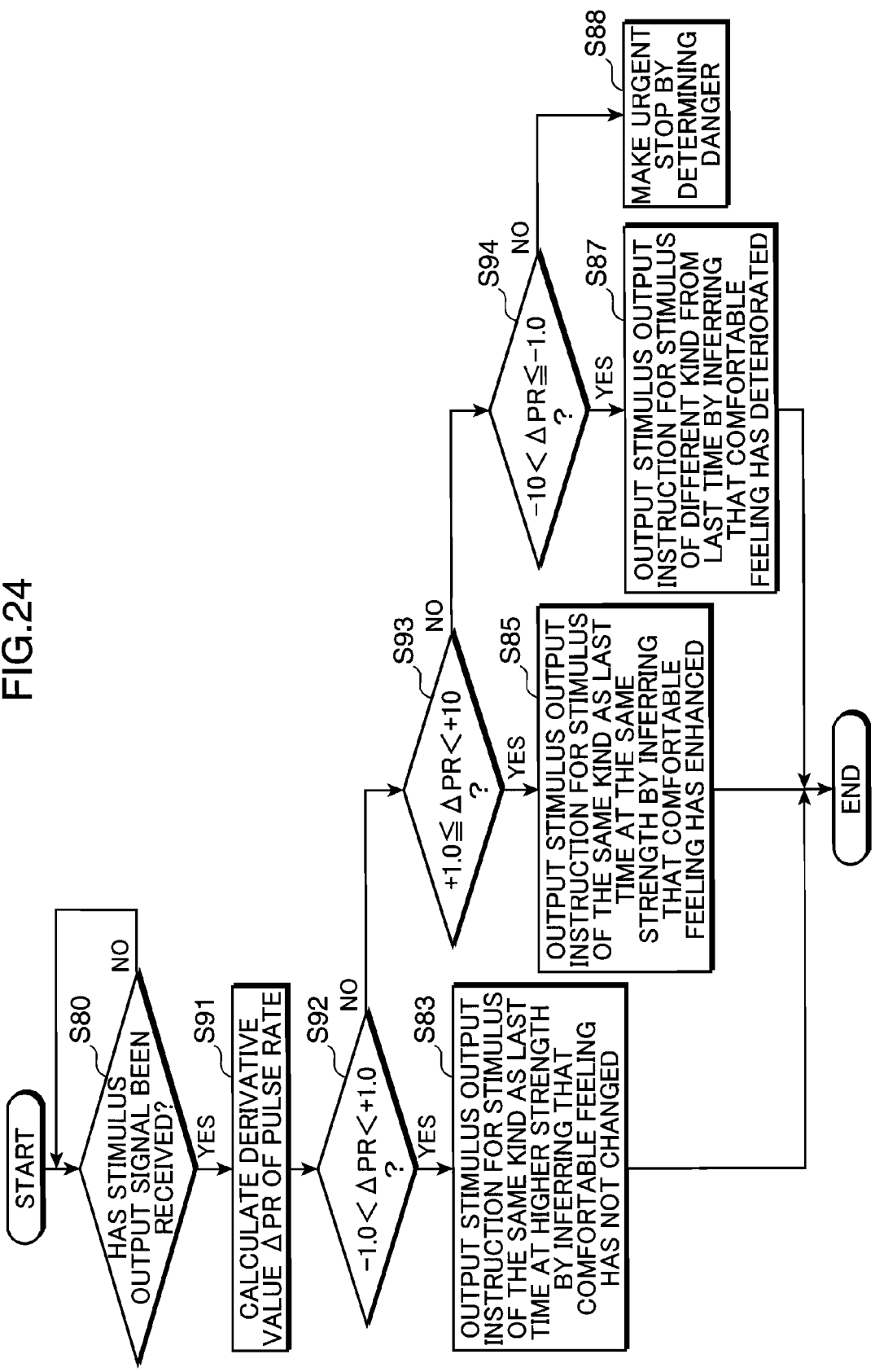
FIG. 24 is a flowchart detailing the processing by a parameter variance determining portion according to a seventh embodiment of the invention.

FIG. 24 is a flowchart detailing the processing by the parameter variance determining portion 303 according to the seventh embodiment of the invention. For the steps in which the same processing as that in the sixth embodiment is performed, the same step numbers are used and descriptions thereof are omitted.

Initially, upon receipt of a stimulus output signal from the stimulus output portion 305 (YES in Step S80), the parameter variance determining portion 303 extracts the pulse rate PR immediately before the reception of the stimulus output signal and the pulse rate PR immediately after the reception among the pulse rates PR extracted by and accumulated in the parameter extracting portion 302, and calculates a derivative value ΔPR of the change (Step S91). Herein, the derivative value ΔPR is obtained by dividing a difference between the pulse rate PR immediately before the reception and the pulse rate immediately after the reception by the sampling cycle.

Subsequently, the parameter variance determining portion 303 determines whether the derivative value ΔPR falls within a particular range 4 (Step S92). The particular range 4 is expressed, for example, as, −1.0<ΔPR<+1.0. In a case where the derivative value ΔPR falls within the particular range 4 (YES in Step S92), it proceeds to the processing in Step S83. In a case where the derivative value ΔPR does not fall within the particular range 4 (NO in Step S92), the parameter variance determining portion 303 determines whether the derivative value ΔPR falls within a particular range 5 different from the particular range 4 (Step S93). The particular range 5 is expressed, for example, as, +1.0≦ΔPR<+10.

In a case where the derivative value ΔPR falls within the particular range 5 (YES in Step S93), it proceeds to the processing in Step S85. Meanwhile, in a case where the derivative value ΔPR does not fall within the particular range 5 (NO in Step S93), the parameter variance determining portion 303 determines whether the derivative value ΔPR falls within a particular range 6 different from the particular range 5 (Step S94). The particular range 6 is expressed, for example, as, −10<ΔPR≦−1.0. In a case where the derivative value ΔPR falls within the particular range 6, the parameter variance determining portion 303 infers that a comfortable feeling of the user has deteriorated and proceeds to the processing in Step S87. Meanwhile, in a case where the derivative value ΔPR does not fall within the particular range 6 (NO in Step S94), it proceeds to the processing in Step S88.

As has been described, according to the environment control system of the seventh embodiment, it is possible to achieve the same function and effect as those in the sixth embodiment.

In the seventh embodiment, the parameter variance determining portion 303 calculates a derivative value on the basis of the pulse rate PR immediately before the reception of the stimulus signal outputted from the stimulus output portion 305 and the pulse rate PR immediately after the reception. However, a difference between the pulse rate PR immediately before the reception and the pulse rate PR immediately after the reception may be calculated, so that a comfortable feeling of the user is inferred on the basis of the difference.

Also, in the seventh embodiment, the parameter variance determining portion 303 calculates a derivative value ΔPR from the pulse rate PR immediately before the reception of the stimulus output signal outputted from the stimulus output portion 305 and the pulse rate PR immediately after the reception. However, an average value of plural pulse rates PR extracted within a specific period in the past since the reception of the stimulus output signal, an average value or a derivative value of respective differences may be calculated, so that a derivative value ΔPR or a difference is calculated on the basis of the calculated value and the pulse rate PR immediately after the reception of the stimulus output signal to infer a comfortable feeling of the user on the basis of the result of calculation.

In this embodiment, the parameter variance determining portion 303 infers a comfortable feeling of the user from a variance of the pulse rate PR. However, the rate of waveform components, c/a, described in the sixth embodiment and the pulse rate PR described in this embodiment may be combined, so that a comfortable feeling of the user is inferred on the basis of variances of the both.

In this embodiment, the stimulus output portion 305 outputs the stimulus output signal indicating that it has outputted a stimulus to the parameter variance determining portion 303, and the parameter variance determining portion 303 calculates the derivative value on the basis of the pulse rates PR immediately before and after the reception of the stimulus output signal. However, it may be configured in such a manner that the stimulus output portion 305 does not output the stimulus output signal, and instead, the parameter variance determining portion 303 is provided with a timer portion that measures a time, so that it calculates the derivative value from the pulse rates PR immediately before and after the elapse of a specific time or immediately before and after the elapse of a stimulus giving time included in the content of stimulus.

Alternatively, a rate of change of the pulse rate PR over a specific time may be used as the derivative value. Further, the timer portion that measures a time may be separated from the parameter variance determining portion 303 as an independent component and the timer portion is connected to the parameter variance determining portion 303 to enable mutual communications, so that the timer portion transmits the start of time measurement and an elapse of time to the parameter variance determining portion 303.

Eighth Embodiment

Figure 25:
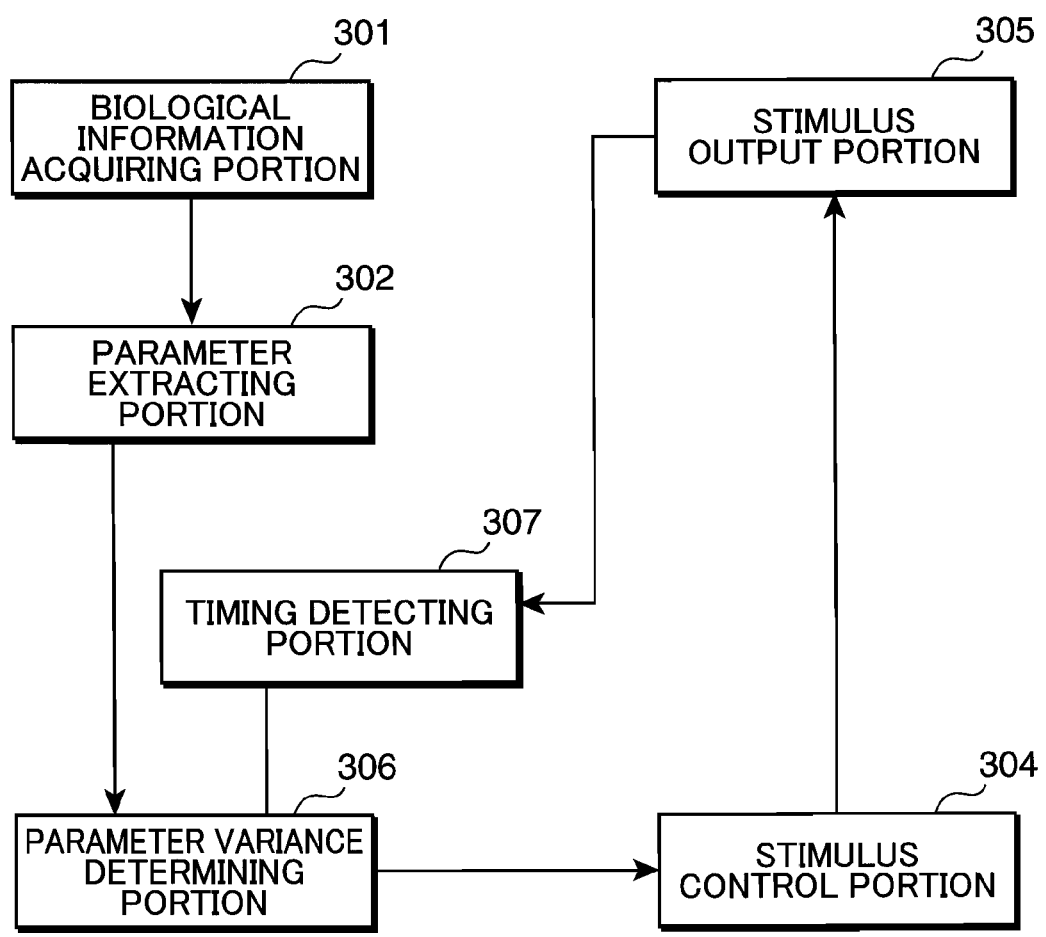
FIG. 25 is a block diagram showing the configuration of an environment control system according to an eighth embodiment of the invention.

FIG. 25 is a block diagram showing the configuration of an environment control system according to an eighth embodiment of the invention. In the eighth embodiment, components same as those in the sixth embodiment are labeled with the same reference numerals and description thereof are omitted. In comparison with the environment control system of the sixth embodiment, the environment control system of the eighth embodiment further includes a timing detecting portion 307 and a parameter variance determining portion 306 functions differently. The timing detection portion 307 also determines and outputs the timing to output a stimulus output instruction.

The timing detecting portion 307 is triggered by the reception of the stimulus output signal from the stimulus output portion 305 and shifts to an active mode. In a case where it is inferred that a comfortable feeling of the user has enhanced by the parameter variance determining portion 306, the timing detection portion 307 sets a comfort flag (initial value is 0), which is a flag indicating enhancement of a comfortable feeling, to 1. Also, the timing detecting portion 307 sets the comfort flag to 0 each time it receives the stimulus output signal.

The parameter variance determining portion 306 includes a counter that continuously counts the number of times it has made determinations that a feeling of the user has not enhanced in a case where the comfort flag set by the timing detecting portion 307 exhibits 1. Hereinafter, the count value of the counter is referred to as the count0.

Figure 26:
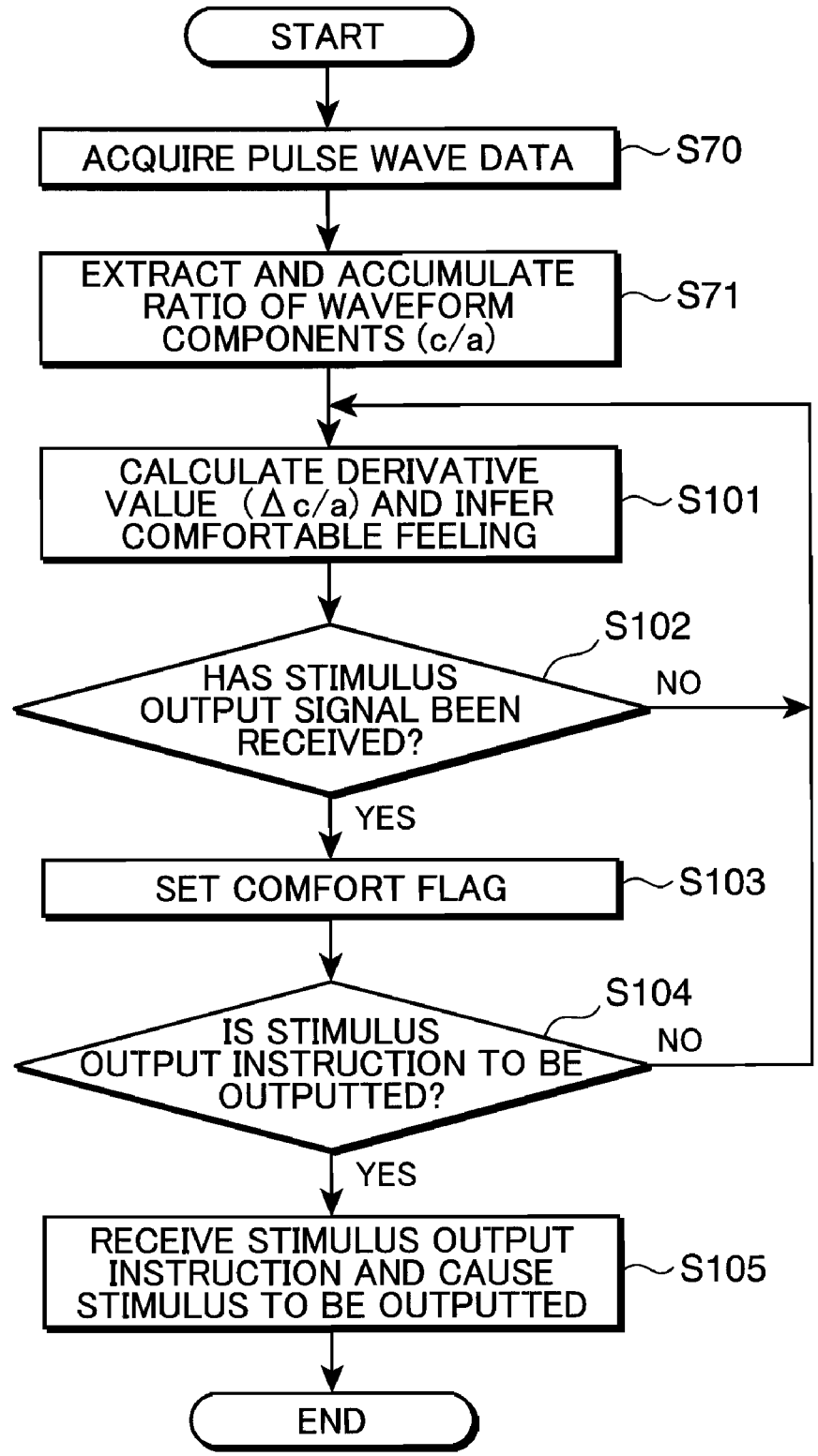
FIG. 26 is a flowchart detailing the processing by the environment control system according to the eighth embodiment of the invention.

FIG. 26 is a flowchart detailing the processing by the environment control system according to the eighth embodiment of the invention. For the steps in which the same processing as that in the sixth embodiment is performed, the same step numbers are used and descriptions thereof are omitted.

Initially, the biological information acquiring portion 301 acquires time-series data of the pulse wave and accumulates it therein (Step S70). Subsequently, the parameter extracting portion 302 extracts the value of the ratio of waveform components, c/a, at regular time intervals from the time-series data of the pulse wave acquired by the biological information acquiring portion 301 and accumulates it therein (Step S71). Subsequently, the parameter variance determining portion 306 finds a variance of the ratio of waveform components on the basis of the ratio of waveform components, c/a, extracted by the parameter extracting portion 302 at a current point in time and the ratio of waveform components, c/a, extracted by the parameter extracting portion 302 immediately before the reception of a stimulus output signal, and infers a comfortable feeling of the user on the basis of the variance (Step S101).

Subsequently, the timing detecting portion 307 determines whether it has received a stimulus output signal from the stimulus output portion 305 (Step S102). Upon receipt of the stimulus output signal from the stimulus output portion 305 (YES in Step S102), the timing detecting portion 307 shifts to the active mode and sets the comfort flag to 0 (Step S103). In a case where it has not received the stimulus output signal from the stimulus output portion 305 (NO in Step S102), it returns to the processing in Step S101.

Meanwhile, in a case where it is inferred that a comfortable feeling of the user has enhanced in Step S101, upon receipt of the stimulus output signal from the stimulus output portion 305 (YES in Step S102), the timing detecting portion 307 sets the comfort flag to 1 (Step S103). Subsequently, the parameter variance determining portion 306 determines whether a stimulus output instruction is to be outputted to the stimulus control portion 304 (Step S104). The parameter variance determining portion 306 determines whether a stimulus is to be outputted or not and the content of stimulus on the basis of the result of inference of a comfortable feeling of the user, the set value of the comfort flag in the timing detecting portion 307, and the value of the count0. In a case where it determines to output a stimulus, it outputs a stimulus output instruction to the stimulus control portion 304. When the stimulus output instruction is outputted to the stimulus control portion 304 (YES in Step S104), the stimulus control portion 304 controls the stimulus output portion 305 to output a stimulus according to the stimulus output instruction outputted from the parameter variance determining portion 306 (Step S105). Meanwhile, in a case where it determines not to output a stimulus output instruction to the stimulus control portion 304 (NO in Step S104), it returns to the processing in Step S101.

A method of inferring a comfortable feeling of the user by the parameter variable determining portion 306 and a method of determining the timing to output a stimulus and the content of stimulus by the timing detecting portion 307 will now be described.

Figure 27:
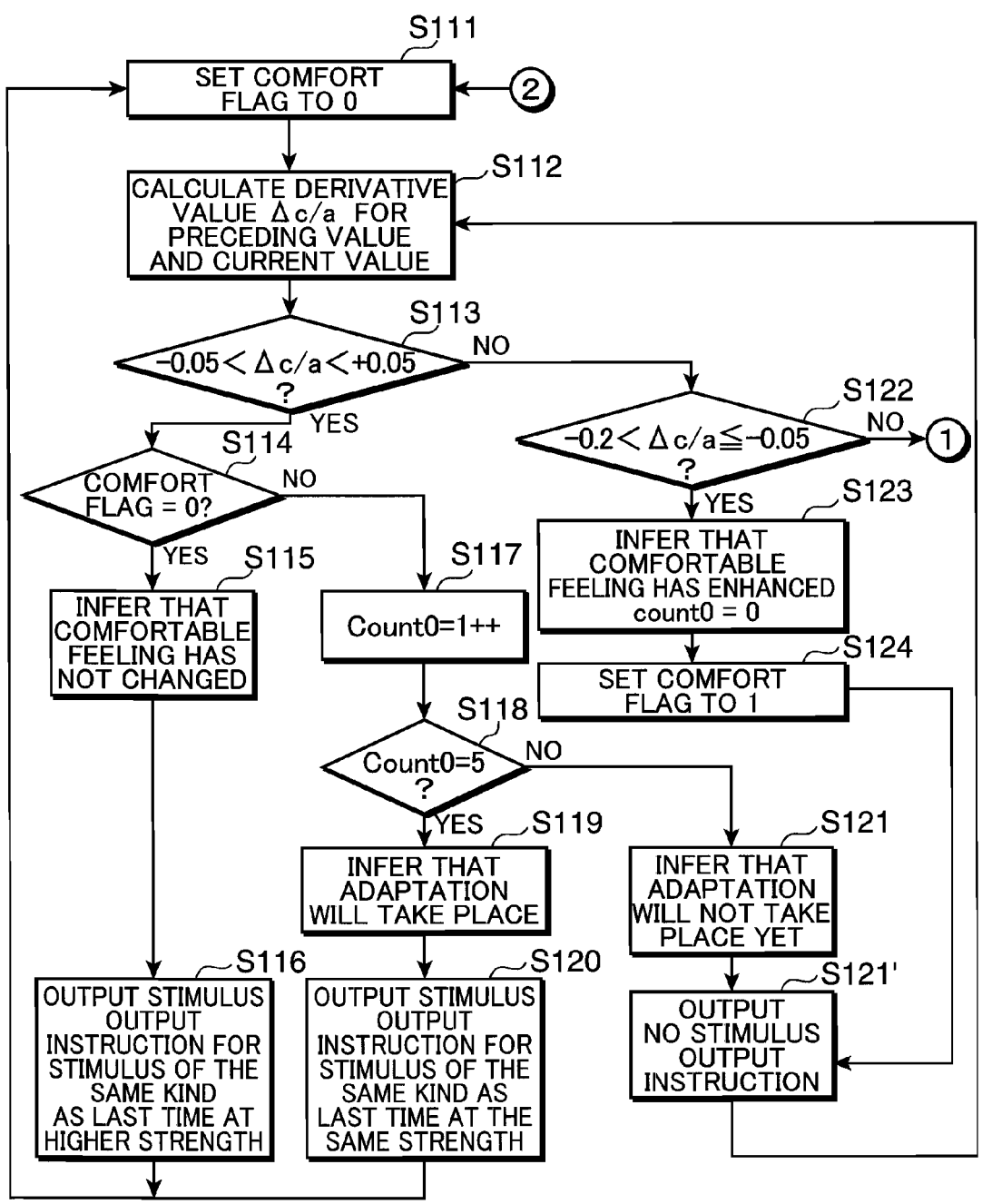
FIG. 27 is a first flowchart detailing the processing by a parameter variance determining portion according to the eighth embodiment of the invention.
Figure 28:
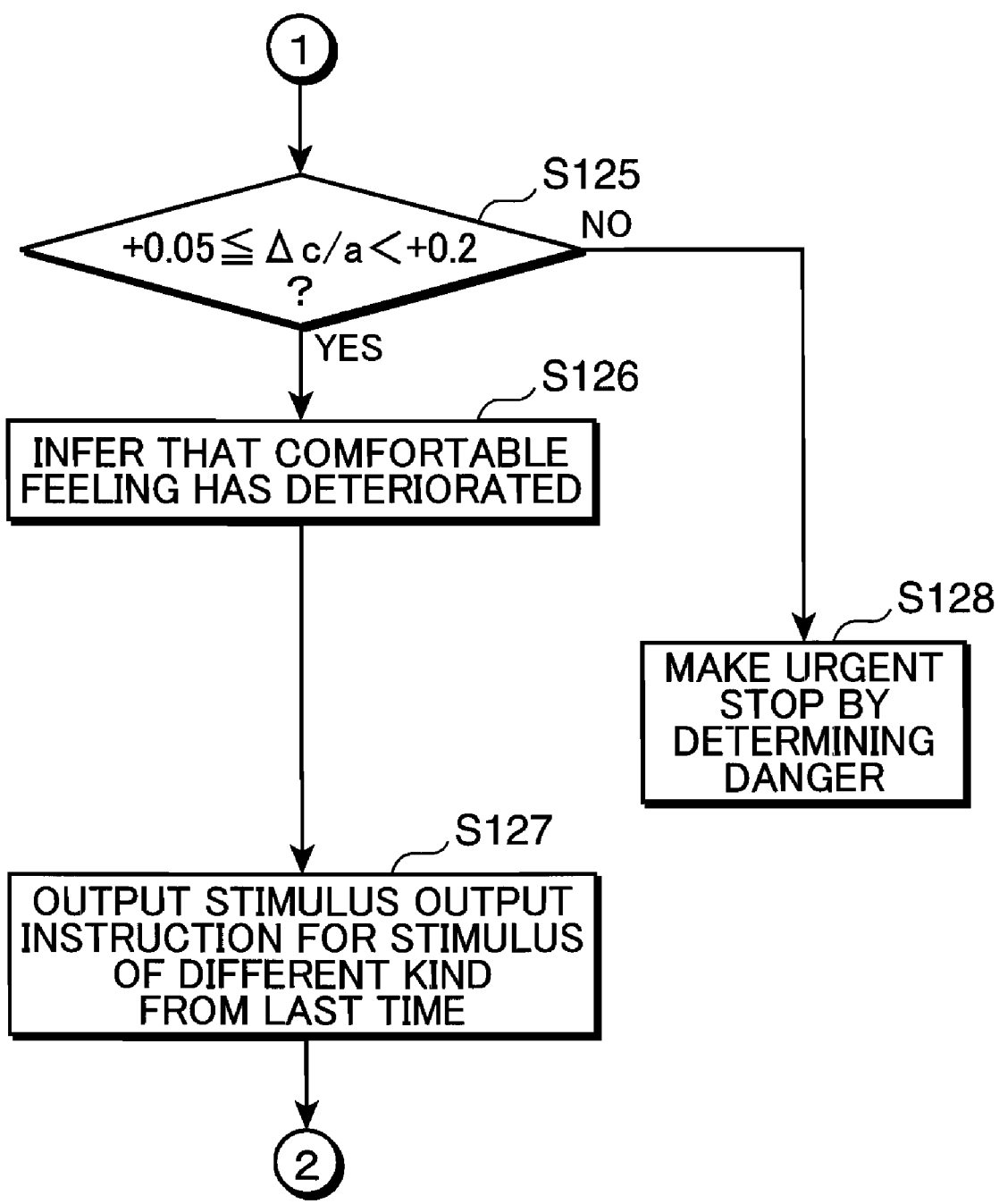
FIG. 28 is a second flowchart detailing the processing by the parameter variance determining portion according to the eighth embodiment of the invention.

FIG. 27 and FIG. 28 are flowcharts detailing the processing by the parameter variance determining portion 306 according to the eighth embodiment of the invention. Initially, the timing detecting portion 307 sets the comfort flag to 0 upon receipt of the stimulus output signal from the stimulus output portion 305 (Step S111). Subsequently, the parameter variance determining portion 306 calculates a derivative value $\Delta c/a$ of the ratio of waveform components on the basis of the ratio of waveform components, c/a, extracted by the parameter extracting portion 302 at a current point in time and the ratio of waveform components, c/a, extracted by the parameter extracting portion 302 immediately before the reception of the stimulus output signal (Step S112).

Subsequently, as in the sixth embodiment, the parameter variance determining portion 306 determines whether the derivative value $\Delta c/a$ falls within a particular range 1 (Step S113). The particular range 1 is expressed, for example, as, $-0.05 < \Delta c/a < +0.05$. In a case where the derivative value $\Delta c/a$ falls within the particular range 1 (YES in Step S113), the parameter variance determining portion 306 determines whether the comfort flag exhibits 0 by referring to the comfort flag set by the timing detecting portion 307 (Step S114). In a case where the comfort flag exhibits 0 (YES in Step S114), the parameter variance determining portion 306 infers that a comfortable feeling of the user has not changed (Step S115). Subsequently, the parameter variance determining portion 306 determines that a stimulus such that enhances a comfortable feeling is necessary, and outputs a stimulus output instruction to the stimulus control portion 304 to heighten the strength of stimulus for a stimulus of the same kind as the stimulus given last time or to extend a stimulus giving time (Step S116). The user thus becomes able to have a comfortable feeling. The flow returns to the processing in Step S111 after the stimulus output instruction is outputted to the stimulus control portion 304.

Meanwhile, in a case where the comfort flag exhibits 1 (NO in Step S114), the parameter variance determining portion 306 increments the value of the count0 (adds one) (Step S117), and determines whether the count0 has reached a specific value, for example, '5' (Step S118). In a case where the count0 has reached '5' (YES in Step S118), the parameter variance determining portion 306 infers that in vivo adaptation will take place in the user (Step S119). Subsequently, the parameter variance determining portion 306 outputs the stimulus output instruction it outputted immediately before it stopped outputting the stimulus output instruction in Processing Step S121' described below again to the stimulus control portion 304 (Step S120). The flow returns to the processing in Step S111 after the stimulus output instruction is outputted to the stimulus control portion 304.

Meanwhile, in a case where the count0 has not reached '5' (NO in Step S118), the parameter variance determining portion 306 infers that in vivo adaptation will not take place yet in the user (Step S121). Subsequently, the parameter variance determining portion 306 determines not to output a stimulus output instruction (Step S121'), and returns to the processing in Step S112 to perform the determination processing for the following derivative value $\Delta c/a$.

Meanwhile, in a case where the derivative value $\Delta c/a$ does not fall within the particular range 1 (NO in Step S113), as in the sixth embodiment, the parameter variance determining portion 306 determines whether the derivative value $\Delta c/a$ falls within a particular range 2 different from the particular range 1 (Step S122). The particular range 2 is defined as, for example, $-0.2 < \Delta c/a \leq -0.05$. In a case where the derivative value $\Delta c/a$ falls within the particular range 2 (YES in Step S122), the parameter variance determining portion 306 infers that a comfortable feeling of the user has enhanced and resets the count0 (Step S123). Subsequently, the timing detecting portion 307 sets the comfort flag to 1 (Step S124). Subsequently, the parameter variance determining portion 306 determines not to output a stimulus output instruction (Step S121), and returns to the processing in Step S112 to perform the determination processing for the following derivative value $\Delta c/a$.

Meanwhile, in a case where the derivative value $\Delta c/a$ does not fall within the particular range 2 (NO in Step S122), as with the sixth embodiment, the parameter variance determining portion 306 determines whether the derivative value $\Delta c/a$ falls within a particular range 3 different from the particular range 2 (Step S125). The particular range 3 is defined, for example, as $+0.05 \leq \Delta c/a < +0.2$. In a case where the derivative value $\Delta c/a$ falls within the particular range 3 (YES in Step S125), the parameter variance determining portion 306 infers that a comfortable feeling by the user has deteriorated (Step S126).

Subsequently, the parameter variance determining portion 306 determines that a stimulus such that enhances a comfortable feeling is necessary, and outputs a stimulus output instruction to the stimulus control portion 304 for a stimulus of a different kind from the stimulus given last time (Step S127). Meanwhile, in a case where the derivative value $\Delta c/a$ does not fall within the particular range 3 (NO in Step S125), the parameter variance determining portion 306 infers that the user is in a state of unexpected danger and stops the system urgently (Step S128).

As has been described, according to the environment control system of the eighth embodiment, it is possible to achieve the function and effect same as those of the sixth embodiment. Further, in this embodiment, even in a case where the derivative value $\Delta c/a$ falls within the particular range 1, no stimulus is outputted from the stimulus output portion 305 when the comfort flag is set to 1 until this setting state has continued for a certain period, that is, until the count0 reaches '5' and adaptation to the stimulus takes place. This configuration makes it possible to achieve the running using the afterglow of a comfortable feeling of the user, which in turn makes it possible to achieve efficient processing. It is thus possible to provide a system with a higher degree of energy saving effect.

Figure 29:
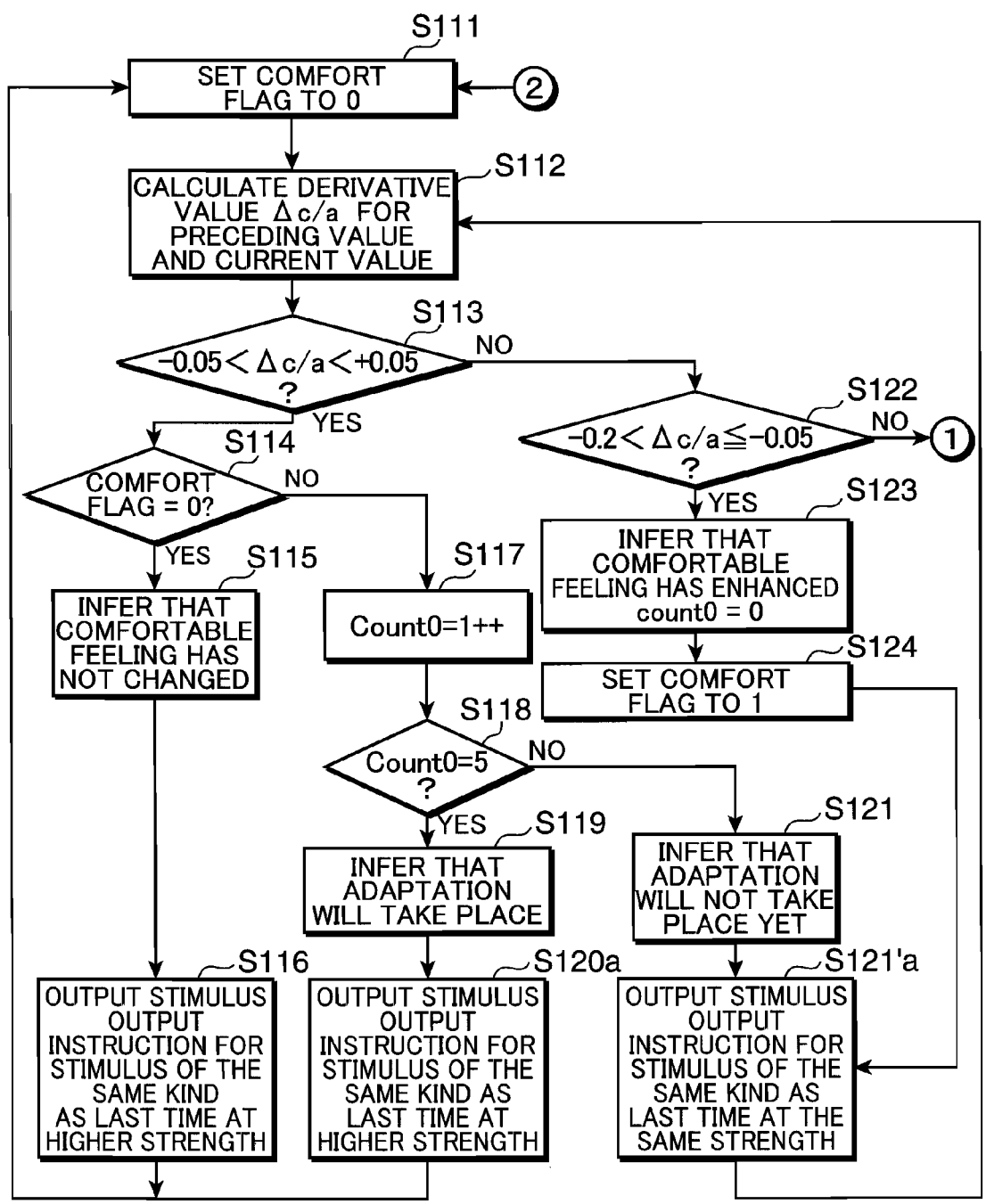
FIG. 29 is a first flowchart detailing the processing by the parameter variance determining portion when the content of stimulus specifies a steady stimulus.
Figure 30:
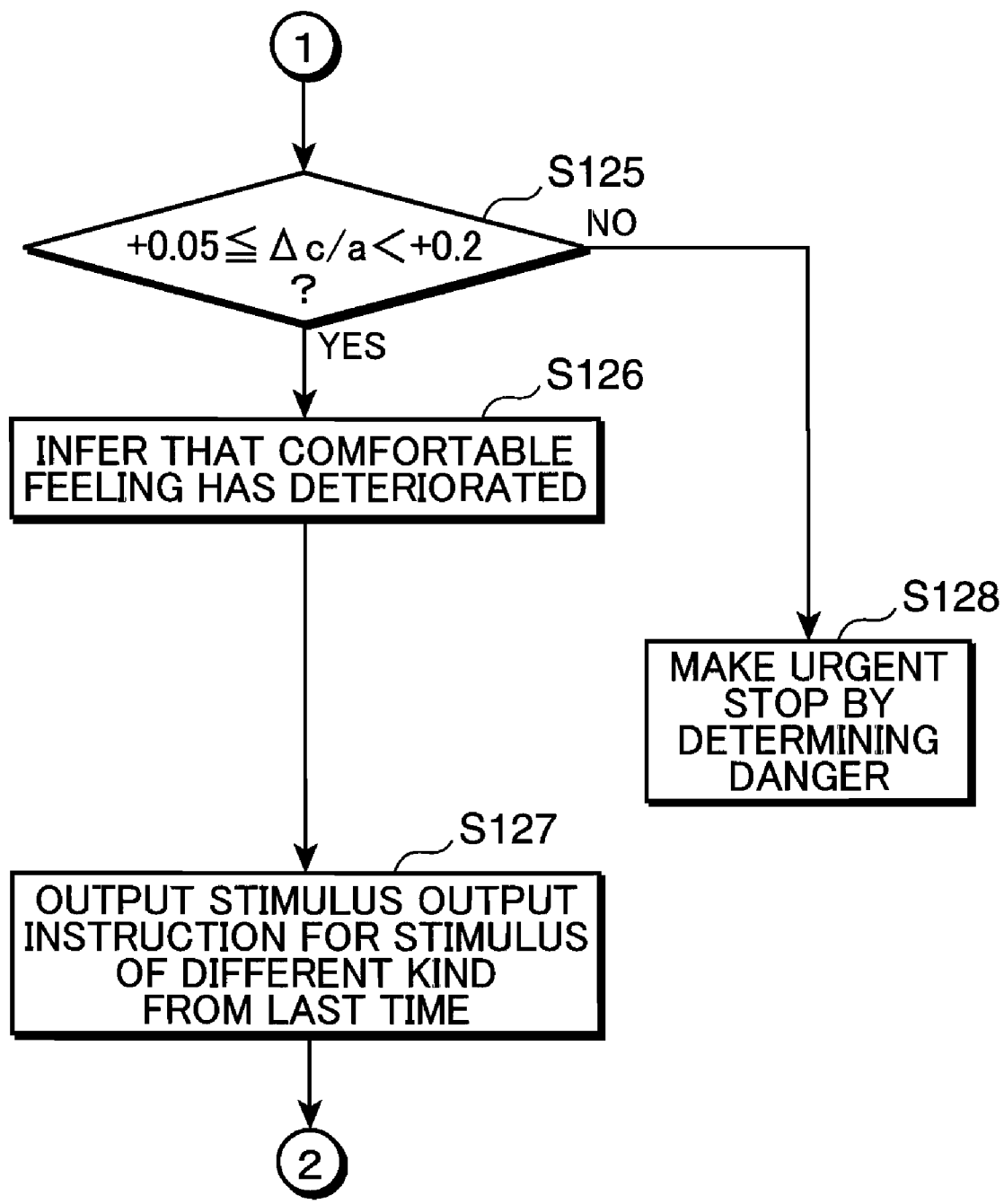
FIG. 30 is a second flowchart detailing the processing by the parameter variance determining portion when the content of stimulus specifies a steady stimulus.

This embodiment was described with reference to FIG. 27 and FIG. 28 on the assumption that the content of stimulus determined by the parameter variance determining portion 303 is a short-term or instantaneous stimulus (for example, an air-flow stimulus, such as cool air or warm air, and a material stimulus, such as oxygen and minus ions). The processing by the parameter variance determining portion 306 in a case where the content of stimulus specifies a steady stimulus (for example, a physical stimulus, such as massage, a warm or cool thermal stimulus, such as cooling or heating by an air conditioner) will now be described. FIG. 29 and FIG. 30 are flowcharts detailing the processing by the parameter variance determining portion 306 in a case where the content of stimulus specifies a steady stimulus.

In FIG. 29 and FIG. 30, processing steps same as those in FIG. 27 and FIG. 28 are labeled with the same reference numerals and description thereof are omitted. In Step S120 shown in FIG. 27, the parameter variance determining portion 303 outputs the stimulus output instruction it outputted immediately before it stopped outputting the stimulus output instruction in Step S121' and returns to the processing in Step S111. However, in Step S120a shown in FIG. 29, it outputs a stimulus output instruction to further enhance a comfortable feeling than the stimulus specified by the content of stimulus outputted in Step S121'a described below, for example, a stimulus output instruction to intensify the stimulus outputted in Step S121'a, and returns to the processing in Step S111.

Also, in Step S121' shown in FIG. 27, the parameter variance determining portion 303 outputs no stimulus output instruction. However, in Step S121'a shown in FIG. 29, it outputs again the stimulus output instruction it outputted just before, and returns to the processing in Step S112. This configuration makes the invention adaptable to a system provided with a device that outputs a steady stimulus, which can broaden a technical applicable range.

In this embodiment, the parameter variance determining portion 303 infers a comfortable feeling of the user from a variance of the rate of waveform components, c/a. However, the pulse rate PR described in the seventh embodiment and the ratio of waveform components, c/a, described in this embodiment may be combined, so that a comfortable feeling of the user is inferred on the basis of the variances of the both.

In this embodiment, the content of stimulus determined by the parameter variance determining portion 303 includes the kinds of stimulus, the strength of stimulus, a stimulus giving time, and so forth. The kinds of stimulus include, in the case for a short-term (momentary) stimulus, an air-flow stimulus, such as cool air and warm air, a material stimulus, such as oxygen and minus ions, a visual stimulus, such as pulse tones, and a visual stimulus, such as light; and in the case of a steady stimulus, a warm or cool thermal stimulus, such as cooling and heating, a physical stimulus, such as massage, an audio stimulus, such as music and ultrasonic waves, and a visual stimulus, such as illumination and video. For the strength of stimulus, assume that the control to heighten or weaken the strength of stimulus is executed, including, for example, for an air-flow stimulus, such as cool air and warm air, the control to increase an amount of air flow and the control to reduce an amount of air flow, for a material stimulus, such as oxygen and minus ions, the control to increase an amount of material and the control to decrease an amount of material, for a warm or cool thermal stimulus, such as cooling and heating, the control to raise the set temperature and the control to lower the set temperature, and for a physical stimulus such as massage, the control to heighten the rubbing strength and the control to weaken the rubbing strength.

In this embodiment, the stimulus output portion 305 outputs the stimulus output signal indicating that it has outputted a stimulus to the timing detecting portion 307, and the timing detecting portion 307 is triggered by the reception of the stimulus output signal from the stimulus output portion 305 and shifts to the active mode. The invention, however, is not particularly limited to this configuration. It may be configured in such a manner that the stimulus output portion 305 does not output the stimulus output signal, and instead, the parameter variance determining portion 303 is provided with a timer portion that measures a time, so that the timing detecting portion 307 is shifted to the active mode as the parameter variance determining portion 303 outputs a signal indicating an elapse of time to the timing detecting portion 307 at the elapse of a specific time or at the elapse of a stimulus giving time included in the content of stimulus.

Alternatively, the timer portion that measures a time may be separated from the parameter variance determining portion 303 as an independent component and the timer portion is connected to the parameter variance determining portion 303 to enable mutual communications, so that the timer portion transmits the start of time measurement and an elapse of time to the parameter variance determining portion 303.

Ninth Embodiment

An environment control system according to a ninth embodiment of the invention will now be described. Because the environment control system of the ninth embodiment is of the same configuration as the environment control system of the sixth embodiment, the configuration thereof will be described using FIG. 21. Also, descriptions of components same as those in the sixth embodiment are omitted and only a difference will be described in the ninth embodiment.

The parameter extracting portion 302 extracts, as a parameter to evaluate the pulse wave, a ratio of waveform components of the accelerated pulse wave obtained by second-order differentiation of the pulse wave waveform obtained from the pulse wave data, and accumulates it in an unillustrated memory. The accelerated pulse wave waveform is the same as that in the sixth embodiment, and c/a is extracted as the ratio of waveform components, where the distance a from the base line to the peak A of the accelerated pulse wave waveform is given as the denominator and the distance c from the base line to the peak C is given as the numerator.

The parameter variance determining portion 303 calculates a variance of the ratio of waveform components extracted by the parameter extracting portion 302 to infer a thermal sensation of the user from the result of calculation. It then determines the content of stimulus from the result of inference, and outputs a stimulus output instruction to the stimulus control portion 304 so that a stimulus according to the determined content of stimulus is outputted from the stimulus output portion 305.

In this embodiment, the parameter variance determining portion 303 calculates a derivative value of the ratio of waveform components by dividing a difference between the ratio of waveform components extracted immediately after the reception of a stimulus output signal that the stimulus output portion 305 outputs when it outputs a stimulus and the ratio of waveform components extracted immediately before the reception of the stimulus output signal by the sampling cycle at which the fingertip pulse wave is sampled, and infers a thermal sensation of the user using this derivative value.

Figure 31:
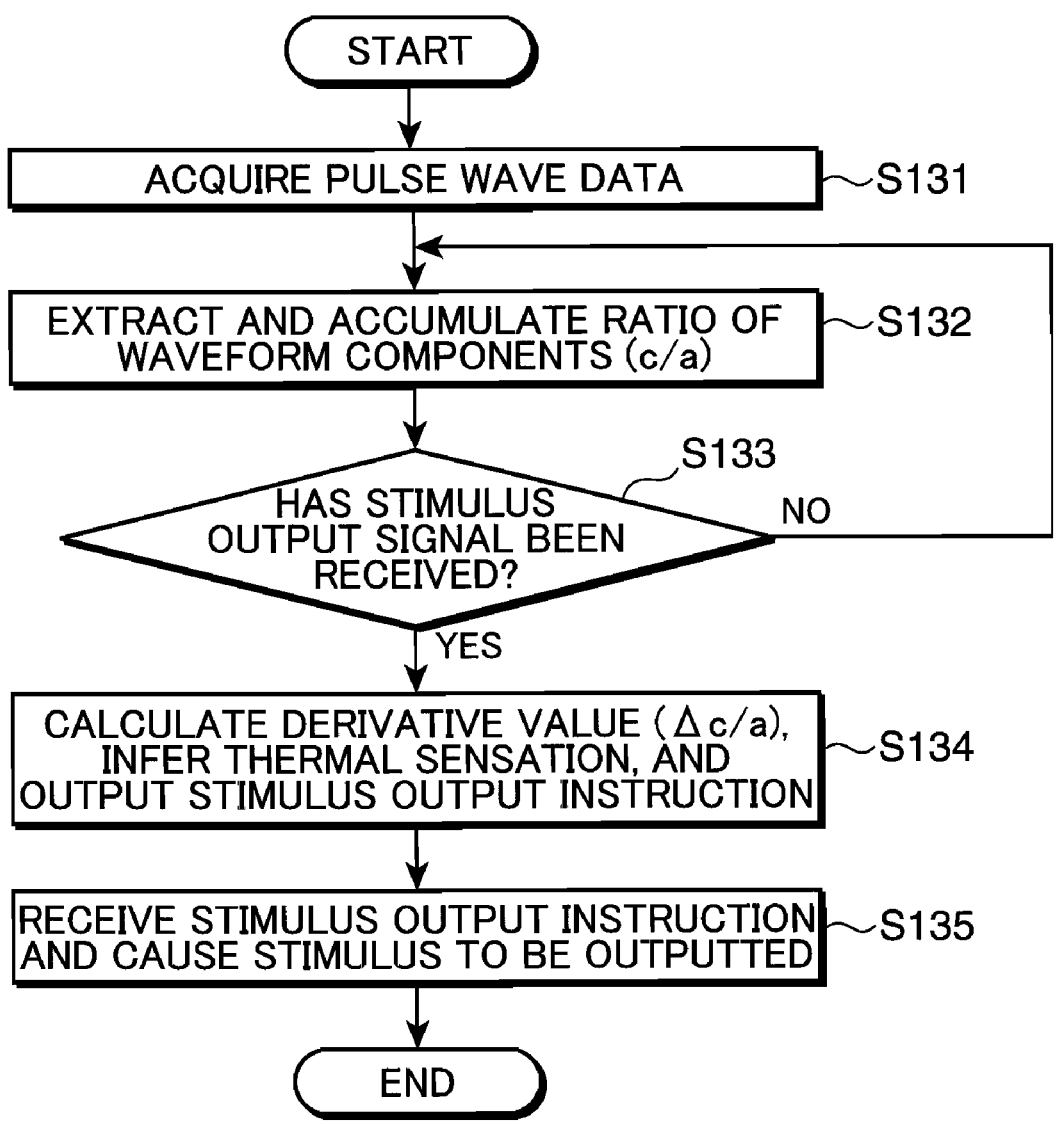
FIG. 31 is a flowchart detailing the processing by an environment control system according to a ninth embodiment of the invention.

FIG. 31 is a flowchart detailing the processing by the environment control system according to the ninth embodiment of the invention. Initially, the biological information acquiring portion 301 acquires time-series data of the pulse wave and accumulates it therein (Step S131). Subsequently, the parameter extracting portion 302 extracts the ratio of waveform components, c/a, at regular time intervals on the basis of the time-series data of the pulse wave acquired by the biological information acquiring portion 301 and accumulates it therein (Step S132).

Subsequently, the parameter variance determining portion 303 determines whether it has received a stimulus output signal from the stimulus output portion 305 (Step S133). In a case where it has not received the stimulus output signal from the stimulus output portion 305 (NO in Step S133), it returns to the processing to Step S132.

Upon receipt of the stimulus output signal from the stimulus output portion 305 (YES in Step S133), the parameter variance determining portion 303 finds a derivative value $\Delta c/a$ of the ratio of waveform components on the basis of the ratio of waveform components, c/a, extracted by the parameter extracting portion 302 immediately after the reception of the stimulus output signal and the ratio of waveform components, c/a, extracted by the parameter extracting portion 302 immediately before the reception of the stimulus output signal, and infers a thermal sensation of the user on the basis of the derivative value. It then determines the content of stimulus from the result of inference, and outputs a stimulus output instruction to the stimulus control portion 304 so that a stimulus according to the determined content of stimulus is outputted from the stimulus output portion 305 (Step S134). Subsequently, the stimulus control portion 304 controls the stimulus output portion 305 to output a stimulus according to the stimulus output instruction outputted from the parameter variance determining portion 303 (Step S135).

Figure 32:
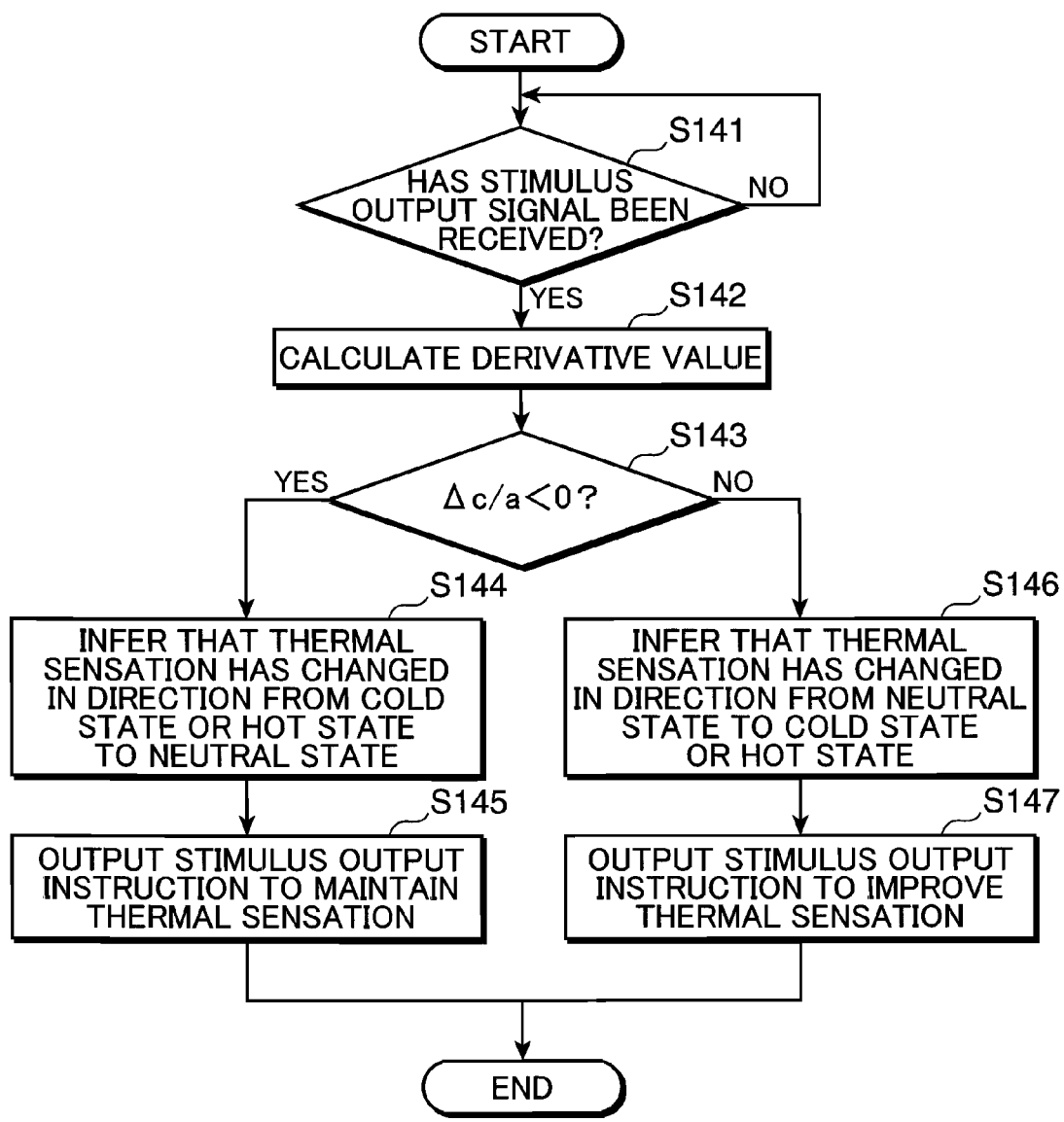
FIG. 32 is a flowchart detailing the processing by a parameter variance determining portion according to the ninth embodiment of the invention.

The processing to infer a thermal sensation of the user and the processing to determine the content of stimulus by the parameter variance determining portion 303 will now be described. FIG. 32 is a flowchart detailing the processing by the parameter variance determining portion 303 in the ninth embodiment of the invention.

Initially, the parameter variance determining portion 303 determines whether it has received a stimulus output signal from the stimulus output portion 305 (Step S141). In a case where it has not received the stimulus output signal from the stimulus output portion 305 (NO in Step S141), the processing in Step S141 is repetitively performed at specific timing until the stimulus output signal is received. Upon receipt of the stimulus output signal from the stimulus output portion 305 (YES in Step S141), the parameter variance determining portion 303 calculates a derivative value $\Delta c/a$ on the basis of the ratio of waveform components, c/a, immediately before the reception of the stimulus output signal and the ratio of waveform components, c/a, immediately after the reception among the ratios of waveform components, c/a, extracted by the parameter extracting portion 302 (Step S142).

Figure 33:
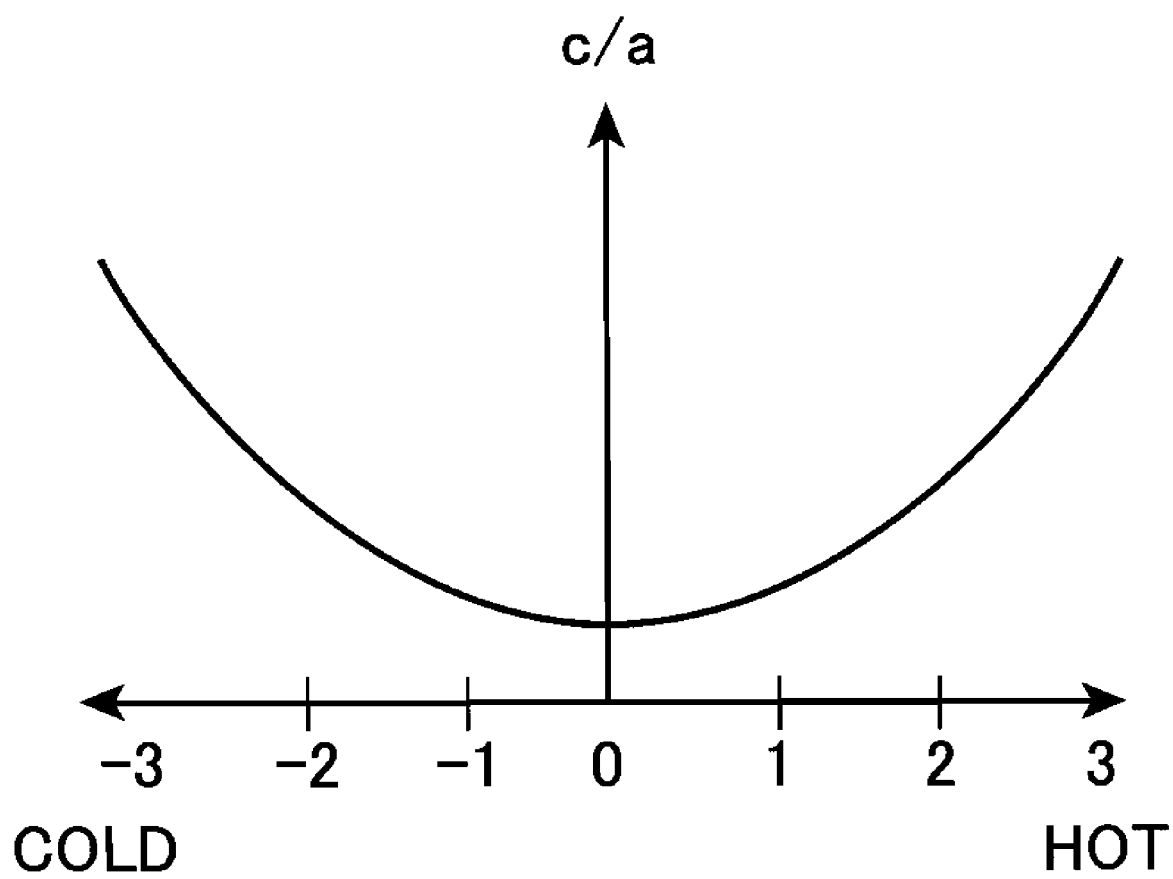
FIG. 33 is a graph indicating a correlation between a ratio of waveform components and a thermal sensation of the user discovered by the inventors from the test conducted on subjects.

The inventors discovered the presence of a high correlation between a variance of the ratio of waveform components and a variance of a thermal sensation of the user. FIG. 33 is a graph indicating a correlation between the ratio of waveform components and a thermal sensation of the user discovered by the inventors from the test conducted on subjects.

In FIG. 33, the abscissa is used for a thermal sensation of the user, and the ordinate is used for the ratio of waveform components. As is shown in this graph, a thermal sensation of the user shapes a downward convex quadratic curve, and the ratio of waveform components shows the minimum value in the vicinity of a point at which a thermal sensation indicates 0. In addition, the ratio of waveform components increases with an increase of a thermal sensation of the user, that is, as the user feels hotter.

The ratio of waveform components also increases with a decrease of a thermal sensation of the user, that is, as the user feels colder. It is thus possible to infer a thermal sensation of the user when a variance of the ratio of waveform components as is indicated by the graph is known. The environment control system therefore infers a thermal sensation of the user on the basis of the characteristic of the ratio of waveform components as indicated by the graph. It should be noted that when a thermal sensation of the user indicates 0, the user feels neither hot nor cold.

In Step S143 shown in FIG. 32, the parameter variance determining portion 303 determines whether the derivative value $\Delta c/a$ of the ratio of waveform components is negative. In a case where the derivative value $\Delta c/a$ is negative (YES in Step S143), the parameter variance determining portion 303 infers that a thermal sensation of the user has changed in a direction from a cold state or a hot state to the neutral state where it is neither hot nor cold, that is, a thermal sensation of the user approximates to 0 and a thermal sensation has improved (Step S144). Subsequently, the parameter variance determining portion 303 outputs a stimulus output instruction to maintain a thermal sensation (Step S145). Meanwhile, in a case where the derivative value $\Delta c/a$ is not negative (NO in Step S143), the parameter variance determining portion 303 infers that a thermal sensation of the user has changed in a direction from the neutral state where it is neither hot nor cold to a cold state or a hot state, that is, a thermal sensation has deteriorated (Step S146). Subsequently, the parameter variance determining portion 303 outputs a stimulus output instruction to improve a thermal sensation (Step S147).

As has been described, according to the environment control system of the ninth embodiment, because a thermal sensation of the user is inferred by employing the principle discovered by the inventors that there is a correlation between a variance of the parameter of the pulse wave and a variance of a thermal sensation of the user, it is possible to infer a thermal sensation of the user at a higher degree of accuracy. Hence, because a thermal sensation of the user can be inferred from the pulse wave, it is possible to infer a thermal sensation of the user without making the user feel uncomfortable. In addition, because a thermal sensation of the user is inferred using the pulse wave, there is no need to configure a system using specialized and expensive equipment as in a case where a thermal sensation of the user is inferred using the brain wave. It is thus possible to provide a system that enables the user to actually have a comfortable feeling in a reliable manner in the residential environment.

In this embodiment, it may be configured in such a manner that the parameter variance determining portion 303 determines whether the derivative value $\Delta c/a$ of the ratio of waveform components falls within a pre-determined particular range (for example, from −0.01 to 0.01) immediately before it determines whether the derivative value $\Delta c/a$ of the ratio waveform components is negative in Step 143, so that in a case where the derivative value $\Delta c/a$ falls within the particular range, it determines that a thermal sensation of the user has hardly changed and outputs a stimulus output instruction to continue to output or stop outputting a stimulus of the current content.

In this embodiment, the content of stimulus determined by the parameter variance determining portion 303 includes a warm or cool thermal stimulus, such as cooling and heating, an air-flow stimulus, such as cool air and warm air, the strength of stimulus, a stimulus giving time, and so forth.

In this embodiment, the parameter variance determining portion 303 calculates a derivative value $\Delta c/a$ on the basis of the ratio of waveform components, c/a, immediately after the output of a stimulus from the stimulus output portion 305 and the ratio of waveform components, c/a, immediately before the output, and infers a thermal sensation of the user using this derivative value $\Delta c/a$. The invention, however, is not limited to this configuration, and a difference between the ratio of waveform components, c/a, immediately before the output and the ratio of waveform components, c/a, immediately after the output may be calculated, so that a thermal sensation of the user is inferred on the basis of the difference.

Alternatively, a derivative value $\Delta c/a$ or a difference of the ratios of waveform components may be calculated on the basis of the average value of plural ratios of waveform components, c/a, extracted over a specific period in the past since the reception of the stimulus output signal and the ratio of waveform components immediately after the reception of the stimulus output signal, so that a thermal sensation of the user is inferred on the basis of the result of calculation. Further, a derivative value Δc/a or a difference of the ratios of waveform components may be calculated on the basis of the average value of differences between the ratios of waveform components, one ahead of the other in time series, among plural ratios of waveform components extracted over a specific period in the past since the reception of the stimulus output signal and the ratio of waveform components immediately after the reception of the stimulus output signal, so that a thermal sensation of the user is inferred using the result of calculation.

Also, in this embodiment, the stimulus output portion 305 outputs the stimulus output signal indicating that it has outputted a stimulus to the parameter variance determining portion 303, and the parameter variance determining portion 303 calculates the derivative value on the basis of the ratios of waveform components immediately before and after the reception of the stimulus output signal. The invention, however, is not particularly limited to this configuration, and it may be configured in such a manner that the stimulus output portion 305 does not output the stimulus output signal, and instead, the parameter variance determining portion 303 is provided with a timer portion that measures a time, so that it calculates the derivative value on the basis of the ratios of waveform components immediately before and after the elapse of a specific time or immediately before and after the elapse of a stimulus giving time included in the content of stimulus.

Alternatively, a rate of change of the ratio of waveform components over a specific time may be used as the derivative value. Further, the timer portion that measures a time may be separated from the parameter variance determining portion 303 as an independent component and the timer portion is connected to the parameter variance determining portion 303 to enable mutual communications, so that the timer portion transmits the start of time measurement and an elapse of time to the parameter variance determining portion 303. Also, in this embodiment, the result of inference of a thermal sensation of the user may be presented to the user by displaying the result on a display portion, such as a monitor.

Tenth Embodiment

An environment control system according to a tenth embodiment will now be described. Because the environment control system of the tenth embodiment is of the same configuration as the environment control system of the sixth embodiment, the configuration thereof will be described using FIG. 21. Also, descriptions of components same as those in the sixth embodiment are omitted and only a difference will be described in the tenth embodiment.

The parameter extracting portion 302 extracts, as a parameter to evaluate the pulse wave, the ratio of waveform components of the accelerated pulse wave obtained by second-order differentiation of the pulse wave waveform obtained from the pulse wave data and the maximum wave height value of the accelerated pulse wave, and accumulates them therein. The accelerated pulse wave waveform is the same as that in the sixth embodiment and shapes the waveform as shown in FIG. 60. In this embodiment, too, given the distance a from the base line to the peak A of the accelerated pulse wave waveform as the denominator and the distance c from the base line to the peak C as the numerator, c/a is extracted as the ratio of waveform components.

The parameter extracting portion 302 extracts the distance a from the base line to the peak A of the accelerated pulse wave waveform as the maximum wave height value of the accelerated pulse wave. The parameter variance determining portion 303 calculates a variance of the ratio of waveform components and a variance of the maximum wave height value of the accelerated pulse wave extracted by the parameter extracting portion 302, and infers a thermal sensation of the user from the result of calculation. It then determines the content of stimulus from the result of inference and outputs a stimulus output instruction to the stimulus control portion 304 so that a stimulus according to the determined content of stimulus is outputted from the stimulus output portion 305.

In this embodiment, the parameter variance determining portion 303 infers a thermal sensation of the user on the basis of a derivative value of the ratio of waveform components and a derivative value of the maximum wave height value of the accelerated pulse wave, which are calculated by dividing differences between the ratio of waveform components and the maximum wave height value of the accelerated pulse wave extracted immediately after the reception of a stimulus output signal that the stimulus output portion 305 outputs when it outputs a stimulus and the ratio of waveform components and the maximum wave height value of the accelerated pulse wave extracted immediately before the reception of the stimulus output signal, respectively, by a specific sampling cycle at which the fingertip pulse wave is sampled.

Figure 34:
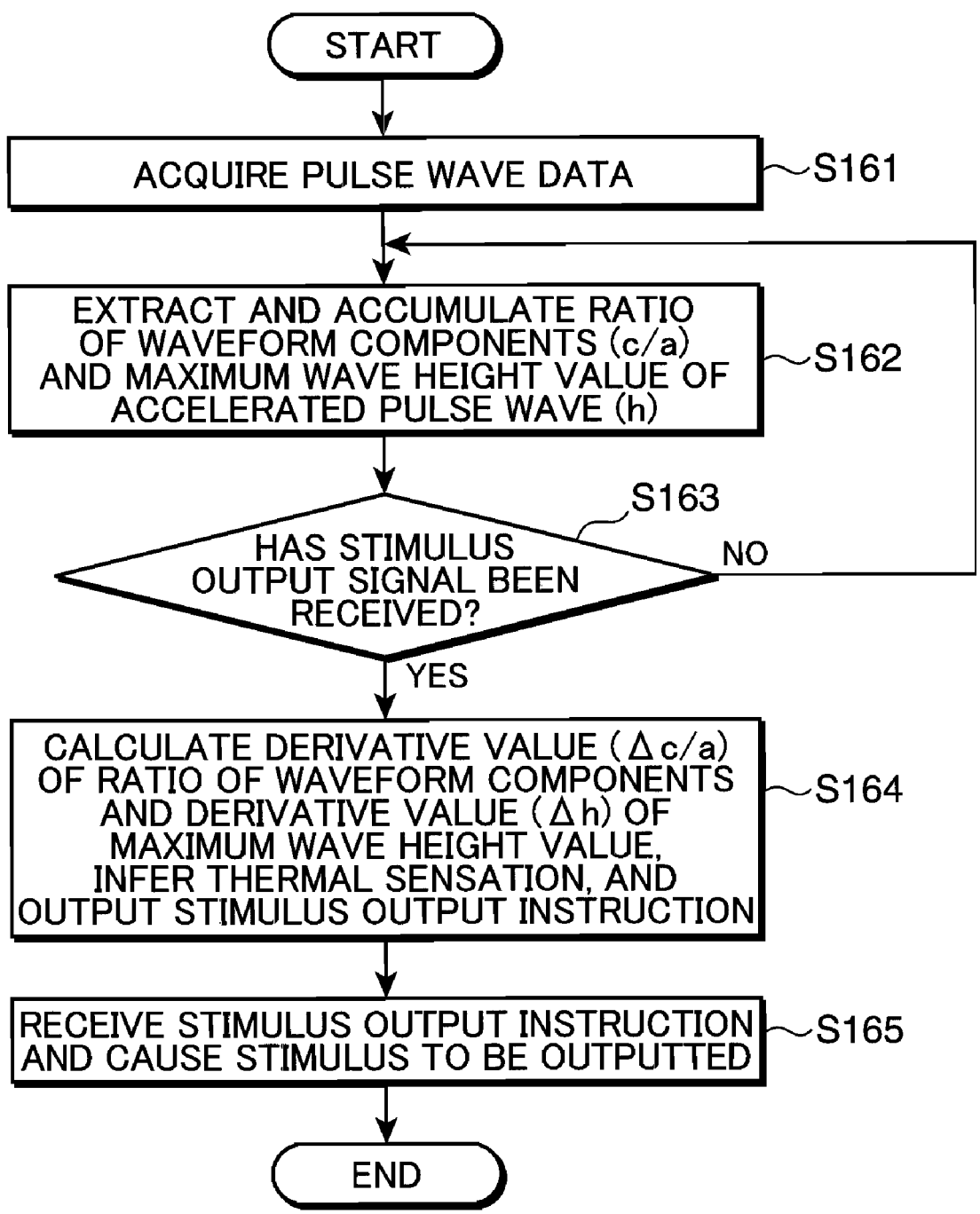
FIG. 34 is a flowchart detailing the processing by an environment control system according to a tenth embodiment of the invention.

FIG. 34 is a flowchart detailing the processing by the environment control system according to the tenth embodiment of the invention. Initially, the biological information acquiring portion 301 acquires time-series data of the pulse wave and accumulates it therein (Step S161). Subsequently, the parameter extracting portion 302 extracts the ratio of waveform components, c/a, and the maximum wave height value of the accelerated pulse wave, h, at regular time intervals from the time-series data of the pulse wave acquired by the biological information acquiring portion 301 and accumulates them therein (Step S162).

Subsequently, the parameter variance determining portion 303 determines whether it has received a stimulus output signal from the stimulus output portion 305 (Step S163). In a case where it has not received the stimulus output signal from the stimulus output portion 305 (NO in Step S163), it returns to the processing in Step S162.

Upon receipt of the stimulus output signal from the stimulus output portion 305 (YES in Step S163), the parameter variance determining portion 303 finds a derivative value Δc/a of the ratio of waveform components on the basis of the ratio of waveform components, c/a, extracted by the parameter extracting portion 302 immediately after the reception of the stimulus output signal and the ratio of waveform components, c/a, extracted by the parameter extracting portion 302 immediately before the reception of the stimulus output signal, and a derivative value Δh of the maximum wave height value of the accelerated pulse wave on the basis of the maximum wave height value of the accelerated pulse wave, h, extracted by the parameter extracting portion 302 immediately after the reception of the stimulus output signal and the maximum wave height value of the accelerated pulse wave, h, extracted by the parameter extracting portion 302 immediately before the reception of the stimulus output signal. The parameter variance determining portion 303 infers a thermal sensation of the user on the basis of these derivative values, determines the content of stimulus from the result of inference, and outputs a stimulus output instruction to the stimulus control portion 304 so that a stimulus according to the determined content of the stimulus is outputted from the stimulus output portion 305 (Step S164). Subsequently, the stimulus control portion 304 controls the stimulus output portion 305 to output the stimulus according to the stimulus output instruction outputted from the parameter variance determining portion 303 (Step S165).

Figure 35:
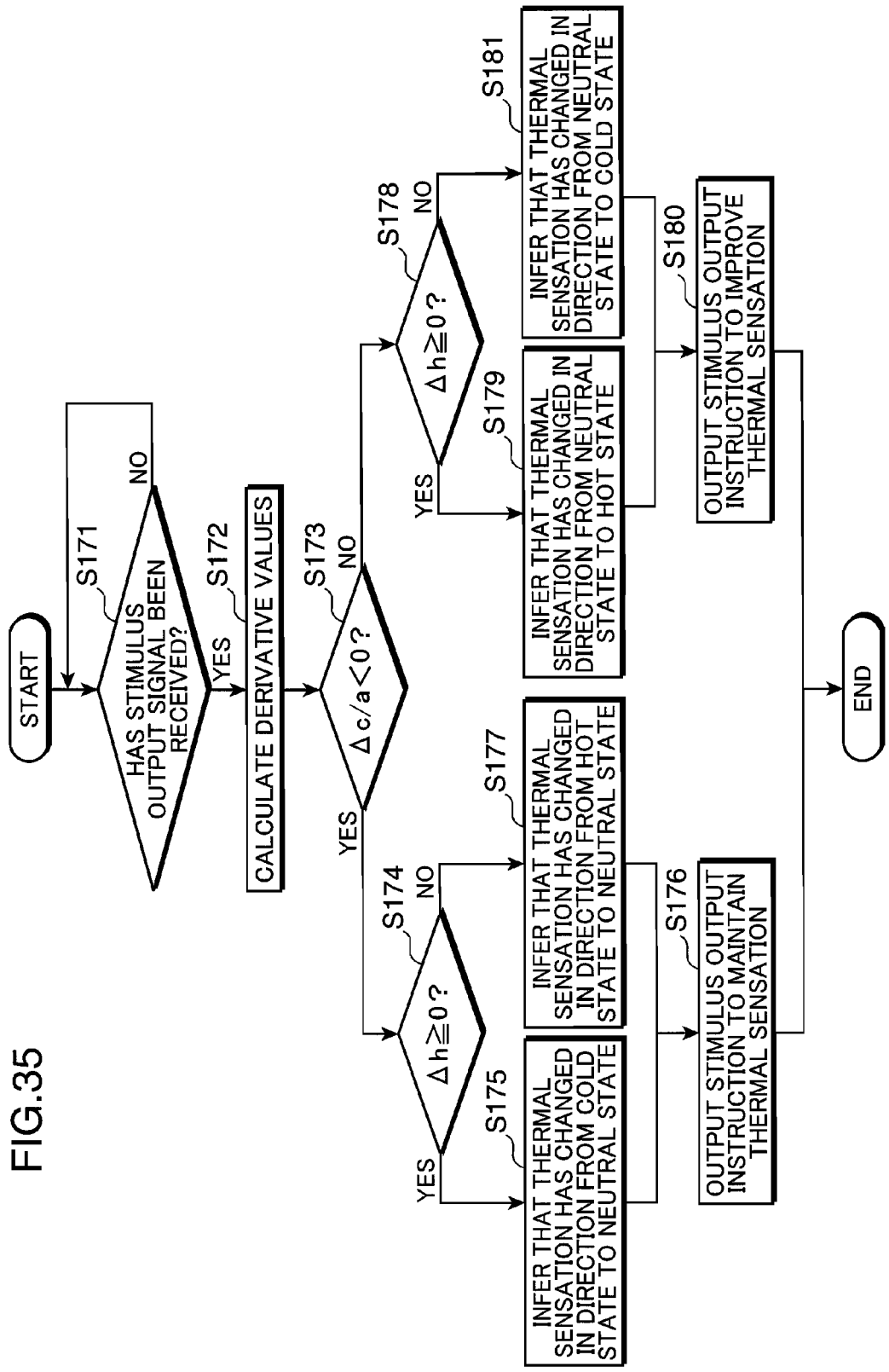
FIG. 35 is a flowchart detailing the processing by a parameter variance determining portion according to the tenth embodiment of the invention.

The processing to infer a thermal sensation of the user and the processing to determine the content of stimulus by the parameter variance determining portion 303 will now be described. FIG. 35 is a flowchart detailing the processing by the parameter variance determining portion 303 according to the tenth embodiment of the invention.

Initially, the parameter variance determining portion 303 determines whether it has received a stimulus output signal from the stimulus output portion 305 (Step S171). In a case where it has not received the stimulus output signal from the stimulus output portion 305 (NO in Step S171), the processing in Step S171 is repetitively performed at specific timing until the stimulus output signal is received. Upon receipt of the stimulus output signal from the stimulus output portion 305 (YES in Step S171), the parameter variance determining portion 303 calculates a derivative value $\Delta c/a$ on the basis of the ratio of waveform components, c/a, immediately before the reception of the stimulus output signal and the ratio of waveform components, c/a, immediately after the reception among the ratios of waveform components, c/a, extracted by the parameter extracting portion 302, and calculates a derivative value $\Delta h$ of the maximum wave height value of the accelerated pulse wave on the basis of the maximum wave height value of the accelerated pulse wave, h, immediately before the reception of the stimulus output signal and the maximum wave height value of the accelerated pulse wave, h, immediately after the reception among the maximum wave height values of the accelerated pulse wave, h, extracted by the parameter extracting portion 302 (Step S172).

Figure 36:
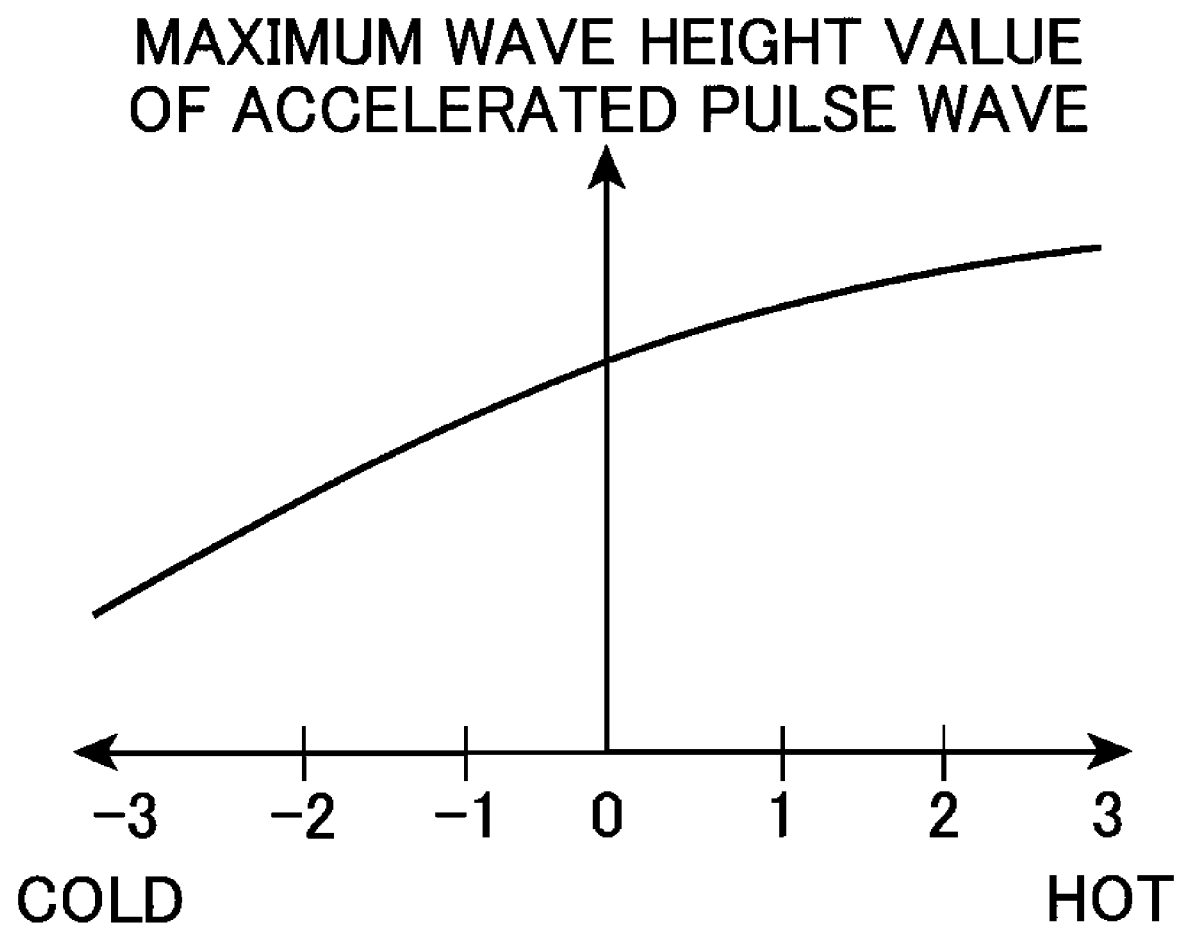
FIG. 36 is a graph indicating a correlation between the maximum wave height value of the accelerated pulse wave and a thermal sensation of the user discovered by the inventors from the test conducted on subjects.

The inventors discovered the presence of a high correlation of a variance of the ratio of waveform components and a variance of the maximum wave height value of the accelerated pulse wave with respect to a variance of a thermal sensation of the user. FIG. 36 is a graph indicating a correlation between the maximum wave height value of the accelerated pulse wave and a thermal sensation of the user discovered by the inventors from the test conducted on subjects. In FIG. 36, the abscissa is used for a thermal sensation of the user and the ordinate is used for the maximum wave height value of the accelerated pulse wave. As is indicated by this graph, because the maximum wave height value of the accelerated pulse wave monotonously increases with an increase of a thermal sensation of the user, it is possible to infer a thermal sensation of the user when the maximum wave height value of the accelerated pulse wave is known.

Accordingly, the environment control system of this embodiment infers a thermal sensation of the user on the basis of a variance of the ratio of waveform components shown in FIG. 33 and a variance of the maximum wave height value of the accelerated pulse wave shown in FIG. 36.

In Step S173 shown in FIG. 35, the parameter variance determining portion 303 determines whether the derivative value $\Delta c/a$ of the ratio of waveform components is negative. In a case where the derivative value $\Delta c/a$ is negative (YES in Step S173), the parameter variance determining portion 303 further determines whether the derivative value $\Delta h$ of the maximum wave height value of the accelerated pulse wave is equal to 0 or greater (Step S174). In a case where the derivative value $\Delta h$ is equal to 0 or greater (YES in Step S174), the parameter variance determining portion 303 infers that a thermal sensation of the user has changed in a direction from a cold state to the neutral state where it is neither hot nor cold, that is, a thermal sensation has improved (Step S175). Subsequently, the parameter variance determining portion 303 outputs a stimulus output instruction to maintain a thermal sensation (Step S176).

Meanwhile, in a case where the derivative value $\Delta h$ is not equal to 0 or greater (NO in Step S174), the parameter variance determining portion 303 infers that a thermal sensation of the user has changed in a direction from a hot state to the neutral state where it is neither hot nor cold, that is, a thermal sensation has improved (Step S177). Subsequently, the parameter variance determining portion 303 outputs a stimulus output instruction to maintain a thermal sensation (Step S176).

In a case where the derivative value $\Delta c/a$ is not negative (NO in Step S173), the parameter variance determining portion 303 determines whether the derivative value $\Delta h$ of the maximum wave height value of the accelerated pulse wave is equal to 0 or greater (Step S178). In a case where the derivative value $\Delta h$ is equal to 0 or greater (YES in Step S178), the parameter variance determining portion 303 infers that a thermal sensation of the user has changed in a direction from the neutral state where it is neither hot nor cold to a hot state, that is, a thermal sensation has deteriorated (Step S179). Subsequently, the parameter variance determining portion 303 outputs a stimulus output instruction to improve a thermal sensation, for example, to give a cool stimulus or to weaken the strength of a warm stimulus (Step S180).

Meanwhile, in a case where the derivative value $\Delta h$ is not equal to 0 or greater, (NO in Step S178), the parameter variance determining portion 303 infers that a thermal sensation of the user has changed in a direction from the neutral state where it is neither hot nor cold to a cold state, that is, a thermal sensation has deteriorated (Step S181). Subsequently, the parameter variance determining portion 303 outputs a stimulus output instruction to improve a thermal sensation, for example, to give a warm stimulus or to weaken the strength of a cool stimulus (Step S180).

As has been described, according to the environment control system of the tenth embodiment, because a thermal sensation of the user is inferred on the basis of the derivative value $\Delta c/a$ of the ratio of waveform components of the accelerated pulse wave and the derivative value $\Delta h$ of the maximum wave height value of the accelerated pulse wave, it is possible to infer a thermal sensation of the user at a further higher degree of accuracy.

In this embodiment, it may be configured in such a manner that the parameter variance determining portion 303 determines whether the derivative value $\Delta c/a$ of the ratio of waveform components falls within a pre-determined particular range (for example, from −0.01 to 0.01) immediately before it determines whether the derivative value $\Delta c/a$ of the ratio waveform components is negative in Step S173, so that in a case where the derivative value $\Delta c/a$ falls within the particular range, it determines that a thermal sensation of the user has hardly changed and outputs a stimulus output instruction to continue to output or stop outputting a stimulus of the current content. Also, it may be configured in such a manner that the parameter variance determining portion 303 determines whether the derivative value $\Delta h$ of maximum wave height value of the accelerated pulse wave falls within a pre-determined particular range (for example, from −0.03 to 0.03) immediately before it determines whether the derivative value $\Delta h$ of the maximum wave height value of the accelerated pulse wave is equal to 0 or greater in Step 174 or Step S178, so that in a case where the derivative value $\Delta h$ falls within the pre-determined particular range, it determines that a thermal sensation of the user has hardly changed and outputs a stimulus output instruction to continue to output or stop outputting a stimulus of the current content.

In this embodiment, the content of stimulus determined by the parameter variance determining portion 303 includes a warm or cool thermal stimulus, such as cooling and heating, an air-flow stimulus, such as cool air and warm air, the strength of stimulus, a stimulus giving time, and so forth.

In this embodiment, the parameter variance determining portion 303 calculates a derivative value $\Delta c/a$ on the basis of the ratio of waveform components, c/a, immediately after the output of a stimulus from the stimulus output portion 305 and the ratio of waveform components, c/a, immediately before the output, and calculates a derivative value $\Delta h$ on the basis of the maximum wave height value of the accelerated pulse wave, h, immediately after the output of a stimulus from the stimulus output portion 305 and the maximum wave height value of the accelerated pulse wave, h, immediately before the output, so that it infers a thermal sensation of the user using these derivative values ($\Delta c/a$ and $\Delta h$). The invention, however, is not limited to this configuration, and it may be configured in such a manner that a difference between the ratio of waveform components, c/a, immediately before the output and the ratio of waveform components, c/a, immediately after the output is calculated and a difference between the maximum wave height value of the accelerated pulse wave, h, immediately before the output and the maximum wave height value of the accelerated pulse wave, h, immediately after the output is calculated, so that a thermal sensation of the user is inferred on the basis of these differences.

In order to calculate a derivative value $\Delta c/a$ or a difference of the ratios of waveform components, the average value of plural ratios of waveform components, c/a, extracted over a specific period in the past since the reception of the stimulus output signal may be calculated, so that a derivative value $\Delta c/a$ or a difference of the ratios of waveform components is calculated on the basis of the average value and the ratio of waveform components, c/a, immediately after the reception of the stimulus output signal. Alternatively, a derivative value $\Delta c/a$ or a difference of the ratios of waveform components may be calculated on the basis of the average value of differences between the ratios of waveform components, one ahead of the other in time series, among plural ratios of waveform components extracted over a specific period in the past since the reception of the stimulus output signal and the ratio of waveform components immediately after the reception of the stimulus output signal, so that a thermal sensation of the user is inferred on the basis of the result of calculation.

Also, in order to calculate a derivative value $\Delta h$ or a difference of the maximum wave height values of the accelerated pulse wave, the average value of plural maximum wave height values of the accelerated pulse wave, h, extracted over a specific period in the past since the reception of the stimulus output signal may be calculated, so that a derivative value $\Delta h$ or a difference of the maximum wave height values of the accelerated pulse wave is calculated on the basis of the average value and the maximum wave height value of the accelerated pulse wave, h, immediately after the reception of the stimulus output signal. Alternatively, a derivative value $\Delta h$ or a difference of the maximum wave height values of the accelerated pulse wave may be calculated on the basis of the average value of differences between the maximum wave height values of the accelerated pulse wave, one ahead of the other in time series, among plural maximum wave height values of the accelerated pulse wave extracted over a specific period in the past since the reception of the stimulus output signal and the maximum wave height value of the accelerated pulse wave immediately after the reception of the stimulus output signal, so that a thermal sensation of the user is inferred on the basis of the result of calculation.

Figure 37:
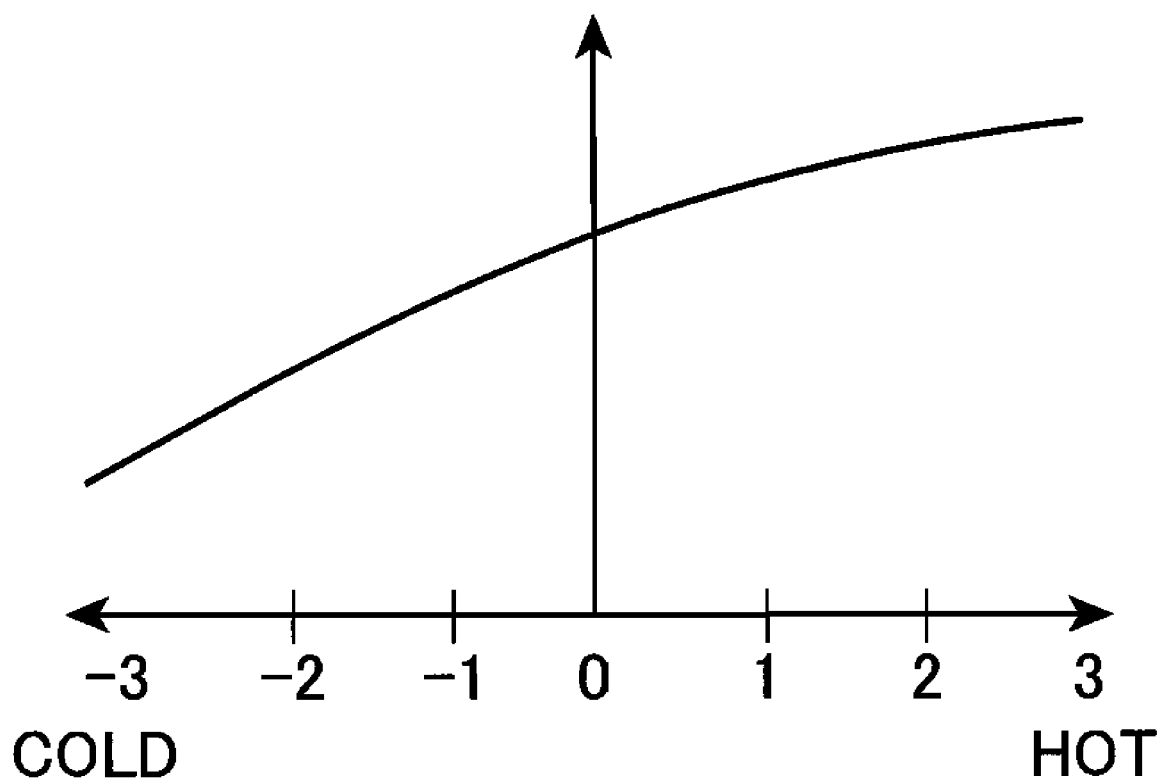
FIG. 37 is a graph indicating a correlation between the maximum wave height value of the pulse wave and a thermal sensation of the user discovered by the inventors from the test conducted on subjects.

The inventors also discovered the presence of a high correlation of a variance of the amplitude of the pulse wave and a variance of the maximum wave height value of the pulse wave with respect to a variance of a thermal sensation of the user. FIG. 37 shows a graph indicating a correlation between a variance of the maximum wave height value of the pulse wave and a thermal sensation of the user discovered by the inventors from the test conducted on subjects. As is shown in FIG. 37, it is understood that the maximum wave height value of the pulse wave increases monotonously with an increase of a thermal sensation of the user. Hence, it is possible to infer a thermal sensation of the user using the maximum wave height value of the pulse wave instead of the maximum wave height value of the accelerated pulse wave.

Also, in this embodiment, the stimulus output portion 305 outputs the stimulus output signal indicating that it has outputted a stimulus to the parameter variance determining portion 303, and the parameter variance determining portion 303 calculates the derivative values on the basis of the ratios of waveform components and the maximum wave height values of the accelerated pulse wave immediately before and after the reception of the stimulus output signal. The invention, however, is not particularly limited to this configuration. It may be configured in such a manner that the stimulus output portion 305 does not output the stimulus output signal, and instead, the parameter variance determining portion 303 is provided with a timer portion that measures a time, so that it calculates the derivative values on the basis of the ratios of waveform components of the accelerated pulse wave and the maximum wave height values of the accelerated pulse wave immediately before and after the elapse of a specific time or immediately before and after the elapse of a stimulus giving time included in the content of stimulus.

Alternatively, rates of change of the ratio of waveform components and the maximum wave height value of the accelerated pulse wave over a specific time may be used as the derivative values. Further, the timer portion that measures a time may be separated from the parameter variance determining portion 303 as an independent component and the timer portion is connected to the parameter variance determining portion 303 to enable mutual communications, so that the timer portion transmits the start of time measurement and an elapse of time to the parameter variance determining portion 303. In addition, in this embodiment, the result of inference of a thermal sensation of the user may be presented to the user by displaying the result on a display portion, such as a monitor.

Eleventh Embodiment

An environment control system according to an eleventh embodiment of the invention will now be described. Because the environment control system of the eleventh embodiment is of the same configuration as the environment control system of the sixth embodiment, the configuration thereof will be described using FIG. 21. Also, descriptions of components same as those in the sixth embodiment are omitted and only a difference will be described in the eleventh embodiment.

The parameter extracting portion 302 extracts, as a parameter to evaluate the pulse wave, a ratio of waveform components of the accelerated pulse wave obtained by second-order differentiation of the pulse wave waveform obtained from the pulse wave data, and accumulates it therein. The accelerated pulse wave waveform is the same as that in the sixth embodiment. In this embodiment, too, given the distance a from the base line to the peak A of the accelerated pulse wave waveform as the denominator and the distance c from the base line to the peak C as the numerator, c/a is extracted as the ratio of waveform components.

The parameter variance determining portion 303 holds the contents of stimulus it has determined in an internal memory, and calculates a variance of the ratio of waveform components extracted by the parameter extracting portion 302. It then infers a thermal sensation of the user on the basis of the result of calculation and the contents of stimulus held therein, and determines the content of stimulus from the result of inference. In this instance, the parameter variance determining portion 303 updates the contents of stimulus held in the internal memory, and outputs a stimulus output instruction to the stimulus control portion 304 so that a stimulus according to the determined content of stimulus is outputted from the stimulus output portion 305. The parameter variance determining portion 303 holds the contents of stimulus given to the user within a specific period in the past. The contents of stimulus held in the memory include the kinds of stimulus, such as cooling and heating, and the strength of stimulus outputted by the cooling and the heating.

In this embodiment, the parameter variance determining portion 303 infers a thermal sensation of the user on the basis of a derivative value of the ratio of waveform components calculated by dividing a difference between the ratio of waveform components extracted immediately after the reception of a stimulus output signal that the stimulus output portion 305 outputs when it outputs a stimulus and the ratio of waveform components extracted immediately before the reception of the stimulus output signal by the sampling cycle, and the contents of the stimulus held in the internal memory at the time of reception of a stimulus output signal that the stimulus output portion 305 outputs when it outputs a stimulus.

Figure 38:
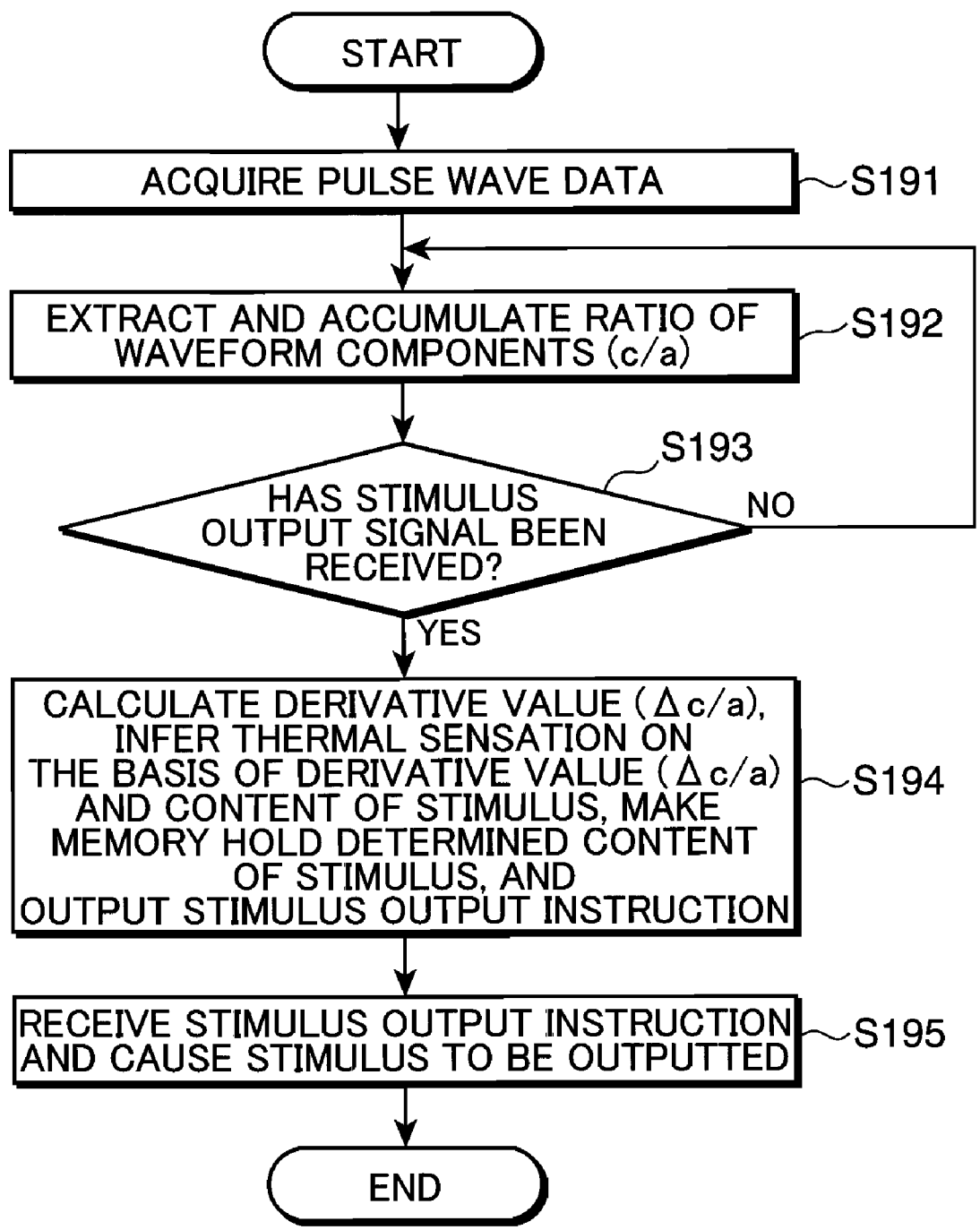
FIG. 38 is a flowchart detailing the processing by an environmental control system according to an eleventh embodiment of the invention.

FIG. 38 is a flowchart detailing the processing by the environment control system according to the eleventh embodiment of the invention. Initially, the biological information acquiring portion 301 acquires time-series data of the pulse wave and accumulates it therein (Step S191). Subsequently, the parameter extracting portion 302 extracts the ratio of waveform components, c/a, at regular time intervals from the time-series data of the pulse wave acquired by the biological information acquiring portion 301 and accumulates it therein (Step S192).

Subsequently, the parameter variance determining portion 303 determines whether it has received a stimulus output signal from the stimulus output portion 305 (Step S193). In a case where it has not received the stimulus output signal from the stimulus output portion 305 (NO in Step S193), it returns to the processing in Step S192.

Meanwhile, upon receipt of the stimulus output signal from the stimulus output portion 305 (YES in Step S193), the parameter variance determining portion 303 finds a derivative value $\Delta c/a$ of the ratio of waveform components on the basis of the ratio of waveform components, c/a, extracted by the parameter extracting portion 302 immediately after the reception of the stimulus output signal and the ratio of waveform components, c/a, extracted by the parameter extracting portion 302 immediately before the reception of the stimulus output signal. The parameter variance determining portion 303 then infers a thermal sensation of the user on the basis of the derivative value and the contents of stimulus held in the memory to determine the content of stimulus from the result of inference. The parameter variance determining portion 303 updates the contents of stimulus held in the internal memory, and outputs a stimulus output instruction to the stimulus control portion 304 so that a stimulus according to the determined content of stimulus is outputted from the stimulus output portion 305 (Step S194). Subsequently, the stimulus control portion 304 controls the stimulus output portion 305 to output a stimulus according to the stimulus output instruction outputted from the parameter variance determining portion 303 (Step S195).

Figure 39:
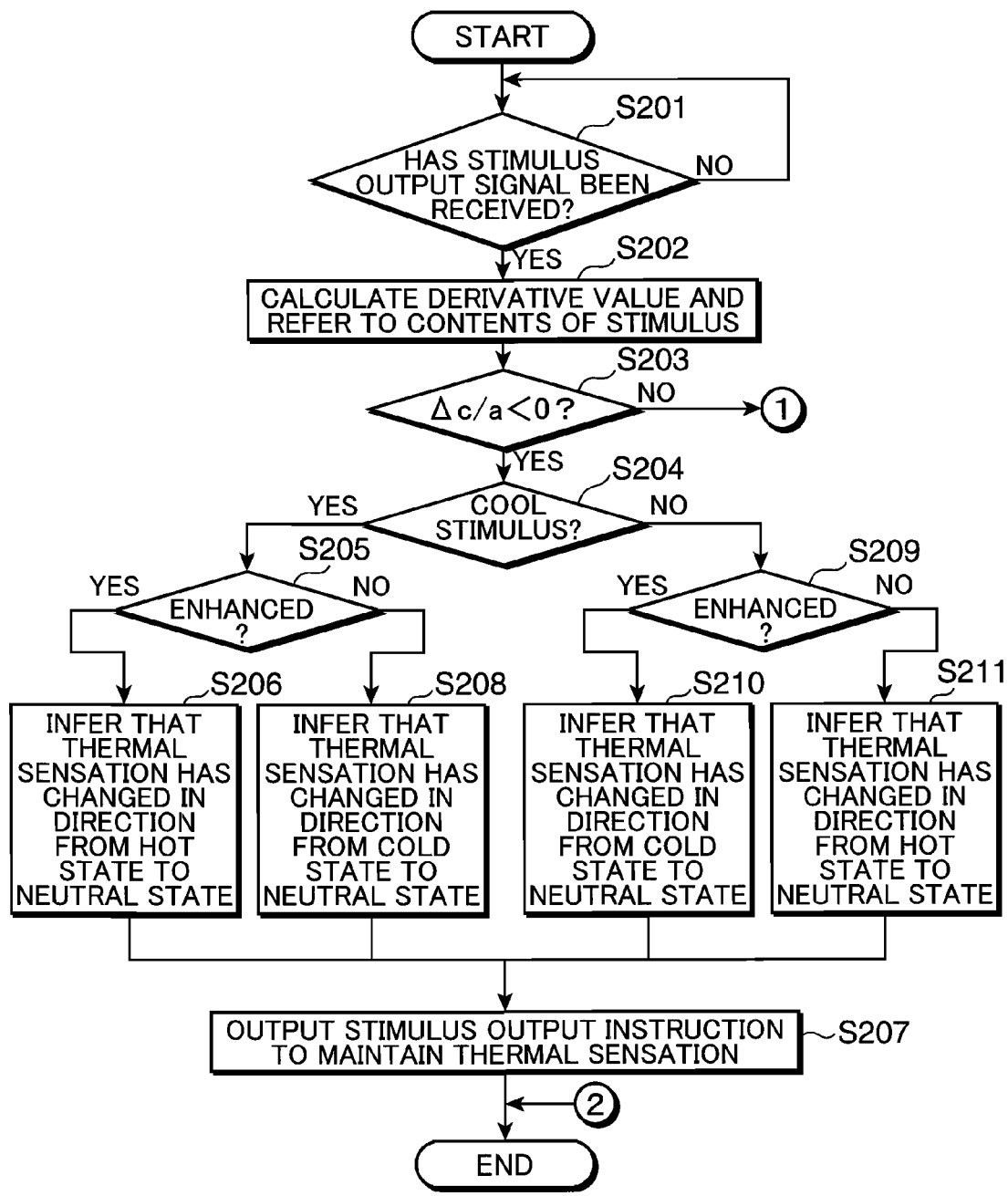
FIG. 39 is a first flowchart detailing the processing by a parameter variance determining portion according to the eleventh embodiment of the invention.
Figure 40:
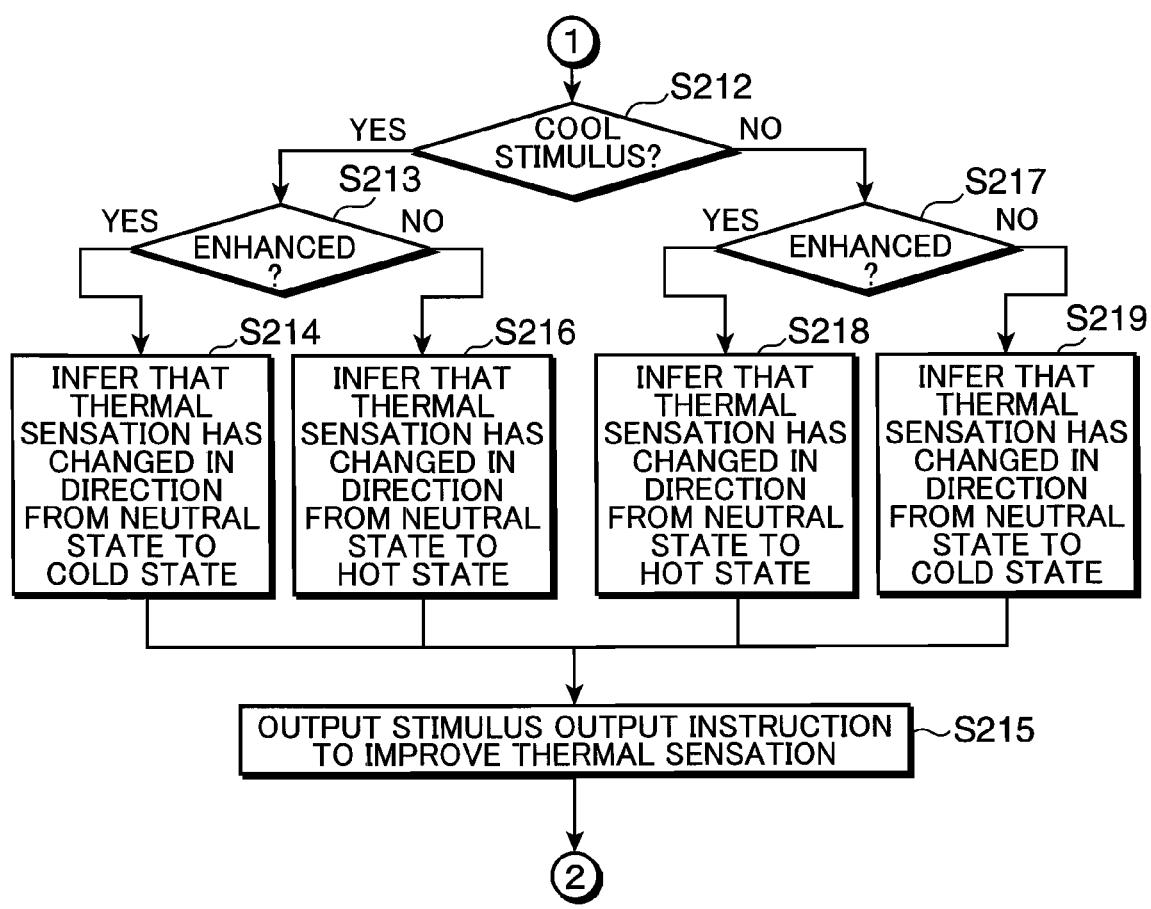
FIG. 40 is a second flowchart detailing the processing by the parameter variance determining portion according to the eleventh embodiment of the invention.

The processing to infer a thermal sensation of the user and the processing to determine the content of stimulus by the parameter variance determining portion 303 will now be described. FIG. 39 and FIG. 40 are flowcharts detailing the processing by the parameter variance determining portion 303 according to the eleventh embodiment of the invention.

Initially, the parameter variance determining portion 303 determines whether it has received a stimulus output signal from the stimulus output portion 305 (Step S201). In a case where it has not received the stimulus output signal from the stimulus output portion 305 (NO in Step S201), the processing in Step S201 is performed repetitively at specific timing until the stimulus output signal is received. Upon receipt of the stimulus output signal from the stimulus output portion 305 (YES in Step S201), the parameter variance determining portion 303 calculates a derivative value $\Delta c/a$ of the ratio of waveform components on the basis of the ratio of waveform components, c/a, immediately before the reception of the stimulus output signal and the ratio of waveform components c/a, immediately after the reception among the ratios of waveform components, c/a, extracted by the parameter extracting portion 302, and refers to the contents of stimulus held in the internal memory (Step S202).

Subsequently, the parameter variance determining portion 303 determines whether the derivative value $\Delta c/a$ of the ratio of waveform components is negative (Step S203). In a case where the derivative value $\Delta c/a$ is negative (YES in Step S203), the parameter variance determining portion 303 determines whether the contents of stimulus referred in Step S202 specify a stimulus such that enhances a cool feeling (Step S204). A stimulus having the content of stimulus such that enhances a cool feeling corresponds, for example, to the cooling. The parameter variance determining portion 303 reads out the contents of stimulus accumulated within a specific period in the past from the memory and determines whether the contents of stimulus specify a stimulus such that enhances a cool feeling.

In a case where the contents of stimulus specify a stimulus such that enhances a cool feeling (YES in Step S204), the parameter variance determining portion 303 further determines the strength of stimulus (Step S205). In a case where the strength of the latest stimulus among the stimuli specified by the contents of stimulus accumulated in the memory within the specific time in the past has heightened from the strengths of stimulus before, the parameter variance determining portion 303 determines that the strength of stimulus has heightened. In a case where it is determined that the strength of stimulus has heightened (YES in Step S205), the parameter variance determining portion 303 infers that a thermal sensation of the user has changed in a direction from a hot state to the neutral state where it is neither hot nor cold, that is, a thermal sensation has improved (Step S206). Subsequently, the parameter variance determining portion 303 outputs a stimulus output instruction to maintain a thermal sensation (Step S207).

Meanwhile, in a case where it is determined that the strength of stimulus has weakened (NO in Step S205), the parameter variance determining portion 303 infers that a thermal sensation of the user has changed in a direction from a cold state to the neutral state where it is neither hot nor cold, that is, a thermal sensation has improved (Step S208). In a case where the strength of the latest stimulus among the stimuli specified by the contents of stimulus accumulated in the memory within the specific time in the past has weakened from the strengths of stimulus before, the parameter variance determining portion 303 determines that the strength of stimulus has weakened. Subsequently, the parameter variance determining portion 303 outputs a stimulus output instruction to maintain a thermal sensation (Step S207).

Meanwhile, in a case where the parameter variance determining portion 303 determines that the contents of stimulus do not specify a stimulus such that enhances a cool feeling, that is, in a case where it determines that the contents of stimulus specify a stimulus such that enhances a warm feeling (NO in Step S204), it further determines the strength of stimulus (Step S209). The contents of stimulus such that enhances a warm feeling correspond, for example, to the heating.

In a case where the parameter variance determining portion 303 determines that the content of stimulus to be outputted specifies a stimulus to heighten the strength of a warm feeling (YES in Step S209), it infers that a thermal sensation of the user has changed in a direction from a cold state to the neutral state where it is neither hot nor cold, that is, a thermal sensation has improved (Step S210). Subsequently, the parameter variance determining portion 303 outputs a stimulus output instruction to maintain a thermal sensation (Step S207).

In a case where, for example, the strength of the latest stimulus among the stimuli specified by the contents of stimulus accumulated in the memory within the specific time in the past has heightened from the strengths of stimulus before, the parameter variance determining portion 303 determines that the strength of stimulus has heightened. In a case where the stimulus is such that weakens the strength of a warm feeling (NO in Step S209), the parameter variance determining portion 303 infers that a thermal sensation of the user has changed in a direction from a hot state to the neutral state where it is neither hot nor cold, that is, a thermal sensation has improved (Step S211). Subsequently, the parameter variance determining portion 303 outputs a stimulus output instruction to maintain a thermal sensation (Step S207).

Meanwhile, in a case where the parameter variance determining portion 303 determines that that the derivative value Δc/a is not negative (NO in Step S203), it further determines whether the contents of stimulus specify a stimulus such that enhances a cool feeling (Step S212). In a case where the parameter variance determining portion 303 determines that the contents of stimulus specify a stimulus such that enhances a cool feeling (YES in Step S212), it further determines the strength of stimulus (Step S213).

In a case where the parameter variance determining portion 303 determines that the stimulus is such that heightens the strength of stimulus (YES in Step S213), it infers that a thermal sensation of the user has changed in a direction from the neutral state where it is neither hot nor cold to a cold state, that is a thermal sensation has deteriorated (Step S214). Subsequently, the parameter variance determining portion 303 outputs a stimulus output instruction to improve a thermal sensation, for example, to give a warm stimulus or weaken the strength of a cool stimulus (Step S215).

Meanwhile, in a case where the strength of stimulus has weakened (NO in Step S213), the parameter variance determining portion 303 infers that a thermal sensation of the user has changed in a direction from the neutral state where it is neither hot nor cold to a hot state, that is, a thermal sensation has deteriorated (Step S216). Subsequently, the parameter variance determining portion 303 outputs a stimulus output instruction to improve a thermal sensation, for example, to heighten the strength of a cool stimulus (Step S215).

In a case where the contents of stimulus do not specify a stimulus such that enhances a cool feeling, that is, the contents of stimulus specify a stimulus such that enhances a warm feeling (NO in Step S212), the parameter variance determining portion 303 further determines the strength of stimulus (Step S217). In a case where the parameter variance determining portion 303 determines that the strength of stimulus has heightened (YES in Step S217), it infers that a thermal sensation of the user has changed in a direction from the neutral state where it is neither hot nor cold to a hot state, that is, a thermal sensation has deteriorated (Step S218). Subsequently, the parameter variance determining portion 303 outputs a stimulus output instruction to improve a thermal sensation, for example, to give a cool stimulus or weaken the strength of a warm stimulus (Step S215).

Meanwhile, in a case where the parameter variance determining portion 303 determines that the strength of stimulus has weakened (NO in Step S217), it infers that a thermal sensation of the user has changed in a direction from the neutral state where it is neither hot nor cold to a cold state, that is, a thermal sensation has deteriorated (Step S219). Subsequently, the parameter variance determining portion 303 outputs a stimulus output instruction to improve a thermal sensation, for example, to heighten the strength of a warm stimulus (Step S215).

As has been described, according to the environment control system of the eleventh embodiment, because a thermal sensation of the user is inferred on the basis of the derivative value Δc/a of the ratio of waveform components of the accelerated pulse wave and the contents of stimulus, it is possible to infer a thermal sensation of the user at a further higher degree of accuracy.

In this embodiment, it may be configured in such a manner that the parameter variance determining portion 303 determines whether the derivative value Δc/a of the ratio of waveform components falls within a pre-determined particular range (for example, from −0.01 to 0.01) immediately before it determines whether the derivative value Δc/a of the ratio waveform components is negative in Step S203, so that in a case where the derivative value Δc/a falls within the particular range, it determines that a thermal sensation of the user has hardly changed and outputs a stimulus output instruction to continue to output or stop outputting a stimulus of the current content.

In this embodiment, the parameter variance determining portion 303 infers a thermal sensation of the user from the kinds of stimulus and the strength of stimulus. However, a thermal sensation of the user may be inferred from a change of the kinds of stimulus alone, for example, from a state in the absence of a stimulus to a warm stimulus or a change from a cool stimulus to a warm stimulus, or a thermal sensation of the user may be inferred by taking into account the number of outputs and a stimulus outputting time of the same stimulus over a specific period in the past.

In this embodiment, the parameter variance determining portion 303 calculates a derivative value Δc/a on the basis of the ratio of waveform components, c/a, immediately after the output of a stimulus from the stimulus output portion 305 and the ratio of waveform components, c/a, immediately before the output, and infers a thermal sensation of the user using this derivative value Δc/a. The invention, however, is not limited to this configuration, and a difference between the ratio of waveform components, c/a, immediately before the output and the ratio of waveform components, c/a, immediately after the output may be calculated, so that a thermal sensation of the user is inferred on the basis of the difference.

Alternatively, the parameter variance determining portion 303 may calculate a derivative value Δc/a or a difference of the ratios of waveform components on the basis of the average value of plural ratios of waveform components, c/a, extracted over a specific period in the past since the reception of the stimulus output signal and the ratio of waveform components immediately after the reception, so that it infers a thermal sensation of the user on the basis of the result of calculation. Further, the parameter variance determining portion 303 may calculate a derivative value Δc/a or a difference of the ratios of waveform components on the basis of the average value of differences between the ratios of waveform components, one ahead of the other in time series, among plural ratios of waveform components extracted over a specific period in the past since the reception of the stimulus output signal and the ratio of waveform components immediately after the reception of the stimulus output signal, so that it infers a thermal sensation of the user on the basis of the result of calculation.

In this embodiment, the stimulus output portion 305 outputs the stimulus output signal indicating that it has outputted a stimulus to the parameter variance determining portion 303. The parameter variance determining portion 303 calculates the derivative value from the ratios of waveform components immediately before and after the reception of the stimulus output signal, and refers to the contents of stimulus held in the internal memory upon receipt of the stimulus output signal that the stimulus output portion 305 outputs when it outputs a stimulus. The invention, however, is not particularly limited to this configuration, and it may be configured in such a manner that the stimulus output portion 305 does not output the stimulus output signal, and instead, the parameter variance determining portion 303 is provided with a timer portion that measures a time, so that it calculates the derivative value from the ratios of waveform components immediately before and after the elapse of a specific time or immediately before and after the elapse of a stimulus giving time included in the content of stimulus and refers to the contents of stimulus. Alternatively, a rate of change of the ratio of waveform components over a specific time may be used as the derivative value. Further, the timer portion that measures a time may be separated from the parameter variance determining portion 303 as an independent component and the timer portion is connected to the parameter variance determining portion 303 to enable mutual communications, so that the timer portion transmits the start of time measurement and an elapse of time to the parameter variance determining portion 303. In addition, in this embodiment, the result of inference of a thermal sensation of the user may be presented to the user by displaying the result on a display portion, such as a monitor.

Twelfth Embodiment

Figure 41:
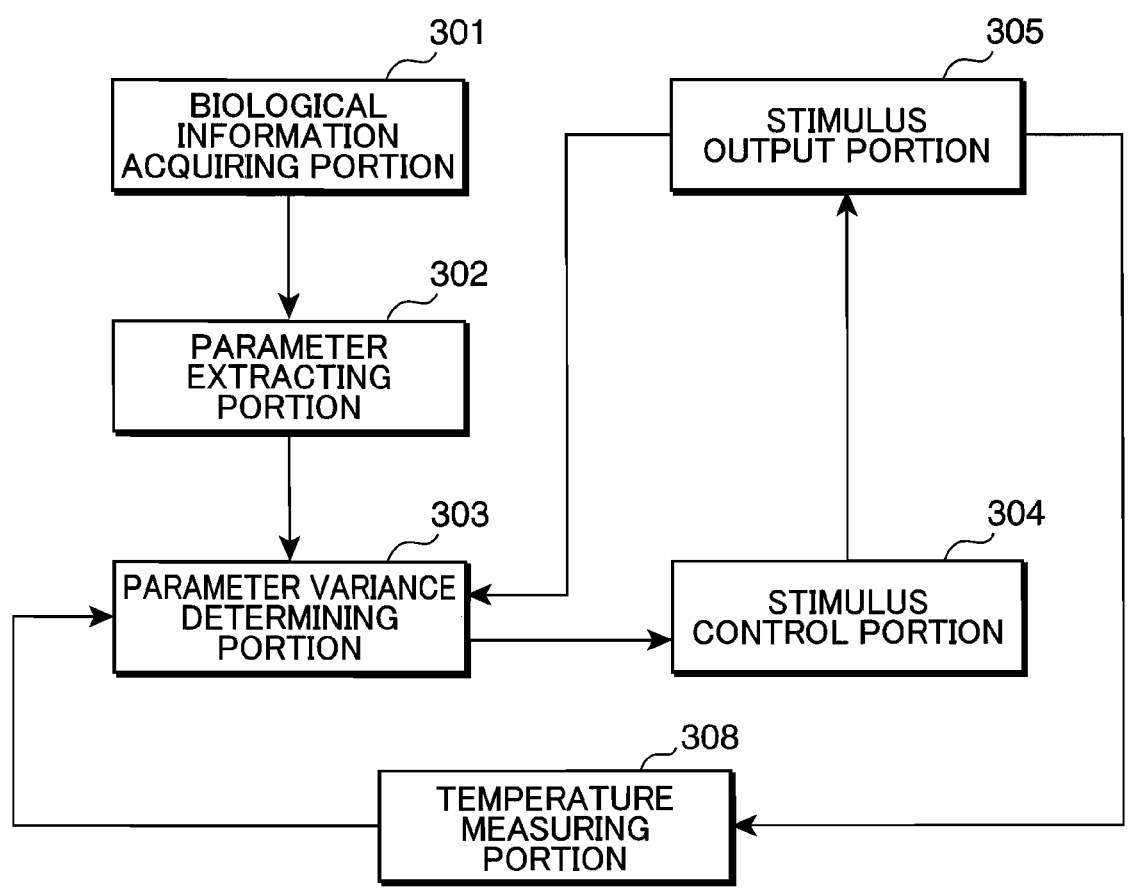
FIG. 41 is a view showing the configuration of an environment control system according to a twelfth embodiment of the invention.

An environment control system of a twelfth embodiment will now be described. FIG. 41 is a view showing the configuration of the environment control system according to the twelfth embodiment of the invention. Descriptions of components in FIG. 41 same as those in FIG. 21 are omitted herein. This embodiment is formed by further including a temperature measuring portion (temperature measuring portion) 503. The temperature measuring portion 308 measures the temperature at a location where the user is in and transmits the result of measurement (temperature data) to the parameter variance determining portion 303. Also, the temperature measuring portion 308 measures the temperature at regular time intervals and never fails to measure the temperature immediately after the reception of a stimulus output signal that the stimulus output portion 305 outputs when it outputs a stimulus.

The parameter extracting portion 302 extracts, as a parameter to evaluate the pulse wave, a ratio of waveform components of the accelerated pulse wave obtained by second-order differentiation of the pulse wave waveform obtained from the pulse wave data, and accumulates it therein. The accelerated pulse wave waveform is the same as that in the sixth embodiment and shapes the waveform as shown in FIG. 60. In this embodiment, too, given the distance a from the base line to the peak A of the accelerated pulse wave waveform as denominator and the distance c from the base line to the peak C as the numerator, c/a is extracted as the ratio of waveform components.

The parameter variance determining portion 303 calculates a variance of the ratio of waveform components extracted by the parameter extracting portion 302, and infers a thermal sensation of the user on the basis of the result of calculation and the temperature data from the temperature measuring portion 308. It then determines the content of stimulus from the result of inference and outputs a stimulus output signal to the stimulus control portion 304 so that a stimulus according to the determined content of stimulus is outputted from the stimulus output portion 305. The parameter variance determining portion 303 holds the temperature data received from the temperature measuring portion 308 within a specific period in the past.

In this embodiment, the parameter variance determining portion 303 calculates a derivative value of the ratio of waveform components by dividing a difference between the ratio of waveform components extracted immediately after the reception of a stimulus output signal that the stimulus output portion 305 outputs when it outputs a stimulus and the ratio of waveform components extracted immediately before the reception of the stimulus output signal by the sampling cycle, and calculates a derivative value of the temperature data by dividing a difference between the temperature data received from the temperature measuring portion 308 immediately after the reception of a stimulus output signal that the stimulus output portion 305 outputs when it outputs a stimulus and the temperature data received from the temperature measuring portion 308 immediately before the reception of the stimulus output signal by a measuring time interval, so that it infers a thermal sensation of the user on the basis of the both derivative values.

Figure 42:
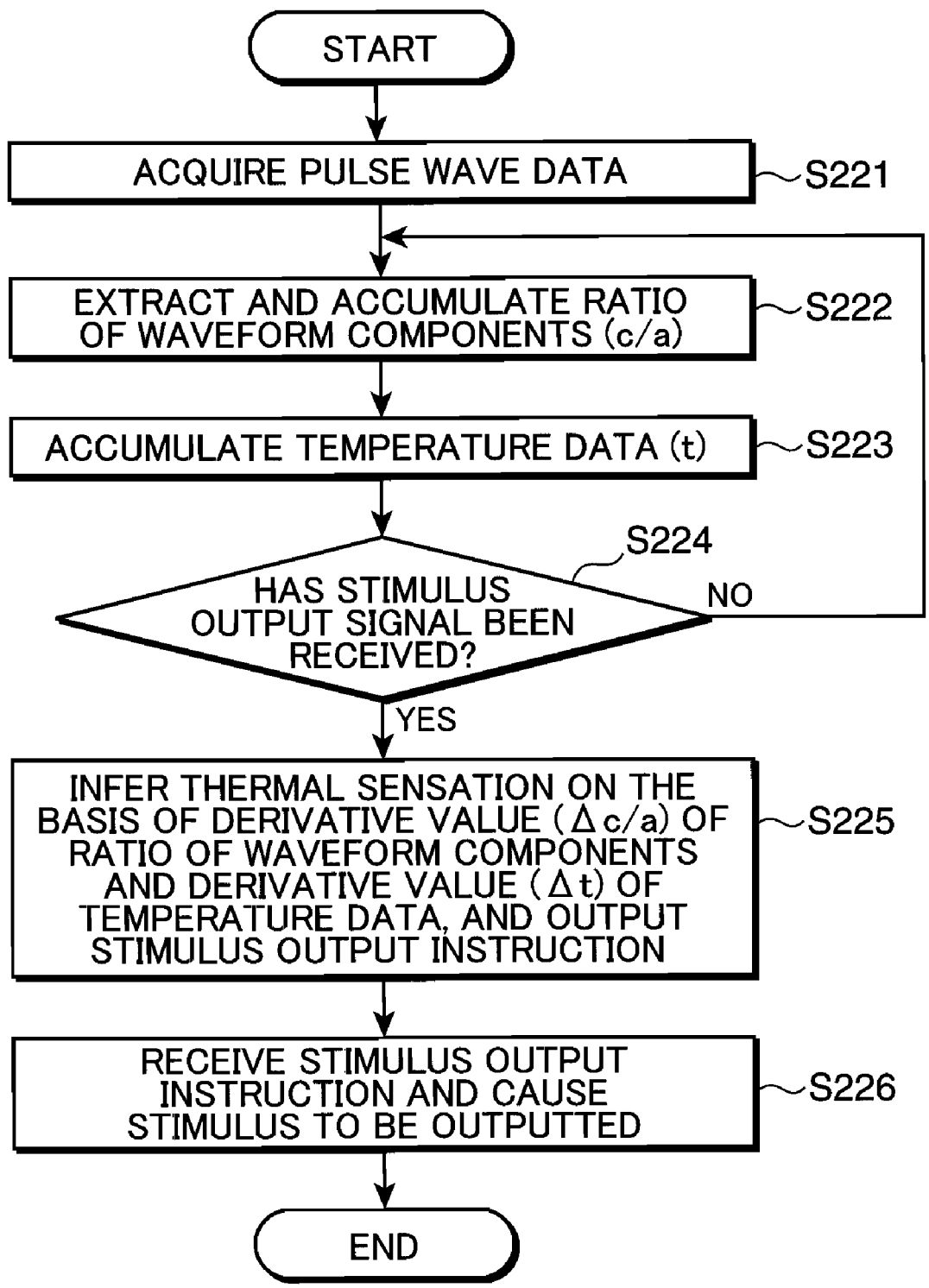
FIG. 42 is a flowchart detailing the processing by the environment control system according to the twelfth embodiment of the invention.

FIG. 42 is a flowchart detailing the processing by the environment control system according to the twelfth embodiment of the invention. Initially, the biological information acquiring portion 301 acquires time-series data of the pulse wave and accumulates it therein (Step S221). Subsequently, the parameter extracting portion 302 extracts the ratio of waveform components, c/a, at regular time intervals from the time-series data of the pulse wave acquired by the biological information acquiring portion 301 and acclimates it therein (Step S222).

Subsequently, the parameter extracting portion 302 accumulates the temperature data t received from the temperature measuring portion 308 (Step S223). Subsequently, the parameter variance determining portion 303 determines whether it has received a stimulus output signal from the stimulus output portion 305 (Step S224). In a case where it has not received the stimulus output signal from the stimulus output portion 305 (NO in Step S224), it returns to the processing in Step S222.

Upon receipt of the stimulus output signal from the stimulus output portion 305 (YES in Step S224), the parameter variance determining portion 303 finds a derivative value Δc/a of the ratio of waveform components on the basis of the ratio of waveform components, c/a, extracted by the parameter extracting portion 302 immediately after the reception of the stimulus output signal and the ratio of waveform components, c/a, extracted by the parameter extracting portion 302 immediately before the reception of the stimulus output signal, and finds a derivative value Δt of the temperature data on the basis of temperature data t received from the temperature measuring portion 308 immediately after the reception of the stimulus output signal and the temperature data t received from the temperature measuring portion 308 immediately before the reception of the stimulus output signal. The parameter variance determining portion 303 infers a thermal sensation of the user on the basis of the both derivative values ($\Delta c/a$ and $\Delta t$). It then determines the content of stimulus from the result of inference, and outputs a stimulus output instruction to the stimulus control portion 304 so that a stimulus according to the determined content of stimulus is outputted from the stimulus output portion 305 (Step S225). Subsequently, the stimulus control portion 304 controls the stimulus output portion 305 to output a stimulus according to the stimulus output instruction outputted from the parameter variance determining portion 303 (Step S226).

Figure 43:
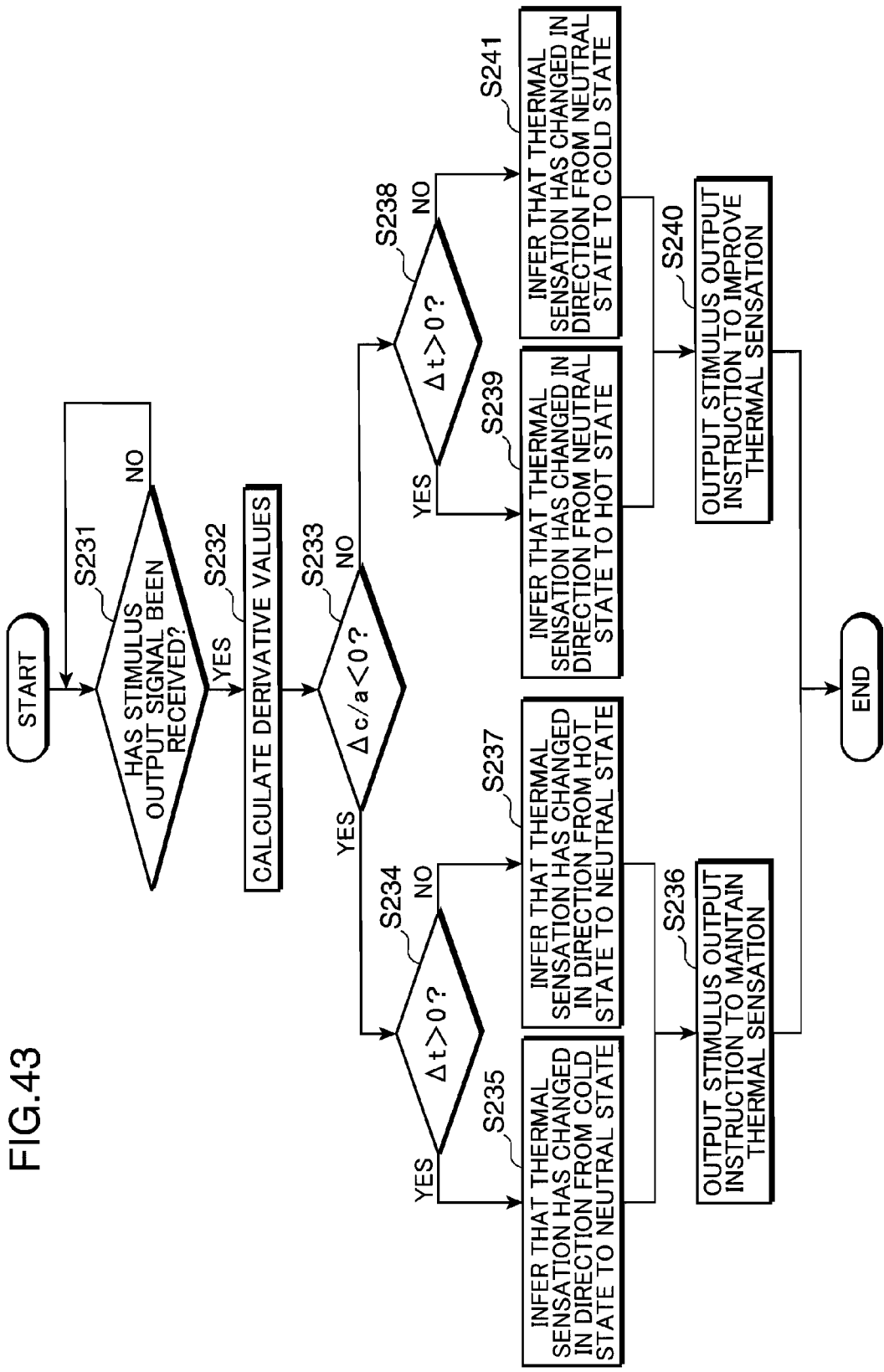
FIG. 43 is a flowchart detailing the processing by a parameter variance determining portion according to the twelfth embodiment of the invention.

The processing to infer a thermal sensation of the user and the processing to determine the content of stimulus by the parameter variance determining portion 303 will now be described. FIG. 43 is a flowchart detailing the processing by the parameter variance determining portion 303 according to the twelfth embodiment of the invention.

Initially, the parameter variance determining portion 303 determines whether it has received a stimulus output signal from the stimulus output portion 305 (Step S231). In a case where it has not received the stimulus output signal from the stimulus output portion 305 (NO in Step S231), the processing in Step S231 is repetitively performed at specific timing until the stimulus output signal is received. Upon receipt of the stimulus output signal from the stimulus output portion 305 (YES in Step S231), the parameter variance determining portion 303 calculates a derivative value $\Delta c/a$ on the basis of the ratio of waveform components, c/a, immediately before the reception of the stimulus output signal and the ratio of waveform components, c/a, immediately after the reception among the ratios of waveform components, c/a, extracted by the parameter extracting portion 302, and calculates a derivative value $\Delta t$ on the basis of the temperature data t immediately before the reception of the stimulus output signal and the temperature data t immediately after the reception among the temperature data t received from the temperature measuring portion 308 (Step S232).

Subsequently, the parameter variance determining portion 303 determines whether the derivative value $\Delta c/a$ of the ratio of waveform components is negative (Step S233). In a case where the derivative value $\Delta c/a$ is negative (YES in Step S233), the parameter variance determining portion 303 further determines whether the derivative value $\Delta t$ of the temperature data is positive (Step S234). In a case where the parameter variance determining portion 303 determines that the derivative value $\Delta t$ is positive (YES in Step 234), it infers that a thermal sensation of the user has changed in a direction from a cold state to the neutral state where it is neither hot nor cold, that is, a thermal sensation has improved (Step S235). Subsequently, the parameter variance determining portion 303 outputs a stimulus output instruction to maintain a thermal sensation (Step S236).

Meanwhile, in a case where the derivative value $\Delta t$ is equal to 0 or smaller (NO in Step S234), the parameter variance determining portion 303 infers that a thermal sensation of the user has changed in a direction from a hot state to the neutral state where it is neither hot nor cold, that is, a thermal sensation has improved (Step S237). Subsequently, the parameter variance determining portion 303 outputs a stimulus output instruction to maintain a thermal sensation (Step S236).

Meanwhile, in a case where the derivative value $\Delta c/a$ is not negative (NO in Step S233), the parameter variance determining portion 303 determines whether the derivative value $\Delta t$ of the temperature data is positive (Step S238). In a case where the parameter variance determining portion 303 determines that the derivative value ($\Delta t$) is positive (YES in Step S238), it infers that a thermal sensation of the user has changed in a direction from the neutral state where it is neither hot nor cold to a hot state, that is, a thermal sensation has deteriorated (Step S239). Subsequently, the parameter variance determining portion 303 outputs a stimulus output instruction to improve a thermal sensation, for example, to give a cool stimulus (Step S240).

Meanwhile, in a case where the derivative value $\Delta t$ is negative (NO in Step S238), the parameter variance determining portion 303 infers that a thermal sensation of the user has changed in a direction from the neutral state where it is neither hot nor cold to a cold state, that is, a thermal sensation has deteriorated (Step S241). Subsequently, the parameter variance determining portion 303 outputs a stimulus output instruction to improve a thermal sensation, for example, to give a warm stimulus (Step S240).

As has been described, according to the environment control system of the twelfth embodiment, because a thermal sensation of the user is inferred on the basis of the derivative value $\Delta c/a$ of the ratio of waveform components of the accelerated pulse wave and the derivative value ($\Delta t$) of the temperature at a location where the user is in, it is possible to infer a thermal sensation of the user at a higher degree of accuracy.

In this embodiment, it may be configured in such a manner that the parameter variance determining portion 303 determines whether the derivative value $\Delta c/a$ of the ratio of waveform components falls within a pre-determined particular range (for example, from −0.01 to 0.01) immediately before it determines whether the derivative value $\Delta c/a$ of the ratio waveform components is negative in Step S233, so that in a case where the derivative value $\Delta c/a$ falls within the particular range, it determines that a thermal sensation of the user has hardly changed and outputs a stimulus output instruction to continue to output or stop outputting a stimulus of the current content. Also, it may be configured in such a manner that the parameter variance determining portion 303 determines whether the derivative value $\Delta t$ of the temperature data falls within a pre-determined particular range (for example, from −0.3 to 0.3) immediately before it determines whether the derivative value $\Delta t$ of the temperature data is positive in Step 234 or Step S238, so that in a case where the derivative value $\Delta t$ falls within the particular range, it determines that the temperature data has hardly changed and outputs a stimulus output instruction to continue to output or stop outputting a stimulus of the current content.

In this embodiment, the content of stimulus determined by the parameter variance determining portion 303 includes a warm or cool thermal stimulus, such as cooling and heating, an air-flow stimulus, such as cool air and warm air, the strength of stimulus, a stimulus giving time, and so forth.

In this embodiment, the parameter variance determining portion 303 calculates the derivative value $\Delta c/a$ on the basis of the ratio of waveform components, c/a, immediately after the output of a stimulus from the stimulus output portion 305 and the ratio of waveform components, c/a, immediately before the output, and calculates the derivative value $\Delta t$ on the basis of the temperature data t immediately after the output of a stimulus from the stimulus output portion 305 and the temperature data t immediately before the output, so that it infers a thermal sensation of the user using these derivative values ($\Delta c/a$ and $\Delta t$). The invention, however, is not limited to this configuration, and a difference between the ratio of waveform components, c/a, immediately before the output and the ratio of waveform components, c/a, immediately after the output may be calculated, so that a thermal sensation of the user is inferred on the basis of the difference, and a difference between the temperature data t immediately before the output and the temperature data t immediately after the output may be calculated, so that a thermal sensation of the user is inferred on the basis of the difference.

Alternatively, the parameter variance determining portion 303 may calculate a derivative value Δc/a or a difference of the ratios of waveform components on the basis of the average value of plural ratios of waveform components, c/a, extracted over a specific period in the past since the reception of the stimulus output signal and the ratio of waveform components immediately after the reception of the stimulus output signal, so that it infers a thermal sensation of the user on the basis of the result of calculation. Further, the parameter variance determining portion 303 may infer a thermal sensation of the user using the average value of differences between the ratios of waveform components, one ahead of the other in time series, among plural ratios of waveform components extracted over a specific period in the past since the reception of the stimulus output signal.

Also, the parameter variance determining portion 303 may calculate a derivative value Δt or a difference of temperature data on the basis of the average value of plural items of the temperature data t extracted over a specific period in the past since the reception of the stimulus output signal and the temperature data t immediately after the reception of the stimulus output signal, so that it infers a thermal sensation of the user on the basis of the result of calculation. Further, the parameter variance determining portion 303 may calculate a derivative value Δt or a difference of temperature data on the basis of the average value of differences between two items of the temperature data, one ahead of the other in time series, among plural items of the temperature data extracted over a specific period in the past since the reception of the stimulus output signal and the ratio of waveform components immediately after the reception of the stimulus output signal, so that it infers a thermal sensation of the user on the basis of the result of calculation.

In this embodiment, the stimulus output portion 305 outputs the stimulus output signal indicating that it has outputted a stimulus to the parameter variance determining portion 303, and the parameter variance determining portion 303 calculates the derivative value of the ratio of waveform components and the derivative value of the temperature data using those immediately before and after the reception of the stimulus output signal. The invention, however, is not particularly limited to this configuration. It may be configured in such a manner that the stimulus output portion 305 does not output the stimulus output signal, and instead, the parameter variance determining portion 303 is provided with a timer portion that measures a time, so that it calculates the derivative value of the ratios of the waveform components and the derivative value of the temperature data using those immediately before and after the elapse of a specific time or immediately before and after the elapse of a stimulus giving time included in the content of stimulus.

Alternatively, rates of change of the ratio of waveform components and the temperature data over a specific time may be used as the derivative values. Further, the timer portion that measures a time may be separated from the parameter variance determining portion 303 as an independent component and the timer portion is connected to the parameter variance determining portion 303 to enable mutual communications, so that the timer portion transmits the start of time measurement and an elapse of time to the parameter variance determining portion 303.

Also, in this embodiment, the temperature measuring portion 308 is configured in such a manner that it never fails to measure the temperature immediately after the reception of the stimulus output signal that the stimulus output portion 305 outputs when it outputs a stimulus. The invention, however, is not limited to this configuration, and it is possible to adopt a method by which the temperature measuring portion 308 does not receive the stimulus output signal that the stimulus output portion 305 outputs when it outputs a stimulus, and instead, it measures the temperature in response to a request from the parameter variance determining portion 303.

The temperature data is accumulated in the parameter variance determining portion 303. However, it is possible to adopt method by which the temperature measuring portion 308 accumulates the temperature data and transmits the temperature data in response to a request from the parameter variance determining portion 303.

Alternatively, it is possible to adopt a method by which the temperature measuring portion 308 accumulates the temperature data therein and calculates the derivative value in response to a request from the parameter variance determining portion 303 to transmit the result of calculation to the parameter variance determining portion 303. The temperature may be measured and the derivative value may be calculated upon receipt of a message informing an elapse of a given time from a timer portion, which is provided apart from the temperature measuring portion 308 to measure a time. In addition, in this embodiment, the result of inference of a thermal sensation of the user may be presented to the user by displaying the result on a display portion, such as a monitor.

Thirteenth Embodiment

Figure 44:
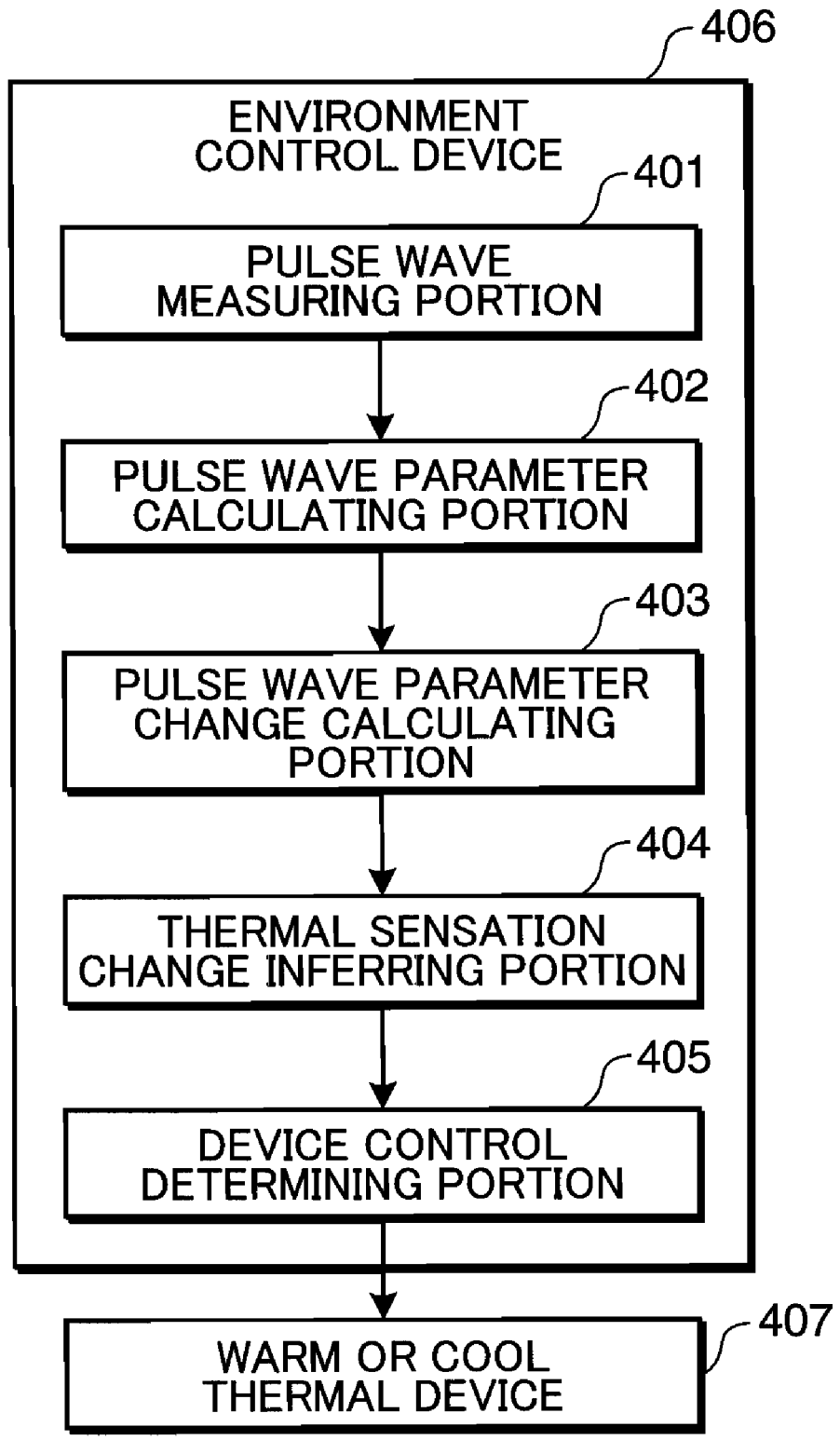
FIG. 44 is a block diagram showing the configuration of an environment control device according to a thirteenth embodiment of the invention.

FIG. 44 is a block diagram showing the configuration of an environment control device according to a thirteenth embodiment of the invention. Referring to FIG. 44, an environment control device 406 includes a pulse wave measuring portion 401, a pulse wave parameter calculating portion 402, a pulse wave parameter change calculating portion 403, a thermal sensation change inferring portion 404, and a device control determining portion 405.

The pulse wave measuring portion 401 measures the pulse wave of the user. The pulse wave parameter calculating portion 402 calculates a pulse wave parameter indicating the characteristic of the pulse wave waveform from the pulse wave data measured by the pulse wave measuring portion 401. The pulse wave parameter change calculating portion 403 calculates a change with time of the value of the pulse wave parameter calculated by the pulse wave parameter calculating portion 402. The thermal sensation change inferring portion 404 infers a change of a thermal sensation of the user on the basis of a change of the pulse wave parameter calculated by the pulse wave parameter change calculating portion 403. The device control determining portion 405 determines the content of control of a warm or cool thermal device 407 on the basis of the result of inference of a change of a thermal sensation of the user made by the thermal sensation change inferring portion 404. The warm or cool thermal device 407 is, for example, an air conditioner, a floor heating system, an electric carpet, a car air conditioner, and a seat heater, and it outputs a warm or cool thermal stimulus to the user.

By running an environment control program of the invention pre-installed in the computer, the central processing unit (CPU) functions as the pulse wave measuring portion 401, the pulse wave parameter calculating portion 402, the pulse wave parameter change calculating portion 403, the thermal sensation change inferring portion 404, and the device control determining portion 405.

The environment control processing by the environment control device shown in FIG. 44 will now be described. FIG.

45 is a flowchart detailing the flow of environment control processing by the environment control device shown in FIG. 44.

Initially, the pulse wave measuring portion 401 acquires time-series data of the pulse wave by measuring the pulse wave (Step S251). For example, the pulse wave measuring portion 401 acquires the time-series data of the pulse wave by irradiating near-infrared light from a light emitting element to the skin surface of the fingers or the earlobe of the user and receiving transmitted or reflected light by a light receiving element to detect a change in amount of blood flow by converting a change of the received light into an electric signal.

Subsequently, the pulse wave parameter calculating portion 402 calculates an accelerated pulse wave waveform parameter obtained by second-order differentiation of the time-series data of the pulse wave measured by the pulse wave measuring portion 401, or a recurrence plot draw white rate (hereinafter, referred to as RP-dw), which is a numerical value indicating a proportion of white in a recurrence plot to obtain a visible form of an unsteady property of an attractor obtained by embedding the time-series data of the pulse wave into the delay coordinate system according to the Takens embedding theorem (Step S252). The accelerated pulse wave waveform parameter or RP-dw is the pulse wave parameter.

Subsequently, the pulse wave parameter change calculating portion 403 calculates a change with time of the value of a pulse wave parameter over a specific time by subtracting the value of an accelerated pulse wave waveform parameter or RP-dw before the pre-set specific time from the value of the accelerated pulse wave waveform parameter or RP-dw calculated by the pulse wave parameter calculating portion 402 (Step S253).

Subsequently, the thermal sensation change inferring portion 404 infers a change of a thermal sensation of the user on the basis of a change with time of the value of the pulse wave parameter over the specific time that is calculated by the pulse wave parameter change calculating portion 403 (Step S254). A method for inferring a change of a thermal sensation will be described below.

Subsequently, the device control determining portion 405 determines the content of control of the warm or cool thermal device 407 on the basis of the result of inference of a change of a thermal sensation of the user made by the thermal sensation change inferring portion 404 (Step S255). For example, in a case where the result of inference of a change of a thermal sensation shows "warm or coolness feeling decreased", the device control determining portion 405 determines the content of control of the warm or cool thermal device 407 to be such that increases a thermal sensation. In a case where the result of inference of a change of a thermal sensation shows "thermal sensation increased", the device control determining portion 405 determines the content of control of the warm or cool thermal device 407 to be such that decreases a thermal sensation. The device control determining portion 405 then outputs the content of control to the warm or cool thermal device 407 (Step S256).

Figure 46:
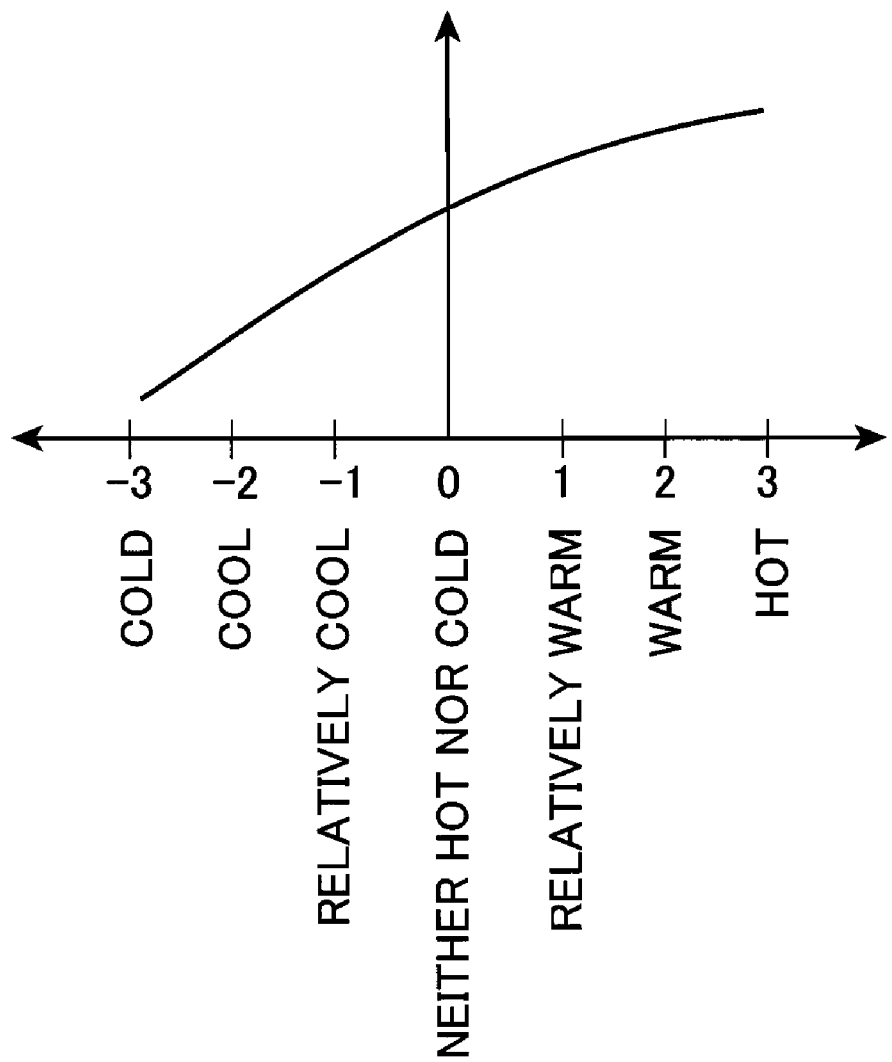
FIG. 46 is a graph indicating a correlation of the ratio of waveform components of the accelerated pulse wave, the accelerated pulse wave amplitude, or RP-dw with respect to a thermal sensation of the user.
Figure 47:
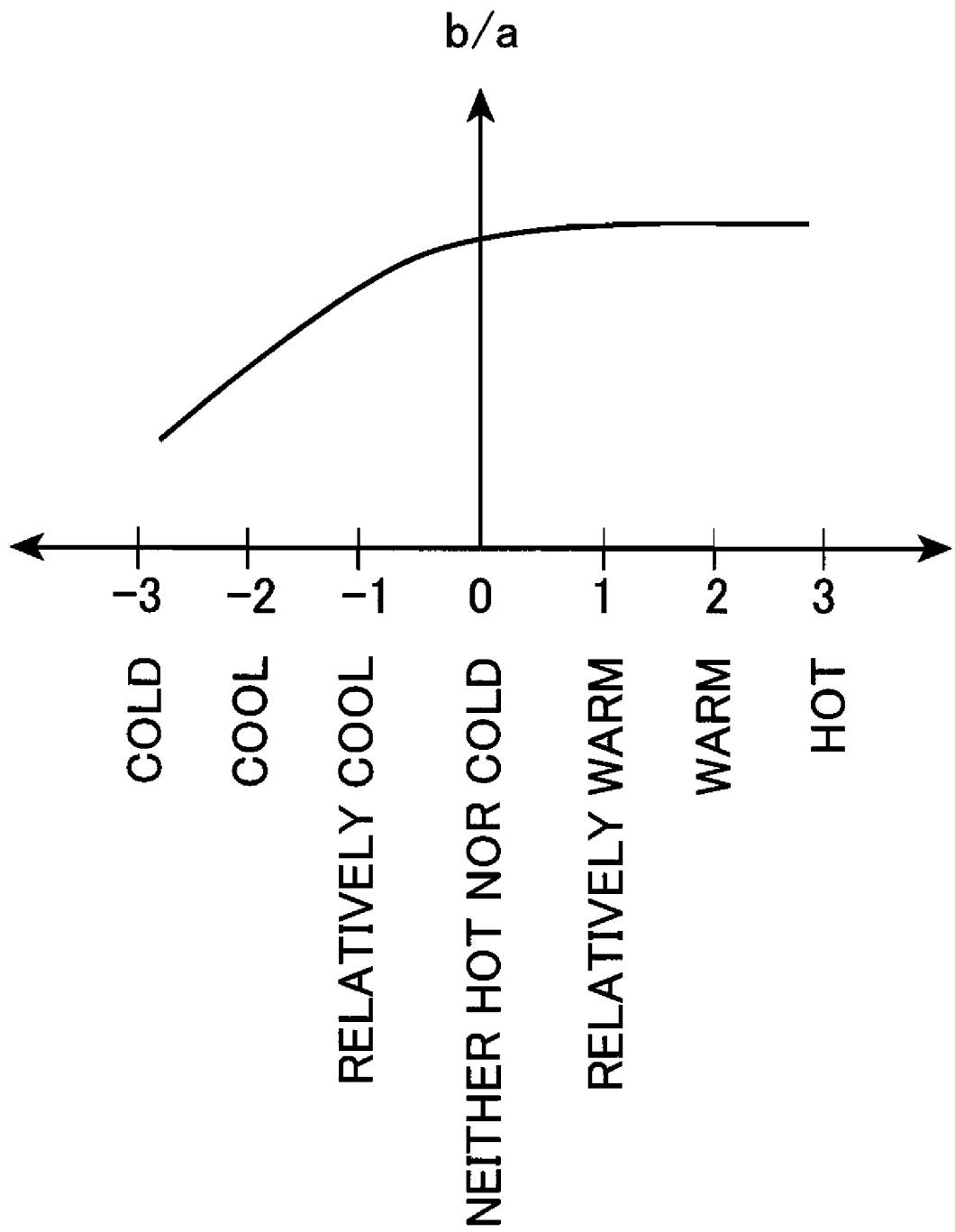
FIG. 47 is a graph indicating a correlation between the ratio of waveform components of the accelerated pulse wave and a thermal sensation of the user discovered by the inventors from the test conducted on subjects.

The processing to infer a change of a thermal sensation of the user in Step S254 shown in FIG. 45 will now be described. The inventors discovered the presence of a high correlation between respective variances of the ratio of waveform components of the accelerated pulse wave, d/a, the accelerated pulse wave amplitude, or RP-dw and a variance of a thermal sensation of the user. FIG. 46 is a graph indicating a correlation between the ratio of waveform components of the accelerated pulse wave, d/a, the accelerated pulse wave amplitude, or RP-dw and a thermal sensation of the user discovered by the inventors from the test conducted on subjects. FIG. 47 is a graph indicating a correlation between the ratio of waveform components of the accelerated pulse wave, b/a, and a thermal sensation of the user discovered by the inventors from the test conducted on subjects.

In FIG. 46, the abscissa is used for a thermal sensation of the user and the ordinate is used for the ratio of waveform components of the accelerated pulse wave, d/a, the accelerated pulse wave amplitude, or RP-dw. In FIG. 47, the abscissa is used for a thermal sensation of the user and the ordinate is used for the ratio of waveform components of the accelerated pulse wave, b/a. As are indicated by these graphs, in a case where a thermal sensation of the user has increased, that is, a thermal sensation has changed in a direction from a cold state to the neutral state where it is neither hot nor cold or in a direction from the neutral state where is neither hot nor cold to a hot state, the ratio of waveform components of the accelerated pulse wave, b/a or d/a, the accelerated pulse wave amplitude, or RP-dw increases. In a case where a thermal sensation of the user has decreased, that is, in a case where a thermal sensation has changed in a direction from a hot state to the neutral state where it is neither hot nor cold or in a direction from the neutral state where it is neither hot nor cold to a cold state, the ratio of waveform components of the accelerated pulse wave, b/a or d/a, the accelerated pulse wave amplitude, or RP-dw decreases. The inventors discovered the presence of the correlation as descried above between the ratio of waveform components of the accelerated pulse wave, b/a or d/a, the accelerated pulse wave amplitude, or RP-dw and a thermal sensation.

It is therefore possible to infer a change of a thermal sensation of the user when a change of the ratio of waveform components of the accelerated pulse wave, b/a or d/a, the accelerated pulse wave amplitude, or RP-dw is known. For one pulse wave parameter (hereinafter, referred to as the ratio of waveform components of the accelerated pulse wave, d/a) among the ratios of waveform components of the accelerated pulse wave, b/a and d/a, the accelerated pulse wave amplitude, and RP-dw, the thermal sensation change inferring portion 404 holds therein in advance the correlation between a change thereof and a change of a thermal sensation of the user.

Figure 48:
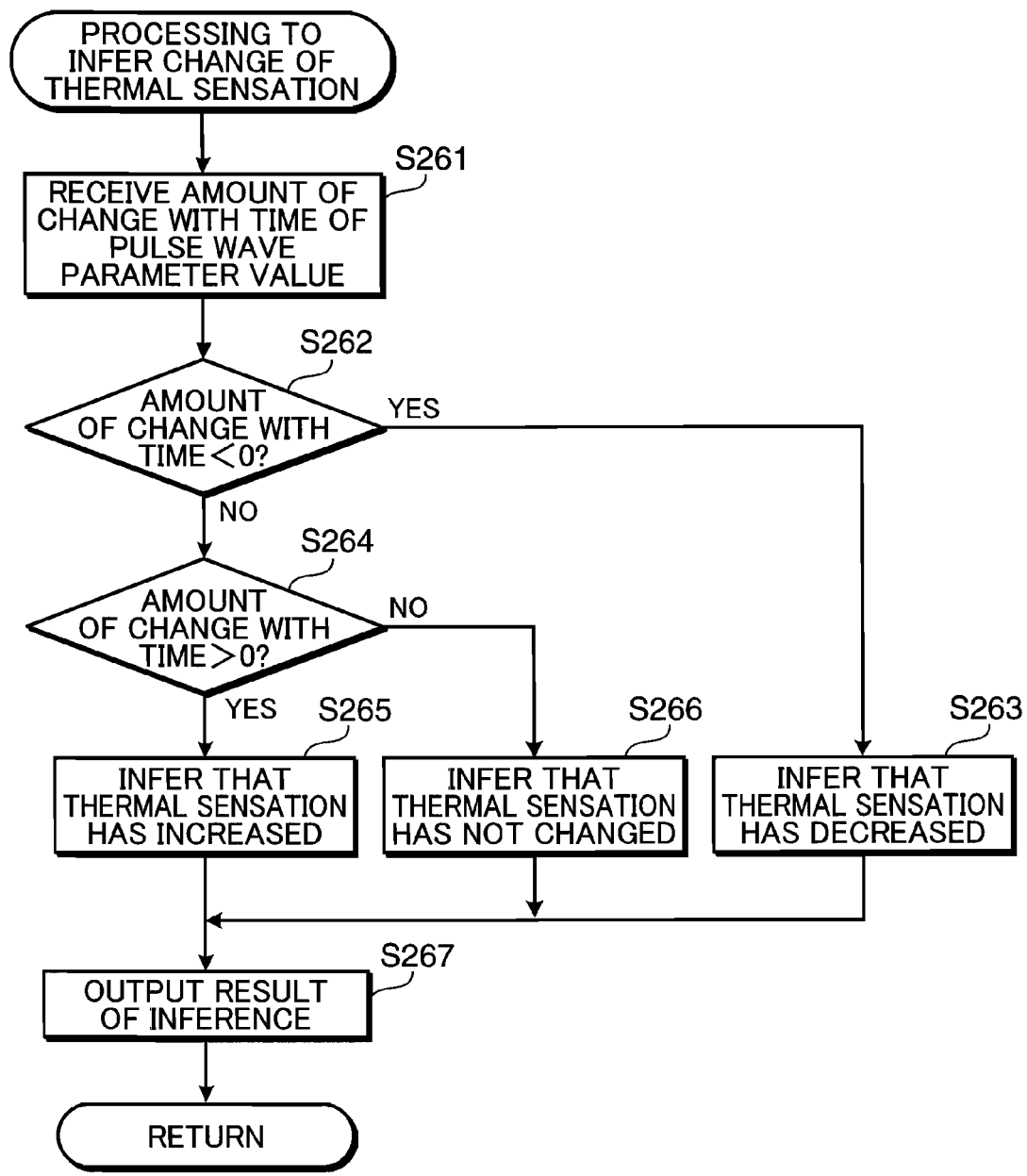
FIG. 48 is a flowchart detailing the processing to infer a change of a thermal sensation by a thermal sensation change inferring portion in the thirteenth embodiment.

FIG. 48 is a flowchart detailing the processing to infer a change of a thermal sensation by the thermal sensation change inferring portion 404 of the thirteenth embodiment. Initially, the thermal sensation change inferring portion 404 receives an amount of change with time within a specific time of the ratio of waveform components of the accelerated pulse wave, d/a, from the pulse wave parameter change calculating portion 403 (Step S261). Subsequently, the thermal sensation change inferring portion 404 determines whether the amount of change with time of the pulse wave parameter is smaller than 0 (Step S262). In short, the thermal sensation change inferring portion 404 determines whether the ratio of waveform components of the accelerated pulse wave, d/a, has decreased.

In a case where it is determined that the amount of change with time of the pulse wave parameter is smaller than 0, that is, in a case where it is determined that the ratio of waveform components of the accelerated pulse wave, d/a, has decreased (YES in Step S262), the thermal sensation change inferring portion 404 infers that a thermal sensation of the user has decreased (Step S263). Meanwhile, in a case where it is determined that the amount of change with time is equal to 0 or greater (NO in Step S262), the thermal sensation change inferring portion 404 determines whether the amount of change with time of the pulse wave parameter is greater than 0 (Step S264). In short, the thermal sensation change inferring portion 404 determines whether the ratio of waveform components of the accelerated pulse wave, d/a, has increased.

In a case where it is determined that the change with time of the pulse wave parameter is greater than 0, that is, in a case where it is determined that the ratio of waveform components of the accelerated pulse wave, d/a, has increased (YES in Step S264), the thermal sensation change inferring portion 404 infers that a thermal sensation of the user has increased (Step S265). Meanwhile, in a case where it is determined that the amount of change with time of the pulse wave parameter is not greater than 0, that is, in a case where it is determined that the amount of change with time is 0 and the ratio of waveform components of the accelerated pulse wave, d/a, has not changed (NO in Step S264), the thermal sensation change inferring portion 404 infers that a thermal sensation of the user has not changed (Step S266). Subsequently, the thermal sensation change inferring portion 404 outputs the result of inference to the device control determining portion 405 (Step S267).

According to the configuration above, by making an inference as to whether a thermal sensation of the user has increased, whether a thermal sensation of the user has decreased, or whether a thermal sensation of the user has not changed on the basis of one parameter among the ratios of waveform components of the accelerated pulse wave, b/a and d/a, the accelerated pulse wave amplitude, and RP-dw, the thermal sensation change inferring portion 404 becomes able to infer a change of a thermal sensation of the user without using the absolute value of the pulse wave parameter that differs from individual to individual. It is thus possible to control the warm or cool thermal device 407 forming the residential environment, such as an air conditioning device, appropriately on the basis of a thermal sensation of the user.

A first modification of this embodiment will now be described. In the embodiment described above, in Step S262 and Step S264 in FIG. 48, a thermal sensation of the user is inferred according to whether an amount of change with time of the value of the pulse wave parameter is negative, 0 or positive. On the contrary, in the first modification of this embodiment, threshold values L1 and L2 (L1<L2) are set, and a change of a thermal sensation of the user is inferred by comparing the amount of change with time with the threshold values L1 and L2.

Figure 49:
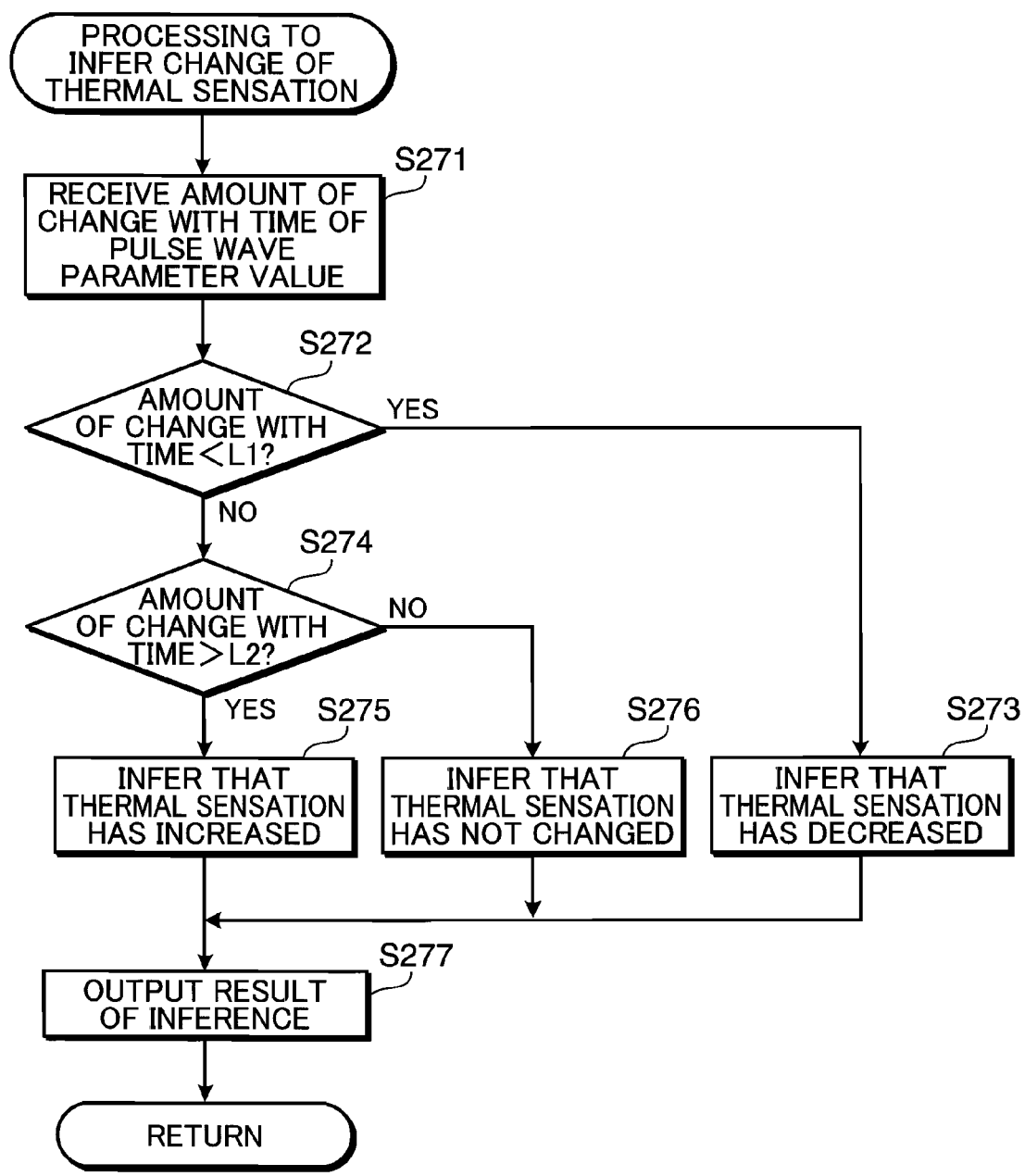
FIG. 49 is a flowchart detailing the processing to infer a change of a thermal sensation by a thermal sensation change inferring portion according to a first modification of the thirteenth embodiment.

FIG. 49 is a flowchart detailing the processing to infer a change of a thermal sensation by the thermal sensation change inferring portion 404 according to the first modification of the thirteenth embodiment. Because the processing in Steps S271, S273, S275, S276, and S277 shown in FIG. 49 is the same as the processing in Steps S261, S263, S265, S266, and S267 shown in FIG. 48, respectively, detailed descriptions of these steps are omitted, and descriptions will be given chiefly to the processing in Steps S272 and S274, which are different from the counterparts in FIG. 48.

In Step S272, the thermal sensation change inferring portion 404 determines whether the amount of change with time of the pulse wave parameter is smaller than the threshold value L1. In short, the thermal sensation change inferring portion 404 determines whether the ratio of waveform components of the accelerated pulse wave, d/a, has substantially decreased.

In a case where it is determined that the amount of change with time of the pulse wave parameter is smaller than the threshold value L1, that is, in a case where it is determined that the ratio of waveform components of the accelerated pulse wave, d/a, has substantially decreased (YES in Step S272), the thermal sensation change inferring portion 404 infers that a thermal sensation of the user has decreased (Step S273). Meanwhile, in a case where it is determined that the amount of change with time is equal to the threshold value L1 or greater (NO in Step S272), the thermal sensation change inferring portion 404 determines whether the amount of change with time of the pulse wave parameter is greater than the threshold value L2 that is greater than the threshold value L1 (Step S274). In short, the thermal sensation change inferring portion 404 determines whether the ratio of waveform components of the accelerated pulse wave, d/a, has substantially increased.

In a case where it is determined that the amount of change with time of the pulse wave parameter is greater than the threshold value L2, that is, in a case where it is determined that the ratio of waveform components of the accelerated pulse wave, d/a, has substantially increased (YES in Step S274), the thermal sensation change inferring portion 404 infers that a thermal sensation of the user has increased (Step S275). Meanwhile, in a case where it is determined that the amount of change with time of the pulse wave parameter is in a range from the threshold value L1 to the threshold value L2, both inclusive, that is, in a case where it is determined that the ratio of waveform components of the accelerated pulse wave, d/a, has not substantially changed (NO in Step S274), the thermal sensation change inferring portion 404 infers that a thermal sensation of the user has not changed (Step S276).

Figure 50:
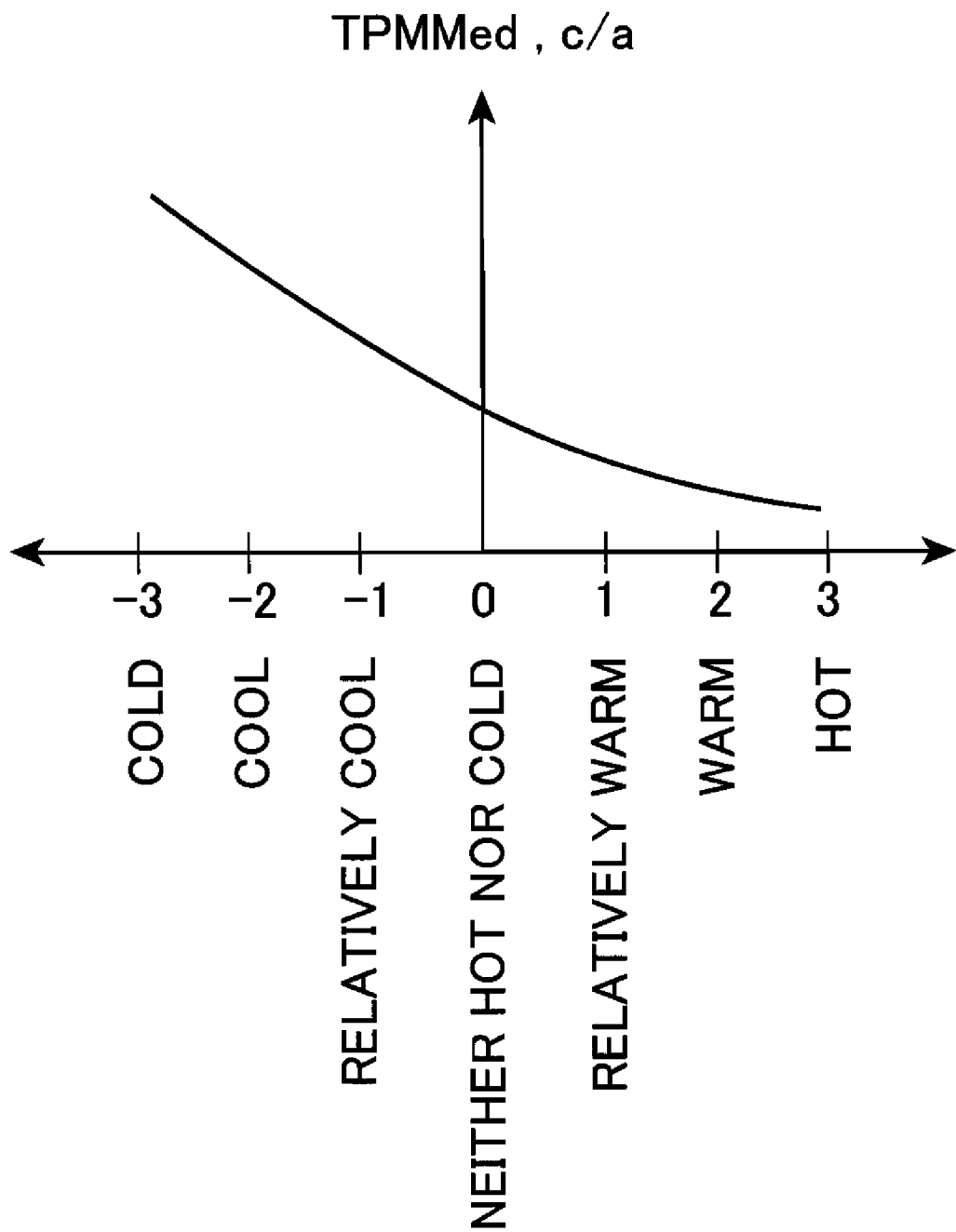
FIG. 50 is a graph indicating a correlation between the median value of trajectory parallel measure and a thermal sensation of the user discovered by the inventors from the test conducted on the subjects.

A second modification of this embodiment will now be described. Regarding the processing to infer a change of a thermal sensation of the user in Step S254 shown in FIG. 45, the inventors also discovered the presence of a high correlation between a variance of the median value of trajectory parallel measure (TPMMed) known as a chaos statistics value, which is used as the pulse wave parameter, and a variance of a thermal sensation of the user. FIG. 50 is a graph indicating a correlation between the median value of trajectory parallel measure and a thermal sensation of the user discovered by the inventors from the test conducted on subjects.

In FIG. 50, the abscissa is used for a thermal sensation of the user and the ordinate is used for the median value of trajectory parallel measure. As is indicated by this graph, the median value of trajectory parallel measure decreases in a case where a thermal sensation of the user has increased, that is, in a case where it has changed in a direction from a cold state to the neutral state where it is neither hot nor cold or in a direction from the neutral state where it is neither hot nor cold to a hot state. The median value of trajectory parallel measure increases in a case where a thermal sensation of the user has decreased, that is, in a case where it has changed in a direction from a hot state to the neutral state where it is neither hot nor cold or in a direction from the neutral direction where it is neither hot nor cold to a cold state. The inventors discovered that the presence of the correlation as described above between the median value of trajectory parallel measure and a thermal sensation.

It is therefore possible to infer a change of a thermal sensation of the user when a change of the medium value of trajectory parallel measure is known. For the median value of trajectory parallel measure described above, the thermal sensation change inferring portion 404 holds therein in advance the correlation between a change thereof and a change of a thermal sensation of the user.

Figure 51:
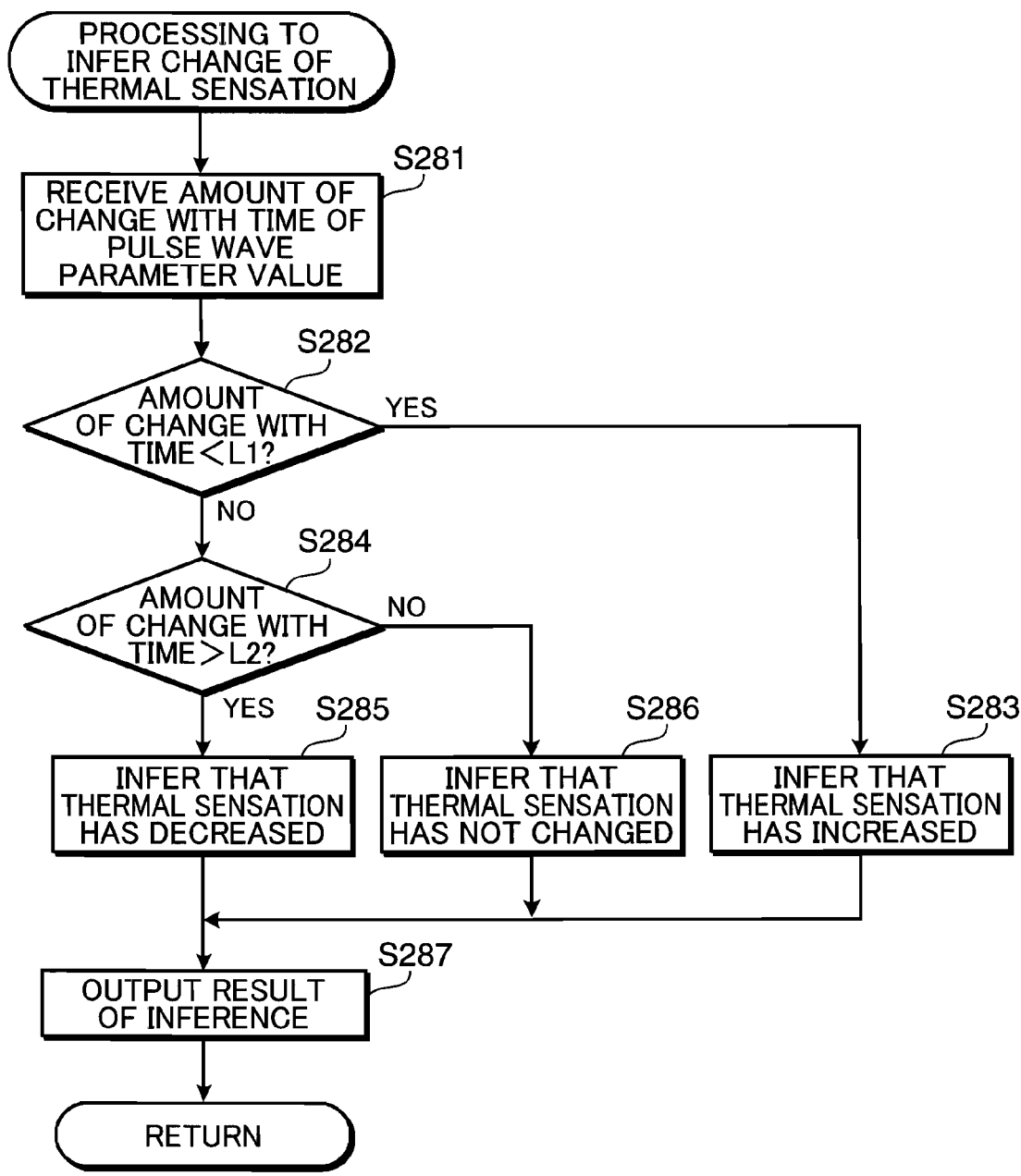
FIG. 51 is a flowchart detailing the processing to infer a change of a thermal sensation by a thermal sensation change inferring portion according to a second modification of the thirteenth embodiment.

FIG. 51 is a flowchart detailing the processing to infer a change of a thermal sensation by the thermal sensation change inferring portion 404 according to the second modification of the thirteenth embodiment. Initially, the thermal sensation change inferring portion 404 receives an amount of change with time within a specific time of the median value of trajectory parallel measure from the pulse parameter change calculating portion 403 (Step S281). Subsequently, the thermal sensation change inferring portion 404 determines whether the amount of change with time of the pulse wave parameter is smaller than the threshold value L1 (Step S282). In short, the thermal sensation change inferring portion 404 determines whether the median value of trajectory parallel measure has substantially decreased.

In a case where it is determined that the amount of change with time is smaller than the pre-set threshold value L1, that is, in a case where it is determined that the median value of trajectory parallel measure has substantially decreased (YES in Step S282), the thermal sensation change inferring portion 404 infers that a thermal sensation of the user has increased (Step S283). Meanwhile, in a case where it is determined that the amount of change with time is equal to the threshold value L1 or greater (NO in Step S282), the thermal sensation change inferring portion 404 determines whether the amount of change with time of the pulse wave parameter is greater than the threshold value L2 that is greater than the threshold value L1 (Step S284). In short, the thermal sensation change inferring portion 404 determines whether the median value of trajectory parallel measure has substantially increased.

In a case where it is determined that the amount of change with time is greater than the pre-set threshold value L2, that is, in a case where it is determined that the median value of trajectory parallel measure has substantially increased (YES in Step S284), the thermal sensation change inferring portion 404 infers that a thermal sensation of the user has decreased (Step S285). Meanwhile, in a case where the amount of change with time is in a range from the threshold value L1 to the threshold value L2, both inclusive, that is, in a case where it is determined that the median value of trajectory parallel measure has not substantially changed (NO in Step S284), the thermal sensation change inferring portion 404 infers that a thermal sensation of the user has not changed (Step S286). Subsequently, the thermal sensation change inferring portion 404 outputs the result of inference to the device control determining portion 405 (Step S287).

Regarding the ratio of waveform components of the accelerated pulse wave, c/a, FIG. 33 of the ninth embodiment shows a graph drawn by finding a quadratic correlation with respect to a thermal sensation of the user set on the abscissa. When this graph is replaced by a linear correlation, it can be deemed as a relation same as the correlation with the median value of trajectory parallel measure (TPMMed) shown in FIG. 50 in which the ratio of waveform components of the accelerated pulse wave, c/a, decreases when a thermal sensation of the user increases and the ratio of waveform components of the accelerated pulse wave, c/a, increases when a thermal sensation of the user decreases. Hence, the processing according to the second modification of this embodiment may be performed as well using an amount of change with time of the ratio of waveform components of the accelerated pulse wave, c/a.

According to this configuration, by making an inference as to whether a thermal sensation of the user has increased, whether a thermal sensation of the user has decreased, or whether a thermal sensation of the user has not changed on the basis of a change of the median value of trajectory parallel measure, the thermal sensation change inferring portion 404 becomes able to infer a change of a thermal sensation of the user without using the absolute value of the pulse wave parameter that differs from individual to individual. It is thus possible to control the warm or cool thermal device 407 forming the residential environment, such as an air conditioning device, appropriately on the basis of a thermal sensation of the user.

Fourteenth Embodiment

Figure 52:
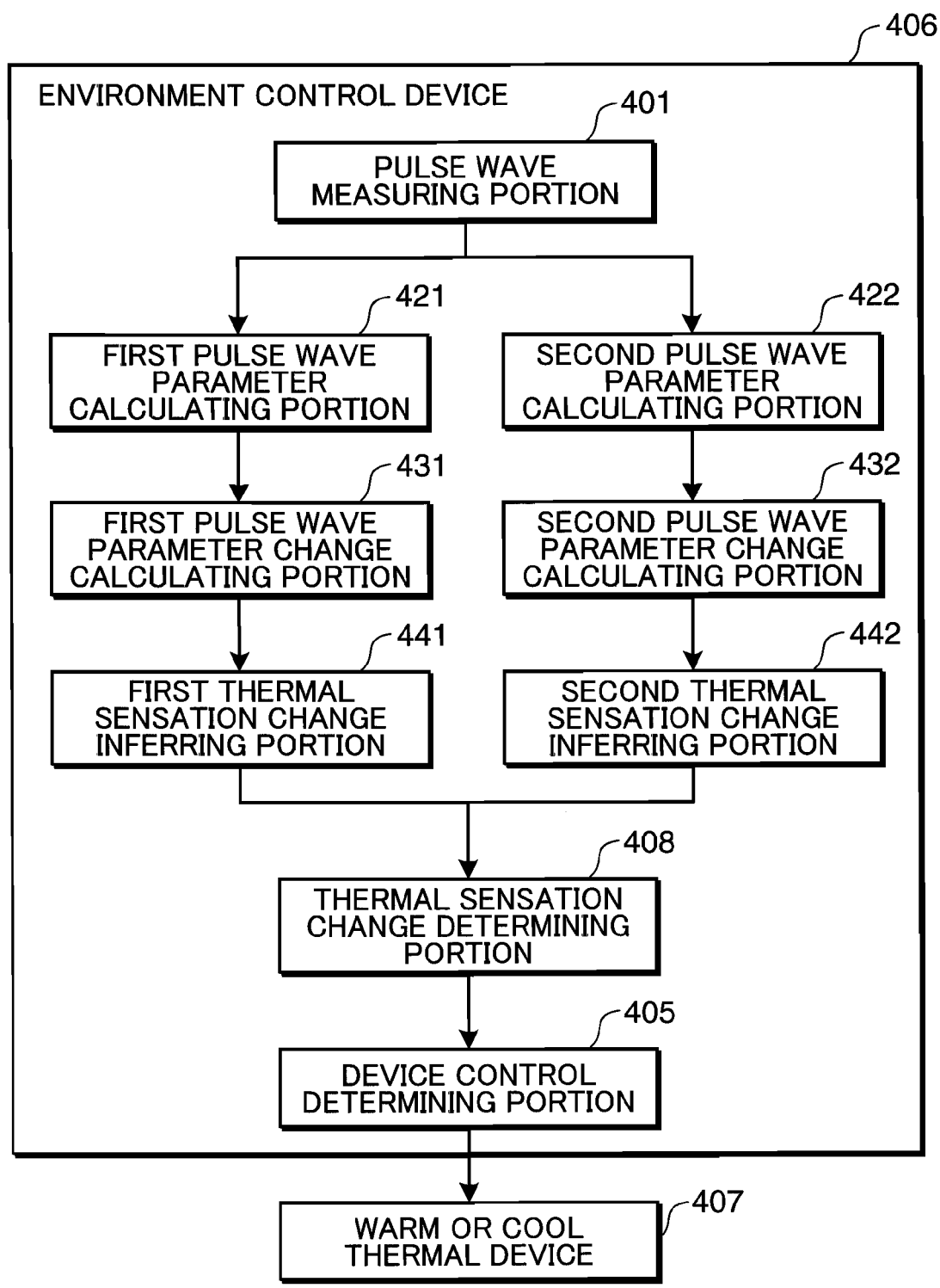
FIG. 52 is a block diagram showing the configuration of an environment control device according to a fourteenth embodiment of the invention.

FIG. 52 is a block diagram showing the configuration of an environment control device according to a fourteenth embodiment of the invention. In FIG. 52, components same as those in FIG. 44 are labeled with the same reference numerals and descriptions of these components are omitted.

Referring to FIG. 52, differences from FIG. 44 of the thirteenth embodiment are that the environment control device 406 includes plural sets of pulse wave parameter calculating portions 421 and 422, pulse wave parameter change calculating portion 431 and 432, and thermal sensation change inferring portions 441 and 442, and that it additionally includes a thermal sensation change determining portion 408. A set of the first pulse wave parameter calculating portion 421, the first pulse wave parameter change calculating portion 431, and the first thermal sensation change inferring portion 441, and another set of the second pulse wave parameter calculating portion 422, the second pulse wave parameter change calculating portion 432, and the second thermal sensation change inferring portion 442 calculate parameters that differ from each other among the ratios of waveform components of the accelerated pulse wave, b/a, d/c, and c/a, the accelerated pulse wave amplitude, RP-dw, and the median value of trajectory parallel measure, which were discovered by the inventors from the test conducted on subjects and described in the thirteenth embodiment, and calculate amounts of change with time. Then, they infer a change of a thermal sensation of the user simultaneously on the basis of the results of calculation of the amounts of change and the correlation between the parameters and a change of a thermal sensation of the user.

The thermal sensation change determining portion 408 determines the result of inference of a change of a thermal sensation of the user by comparing the result of inference of a change of a thermal sensation of the user made by the first pulse wave parameter calculating portion 421, the first pulse wave parameter change calculating portion 431, and the first thermal sensation change inferring portion 441 with the result of inference of a change of a thermal sensation of the user made by the second pulse wave parameter calculating portion 422, the second pulse wave parameter change calculating portion 432, and the second thermal sensation change inferring portion 442.

Figure 53:
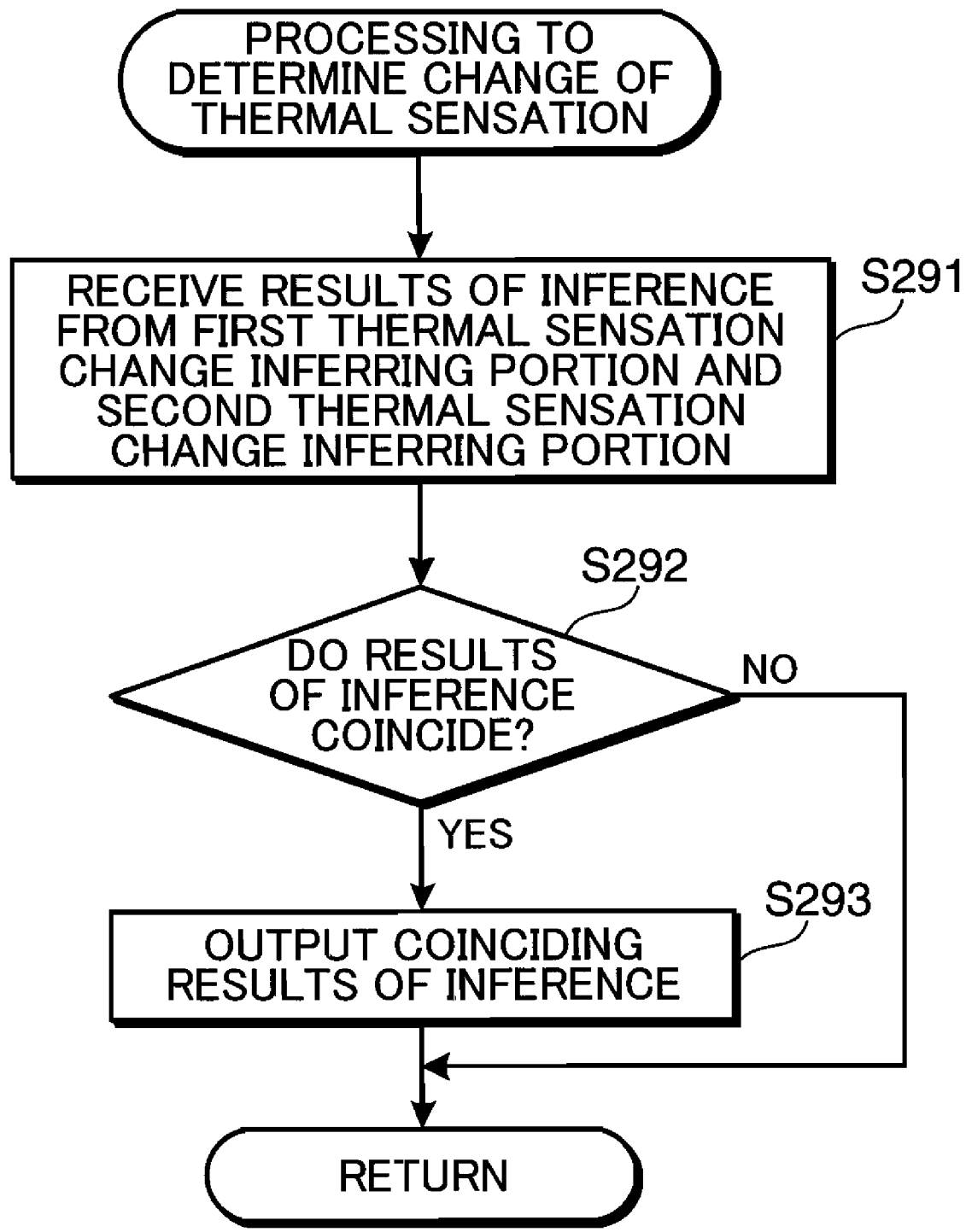
FIG. 53 is a flowchart detailing the flow of the processing to determine a change of a thermal sensation by a thermal sensation change determining portion of the fourteenth embodiment.

FIG. 53 is a flowchart detailing the flow of the processing to determine a change of a thermal sensation by the thermal sensation change determining portion 408 of the fourteenth embodiment. Initially, the thermal sensation change determining portion 408 receives the results of inference of a change of a thermal sensation of the user made on the basis of parameters that differ from each other from the first thermal sensation change inferring portion 441 and the second thermal sensation change inferring portion 442 (Step S291). Subsequently, the thermal sensation change determining portion 408 determines whether the two results of inference of a thermal sensation coincide with each other by comparing the two results of inference of a thermal sensation it has received (Step S292). In a case where it is determined that the two results of inference of a thermal sensation coincide with each other (YES in Step S292), the thermal sensation change determining portion 408 outputs the results of inference of a change of a thermal sensation that coincide with each other to the device control determining portion 405 (Step S293). Meanwhile, in a case where it is determined that the two results of inference of a thermal sensation do not coincide with each other (NO in Step S292), the thermal sensation change determining portion 408 ends the processing without outputting the results of inference of a thermal sensation to the device control determining portion 405.

Figure 45:
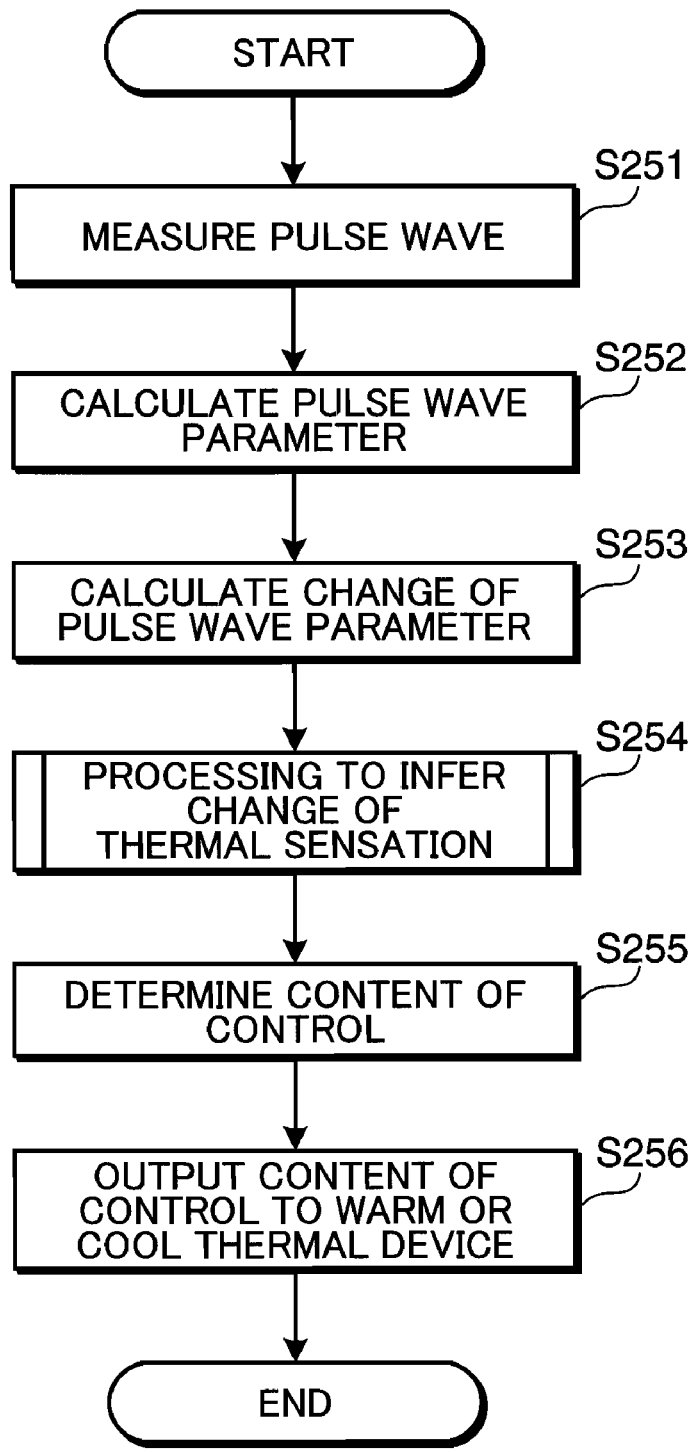
FIG. 45 is a flowchart detailing the flow of the environment control processing by the environment control device shown in FIG. 44.

Consequently, upon receipt of the results of inference of a change of a thermal sensation, the device control determining portion 405 determines the content of control of the warm or cool thermal device 407 on the basis of the results of inference of a thermal sensation it has received (Step S255 in FIG. 45). For example, in a case where the results of inference of a change of a thermal sensation indicate "a thermal sensation decreased", the device control determining portion 405 determines the content of control of the warm or cool thermal device 407 to be such that increases a thermal sensation. In a case where the results of inference of a change of a thermal sensation indicate "a thermal sensation increased", the device control determining portion 405 determines the content of control of the warm or cool thermal device 407 to be such that decreases a thermal sensation. The device control determining portion 405 then outputs the content of control to the warm or cool thermal device 407 (Step S256 in FIG. 45).

In a case where the results of inference of a change of a thermal sensation are not received from the device control determining portion 405, that is, in a case where the results of inference of a change of a thermal sensation are not outputted because the two results of inference of a thermal sensation do not coincide with each other in the thermal sensation change determining portion 408, the device control determining portion 405 determines that there is no obvious change of a thermal sensation of the user, and maintains the current content of control of the warm or cool thermal device 407.

According to this configuration, because a change of a thermal sensation of the user is inferred simultaneously on the basis of plural different pulse wave parameters and a change of a thermal sensation is determined by comparing the plural results of inference, although the pulse wave may change by an influence other than a change in the warm or cool thermal environment, it is possible to infer a change of a thermal sensation of the user in response to a change in the warm or cool thermal environment at a higher degree of accuracy. Also, the results of inference are outputted when the plural results of inference of a thermal sensation coincide with each other, and they are not outputted when they do not coincide with each other. Hence, even in a case where one pulse wave parameter has changed because of a factor other than a change in the warm or cool thermal environment, the content of control of the warm or cool thermal device 407 is not changed, which makes it possible to avoid an event that the user is made feel uncomfortable.

The environment control device of this embodiment includes two sets of the pulse wave parameter calculating portions, the pulse wave parameter change calculating portions, and the thermal sensation change inferring portions. The invention, however, is not particularly limited to this configuration, and three or more sets may be provided. In this case, each pulse wave parameter calculating portion calculates a different pulse wave parameter.

Fifteenth Embodiment

Hereinafter, a fifteenth embodiment of the invention will be described. A difference of the fifteenth embodiment from the thirteenth embodiment and the fourteenth embodiment described above is the processing by the thermal sensation change determining portion 408 in FIG. 52. Because the configuration of the environment control device of the fifteenth embodiment is the same as the configuration of the environment control device of the fourteenth embodiment, descriptions thereof are omitted.

Figure 54:
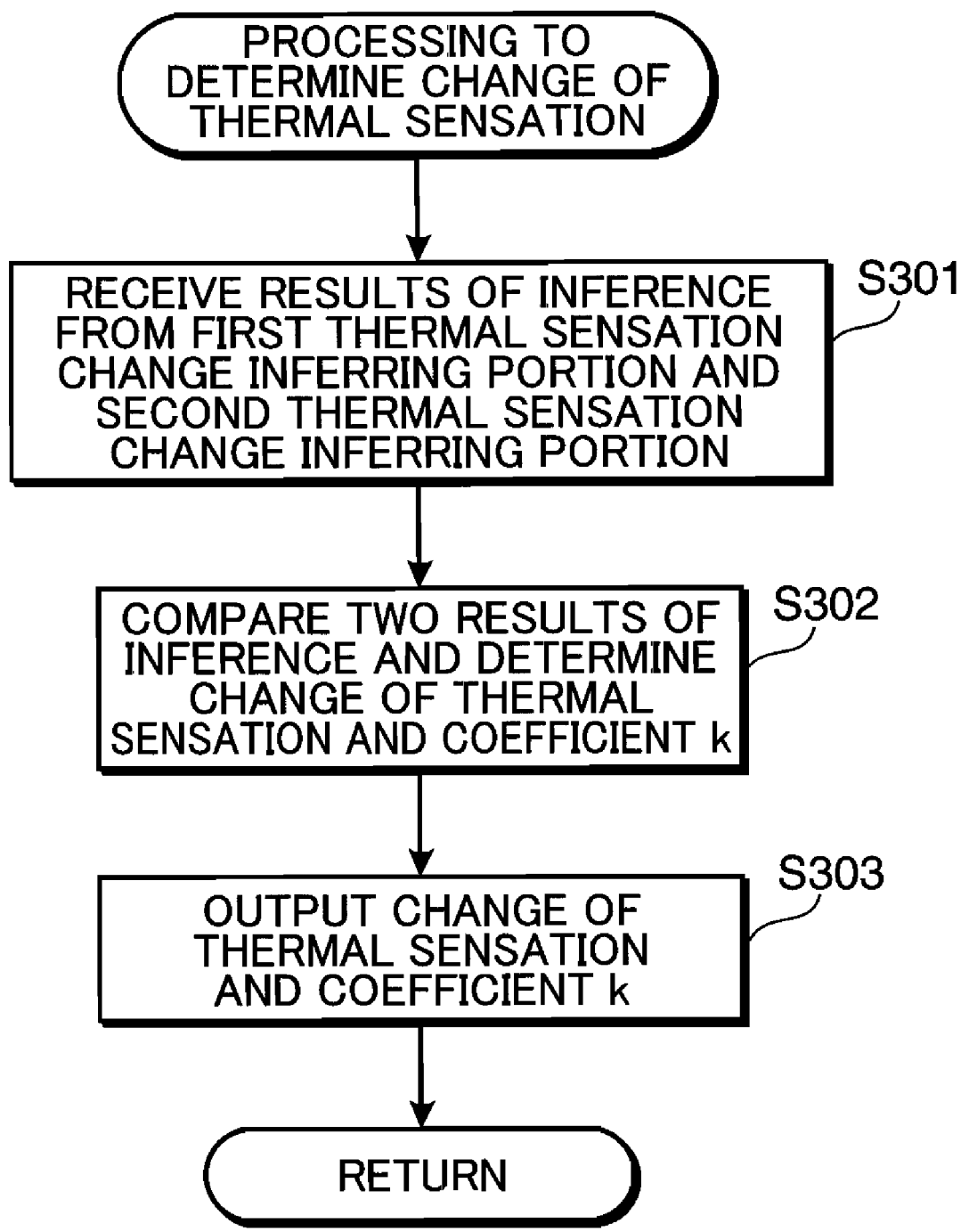
FIG. 54 is a flowchart detailing the processing to determine a change of a thermal sensation by a thermal sensation change determining portion of a fifteenth embodiment.

FIG. 54 is a flowchart detailing the flow of the processing to determine a change of a thermal sensation by the thermal sensation change determining portion 408 of the fifteenth embodiment. Initially, the thermal sensation change determining portion 408 receives the results of inference of a change of a thermal sensation of the user made on the basis of parameters that differ from each other from the first thermal sensation change inferring portion 441 and the second thermal sensation change inferring portion 442 (Step S301). Subsequently, the thermal sensation change determining portion 408 compares the two results of inference of a thermal sensation it has received and determines the result of inference of a thermal sensation and a coefficient k of a thermal sensation according to a table shown in FIG. 55 (Step S302).

FIG. 55 is a view showing an example of a table in the fifteenth embodiment in which the results of inference made by the first thermal sensation change inferring portion and the second thermal sensation change inferring portion, and a change of a thermal sensation and the coefficient k determined by the thermal sensation change determining portion are correlated with one another. This table is pre-stored in the internal memory of the thermal sensation change determining portion 408.

More specifically, in a case where both of the result of inference made by the first thermal sensation change inferring portion 441 and the result of inference made by the second thermal sensation change inferring portion 442 indicate an increase of a thermal sensation, the thermal sensation change determining portion 408 determines that a thermal sensation has increased, and, for example, the coefficient k=1. In a case where both of the result of inference made by the first thermal sensation change inferring portion 441 and the result of inference made by the second thermal sensation change inferring portion 442 indicate a decrease of a thermal sensation, the thermal sensation change determining portion 408 determines that a thermal sensation has decreased, and, for example, the coefficient k=1. In a case where both of the result of inference made by the first thermal sensation change inferring portion 441 and the result of inference made by the second thermal sensation change inferring portion 442 indicate the absence of a change of a thermal sensation, the thermal sensation change determining portion 408 determines that a thermal sensation has not changed, and, for example, the coefficient k=0.

Of the result of inference made by the first thermal sensation change inferring portion 441 and the result of inference made by the second thermal sensation change inferring portion 442, in a case where one indicates an increase of a thermal sensation and the other indicates a decrease of a thermal sensation, the thermal sensation change determining portion 408 determines that a thermal sensation has not changed, and for example, the coefficient k=0. Also, of the result of inference made by the first thermal sensation change inferring portion 441 and the result of inference made by the second thermal sensation change inferring portion 442, in a case where one indicates an increase of a thermal sensation and the other indicates the absence of a change of a thermal sensation, the thermal sensation change determining portion 408 determines that a thermal sensation has increased, and for example, the coefficient k=0.5. Further, of the result of inference made by the first thermal sensation change inferring portion 441 and the result of inference made by the second thermal sensation change inferring portion 442, in a case where one indicates a decrease of a thermal sensation and the other indicates the absence of a change of a thermal sensation, the thermal sensation change determining portion 408 determines that a thermal sensation has decreased, and for example, the coefficient k=0.5. The thermal sensation change determining portion 408 then outputs the change of a thermal sensation and the coefficient k it has determined to the device control determining portion 405 (Step S303).

Figure 56:
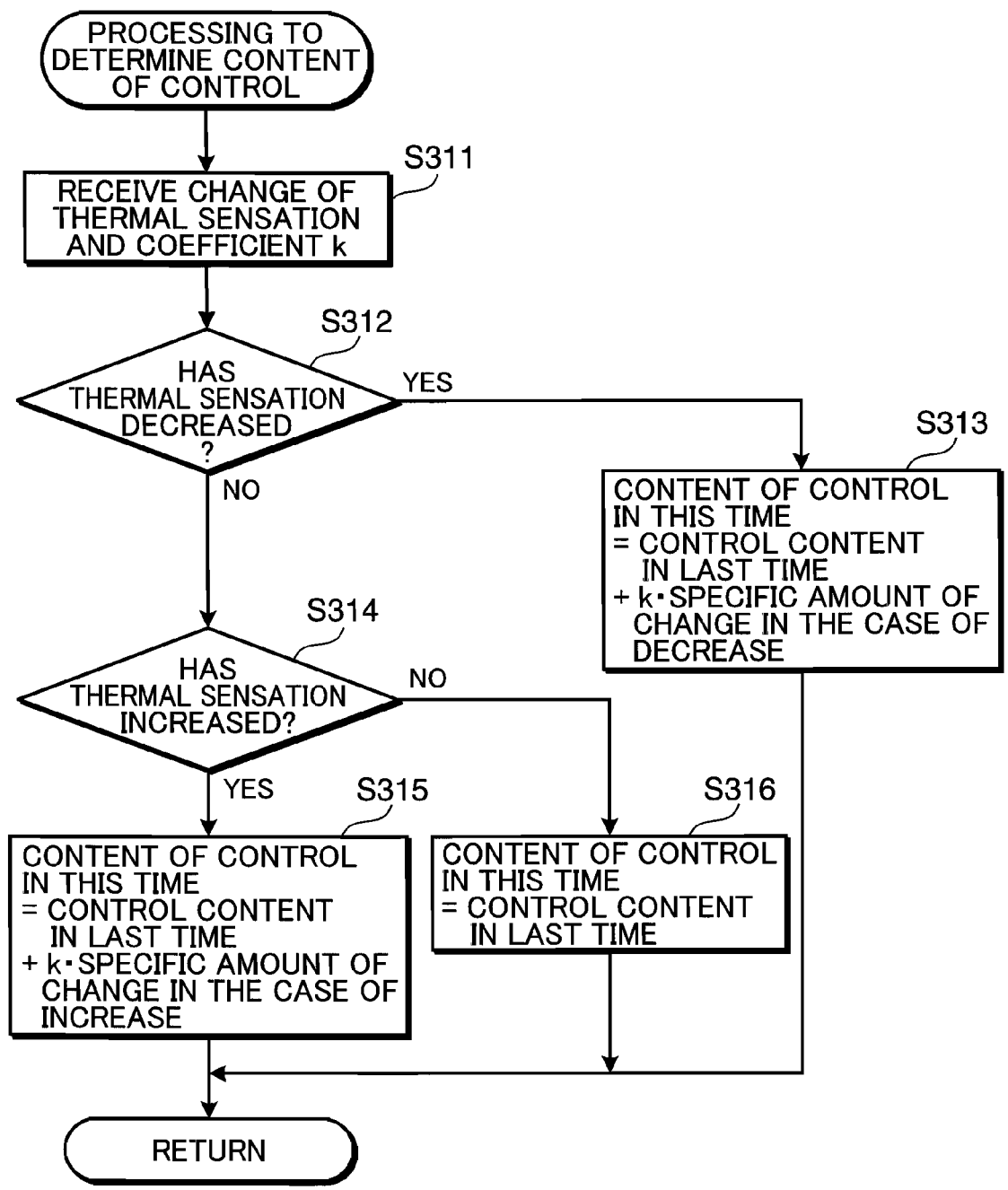
FIG. 56 is a flowchart detailing the flow of the processing to determine the content of control by a device control determining portion of the fifteenth embodiment.

FIG. 56 is a flowchart detailing the flow of the processing to determine the content of control by the device control determining portion 405 of the fifteenth embodiment. Initially, the device control determining portion 405 receives the change of a thermal sensation and the coefficient k determined by the thermal sensation change determining portion 408 (Step S311). Subsequently, the device control determining portion 405 determines whether the change of a thermal sensation it received indicates a decrease of a thermal sensation (Step S312). In a case where it is determined that the change of a thermal sensation is a decrease of a thermal sensation (YES in Step S312), the device control portion 405 calculates the content of control of the warm or cool thermal device 407 in this time by adding a value, which is found by multiplying a specific amount of change in the case of a decrease of a thermal sensation by the coefficient k, to the control of control in the last time (Step S313).

Meanwhile, in a case where it is determined that the change of a thermal sensation is not a decrease of a thermal sensation (NO in Step S312), the device control determining portion 405 determines whether the change of a thermal sensation is an increase of a thermal sensation (Step S314). In a case where it is determined that that the change of a thermal sensation is an increase of a thermal sensation (YES in Step S314), the device control determining portion 405 calculates the content of control of the warm or cool thermal device 407 in this time by adding a value, which is found by multiplying a specific amount of change in the case of an increase of a thermal sensation by the coefficient k, to the control of control in the last time (Step S315).

In a case where it is determined that the change of a thermal sensation is not an increase of a thermal sensation, that is, in a case where a thermal sensation has not changed (NO in Step S314), the device control determining portion 405 makes the content of control of the warm or cool thermal device 407 in this time same as the content of control in the last time (Step S316). Subsequently, the device control determining portion 405 outputs the content of control it has calculated to the warm or cool thermal device 407 (Step S256 in FIG. 45). The warm or cool thermal device 407 is thus controlled according to the content of control based on the result of inference and the coefficient k of a thermal sensation.

According to this configuration, because a change of a thermal sensation of the user is inferred simultaneously on the basis of plural different pulse wave parameters and a change of a thermal sensation is determined by comparing the plural results of inference, it is possible to infer a change of a thermal sensation of the user in response to a change in the warm or cool thermal environment at a higher degree of accuracy. Also, the results of inference are outputted when the plural results of inference of a thermal sensation coincide with each other, and they are not outputted when they do not coincide with each other. Hence, even in a case where one pulse wave parameter has changed because of a factor other than a change in the warm or cool thermal environment, the content of control of the warm or cool thermal device 407 is not changed, which makes it possible to avoid an event that the user is made feel uncomfortable. Further, because an amount of change of the content of control is determined adequately according to the results of inference of a change of a thermal sensation based on the plural pulse wave parameters, it is possible to provide more comfortable warm or cool thermal environment to the user.

The amount of change of the content of control referred to herein includes, for example, a change of an amount of air flow, a change of an amount of set room temperature, an amount of a change of the set temperature of blowing air, an amount of a change of the frequency of a compressor, an amount of a change of the opening of an expansion valve of an air conditioner, an amount of a change of the set temperature of the floor heating system, an amount of a change of a heater ON-time of an electric carpet or a seat heater, and an amount of a change of a heater capacity.

In the description above, the coefficient k was described as 0, 0.5, and 1. The invention, however, is not particularly limited to this configuration, and it may be configured in such a manner that of all the results of inference of a change of a thermal sensation made on the basis of changes of plural pulse wave parameters, the value of the coefficient k is increased for those having a higher coinciding rate.

Sixteenth Embodiment

Hereinafter, a sixteenth embodiment of the invention will be described. A difference of the sixteenth embodiment from the thirteenth embodiment through the fifteenth embodiment described above is that, regarding the correlation between the ratio of waveform components of the accelerated pulse wave, b/a, and a thermal sensation of the user discovered by the inventors from the test conducted on subjects and shown in FIG. 47, the inventors further discovered that the accelerated pulse wave parameter b/a no longer changes substantially in response to a change of a thermal sensation, in particular, when a thermal sensation is equal to 1 or greater, and put this discovery into practical use. To be more concrete, the processing by the thermal sensation change inferring portion 404 in FIG. 44 is different. Because the configuration of the environment control device of the sixteenth embodiment is the same as the configuration of the environment control device of the thirteenth embodiment, descriptions thereof are omitted.

Figure 57:
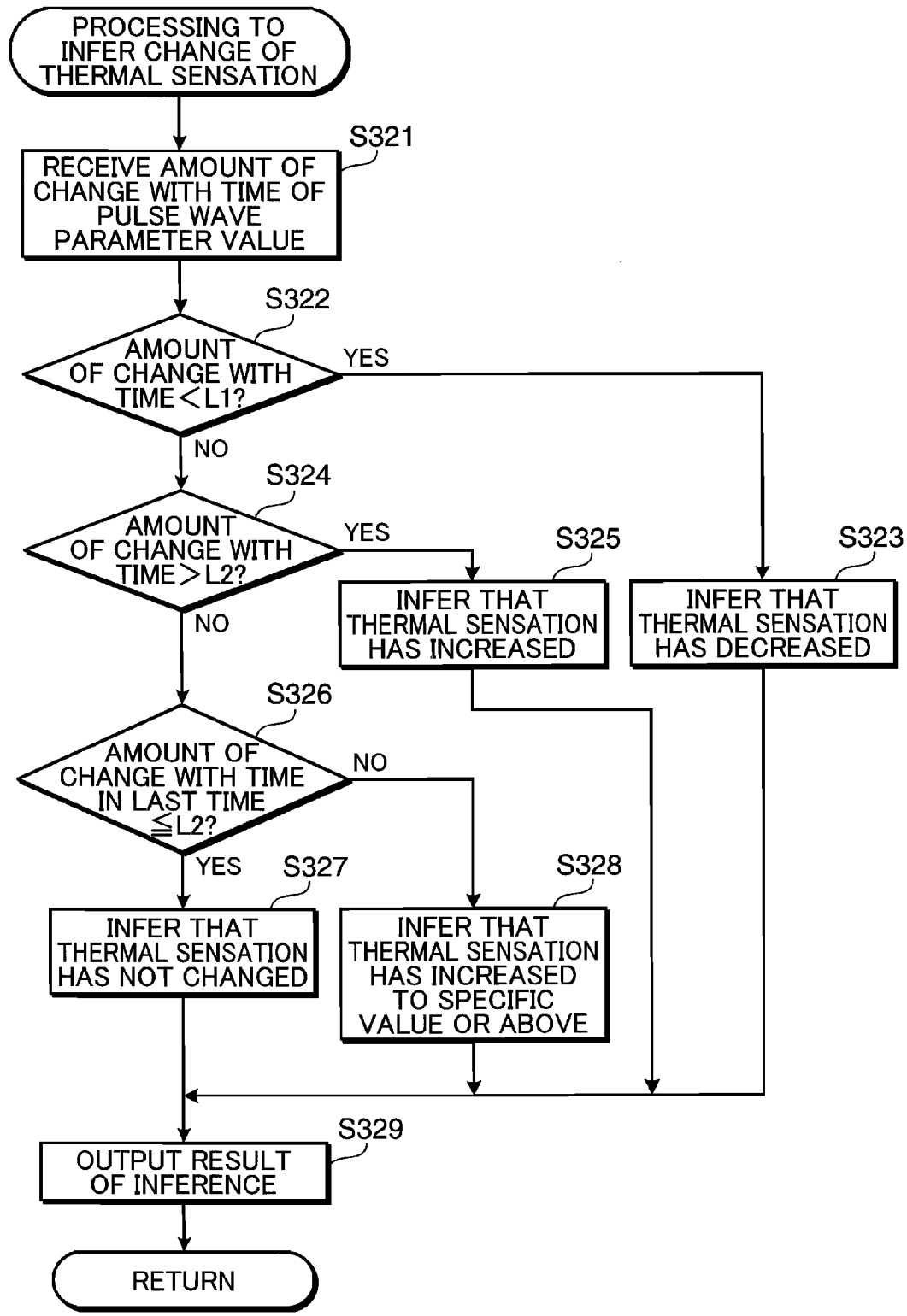
FIG. 57 is a flowchart detailing the flow of the processing to infer a change of a thermal sensation by a thermal sensation change inferring portion of a sixteenth embodiment of the invention.

FIG. 57 is a flowchart detailing the flow of the processing to infer a change of a thermal sensation by the thermal sensation change inferring portion 404 of the sixteenth embodiment. Initially, the thermal sensation change inferring portion 404 receives an amount of change with time within a specific time of the ratio of waveform components of the accelerated pulse wave, b/a, from the pulse wave parameter change calculating portion 403 (Step S321).

Subsequently, the thermal sensation change inferring portion 404 determines whether the amount of change with time is smaller than a pre-set threshold value L1 (Step S322). In a case where it is determined that the amount of change with time is smaller than the pre-set threshold value L1, that is, in a case where it is determined that the ratio of waveform components of the accelerated pulse wave, b/a, has substantially deceased (YES in Step S322), the thermal sensation change inferring portion 404 infers that a thermal sensation of the user has decreased (Step S323). Subsequently, the thermal sensation change inferring portion 404 outputs the result of inference to the device control determining portion 405 (Step S329).

Meanwhile, in a case where it is determined that the amount of change with time is equal to the threshold value L1 or greater (NO in Step S322), the thermal sensation change inferring portion 404 determines whether the amount of change with time is greater than a threshold value L2 that is greater than the threshold value L1 (Step S324). In a case where it is determined that the amount of change with time is greater than the pre-set threshold value L2, that is, in a case where the ratio of waveform components of the accelerated pulse wave, b/a, has substantially increased (YES in Step S324), the thermal sensation change inferring portion 404 infers that a thermal sensation of the user has increased (Step S325). In a case where it is determined that the amount of change with time is in a range from the threshold value L1 to the threshold value L2, both inclusive, that is, in a case where the ratio of waveform components of the accelerated pulse wave, b/a, has not substantially changed (NO in Step S324), the thermal sensation change inferring portion 404 further refers to the amount of change with time in the last time and determines whether the amount of change with time in the last time is equal to the pre-set threshold value L2 or smaller (Step S326).

In a case where it is determined that the amount of change with time in the last time is equal to the threshold value L2 or smaller, that is, in a case where the ratio of waveform components of the accelerated pulse wave, b/a, has not substantially changed, either, or substantially decreased in the last time (YES in Step S326), the thermal sensation change inferring portion 404 infers that a thermal sensation of the user has not changed (Step S327). Subsequently, the thermal sensation change inferring portion 404 outputs the result of inference to the device control determining portion 405 (Step S329).

Meanwhile, in a case where it is determined that the amount of change with time in the last time is greater than the pre-set threshold value L2, that is, in a case where the ratio of waveform components of the accelerated pulse wave, b/a, has substantially increased in the last time (NO in Step S326), the thermal sensation change inferring portion 404 infers that a thermal sensation of the user has increased to a specific value or above (Step S328). Subsequently, the thermal sensation change inferring portion 404 outputs the result of inference to the device control determining portion 405 (Step S329).

According to this configuration, by applying the discovery by the inventors that the ratio of waveform components of the accelerated pulse wave, b/a, no longer changes substantially in response to a change of a thermal sensation when a thermal sensation of the user reaches a specific value (1: relatively warm), not only is it possible to make an inference as to whether a thermal sensation of the user has increased, whether a thermal sensation of the user has decreased, or whether a thermal sensation of the user has not changed on the basis of a change of the ratio of waveform components of the accelerated pulse wave, b/a, but it is also possible to make an inference as to whether a thermal sensation of the user is warmed to the specific value (1: relatively warm) or above. It is thus possible to infer a change of a thermal sensation of the user without using the absolute value of the pulse wave parameter that differs from individual to individual, which makes it possible to control the warm or cool thermal device 407 forming the residential environment appropriately on the basis of a thermal sensation.

Further, because whether the user is being warmed can be inferred as well, when the user is warmed more than necessary, it is possible to make a contribution to energy saving by suppressing the heating performance of the warm or cool thermal device 407, or it is possible to achieve the comfortable warm or cool thermal environment where it is neither hot nor cold swiftly by upgrading the cooling performance of the warm or cool thermal device 407.

Seventeenth Embodiment

Hereinafter, a seventeenth embodiment of the invention will be described. A difference of the seventeenth embodiment from the thirteenth embodiment through the sixteenth embodiment described above is that, regarding the correlation between the ratio of waveform components of the accelerated pulse wave, b/a, and a thermal sensation of the user discovered by the inventors from the test conducted on subjects and shown in FIG. 47, the inventors further discovered that the accelerated pulse wave parameter b/a no longer changes substantially in response to a change of a thermal sensation, in particular, when a thermal sensation is equal to 1 or greater, and put this discovery into practical use. To be more concrete, the processing by the thermal sensation change determining portion 408 of FIG. 52 that has received the result of inference of a change of a thermal sensation described in the sixteenth embodiment is different, and to be furthermore concrete, a method of determining a change of a thermal sensation and a method of determining the coefficient k in Step S302 of FIG. 54 are different.

Hereinafter, the seventeenth embodiment will be described using FIG. 52, FIG. 54, and FIG. 58. Referring to FIG. 54, initially, the thermal sensation change determining portion 408 receives the results of inference of a change of a thermal sensation of the user made on the basis of different parameters from the first thermal sensation change inferring portion 441 and the second thermal sensation change inferring portion 442 (step S301). The first thermal sensation change inferring portion 441 infers a change of a thermal sensation of the user on the basis of an amount of change with time of the ratio of waveform components of the accelerated pulse wave, b/a. Subsequently, the thermal sensation change determining portion 408 compares the two results of inference of a thermal sensation it has received, and determines the result of inference and the coefficient k of a thermal sensation according to a table shown in FIG. 58 (Step S302).

FIG. 58 is a view showing an example of a table in the seventeenth embodiment in which the results of inference made by the first thermal sensation change inferring portion and the second thermal sensation change inferring portion, and a change of a thermal sensation and the coefficient k determined by the thermal sensation change determining portion are correlated with one another. This table is pre-stored in the internal memory of the thermal sensation change determining portion 408.

More specifically, in a case where both of the result of inference made by the first thermal sensation change inferring portion 441 and the result of inference made by the second thermal sensation change inferring portion 442 indicate an increase of a thermal sensation, the thermal sensation change determining portion 408 determines that a thermal sensation has increased and the coefficient k=1. In a case where both of the result of inference made by the first thermal sensation change inferring portion 441 and the result of inference made by the second thermal sensation change inferring portion 442 indicate a decrease of a thermal sensation, the thermal sensation change determining portion 408 determines that a thermal sensation has decreased and the coefficient k=1. In a case where both of the result of inference made by the first thermal sensation change inferring portion 441 and the result of inference made by the second thermal sensation change inferring portion 442 indicate the absence of a change of a thermal sensation, the thermal sensation change determining portion 408 determines that a thermal sensation has not changed and the coefficient k=0.

Of the result of inference made by the first thermal sensation change inferring portion 441 and the result of inference made by the second thermal sensation change inferring portion 442, in a case where one indicates an increase of a thermal sensation and the other indicates a decrease of a thermal sensation, the thermal sensation change determining portion 408 determines that a thermal sensation has not changed and the coefficient k=0. Also, of the result of inference made by the first thermal sensation change inferring portion 441 and the result of inference made by the second thermal sensation change inferring portion 442, in a case where one indicates a decrease of a thermal sensation and the other indicates the absence of a change of a thermal sensation, the thermal sensation change determining portion 408 determines that a thermal sensation has decreased and the coefficient k=0.5. In a case where the result of inference made by the first thermal sensation change inferring portion 441 on the basis of an amount of change with time of the ratio of waveform components of the accelerated pulse wave, b/a, indicates an increase of a thermal sensation and the result of inference made by the second thermal sensation change inferring portion 442 on the basis of an amount of change with time of a parameter other than the ratio of waveform components of the accelerated pulse wave, b/a, indicates the absence of a change, the thermal sensation change determining portion 408 determines that a thermal sensation has increased and the coefficient k=0.5. The steps thus far are the same as those in the fifteenth embodiment.

In a case where the result of inference made by the first thermal sensation change inferring portion 441 on the basis of an amount of change with time of the ratio of waveform components of the accelerated pulse wave, b/a indicates the absence of a change and the result of inference made by the second thermal sensation change inferring portion 442 on the basis of on an amount of change with time of a parameter other than the ratio of waveform components of the accelerated pulse wave, b/a, indicates an increase of a thermal sensation, the thermal sensation change determining portion 408 infers that the heating performance is too high when the warm or cool thermal device 407 is run for heating, or infers that the cooling performance is insufficient when the warm or cool thermal device 407 is run for cooling. It thus determines that a thermal sensation has increased to the specific value (1: relatively warm to 3: hot) or above and determines the coefficient k=1. Subsequently, the thermal sensation change determining portion 408 outputs the change of a thermal sensation and the coefficient k it has determined to the device control determining portion 405 (Step S303).

Figure 59:
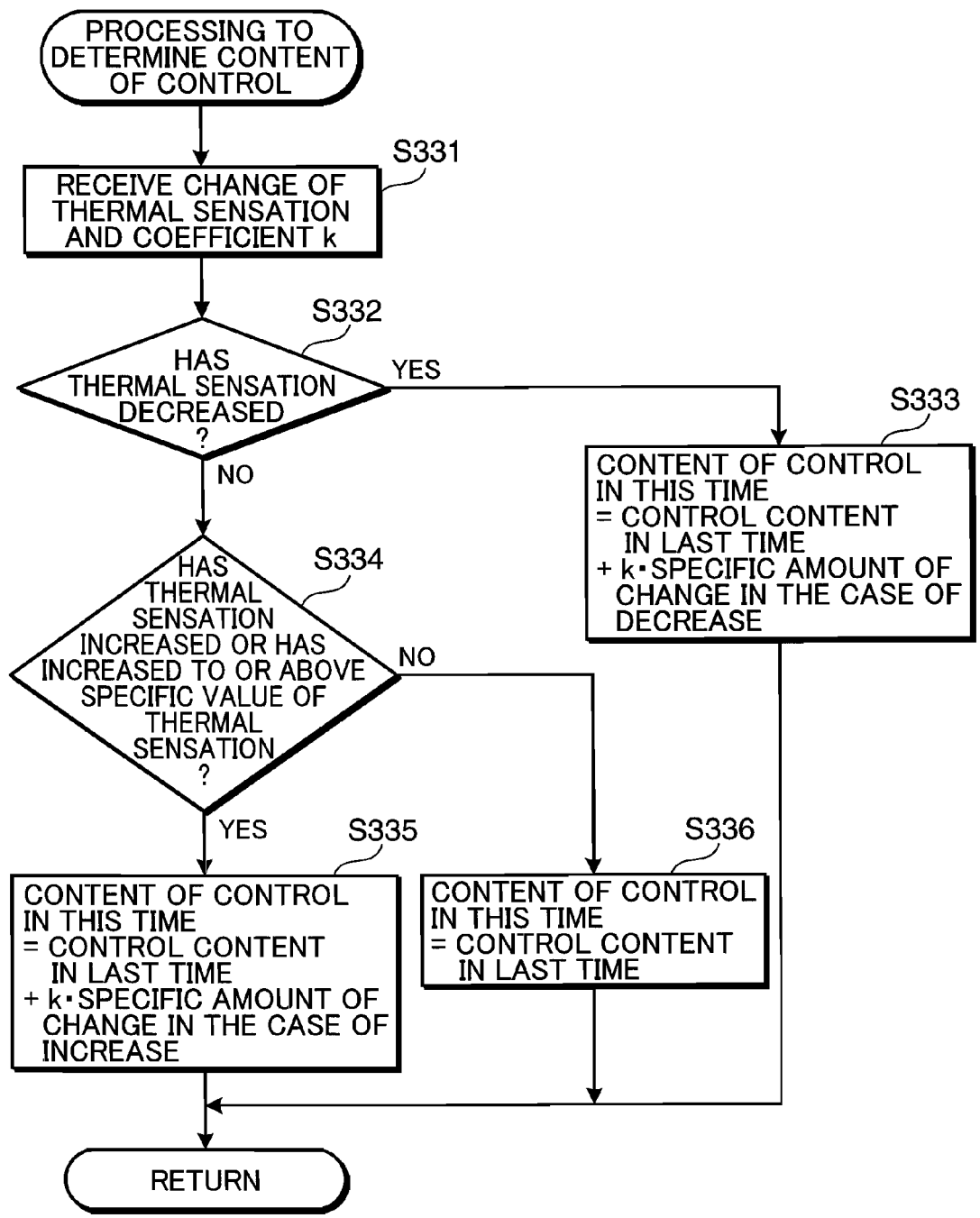
FIG. 59 is a flowchart detailing the flow of the processing by a device control determining portion of the seventeenth embodiment.

Hereinafter, the processing to determine the content of control by the device control determining portion 405 in the seventeenth embodiment will be described continuously using FIG. 59. FIG. 59 is a flowchart detailing the flow of the processing by the device control determining portion 405 in the seventeenth embodiment. Initially, the device control determining portion 405 receives the change of a thermal sensation and the coefficient k determined by the thermal sensation change determining portion 408 (Step S331). Subsequently, the device control determining portion 405 determines whether the change of a thermal sensation it received indicates a decrease of a thermal sensation (Step S332).

In a case where it is determined that the change of a thermal sensation is a decrease of a thermal sensation (YES in Step S332), the device control determining portion 405 calculates the content of control of the warm or cool thermal device 407 in this time by adding a value, which is found by multiplying a specific amount of change in the case of a decrease of a thermal sensation by the coefficient k, to the control of control in the last time (Step S333). Meanwhile, in a case where it is determined that the change of a thermal sensation is not a decrease of a thermal sensation (NO in Step S332), the device control determining portion 405 determines whether the change of a thermal sensation is an increase of a thermal sensation or an increase to or above the specific value of a thermal sensation (Step S334).

In a case where it determined that that the change of a thermal sensation is an increase of a thermal sensation or an increase to or above the specific value of a thermal sensation (YES in Step S334), the device control determining portion 405 calculates the content of control of the warm or cool thermal device 407 in this time by adding a value, which is found by multiplying a specific amount of change in the case of an increase of a thermal sensation by the coefficient k, to the control of control in the last time (Step S335). In a case where it is determined that the change of a thermal sensation is not an increase of a thermal sensation or an increase to or above the specific value of a thermal sensation, that is, in a case where a thermal sensation has not changed (NO in Step S334), the device control determining portion 405 makes the content of control of the warm or cool thermal device 407 in this time same as the content of control in the last time (Step S336). Subsequently, the device control determining portion 405 outputs the content of control it has calculated to the warm or cool thermal device 407 (Step S256 in FIG. 45). The warm or cool thermal device 407 is thus controlled according to the content of control based on the result of inference and the coefficient k of a thermal sensation.

According to this configuration, because a change of a thermal sensation of the user is inferred simultaneously on the basis of plural different pulse wave parameters and a change of a thermal sensation is determined by comparing the plural results of inference, it is possible to infer a change of a thermal sensation of the user in response to a change in the warm or cool thermal environment at a higher degree of accuracy. The results of inference are outputted when the plural results of inference of a thermal sensation coincide with each other, and they are not outputted when they do not coincide with each other. Hence, even in a case where one pulse wave parameter has changed because of a factor other than a change in the warm or cool thermal environment, the content of control of the warm or cool thermal device 407 is not changed, which makes it possible to avoid an event that the user is made feel uncomfortable.

Further, because an amount of change of the content of control is also determined adequately according to the results of inference of a change of a thermal sensation based on the plural pulse wave parameters, it is possible to provide a more comfortable warm or cool thermal environment to the user. The amount of change of the content of control referred to herein includes, for example, a change of an amount of air flow, a change of an amount of set room temperature, an amount of a change of the set temperature of blowing air, an amount of a change of the frequency of a compressor, an amount of a change of the opening of an expansion valve of an air conditioner, an amount of a change of the set temperature of the floor heating system, an amount of a change of a heater ON-time of an electric carpet or a seat heater, and an amount of a change of a heater capacity.

Further, as in the sixteenth embodiment, by applying the discovery by the inventors that the accelerated pulse wave parameter b/a no longer changes substantially in response to a change of a thermal sensation when a thermal sensation of the user reaches the specific value (1: relatively warm) or above, whether the user is being warmed can be inferred as well. Hence, when the user is warmed more than necessary, it is possible to make a contribution to energy saving by suppressing the heating performance of the warm or cool thermal device 407, or it is possible to achieve the comfortable warm or cool thermal environment for the user swiftly where it is neither hot nor cold, that is, hotness or coldness are removed, by upgrading the cooling performance of the warm or cool thermal device 407.

In the description above, the coefficient k was described as 0, 0.5, and 1. The invention, however, is not particularly limited to this configuration, and it may be configured in such a manner that of all the results of inference of a change of thermal sensation made on the basis of changes of plural pulse wave parameters, the value of the coefficient k is increased for those having a higher coinciding rate.

The specific embodiments described above chiefly contain inventions having the following configurations.

An environment control device according to an aspect of the invention includes: a biological information acquiring portion for acquiring time-series data of biological information of a user; a parameter calculating portion for calculating a parameter about the biological information through chaos analysis of the time-series data acquired by the biological information acquiring portion; an inferring portion for inferring a comfortable feeling of the user on the basis of the parameter calculated by the parameter calculating portion; and a stimulus control portion for controlling generation of a stimulus to be given to the user on the basis of a result of inference made by the inferring portion.

An environment control method according to another aspect of the invention includes: a biological information acquiring step of acquiring time-series data of biological information of a user; a parameter calculating step of calculating a parameter about the biological information through chaos analysis of the time-series data acquired in the biological information acquiring step; an inferring step of inferring a comfortable feeling of the user on the basis of the parameter calculated in the parameter calculating step; and a stimulus controlling step of controlling generation of a stimulus to be given to the user on the basis of a result of inference made in the inferring step.

An environment control program according to still another aspect of the invention causes a computer to function as: a biological information acquiring portion for acquiring time-series data of biological information of a user; a parameter calculating portion for calculating a parameter about the biological information through chaos analysis of the time-series data acquired by the biological information acquiring portion; an inferring portion for inferring a comfortable feeling of the user on the basis of the parameter calculated by the parameter calculating portion; and a stimulus control portion for controlling generation of a stimulus to be given to the user on the basis of a result of inference made by the inferring portion.

A computer-readable recording medium containing an environment control program according to still another aspect of the invention has recorded therein an environment control program that causes a computer to function as: a biological information acquiring portion for acquiring time-series data of biological information of a user; a parameter calculating portion for calculating a parameter about the biological information through chaos analysis of the time-series data acquired by the biological information acquiring portion; an inferring portion for inferring a comfortable feeling of the user on the basis of the parameter calculated by the parameter calculating portion; and a stimulus control portion for controlling generation of a stimulus to be given to the user on the basis of a result of inference made by the inferring portion.

According to these configurations, the parameter about the biological information is calculated through chaos analysis of the time-series data of the biological information of the user. A comfortable feeling of the user in response to a stimulus is inferred on the basis of the parameter thus calculated, and the generation of a stimulus to be given to the user is controlled on the basis of the result of inference. In other words, in a case where the result of inference obtained indicates a deterioration of a comfortable feeling of the user, a stimulus such that enhances a comfortable feeling is given to the user.

Hence, because a comfortable feeling is inferred on the basis of the parameter calculated through chaos analysis of the time-series data of the biological information of the user and the generation of a stimulus to be given to the user is controlled on the basis of the result of inference, it is possible to enable the user to actually have a comfortable feeling in a reliable manner and further to maintain such a comfortable state.

Also, in the environment control device described above, it is preferable that: the biological information is a pulse wave of the user; the stimulus control portion controls generation of a warm or cool thermal stimulus to be given to the user; and the inferring portion infers a thermal sensation of the user in response to the warm or cool thermal stimulus.

According to this configuration, a thermal sensation of the user is inferred on the basis of the parameter to evaluate the pulse wave, and the generation of a stimulus to be given to the user is controlled on the basis of the result of inference. Hence, because a thermal sensation of the user is inferred from the pulse wave, which is a kind of the biological information that can be readily obtained among others, it is possible to infer a thermal sensation of the user easily without making the user feel uncomfortable. In addition, because a thermal sensation of the user is inferred using the pulse wave, unlike the case of inferring a thermal sensation of the user using the brain wave, there is no need to form the device using special and expensive equipment, which makes it possible to form the device using simple and inexpensive equipment.

Also, in the environment control device described above, it is preferable that the parameter calculating portion calculates, as the parameter, any one of a maximum Lyapunov exponent, a recurrence plot draw white rate, and a median value of trajectory parallel measure through the chaos analysis of the time-series data, and that the inferring portion infers the thermal sensation of the user on the basis of the parameter calculated by the parameter calculating portion.

According to this configuration, any one of the maximum Lyapunov exponent, the recurrence plot draw white rate, and the median value of trajectory parallel measure is calculated as the parameter through chaos analysis of the time-series data, and a thermal sensation of the user is inferred on the basis of the parameter thus calculated. Hence, unlike the conventional case, a thermal sensation of the user can be inferred without using the absolute value of the biological information (pulse wave parameter) that varies from individual to individual. It is therefore possible to control a warm or cool thermal device forming the residential environment, such as an air conditioning device, appropriately on the basis of a thermal sensation of the user.

Also, in the environment control device described above, it is preferable that the parameter calculating portion calculates the maximum Lyapunov exponent as the parameter through the chaos analysis of the time-series data, and that the inferring portion infers that the thermal sensation has deteriorated as the thermal sensation of the user has changed in a direction from a neutral state to a cold state or in a direction from the neutral state to a hot state in a case where the maximum Lyapunov exponent has increased, and infers that the thermal sensation has improved as the thermal sensation of the user has changed in a direction from the cold state to the neutral state or in a direction from the hot state to the neutral state in a case where the maximum Lyapunov exponent has decreased.

According to this configuration, the maximum Lyapunov exponent is calculated as the parameter through chaos analysis of the time-series data. In a case where the maximum Lyapunov exponent has increased, a thermal sensation is inferred to have deteriorated as a thermal sensation of the user has changed in a direction from the neutral state to a cold state or in a direction from the neutral state to a hot state, and in a case where the maximum Lyapunov exponent has decreased, a thermal sensation is inferred to have improved as a thermal sensation of the user has changed in a direction from a cold state to the neutral state or in a direction from a hot state to the neutral state.

Hence, in a case where it is inferred that a thermal sensation has deteriorated, it is possible to give a warm or cool thermal stimulus such that enhances a thermal sensation of the user, and in a case where it is inferred that a thermal sensation has improved, it is possible to give a warm or cool thermal stimulus for the current control to be maintained. In other words, it is possible to control the device forming the residential environment of the user, for example, an air conditioning device, to maintain a thermal sensation of the user in a moderate state where it is neither hot nor cold.

Also, in the environment control device described above, it is preferable that the parameter calculating portion calculates the recurrence plot draw white rate as the parameter through the chaos analysis of the time-series data, and that the inferring portion infers that the thermal sensation of the user has changed in a direction from a hot state to a neutral state or in a direction from the neutral state to a cold state in a case where the recurrence plot draw white rate has decreased, and infers that the thermal sensation of the user has changed in a direction from the cold state to the neutral state or in a direction from the neutral state to the hot state in a case where the recurrence plot draw white rate has increased.

According to this configuration, the recurrence plot draw white rate is calculated as the parameter through chaos analysis of the time-series data. In a case where the recurrence plot draw white rate has decreased, a thermal sensation of the user is inferred to have changed in a direction from a hot state to the neutral state or in a direction from the neutral state to a cold state, and in a case where the recurrence plot draw white rate has increased, a thermal sensation of the user is inferred to have changed in a direction from a cold state to the neutral state or in a direction from the neutral state to a hot state.

Hence, in a case where it is inferred that a thermal sensation has deteriorated, it is possible to give a warm or cool thermal stimulus such that enhances a thermal sensation of the user, and in a case where it is inferred that a thermal sensation has improved, it is possible to give a warm or cool thermal stimulus for the current control to be maintained. In other words, it is possible to control the device forming the residential environment of the user, for example, an air conditioning device, to maintain a thermal sensation of the user in a moderate state where it is neither hot nor cold.

Also, in the environment control device described above, it is preferable that the parameter calculating portion calculates the median value of trajectory parallel measure as the parameter through the chaos analysis of the time-series data, and that the inferring portion infers that the thermal sensation of the user has changed in a direction from a hot state to a neutral state or in a direction from the neutral state to a cold state in a case where the median value of trajectory parallel measure has increased, and infers that the thermal sensation of the user has changed in a direction from the cold state to the neutral state or in a direction from the neutral state to the hot state in a case where the median value of trajectory parallel measure has decreased.

According to this configuration, the median value of trajectory parallel measure is calculated as the parameter through chaos analysis of the time-series data. In a case where the median value of the trajectory parallel measure has increased, a thermal sensation of the user is inferred to have changed in a direction from a hot state to the neutral state or in a direction from the neutral state to a cold state, and in a case where the median value of the trajectory parallel measure has decreased, a thermal sensation of the user is inferred to have changed in a direction from a cold state to the neutral state or in a direction from the neutral state to a hot state.

Hence, in a case where it is inferred that a thermal sensation has deteriorated, it is possible to give a warm or cool thermal stimulus such that enhances a thermal sensation of the user, and in a case where it is inferred that a thermal sensation has improved, it is possible to give a warm or cool thermal stimulus for the current control to be maintained. In other words, it is possible to control the device forming the residential environment of the user, for example, an air conditioning device, to maintain a thermal sensation of the user in a moderate state where it is neither hot nor cold.

Also, in the environment control device described above, it is preferable that the parameter calculating portion includes a first parameter calculating portion for calculating a first parameter about the biological information through the chaos analysis of the time-series data and a second parameter calculating portion for calculating a second parameter about the biological information on the basis of a change of the time-series data, and that the inferring portion infers the comfortable feeling of the user on the basis of the first parameter calculated by the first parameter calculating portion and the second parameter calculated by the second parameter calculating portion.

According to this configuration, the first parameter about the biological information is calculated through chaos analysis of the time-series data, and the second parameter about the biological information is calculated on the basis of a change of the time-series data, so that a comfortable feeling of the user is inferred on the basis of the first parameter and the second parameter thus calculated.

Hence, because a comfortable feeling of the user is inferred using two different kinds of parameters, it is possible to infer a thermal sensation of the user at a higher degree of accuracy by eliminating an influence of differences of the biological information among individuals. In addition, because a stimulus to be given to the user is generated on the basis of the result of inference, it is possible to lead a thermal sensation of the user to a moderate state where it is neither hot nor cold in a reliable manner.

Also, in the environment control device described above, it is preferable that: the first parameter calculating portion calculates a maximum Lyapunov exponent through the chaos analysis of the time-series data; the second parameter calculating portion calculates amplitude of a pulse wave or a maximum wave height value of the pulse wave from the time-series data; and the inferring portion infers that a thermal sensation of the user has changed in a direction from a neutral state to a hot state in a case where the maximum Lyapunov exponent has increased and the amplitude of the pulse wave or the maximum wave height value of the pulse wave has increased, infers that the thermal sensation of the user has changed in a direction from a cold state to the neutral state in a case where the maximum Lyapunov exponent has decreased and the amplitude of the pulse wave or the maximum wave height value of the pulse wave has increased, infers that the thermal sensation of the user has changed in a direction from the neutral state to the cold state in a case where the maximum Lyapunov exponent has increased and the amplitude of the pulse wave or the maximum wave height value of the pulse wave has decreased, and infers that the thermal sensation of the user has changed in a direction from the hot state to the neutral state in a case where the maximum Lyapunov exponent has decreased and the amplitude of the pulse wave or the maximum wave height value of the pulse wave has decreased.

According to this configuration, not only the maximum Lyapunov exponent is calculated through chaos analysis of the time-series data, but also the amplitude of the pulse wave or the maximum wave height value of the pulse wave is calculated from the time-series data. In a case where the maximum Lyapunov exponent has increased and the amplitude of the pulse wave or the maximum wave height value of the pulse wave has increased, a thermal sensation of the user is inferred to have changed in a direction from the neutral state to a hot state. In a case where the maximum Lyapunov exponent has decreased and the amplitude of the pulse wave or the maximum wave height value of the pulse wave has increased, a thermal sensation of the user is inferred to have changed in a direction from a cold state to the neutral state. In a case where the maximum Lyapunov exponent has increased and the amplitude of the pulse wave or the maximum wave height value of the pulse wave has decreased, a thermal sensation of the user is inferred to have changed in a direction from the neutral state to a cold state. In a case where the maximum Lyapunov exponent has decreased and the amplitude of the pulse wave or the maximum wave height value of the pulse wave has decreased, a thermal sensation of the user is inferred to have changed in a direction from a hot state to the neutral state.

Hence, because a comfortable feeling is inferred using two different kinds of parameters, including the maximum Lyapunov exponent and the amplitude of the pulse wave or the maximum wave height value of the pulse wave, it is possible to infer a thermal sensation of the user at a higher degree of accuracy by eliminating an influence of differences of the biological information among individuals. In addition, because a stimulus to be given to the user is generated on the basis of the result of inference, it is possible to lead a thermal sensation of the user to a moderate state where it is neither hot nor cold in a reliable manner.

Also, in the environment control device described above, it is preferable that the stimulus control portion generates control data to control a stimulus to be given to the user on the basis of the result of inference made by the inferring portion and outputs the control data that has been generated to the inferring portion, and that the inferring portion infers a warm or cold feeling of the user on the basis of a variance of a maximum Lyapunov exponent obtained through the chaos analysis and the control data generated by the stimulus control portion.

According to this configuration, the inferring portion infers a thermal sensation of the user using the control data generated by the stimulus control portion and the maximum Lyapunov exponent. In other words, because a thermal sensation is inferred using two different kinds of parameters, including not only the maximum Lyapunov exponent but also the control data, it is possible to infer a thermal sensation of the user at a higher degree of accuracy by eliminating an influence of differences of the biological information among individuals. In addition, because a stimulus to be given to the user is generated on the basis of the result of inference, it is possible to lead a thermal sensation of the user to a moderate state where it is neither hot nor cold in a reliable manner.

Also, in the environment control device described above, it is preferable that the control data includes data indicating output strength of a cooling device that generates a stimulus, and that the inferring portion determines whether the output strength of the cooling device has heightened or weakened from the control data, and infers that the thermal sensation of the user has changed in a direction from a neutral state to a cold state in a case where a maximum Lyapunov exponent obtained through the chaos analysis has increased and the output strength of the cooling device has heightened, infers that the thermal sensation of the user has changed in a direction from a hot state to the neutral state in a case where the maximum Lyapunov exponent has decreased and the output strength of the cooling device has heightened, infers that the thermal sensation of the user has changed in a direction from the neutral state to the hot state in a case where the maximum Lyapunov exponent has increased and the output strength of the cooling device has weakened, and infers that the thermal sensation of the user has changed in a direction from the cold state to the neutral state in a case where the maximum Lyapunov exponent has decreased and the output strength of the cooling device has weakened.

According to this configuration, in a case where the output strength of the cooling device has heightened and the maximum Lyapunov exponent has increased, the inferring portion infers that a thermal sensation of the user has changed in a direction from the neutral state to a cold state. In a case where the output strength of the cooling device has heightened and the maximum Lyapunov exponent has decreased, the inferring portion infers that a thermal sensation of the user has changed in a direction from a hot state to the neutral state. In a case where the output strength of the cooling device has weakened and the Lyapunov exponent has increased, the inferring portion infers that a thermal sensation of the user has changed in a direction from the neutral state to a hot state. In a case where the output strength of the cooling device has weakened and the maximum Lyapunov exponent has decreased, the inferring portion infers that a thermal sensation of the user has changed in a direction from a cold state to the neutral state. The generation of a warm or cool stimulus is controlled from these results of inference. In other words, because a thermal sensation of the user is inferred from the combination of an increase or a decrease of the maximum Lyapunov exponent and heightening or weakening of the output strength of the cooling device, it is possible to infer a thermal sensation of the user at a higher degree of accuracy by eliminating an influence of differences of the biological information among individuals. In addition, because a stimulus to be given to the user is generated on the basis of the result of inference, it is possible to lead a thermal sensation of the user to a moderate state where it is neither hot nor cold in a reliable manner.

Also, in the environment control device described above, it is preferable that the control data includes data indicating output strength of a heating device that generates a stimulus, and that the inferring portion determines whether the output strength of the heating device has heightened or weakened from the control data, and infers that the thermal sensation of the user has changed in a direction from a neutral state to a hot state in a case where a maximum Lyapunov exponent obtained through the chaos analysis has increased and the output strength of the heating device has heightened, infers that the thermal sensation of the user has changed in a direction from a cold state to the neutral state in a case where the maximum Lyapunov exponent has decreased and the output strength of the cooling device has heightened, infers that the thermal sensation of the user has changed in a direction from the neutral state to the cold state in a case where the maximum Lyapunov exponent has increased and the output strength of the heating device has weakened, and infers that the thermal sensation of the user has changed in a direction from the hot state to the neutral state in a case where the maximum Lyapunov exponent has decreased and the output strength of the heating device has weakened.

According to this configuration, in a case where the output strength of the heating device has heightened and the maximum Lyapunov exponent has increased, the inferring portion infers that a thermal sensation of the user has changed in a direction from the neutral state to a hot state. In a case where the output strength of the heating device has heightened and the maximum Lyapunov exponent has decreased, the inferring portion infers that a thermal sensation of the user has changed in a direction from a cold state to the neutral state. In a case where the output strength of the heating device has weakened and the Lyapunov exponent has increased, the inferring portion infers that a thermal sensation of the user has changed in a direction from the neutral state to a cold state. In a case where the output strength of the heating device has weakened and the maximum Lyapunov exponent has decreased, the inferring portion infers that a thermal sensation of the user has changed in a direction from a hot state to the neutral state. The generation of a warm or cool stimulus is controlled from these results of inference. In other words, because a thermal sensation of the user is inferred from the combination of an increase or a decrease of the maximum Lyapunov exponent and heightening or weakening of the output strength of the heating device, it is possible to infer a thermal sensation of the user at a higher degree of accuracy by eliminating an influence of differences of the biological information among individuals. In addition, because a stimulus to be given to the user is generated on the basis of the result of inference, it is possible to lead a thermal sensation of the user to a moderate state where it is neither hot nor cold in a reliable manner.

Also, in the control device described above, it is preferable that: the parameter calculating portion includes a first parameter calculating portion for calculating a first parameter about the biological information through the chaos analysis of the time-series data and a second parameter calculating portion for calculating a second parameter about the biological information on the basis of a change of the time-series data; the inferring portion includes a first inferring portion for inferring the comfortable feeling of the user on the basis of the first parameter calculated by the first parameter calculating portion and a second inferring portion for inferring the comfortable feeling of the user on the basis of the second parameter calculated by the second parameter calculating portion; the stimulus control portion includes a first stimulus control portion for controlling the generation of the stimulus to be given to the user on the basis of a result of inference made by the first inferring portion and a second stimulus control portion for controlling the generation of the stimulus to be given to the user on the basis of a result of inference made by the second inferring portion; and the environment control device further includes a stimulus control switching portion for switching control by the first stimulus control portion and control by the second stimulus control portion on the basis of the change of the time-series data.

According to this configuration, not only the first parameter about the biological information is calculated through chaos analysis of the time-series data, but also the second parameter about the biological information is calculated on the basis of a change of the time-series data. A comfortable feeling of the user is inferred on the basis of the first parameter, and the generation of a stimulus to be given to the user is controlled by the first stimulus control portion on the basis of the result of inference. Also, a comfortable feeling of the user is inferred on the basis of the second parameter, and the generation of a stimulus to be given to the user is controlled by the second stimulus control portion on the basis of the result of inference. The control by the first stimulus control portion the control by the second stimulus control portion are switched on the basis of a change of the time-series data.

In order to infer a state of the user through chaos analysis of the time-series data, a sufficiently long period, for example, about a few minutes to 15 minutes, is necessary. On the contrary, in a case where a state of the user is inferred on the basis of a change of the time-series data, it is possible to infer a state of the user in a short time, for example, about five seconds to about ten seconds, at a certain degree of accuracy.

Hence, in a case where the strength of a stimulus currently given to the user needs to be weakened or heightened urgently, that is, when the time-series data obviously indicates that the stimulus to the user is too high or the time-series data obviously indicates that the stimulus to the user is too weak, it is possible to move a stimulus to be given to the user swiftly to a range that is suitable to some extent by controlling the generation of a stimulus by the second stimulus control portion that is capable of inferring a state of the user in a short time.

Meanwhile, in a case where the time-series data obviously indicates that the stimulus to the user is not too high or not too weak, there is no need to change the strength of the stimulus currently given to the user urgently. Hence, by inferring a state of the user by the first stimulus control portion and giving a moderate stimulus to the user on the basis of the result of inference, the user will not feel a pain or be adversely affected. Hence, even in a case where the time-series data of a sufficiently long period cannot be acquired, it is possible to infer a state of the user precisely to some extent. It is thus possible to give the user a stimulus such that enhances a comfortable feeling by avoiding an event that the user feels a pain or is adversely affected. Consequently, the configuration can be applied adequately to the control of a device forming the residential environment of the user, for example, an air conditioning device, a lighting device, a video device, and an audio device.

Also, in the environment control device described above, it is preferable that: the first stimulus control portion calculates, on the basis of the result of inference made by the first inferring portion, a first stimulus value for a stimulus to be generated at strength to enhance a relaxed feeling, a comfortable feeling, or a thermal sensation of the user; the second stimulus control portion calculates, on the basis of the result of inference made by the second inferring portion, a second stimulus value for the stimuli generating portion to generate a stimulus at strength to enhance the relaxed feeling, the comfortable feeling, or the thermal sensation of the user; and the stimulus control switching portion calculates a stimulus output value on the basis of the first stimulus value and the second stimulus value for a stimulus specified by the stimulus output value that has been calculated to be generated.

According to this configuration, because the stimulus output value is calculated on the basis of the first stimulus value and the second stimulus value and a stimulus specified by the stimulus output value thus calculated is generated, it is possible to give the user a stimulus at a strength suitable to a state of the user.

Also, in the environment control device described above, it is preferable that the stimulus control switching portion calculates a stimulus output value to control the generation of the stimulus to be given to the user, and in a case where a change of the time-series data is equal to a predetermined lower limit specified value or smaller, uses the second stimulus value as the stimulus output value, and in a case where the change of the time-series data is greater than a predetermined upper limit specified value, uses the second stimulus value as the stimulus output value.

According to this configuration, in a case where a change of the time-series data is equal to the predetermined lower limit specified value or smaller and the strength of a stimulus to the user is too weak, or in case where a change of the time-series data is equal to the predetermined upper limit specified value or greater and the strength of a stimulus to the user is too high, the second stimulus value is used as the stimulus output value. Hence, because a stimulus to be given to the user is controlled by the second stimulus control portion, it is possible to bring the user in a relaxed state swiftly.

Also, in the environment control device described above, it is preferable that the stimulus control switching portion uses the first stimulus value as the stimulus output value in a case where the change of the time-series data is greater than a predetermined first specified value (>the lower limit specified value) and is equal to a predetermined second specified value (the first specified value<the second specified value<the upper limit specified value) or smaller.

According to this configuration, in a case where a change of the time-series data is greater than the first specified value and is equal to the second specified value or smaller, it is determined that the user is relaxed, and the first stimulus value is used as the stimulus output value. Hence, because a stimulus to be given to the user is controlled by the first stimulus control portion, it is possible to bring the user in a relaxed state in a more reliable manner.

Also, in the environment control device described above, it is preferable that the stimulus control switching portion determines weighting factors of the both stimulus values in such a manner that, in a case where the change of the time-series data is greater than the lower limit specified value and equal to the first specified value or smaller, a weighting factor for the first stimulus value increases and a weighting factor for the second stimulus value decreases as the change of the time-series data approximates to the first specified value, and uses, as the stimulus output value, a value obtained by adding the both stimulus values in accordance with the weighting factors that have been determined.

According to this configuration, in a case where a change of the time-series data is greater than the lower limit specified value and equal to the first specified value or smaller, the weighting factor for the first stimulus value is increased as the change of the time-series data approximates to the first specified value. It is thus possible to control a stimulus to be given to the user by combining the control by the first stimulus control portion and the control by the second stimulus control portion at an appropriate ratio.

Also, in the environment control device described above, it is preferable that the stimulus control switching portion determines weighting factors of the both stimulus values in such a manner that, in a case where the change of the time-series data is greater than the second specified value and equal to the upper limit specified value or smaller, a weighting factor for the first stimulus value decreases and a weighting factor for the second stimulus value increases as the change of the time-series data approximates to the upper limit specified value, and uses, as the stimulus output value, a value obtained by adding the both stimulus values in accordance with the weighting factors that have been determined.

According to this configuration, in a case where a change of the time-series data is greater than the second specified value and equal to the upper limit specified value or smaller, the weighting factor for the second stimulus value is increased as the change of the time-series data approximates to the second specified value. It is thus possible to control a stimulus to be given to the user by combining the control by the first stimulus control portion and the control by the second stimulus control portion at an appropriate ratio.

Also, in the environment control device described above, it is preferable that the first inferring portion calculates a maximum Lyapunov exponent of the biological information as a pulse wave chaos parameter and infers that a relaxed feeling, a comfortable feeling, or a thermal sensation of the user has enhanced in a case where the pulse wave chaos parameter that has been calculated is equal to a predetermined third specified value or greater, and infers that the relaxed feeling, the comfortable feeling, or the thermal sensation of the user has not enhanced in case where the pulse wave chaos parameter is smaller than the third specified value. According to this configuration, because a state of the user is inferred on the basis of the maximum Lyapunov exponent, it is possible to infer a state of the user precisely.

Also, in the environment control device described above, it is preferable that the first stimulus control portion outputs the first stimulus value for current strength of stimulus to be maintained in a case where the first inferring portion infers that the relaxed feeling, the comfortable feeling, or the thermal sensation of the user has enhanced, and calculates the first stimulus value for the current strength of stimulus to be heightened in a case where the first inferring portion infers that the relaxed feeling, the comfortable feeling, or the thermal sensation of the user has not enhanced.

According to this configuration, in a case where it is inferred that a relaxed feeling, a comfortable feeling, a thermal sensation, or the like of the user has enhanced, the current strength of stimulus is maintained, and in a case where it is inferred that a relaxed feeling, a comfortable feeling, or a thermal sensation of the user has not enhanced, the current strength of stimulus is heightened. It is thus possible to provide a relaxed feeling, a comfortable feeling, or a thermal sensation to the user swiftly.

Also, in the environment control device described above, it is preferable that the first inferring portion infers the comfortable feeling of the user on the basis of the first parameter calculated by the first parameter calculating portion and the second parameter calculated by the second parameter calculating portion.

According to this configuration, not only the first parameter about the biological information is calculated through chaos analysis of the time-series data, but also the second parameter about the biological information is calculated on the basis of a change of the time-series data. A comfortable feeling of the user is inferred on the basis of the first parameter and the second parameter, and the generation of a stimulus to be given to the user is controlled by the first stimulus control portion on the basis of the result of inference. Also, a comfortable feeling of the user is inferred on the basis of the second parameter, and the generation of a stimulus to be given to the user is controlled by the second stimulus control portion on the basis of the result of stimulus. The control by the first stimulus control portion and the control by the second stimulus control portion are switched on the basis of a change of the time-series data.

Hence, because a comfortable feeling of the user is not inferred using the first parameter alone, but it is inferred using two different kinds of parameters, it is possible to infer a thermal sensation of the user at a higher degree of accuracy by eliminating an influence of differences of the biological information among individuals.

Also, in the environment control device described above, it is preferable to further include a room temperature measuring portion for measuring room temperature in a room where the user is in, and it is preferable that the parameter calculating portion calculates a maximum Lyapunov exponent through the chaos analysis of the time-series data, and that the inferring portion infers that the thermal sensation of the user has changed in a direction from a neutral state to a hot state in a case where the maximum Lyapunov exponent has increased and the room temperature has risen, infers that the thermal sensation of the user has changed in a direction from a cold state to the neutral state in a case where the maximum Lyapunov exponent has decreased and the room temperature has risen, infers that the thermal sensation of the user has changed in a direction from the neutral state to the cold state in a case where the maximum Lyapunov exponent has increased and the room temperature has dropped, and infers that the thermal sensation of the user has changed in a direction from the hot state to the neutral state in a case where the maximum Lyapunov exponent has decreased and the room temperature has dropped.

According to this configuration, the room temperature of the room where the user is in is measured, and the maximum Lyapunov exponent is calculated through chaos analysis of the time-series data. In a case where the maximum Lyapunov exponent has increased and the room temperature has risen, a thermal sensation of the user is inferred to have changed in a direction from the neutral state to a hot state. In a case where the maximum Lyapunov exponent has decreased and the room temperature has risen, a thermal sensation of the user is inferred to have change in a direction from a cold state to the neutral state. In a case where the maximum Lyapunov exponent has increased and the room temperature has dropped, a thermal sensation of the user is inferred to have changed in a direction from the neutral state to a cold state. In a case where the maximum Lyapunov exponent has decreased and the room temperature has dropped, a thermal sensation of the user is inferred to have changed in a direction from a hot state to the neutral state.

Hence, because a thermal sensation is not inferred using the maximum Lyapunov exponent alone, but it is inferred using two kinds of parameters, including the maximum Lyapunov exponent and the room temperature, it is possible to infer a thermal sensation of the user at a higher degree of accuracy by eliminating an influence of differences of the biological information among individuals. In addition, because a stimulus to be given to the user is generated on the basis of the result of inference, it is possible to lead a thermal sensation of the user to a moderate state where it is neither hot nor cold in a reliable manner.

An environment control device according to still another aspect of the invention includes: a biological information acquiring portion for acquiring time-series data of biological information of a user; a parameter calculating portion for calculating a parameter about the biological information on the basis of a change of the time-series data acquired by the biological information acquiring portion; an inferring portion for inferring a comfortable feeling of the user on the basis of the parameter calculated by the parameter calculating portion; and a stimulus control portion for controlling generation of a stimulus to be given to the user on the basis of a result of inference made by the inferring portion.

An environment control method according to still another aspect of the invention includes: a biological information acquiring step of acquiring time-series data of biological information of a user; a parameter calculating step of calculating a parameter about the biological information on the basis of a change of the time-series data acquired in the biological information acquiring step; an inferring step of inferring a comfortable feeling of the user on the basis of the parameter calculated in the parameter calculating step; and a stimulus controlling step of controlling generation of a stimulus to be given to the user on the basis of a result of inference made in the inferring step.

An environment control program according to still another aspect of the invention causes a computer to function as: a biological information acquiring portion for acquiring time-series data of biological information of a user; a parameter calculating portion for calculating a parameter about the biological information on the basis of a change of the time-series data acquired by the biological information acquiring portion; an inferring portion for inferring a comfortable feeling of the user on the basis of the parameter calculated by the parameter calculating portion; and a stimulus control portion for controlling generation of a stimulus to be given to the user on the basis of a result of inference made by the inferring portion.

A computer-readable recording medium containing an environment control program according to still another aspect of the invention has recorded therein an environment control program that causes a computer to function as: a biological information acquiring portion for acquiring time-series data of biological information of a user; a parameter calculating portion for calculating a parameter about the biological information on the basis of a change of the time-series data acquired by the biological information acquiring portion; an inferring portion for inferring a comfortable feeling of the user on the basis of the parameter calculated by the parameter calculating portion; and a stimulus control portion for controlling generation of a stimulus to be given to the user on the basis of a result of inference made by the inferring portion.

According to these configurations, the parameter about the biological information is calculated on the basis of a change of the time-series data of the biological information of the user. A comfortable feeling of the user in response to a stimulus is inferred on the basis of the parameter thus calculated, and the generation of a stimulus to be given to the user is controlled on the basis of the result of inference. In other words, in a case where the result of inference obtained indicates a deterioration of a comfortable feeling of the user, a stimulus such that enhances a comfortable feeling is given to the user.

Hence, because a comfortable feeling is inferred on the basis of the parameter calculated on the basis of a change of the time-series data of the biological information of the user and the generation of a stimulus to be given to the user is controlled on the basis of the result of inference, it is possible to enable the user to actually have a comfortable feeling in a reliable manner and further to maintain such a comfortable state.

Also, in the environment control device described above, it is preferable that: the biological information is a pulse wave of the user; the stimulus control portion controls generation of a warm or cool thermal stimulus to be given to the user; and the inferring portion infers a thermal sensation of the user in response to the warm or cool thermal stimulus.

According to this configuration, a thermal sensation of the user is inferred on the basis of the parameter to evaluate the pulse wave, and the generation of a stimulus to be given to the user is controlled on the basis of the result of inference. Hence, because a thermal sensation of the user is inferred from the pulse wave, which is a kind of the biological information that can be readily obtained among others, it is possible to infer a thermal sensation of the user easily without making the user feel uncomfortable. In addition, because a thermal sensation of the user is inferred using the pulse wave, unlike the case of inferring a thermal sensation of the user using the brain wave, there is no need to form the device using special and expensive equipment, which makes it possible to form the device using simple and inexpensive equipment.

Also, in the environment control device described above, it is preferable that the parameter calculating portion calculates, as the parameter, at least one of pulse wave amplitude of a pulse wave waveform obtained from the biological information, a maximum wave height value of the pulse wave, a ratio of waveform components of an accelerated pulse wave waveform obtained by second-order differentiation of the pulse wave waveform obtained from the biological information, accelerated pulse wave amplitude, and a pulse rate, and that the inferring portion infers the thermal sensation of the user on the basis of a variance of the parameter calculated by the parameter calculating portion.

According to this configuration, at least one of the pulse wave waveform amplitude obtained from the biological information, the maximum wave height value of the pulse wave, the ratio of waveform components of an accelerated pulse wave waveform obtained by second-order differentiation of the pulse wave waveform obtained from the biological information, the accelerated pulse wave amplitude, and the pulse rate is calculated as the parameter, and a thermal sensation of the user is inferred on the basis of a variance of the parameter thus calculated.

Hence, unlike the conventional case, a thermal sensation of the user can be inferred without using the absolute value of the biological information (pulse wave parameter) that varies from individual to individual. It is therefore possible to control a warm or cool thermal device forming the residential environment, such as an air conditioning device, appropriately on the basis of a thermal sensation of the user.

Also, in the environment control device described above, it is preferable that the parameter calculating portion calculates a ratio of waveform components of the accelerated pulse wave waveform, c/a, on the basis of the time-series data, and that the inferring portion infers that the thermal sensation has deteriorated as the thermal sensation of the user has changed in a direction from a neutral state to a cold state or in a direction from the neutral state to a hot state in a case where the ratio of waveform components of the accelerated pulse wave waveform, c/a, has increased, and infers that the thermal sensation has improved as the thermal sensation of the user has changed in a direction from the cold state to the neutral state or in a direction from the hot state to the neutral state in a case where the ratio of waveform components of the accelerated pulse wave waveform, c/a, has decreased.

According to this configuration, the ratio of waveform components of the accelerated pulse wave waveform, c/a, is calculated on the basis of the time-series data. In a case where the ratio of waveform components of the accelerated pulse wave waveform, c/a, has increased, a thermal sensation is inferred to have deteriorated as a thermal sensation of the user has changed in a direction from the neutral state to a cold state or in a direction from the neutral state to a hot state, and in a case where the ratio of waveform components of the accelerated pulse wave waveform, c/a, has decreased, a thermal sensation is inferred to have improved as a thermal sensation of the user has changed in a direction from a cold state to the neutral state or in a direction from a hot state to the neutral state.

Hence, it is possible to infer whether a thermal sensation of the user has deteriorated or improved by determining whether the ratio of waveform components of the accelerated pulse wave waveform, c/a, has increased or decreased, which makes it possible to control the generation of a stimulus appropriately according to the result of inference.

Also, in the environment control device described above, it is preferable that the parameter calculating portion calculates a ratio of waveform components of the accelerated pulse wave waveform, c/a, on the basis of the time-series data, and that the inferring portion infers that the thermal sensation of the user has changed in a direction from a hot state to a neutral state or in a direction from the neutral state to a cold state in a case where the ratio of waveform components of the accelerated pulse wave waveform, c/a, has increased, and infers that the thermal sensation of the user has changed in a direction from the cold state to the neutral state or in a direction from the neutral state to the hot state in a case where the ratio of waveform components of the accelerated pulse wave waveform, c/a, has decreased.

According to this configuration, the ratio of waveform components of the accelerated pulse wave waveform, c/a, is calculated on the basis of the time-series data. In a case where the ratio of waveform components of the accelerated pulse wave waveform, c/a, has increased, a thermal sensation of the user is inferred to have changed in a direction from a hot state to the neutral state or in a direction from the neutral state to a cold state, and in a case where the ratio of waveform components of the accelerated pulse wave waveform, c/a, has decreased, a thermal sensation of the user is inferred to have changed in a direction from a cold state to the neutral state or in a direction from the neutral state to a hot state.

Hence, in a case where it is inferred that a thermal sensation has deteriorated, it is possible to give a warm or cool thermal stimulus such that enhances a thermal sensation of the user, and in a case where it is inferred that a thermal sensation has improved, it is possible to give a warm or cool thermal stimulus for the current control to be maintained. In other words, it is possible to control the device forming the residential environment of the user, for example, an air conditioning device, to maintain a thermal sensation of the user in a moderate state where it is neither hot nor cold.

Also, in the environment control device described above, it is preferable that the parameter calculating portion calculates the pulse wave amplitude or the maximum wave height value of the pulse wave and a ratio of waveform components of the accelerated pulse wave waveform, c/a, on the basis of the time-series data, and that the inferring portion infers that the thermal sensation of the user has changed in a direction from a neutral state to a hot state in a case where the ratio of waveform components of the accelerated pulse wave waveform, c/a, has increased and the pulse wave amplitude or the maximum wave height value of the pulse wave has increased, infers that the thermal sensation of the user has changed in a direction from a cold state to the neutral state in a case where the ratio of waveform components of the accelerated pulse wave waveform, c/a, has decreased and the pulse wave amplitude or the maximum wave height value of the pulse wave has increased, infers that the thermal sensation of the user has changed in a direction from the neutral state to the cold state in a case where the ratio of waveform components of the accelerated pulse wave waveform, c/a, has increased and the pulse wave amplitude or the maximum wave height value of the pulse wave has decreased, and infers that the thermal sensation of the user has changed in a direction from the hot state to the neutral state in a case where the ratio of waveform components of the accelerated pulse wave waveform, c/a, has decreased and the pulse wave amplitude or the maximum wave height value of the pulse wave has decreased.

According to this configuration, the pulse wave amplitude or the maximum wave height value of the pulse wave and the ratio of waveform components of the accelerated pulse wave waveform, c/a, are calculated on the basis of the time-series data. In a case where the ratio of waveform components of the accelerated pulse wave waveform, c/a, has increased and the pulse wave amplitude or the maximum wave height value of the pulse wave has increased, a thermal sensation of the user is inferred to have changed in a direction from the neutral state to a hot state. In a case where the ratio of waveform components of the accelerated pulse wave waveform, c/a, has decreased and the pulse wave amplitude or the maximum wave height value of the pulse wave has increased, a thermal sensation of the user is inferred to have changed in a direction from a cold state to the neutral state. In a case where the ratio of waveform components of the accelerated pulse wave waveform, c/a, has increased and the pulse wave amplitude or the maximum wave height value of the pulse wave has decreased, a thermal sensation of the user is inferred to have changed in a direction from the neutral state to a cold state. In a case where the ratio of waveform components of the accelerated pulse wave waveform, c/a, has decreased and the pulse wave amplitude or the maximum wave height value of the pulse wave has decreased, a thermal sensation of the user is inferred to have changed in a direction from a hot state to the neutral state.

Hence, because a thermal sensation is inferred using two kinds of parameters, including the ratio of waveform components of the accelerated pulse wave waveform, c/a, and the pulse wave amplitude or the maximum wave height value of the pulse wave, it is possible to infer a thermal sensation of the user at a higher degree of accuracy by eliminating an influence of differences of the biological information among individuals. In addition, because a stimulus to be given to the user is generated on the basis of the result of inference, it is possible to lead a warm or cool of the user to a moderate state where it is neither hot nor cold in a reliable manner.

Also, in the environment control device described above, it is preferable that the parameter calculating portion calculates at least one of the accelerated pulse wave amplitude, a ratio of waveform components of the accelerated pulse wave waveform, b/a, and a ratio of waveform components of the accelerated pulse wave waveform, d/a, on the basis of the time-series data, and that the inferring portion infers that the thermal sensation of the user has changed in a direction from a neutral state to a hot state or in a direction from a cold state to the neutral state in a case where at least one of the accelerated pulse wave amplitude, the ratio of waveform components of the accelerated pulse wave waveform, b/a, and the ratio of waveform components of the accelerated pulse wave waveform, d/a, has increased, and infers that the thermal sensation of the user has changed in a direction from the neutral state to the cold state or in a direction from the hot state to the neutral state in a case where at least one of the accelerated pulse wave amplitude, the ratio of waveform components of the accelerated pulse wave waveform, b/a, and the ratio of waveform components of the accelerated pulse wave waveform, d/a, has decreased.

According to this configuration, at least one of the accelerated pulse wave amplitude, the ratio of waveform components of the accelerated pulse wave waveform, b/a, and the ratio of waveform components of the accelerated pulse wave waveform, d/a, is calculated on the basis of the time-series data. In a case where at least one of the accelerated pulse wave amplitude, the ratio of waveform components of the accelerated pulse wave waveform, b/a, and the ratio of waveform components of the accelerated pulse wave waveform, d/a, has increased, a thermal sensation of the user is inferred to have changed in a direction from the neutral state to a hot state or in a direction from a cold state to the neutral state. In a case where at least one of the accelerated pulse wave amplitude, the ratio of waveform components of the accelerated pulse wave waveform, b/a, and the ratio of waveform components of the accelerated pulse wave waveform, d/a, has decreased, a thermal sensation of the user is inferred to have changed in a direction from the neutral state to a cold state or in a direction from a hot state to the neutral state.

Hence, it is possible to infer a change of a thermal sensation of the user by determined whether at least one of the accelerated pulse wave amplitude, the ratio of waveform components of the accelerated pulse wave waveform, b/a, and the ratio of waveform components of the accelerated pulse wave waveform, d/a, has increased or decreased, which makes it possible to control the generation of a stimulus appropriately according to the result of inference.

Also, in the environment control device described above, it is preferable that: the parameter calculating portion includes a first parameter calculating portion for calculating a first parameter about the biological information through the chaos analysis of the time-series data and a second parameter calculating portion for calculating a second parameter about the biological information on the basis of a change of the time-series data; the inferring portion includes a first inferring portion for inferring the comfortable feeling of the user on the basis of the first parameter calculated by the first parameter calculating portion and a second inferring portion for inferring the comfortable feeling of the user on the basis of the second parameter calculated by the second parameter calculating portion; the first parameter calculating portion in a plural form, the second parameter calculating portion in a plural form, or the first parameter calculating portion at least in a singular form and the second parameter calculating portion at least in a singular form are included; the environment control device further includes a determining portion for determining whether all results of inference made by the first inferring portion or the second inferring portion coincide with each other; and the stimulus control portion controls the generation of the stimulus to be given to the user on the basis of the results of inference that are determined as coinciding with each other by the determining portion.

According to this configuration, the first parameter about the biological information is calculated by the first parameter calculating portion through chaos analysis of the time-series data, and a comfortable feeling of the user is inferred on the basis of the first parameter by the first inferring portion. Also, the second parameter about the biological information is calculated by the second parameter calculating portion on the basis of a change of the time-series data, and a comfortable feeling of the user is inferred on the basis of the second parameter by the first inferring portion. The environment control device is provided with the first parameter calculating portion in a plural form, the second parameter calculating portion in a plural form, or the first parameter calculating portion at least in a singular form and the second parameter calculating portion at least in a singular from. Whether all the results of inference made by the first inferring portion or the second inferring portion coincide with each other is determined. In a case where it is determined that all the results of inference coincide with each other, the generation of a stimulus to be given to the user is controlled on the basis of the results of inference.

Hence, because a thermal sensation of the user is inferred simultaneously on the basis of the plural parameters and a thermal sensation is determined by comparing the plural results of inference, it is possible to infer a thermal sensation of the user in response to a change in the warm or cool thermal environment at a higher degree of accuracy. Even when the parameter changes because of a factor other than a change in the warm or cool thermal environment, because the content of control is changed appropriately, it is possible to avoid an event that the user is made feel uncomfortable, which makes it possible to provide a satisfactorily comfortable feeling to the user constantly.

Also, in the environment control device described above, it is preferable that when a stimulus is outputted by a stimulus output portion for outputting a stimulus to the user, the stimulus output portion outputs a stimulus output signal indicating that the stimulus output portion has outputted the stimulus to the inferring portion, and that the inferring portion calculates a variance of the parameter from a parameter extracted before reception of the stimulus output signal and a parameter extracted after the reception.

According to this configuration, because a comfortable feeling of the user is inferred from a variance of the pulse wave before and after the reception of a stimulus by the user, it is possible to understand a response of the user to the stimulus in a reliable manner. Also, by inferring a comfortable feeling on the basis of a response of the user to the stimulus and by outputting the content of stimulus determined on the basis of the result of inference, it is possible to address differences among individuals, which makes it possible to enable the user to actually have a comfortable feeling in a reliable manner. Further, by repetitively performing a series of these processing steps, it is possible to enable the user to maintain a comfortable state in a reliable manner.

Also, in the environment control device described above, it is preferable that the parameter calculating portion calculates the variance of the parameter from parameters extracted at pre-set specific time intervals. According to this configuration, it is possible to understand the variance of a response of the user to a stimulus. Also, by inferring a comfortable feeling on the basis of a response of the user to a stimulus and outputting the content of stimulus determined on the basis of the result of inference, it is possible to address differences among individuals, which makes it possible to enable the user to actually have a comfortable feeling in a reliable manner.

Also, in the environment control device described above, it is preferable that the inferring portion infers that the comfortable feeling of the user has not changed in a case where a variance of the parameter falls within a specific first range indicating that the comfortable feeling of the user has not changed, and outputs a stimulus output instruction to enhance the comfortable feeling to the stimulus control portion.

According to this configuration, by employing the principle discovered by the inventors that there is a correlation between a variance of a parameter of the pulse wave and a comfortable feeling of the user, the first range indicating that a comfortable feeling of the user has not changed is set in advance, and a comfortable feeling of the user is inferred not to have changed in a case where a variance of the parameter falls within the first range. It is thus possible to infer precisely that a comfortable feeling of the user has not changed. Also, in a case where the result of inference obtained indicates the absence of a change of a comfortable feeling of the user, because a stimulus to enhance a comfortable feeling is outputted, it is possible to provide a comfortable feeling to the user.

Also, in the environment control device described above, it is preferable that the inferring portion infers that the comfortable feeling of the user has enhanced in a case where the variance of the parameter falls within a specific second range that is different from the first range and indicates that the comfortable feeling of the user has enhanced, and outputs a stimulus output instruction to maintain the comfortable feeling to the stimulus control portion.

According to this configuration, by employing the principle discovered by the inventors that there is a correlation between a variance of a parameter to evaluate the pulse wave and a comfortable feeling of the user, the second range indicating that a comfortable feeling of the user has enhanced is set in advance, and a comfortable feeling of the user is inferred to have enhanced in a case where a variance of the parameter falls within the second range. It is thus possible to infer precisely that a comfortable feeling of the user has enhanced. Also, in a case where the result of inference obtained indicates enhancement of a comfortable feeling of the user, because a stimulus for the user to maintain a comfortable feeling is outputted, it is possible to maintain a comfortable feeling of the user.

Also, in the environment control device described above, it is preferable that the inferring portion infers that the comfortable feeling of the user has deteriorated in a case where the variance of the parameter falls within a specific third range that is different from the second range and indicates that the comfortable feeling of the user has deteriorated, and outputs a stimulus output instruction to enhance the comfortable feeling to the stimulus control portion, and in a case where the variance of the parameter does no fall within any of the first through third ranges, infers that the user in a state of danger and stops a system urgently.

According to this configuration, by employing the principle discovered by the inventors that there is a correlation between a variance of a parameter to evaluate the pulse wave and a comfortable feeling of the user, the third range indicating that a comfortable feeling of the user has deteriorated is set in advance, and a comfortable feeling of the user is inferred to have deteriorated in a case where a variance of the parameter falls within the third range. It is thus possible to infer precisely that a comfortable feeling of the user has deteriorated. Also, in a case where the result of inference obtained indicates deterioration of a comfortable feeling of the user, because a stimulus to enhance a comfortable feeling is outputted, it is possible to provide a comfortable feeling to the user. Also, in a case where a variance of the parameter does not fall within any of the first through third ranges, the system is stopped urgently because a danger for the user is predicted. It is thus possible to achieve a safe system for the user.

Also, in the environment control system described above, it is preferable that the inferring portion outputs a stimulus output instruction for the variance of the parameter to fall within the second range in a case where the variance of the parameter falls within the first range, outputs a stimulus output instruction to stop a stimulus in a case where the variance of the parameter falls within the second range, and outputs again the stimulus output instruction outputted to the stimulus control portion immediately before the stimulus was stopped in a case where the variance of the parameter later falls again within the first range and continues to stay in the first range over a specific period by inferring that the user has adapted to the stimulus.

According to this configuration, it is possible to control a stimulus output by also detecting that adaptation to the stimulus takes place, which makes it possible to achieve a system capable of maintaining a comfortable state for the user in a reliable manner. Also, by outputting a stimulus after determining the most appropriate content of stimulus and timing from a change of the pulse wave of the user, it is possible to achieve efficient running, which makes in possible to achieve an efficient system also in terms of energy saving.

Also, in the environment control device described above, it is preferable that the parameter calculating portion calculates a first parameter and a second parameter different from the first parameter to evaluate a pulse wave from the time-series data, and that the inferring portion infers a warm or cold feeling of the user on the basis of a variance of the first parameter and a variance of the second parameter.

According to this configuration, two kinds of parameters to evaluate the pulse wave, including the first and second parameters, are extracted, and a warm or cold feeling of the user is inferred by employing the principle discovered by the inventors that there is a correlation between variances of the first and second parameters and a thermal sensation of the user. It is thus possible to infer a thermal sensation of the user at a higher degree of accuracy as to whether a warm or cold feeling has changed in a direction to a hot state, whether it has changed in a direction to a cold state, or whether it has changed in a direction to the neutral state.

Also, in the environment control device described above, it is preferable that the inferring portion infers a thermal sensation of the user on the basis of a content of stimulus to be given to the user and a variance of the parameter. According to this configuration, because a thermal sensation of the user is inferred on the basis of a variance of the parameter of the wave pulse and the content of stimulus specifying whether a stimulus is a warm stimulus or a cool stimulus, the kinds and the strength of stimulus, and so forth, it is possible to infer a thermal sensation of the user at a higher degree of accuracy as to whether a warm or cold feeling has changed in a direction to a hot state, whether it has changed in a direction to a cold state, or whether it has changed in a direction to the neutral state.

Also, in the environment control device described above, it is preferable to further include a temperature measuring portion for measuring a temperature of a location where the user is in, and it is preferable that the inferring portion infers a thermal sensation of the user on the basis of a variance of parameter and a result of temperature measurement by the temperature measuring portion.

According to this configuration, because a thermal sensation of the user is inferred on the basis of a variance of the parameter of the pulse wave and the result indicating whether the temperature of the location where the user is in has risen or dropped, it is possible to infer a thermal sensation of the user at a higher degree of accuracy as to whether a warm or cold feeling of the user has changed in a direction to a hot state, whether it has changed in a direction to a cold state, or whether it has changed in a direction to the neutral state.

In the environment control device described above, it is preferable that the parameter is a ratio of waveform components of an accelerated pulse wave obtained by second-order differentiation of a pulse wave waveform obtained from the time-series data, and that the inferring portion infers that a thermal sensation has improved as the thermal sensation of the user has changed in a direction from a cold state to a neutral state or in a direction from a hot state to the neutral state in a case where the ratio of waveform components of the accelerated pulse wave has decreased, and infers that the thermal sensation has deteriorated as the thermal sensation of the user has changed in a direction from the neutral state to the cold state or in a direction from the neutral state to the hot state in a case where the ratio of waveform components of the accelerated pulse wave has increased.

According to this configuration, of many parameters of the pulse wave, the ratio of waveform components of the accelerated pulse wave is used as the parameter. Hence, because complicated processing can be omitted, it is possible to achieve a system with a simple configuration. Also, because a direction of a change of a thermal sensation of the user is inferred from a variance of the parameter, it is possible to extract a response of the user to a stimulus in a more reliable manner.

Also, in the environment control device described above, it is preferable that: the first parameter is a ratio of waveform components of an accelerated pulse wave obtained by second-order differentiation of a pulse wave waveform obtained from the time-series data, and the second parameter is a maximum value of a wave height of an accelerated pulse wave obtained by second-order differentiation of the pulse wave waveform obtained from the time series data or a maximum value of a wave height of the pulse wave obtained from the time series data, and that the inferring portion infers that a thermal sensation of the user has changed in a direction from a cold state to a neutral state in a case where the ratio of waveform components of the accelerated pulse wave has decreased and the maximum value of the wave height of the accelerated pulse wave or the maximum value of the wave height of the pulse wave has increased, infers that the thermal sensation of the user has changed in a direction from a hot state to the neutral state in a case where the ratio of waveform components of the accelerated pulse wave has decreased and the maximum value of the wave height of the accelerated pulse wave or the maximum value of the wave height of the pulse wave has decreased, infers that the thermal sensation of the user has changed in a direction from the neutral state to the hot state in a case where the ratio of waveform components of the accelerated pulse wave has increased and the maximum value of the wave height of the accelerated pulse wave or the maximum value of the wave height of the pulse wave has increased, and infers that the thermal sensation of the user has changed in a direction from the neutral state to the cold state in a case where the ratio of waveform components of the accelerated pulse wave has increased and the maximum value of the wave height of the accelerated pulse wave or the maximum value of the wave height of the pulse wave has decreased.

According to this configuration, of many pulse wave parameters, the ratio of waveform components of the accelerated pulse wave obtained by second-order differentiation of the pulse wave waveform obtained from the pulse wave data is used as the first parameter, and the maximum value of the wave height of the accelerated pulse wave or the maximum value of the wave height of the pulse wave is used as the second parameter. Hence, because complicated processing can be omitted, it is possible to achieve a system with a simple configuration. Also, because a direction of a change of a thermal sensation of the user is inferred from a variance of the ratio of waveform components of the accelerated pulse wave and the maximum value of the wave height of the accelerated pulse wave or the maximum value of the wave height of the pulse wave, all of which are the parameters, it is possible to extract a response of the user to a stimulus in a more reliable manner.

Also, in the environment control device described above, it is preferable that the parameter is a ratio of waveform components of an accelerated pulse wave obtained by second-order differentiation of a pulse wave waveform obtained from the time-series data, and that the inferring portion infers that a thermal sensation of the user has changed in a direction from a hot state to a neutral state in a case where the ratio of waveform components of the accelerated pulse wave has decreased, a content of stimulus specifies a stimulus of a kind that enhances a cool feeling, and strength of stimulus has heightened or in a case where the ratio of waveform components of the accelerated pulse wave has decreased, the content of stimulus specifies a stimulus of a kind that enhances a warm feeling, and the strength of stimulus has weakened, infers that the thermal sensation of the user has changed in a direction from a cold state to the neutral state in a case where the ratio of waveform components of the accelerated pulse wave has decreased, the content of stimulus specifies a stimulus of a kind that enhances the cool feeling, and the strength of stimulus has weakened or in a case where the ratio of waveform components of the accelerated pulse wave has decreased, the content of stimulus specifies a stimulus of a kind that enhances the warm feeling, and the strength of stimulus has heightened, infers that the thermal sensation of the user has changed in a direction from the neutral state to the cold state in a case where the ratio of waveform components of the accelerated pulse wave has increased, the content of stimulus specifies a stimulus of a kind that enhances the cool feeling, and the strength of stimulus has heightened or in a case where the ratio of waveform components of the accelerated pulse wave has increased, the content of stimulus specifies a stimulus of a kind that enhances the warm feeling, and the strength of stimulus has weakened, and infers that the thermal sensation of the user has changed in a direction from the neutral state to the hot state in a case where the ratio of waveform components of the accelerated pulse wave has increased, the content of stimulus specifies a stimulus of a kind that enhances the cool feeling, and the strength of stimulus has weakened or in a case where the ratio of waveform components of the accelerated pulse wave has increased, the content of stimulus specifies a stimulus of a kind that enhances the warm feeling, and the strength of stimulus has heightened.

According to this configuration, of many parameters of the pulse wave, the ratio of waveform components of the accelerated pulse wave is used as the parameter. Hence, because complicated processing can be omitted, it is possible to achieve a system with a simple configuration. Also, because a direction of a change of a thermal sensation of the user is inferred on the basis of a variance of the waveform components of the accelerated pulse wave, which is the parameter, and the content of stimulus, it is possible to extract a response of the user to a stimulus in a more reliable manner.

Also, in the environment control device described above, it is preferable that the inferring portion calculates a derivative value of the parameter and infers a thermal sensation of the user on the basis of the derivative value that has been calculated. According to this configuration, because a thermal sensation of the user is inferred from the derivative value of the ratio of waveform components of the accelerated pulse wave, which is the parameter, it is possible to extract a response of the user to a stimulus in a more reliable manner.

Also, in the environment control device described above, it is preferable that the inferring portion infers a thermal sensation of the user by calculating derivative values of the first and second parameters. According to this configuration, because a thermal sensation of the user is inferred on the basis of the derivative value of the ratio of waveform components of the accelerated pulse wave as the first parameter and the derivative value of the maximum value of the wave height of the accelerated pulse wave or the maximum value of the wave height of the pulse wave as the second parameter, it is possible to extract a response of the user to a stimulus in a more reliable manner.

Also, in the environment control device described above, it is preferable that the inferring portion determines that a thermal sensation of the user has not changed in a case where a variance of the parameter falls within a specific range, and outputs no stimulus output instruction. According to this configuration, it is possible to reduce frequent changes of the content of stimulus and the inference processing that take place for a slight variance of the parameter.

Also, in the environment control device described above, it is preferable that the inferring portion determines that a thermal sensation of the user has not changed in a case where a variance of the first parameter falls within a specific first range or in a case where a variance of the second parameter falls within a specific second range, and outputs no stimulus output instruction. According to this configuration, it is possible to reduce frequent changes of the content of stimulus and the inference processing that take place for slight variances of the first and second parameters.

INDUSTRIAL APPLICABILITY

An environment control device, an environment control method, an environment control program, and a computer-readable recording medium containing the environment control program of the invention enable the user to actually have a comfortable feeling in a reliable manner and further to maintain such a comfortable state. Hence, they are useful as an environment control device, an environment control method, an environment control program, and a computer-readable recording medium containing the environment control program to control a device forming the residential environment, for example, an air conditioning device, a lighting device, a video device, and an audio device.

The invention claimed is:

1. An environment control device, comprising:
a biological information acquiring portion for acquiring time-series data of biological information of a user;
a parameter calculating portion for calculating a parameter about the biological information through chaos analysis of the time-series data acquired by the biological information acquiring portion;
an inferring portion for inferring a comfortable feeling of the user on the basis of the parameter calculated by the parameter calculating portion; and
a stimulus control portion for controlling generation of a stimulus to be given to the user on the basis of a result of inference made by the inferring portion,
wherein the parameter calculating portion includes a first parameter calculating portion for calculating a first parameter about the biological information through the chaos analysis of the time-series data and a second parameter calculating portion for calculating a second parameter about the biological information on the basis of a change of the time-series data,
wherein the inferring portion infers the comfortable feeling of the user on the basis of the first parameter calculated by the first parameter calculating portion and the second parameter calculated by the second parameter calculating portion,
wherein the first parameter calculating portion calculates a maximum Lyapunov exponent through the chaos analysis of the time-series data,
wherein the second parameter calculating portion calculates an amplitude of a pulse wave or a maximum wave height value of the pulse wave from the time-series data, and
wherein the inferring portion infers that a thermal sensation of the user has changed in a direction from a neutral state to a hot state in a case where the maximum Lyapunov exponent has increased and the amplitude of the pulse wave or the maximum wave height value of the pulse wave has increased, infers that the thermal sensation of the user has changed in a direction from a cold state to the neutral state in a case where the maximum Lyapunov exponent has decreased and the amplitude of the pulse wave or the maximum wave height value of the pulse wave has increased, infers that the thermal sensation of the user has changed in a direction from the neutral state to the cold state in a case where the maximum Lyapunov exponent has increased and the amplitude of the pulse wave or the maximum wave height value of the pulse wave has decreased, and infers that the thermal sensation of the user has changed in a direction from the hot state to the neutral state in a case where the maximum Lyapunov exponent has decreased and the amplitude of the pulse wave or the maximum wave height value of the pulse wave has decreased.

2. An environment control device, comprising:
a biological information acquiring portion for acquiring time-series data of biological information of a user;
a parameter calculating portion for calculating a parameter about the biological information through chaos analysis of the time-series data acquired by the biological information acquiring portion;
an inferring portion for inferring a comfortable feeling of the user on the basis of the parameter calculated by the parameter calculating portion; and
a stimulus control portion for controlling generation of a stimulus to be given to the user on the basis of a result of inference made by the inferring portion,
wherein the parameter calculating portion includes a first parameter calculating portion for calculating a first parameter about the biological information through the chaos analysis of the time-series data and a second parameter calculating portion for calculating a second parameter about the biological information on the basis of a change of the time-series data,
wherein the inferring portion includes a first inferring portion for inferring the comfortable feeling of the user on the basis of the first parameter calculated by the first parameter calculating portion and a second inferring portion for inferring the comfortable feeling of the user on the basis of the second parameter calculated by the second parameter calculating portion,
wherein the stimulus control portion includes a first stimulus control portion for controlling the generation of the stimulus to be given to the user on the basis of a result of inference made by the first inferring portion and a second stimulus control portion for controlling the generation of the stimulus to be given to the user on the basis of a result of inference made by the second inferring portion, and
wherein the environment control device further comprises a stimulus control switching portion for switching control by the first stimulus control portion and control by the second stimulus control portion on the basis of the change of the time-series data.

3. The environment control device according to claim 2,
wherein the first inferring portion infers the comfortable feeling of the user on the basis of the first parameter calculated by the first parameter calculating portion and the second parameter calculated by the second parameter calculating portion.

4. An environment control device, comprising:
a biological information acquiring portion for acquiring time-series data of biological information of a user;
a parameter calculating portion for calculating a parameter about the biological information on the basis of a change of the time-series data acquired by the biological information acquiring portion;
an inferring portion for inferring a comfortable feeling of the user on the basis of the parameter calculated by the parameter calculating portion; and
a stimulus control portion for controlling generation of a stimulus to be given to the user on the basis of a result of inference made by the inferring portion,
wherein the biological information is a pulse wave of the user,
wherein the stimulus control portion controls generation of a warm or cool thermal stimulus to be given to the user,
wherein the inferring portion infers a thermal sensation of the user in response to the warm or cool thermal stimulus,
wherein the parameter calculating portion calculates, as the parameter, at least one of a pulse wave amplitude of a pulse wave waveform obtained from the biological information, a maximum wave height value of the pulse wave, a ratio of waveform components of an accelerated pulse wave waveform obtained by second-order differentiation of the pulse wave waveform obtained from the biological information, an accelerated pulse wave amplitude, and a pulse rate,
wherein the inferring portion infers the thermal sensation of the user on the basis of a variance of the parameter calculated by the parameter calculating portion,
wherein the parameter calculating portion calculates the pulse wave amplitude or the maximum wave height value of the pulse wave and a ratio of waveform components of the accelerated pulse wave waveform, c/a, on the basis of the time-series data, and
wherein the inferring portion infers that the thermal sensation of the user has changed in a direction from a neutral state to a hot state in a case where the ratio of waveform components of the accelerated pulse wave waveform, c/a, has increased and the pulse wave amplitude or the maximum wave height value of the pulse wave has increased, infers that the thermal sensation of the user has changed in a direction from a cold state to the neutral state in a case where the ratio of waveform components of the accelerated pulse wave waveform, c/a, has decreased and the pulse wave amplitude or the maximum wave height value of the pulse wave has increased, infers that the thermal sensation of the user has changed in a direction from the neutral state to the cold state in a case where the ratio of waveform components of the accelerated pulse wave waveform, c/a, has increased and the pulse wave amplitude or the maximum wave height value of the pulse wave has decreased, and infers that the thermal sensation of the user has changed in a direction from the hot state to the neutral state in a case where the ratio of waveform components of the accelerated pulse wave waveform, c/a, has decreased and the pulse wave amplitude or the maximum wave height value of the pulse wave has decreased.

5. An environment control device, comprising:
a biological information acquiring portion for acquiring time-series data of biological information of a user;
a parameter calculating portion for calculating a parameter about the biological information through chaos analysis of the time-series data acquired by the biological information acquiring portion;

an inferring portion for inferring a comfortable feeling of the user on the basis of the parameter calculated by the parameter calculating portion; and a stimulus control portion for controlling generation of a stimulus to be given to the user on the basis of a result of inference made by the inferring portion, wherein the parameter calculating portion includes a first parameter calculating portion for calculating a first parameter about the biological information through the chaos analysis of the time-series data and a second parameter calculating portion for calculating a second parameter about the biological information on the basis of a change of the time-series data, wherein the inferring portion includes a first inferring portion for inferring the comfortable feeling of the user on the basis of the first parameter calculated by the first parameter calculating portion and a second inferring portion for inferring the comfortable feeling of the user on the basis of the second parameter calculated by the second parameter calculating portion, wherein the first parameter calculating portion in a plural form, the second parameter calculating portion in a plural form, or the first parameter calculating portion at least in a singular form and the second parameter calculating portion at least in a singular form are included, wherein the environment control device further comprises a determining portion for determining whether all results of inference made by the first inferring portion or the second inferring portion coincide with each other, and wherein the stimulus control portion controls the generation of the stimulus to be given to the user on the basis of the results of inference that are determined as coinciding with each other by the determining portion.

6. An environment control method, comprising:

a biological information acquiring step of acquiring time-series data of biological information of a user;

a parameter calculating step of calculating a parameter about the biological information through chaos analysis of the time-series data acquired in the biological information acquiring step;

an inferring step of inferring a comfortable feeling of the user on the basis of the parameter calculated in the parameter calculating step; and a stimulus controlling step of controlling generation of a stimulus to be given to the user on the basis of a result of inference made in the inferring step, wherein the parameter calculating step includes a first parameter calculating step of calculating a first parameter about the biological information through the chaos analysis of the time-series data and a second parameter calculating step of calculating a second parameter about the biological information on the basis of a change of the time-series data, wherein the inferring portion step the comfortable feeling of the user on the basis of the first parameter calculated by the first parameter calculating step and the second parameter calculated by the second parameter calculating step, wherein the first parameter calculating step calculates a maximum Lyapunov exponent through the chaos analysis of the time-series data, wherein the second parameter calculating step calculates an amplitude of a pulse wave or a maximum wave height value of the pulse wave from the time-series data, and wherein the inferring step infers that a thermal sensation of the user has changed in a direction from a neutral state to a hot state in a case where the maximum Lyapunov exponent has increased and the amplitude of the pulse wave or the maximum wave height value of the pulse wave has increased, infers that the thermal sensation of the user has changed in a direction from a cold state to the neutral state in a case where the maximum Lyapunov exponent has decreased and the amplitude of the pulse wave or the maximum wave height value of the pulse wave has increased, infers that the thermal sensation of the user has changed in a direction from the neutral state to the cold state in a case where the maximum Lyapunov exponent has increased and the amplitude of the pulse wave or the maximum wave height value of the pulse wave has decreased, and infers that the thermal sensation of the user has changed in a direction from the hot state to the neutral state in a case where the maximum Lyapunov exponent has decreased and the amplitude of the pulse wave or the maximum wave height value of the pulse wave has decreased.

7. A non-transitory computer-readable recording medium storing thereon an environment control program, wherein, when executed, the environment control program causes a computer to function as:

a biological information acquiring portion for acquiring time-series data of biological information of a user;

a parameter calculating portion for calculating a parameter about the biological information through chaos analysis of the time-series data acquired by the biological information acquiring portion;

an inferring portion for inferring a comfortable feeling of the user on the basis of the parameter calculated by the parameter calculating portion; and a stimulus control portion for controlling generation of a stimulus to be given to the user on the basis of a result of inference made by the inferring portion, wherein the parameter calculating portion includes a first parameter calculating portion for calculating a first parameter about the biological information through the chaos analysis of the time-series data and a second parameter calculating portion for calculating a second parameter about the biological information on the basis of a change of the time-series data, wherein the inferring portion infers the comfortable feeling of the user on the basis of the first parameter calculated by the first parameter calculating portion and the second parameter calculated by the second parameter calculating portion, wherein the first parameter calculating portion calculates a maximum Lyapunov exponent through the chaos analysis of the time-series data, wherein the second parameter calculating portion calculates an amplitude of a pulse wave or a maximum wave height value of the pulse wave from the time-series data, and wherein the inferring portion infers that a thermal sensation of the user has changed in a direction from a neutral state to a hot state in a case where the maximum Lyapunov exponent has increased and the amplitude of the pulse wave or the maximum wave height value of the pulse wave has increased, infers that the thermal sensation of the user has changed in a direction from a cold state to the neutral state in a case where the maximum Lyapunov exponent has decreased and the amplitude of the pulse wave or the maximum wave height value of the pulse wave has increased, infers that the thermal sensation of the user has changed in a direction from the neutral state to the cold state in a case where the maximum Lyapunov exponent has increased and the amplitude of the pulse wave or the maximum wave height value of the pulse wave has decreased, and infers that the thermal sensation of the user has changed in a direction from the hot state to the neutral state in a case where the maximum Lyapunov exponent has decreased and the amplitude of the pulse wave or the maximum wave height value of the pulse wave has decreased.

8. An environment control method, comprising:
a biological information acquiring step of acquiring time-series data of biological information of a user;
a parameter calculating step of calculating a parameter about the biological information on the basis of a change of the time-series data acquired in the biological information acquiring step;
an inferring step of inferring a comfortable feeling of the user on the basis of the parameter calculated in the parameter calculating step; and
a stimulus controlling step of controlling generation of a stimulus to be given to the user on the basis of a result of inference made in the inferring step,
wherein the biological information is a pulse wave of the user,
wherein the stimulus controlling step controls generation of a warm or cool thermal stimulus to be given to the user,
wherein the inferring step infers a thermal sensation of the user in response to the warm or cool thermal stimulus,
wherein the parameter calculating step calculates, as the parameter, at least one of a pulse wave amplitude of a pulse wave waveform obtained from the biological information, a maximum wave height value of the pulse wave, a ratio of waveform components of an accelerated pulse wave waveform obtained by second-order differentiation of the pulse wave waveform obtained from the biological information, an accelerated pulse wave amplitude, and a pulse rate,
wherein the inferring step infers the thermal sensation of the user on the basis of a variance of the parameter calculated by the parameter calculating step,
wherein the parameter calculating step calculates the pulse wave amplitude or the maximum wave height value of the pulse wave and a ratio of waveform components of the accelerated pulse wave waveform, c/a, on the basis of the time-series data, and
wherein the inferring step infers that the thermal sensation of the user has changed in a direction from a neutral state to a hot state in a case where the ratio of waveform components of the accelerated pulse wave waveform, c/a, has increased and the pulse wave amplitude or the maximum wave height value of the pulse wave has increased, infers that the thermal sensation of the user has changed in a direction from a cold state to the neutral state in a case where the ratio of waveform components of the accelerated pulse wave waveform, c/a, has decreased and the pulse wave amplitude or the maximum wave height value of the pulse wave has increased, infers that the thermal sensation of the user has changed in a direction from the neutral state to the cold state in a case where the ratio of waveform components of the accelerated pulse wave waveform, c/a, has increased and the pulse wave amplitude or the maximum wave height value of the pulse wave has decreased, and infers that the thermal sensation of the user has changed in a direction from the hot state to the neutral state in a case where the ratio of waveform components of the accelerated pulse wave waveform, c/a, has decreased and the pulse wave amplitude or the maximum wave height value of the pulse wave has decreased.

9. A non-transitory computer-readable recording medium storing thereon an environment control program, wherein, when executed, the environment control program causes a computer to function as:
a biological information acquiring portion for acquiring time-series data of biological information of a user;
a parameter calculating portion for calculating a parameter about the biological information on the basis of a change of the time-series data acquired by the biological information acquiring portion;
an inferring portion for inferring a comfortable feeling of the user on the basis of the parameter calculated by the parameter calculating portion; and
a stimulus control portion for controlling generation of a stimulus to be given to the user on the basis of a result of inference made by the inferring portion,
wherein the biological information is a pulse wave of the user,
wherein the stimulus control portion controls generation of a warm or cool thermal stimulus to be given to the user,
wherein the inferring portion infers a thermal sensation of the user in response to the warm or cool thermal stimulus,
wherein the parameter calculating portion calculates, as the parameter, at least one of a pulse wave amplitude of a pulse wave waveform obtained from the biological information, a maximum wave height value of the pulse wave, a ratio of waveform components of an accelerated pulse wave waveform obtained by second-order differentiation of the pulse wave waveform obtained from the biological information, an accelerated pulse wave amplitude, and a pulse rate,
wherein the inferring portion infers the thermal sensation of the user on the basis of a variance of the parameter calculated by the parameter calculating portion,
wherein the parameter calculating portion calculates the pulse wave amplitude or the maximum wave height value of the pulse wave and a ratio of waveform components of the accelerated pulse wave waveform, c/a, on the basis of the time-series data, and
wherein the inferring portion infers that the thermal sensation of the user has changed in a direction from a neutral state to a hot state in a case where the ratio of waveform components of the accelerated pulse wave waveform, c/a, has increased and the pulse wave amplitude or the maximum wave height value of the pulse wave has increased, infers that the thermal sensation of the user has changed in a direction from a cold state to the neutral state in a case where the ratio of waveform components of the accelerated pulse wave waveform, c/a, has decreased and the pulse wave amplitude or the maximum wave height value of the pulse wave has increased, infers that the thermal sensation of the user has changed in a direction from the neutral state to the cold state in a case where the ratio of waveform components of the accelerated pulse wave waveform, c/a, has increased and the pulse wave amplitude or the maximum wave height value of the pulse wave has decreased, and infers that the thermal sensation of the user has changed in a direction from the hot state to the neutral state in a case where the ratio of waveform components of the accelerated pulse wave waveform, c/a, has decreased and the pulse wave amplitude or the maximum wave height value of the pulse wave has decreased.

* * * * *